(12) United States Patent
Liew

(10) Patent No.: US 8,133,675 B2
(45) Date of Patent: *Mar. 13, 2012

(54) METHOD OF PROFILING GENE EXPRESSION IN A SUBJECT HAVING AN INFECTIOUS DISEASE

(75) Inventor: Choong-Chin Liew, Toronto (CA)

(73) Assignee: GeneNews Corporation, Richmond Hill (CA)

( * ) Notice: Subject to any disclaimer, the term of this patent is extended or adjusted under 35 U.S.C. 154(b) by 3 days.

This patent is subject to a terminal disclaimer.

(21) Appl. No.: 12/757,934

(22) Filed: Apr. 9, 2010

(65) Prior Publication Data

US 2011/0014614 A1     Jan. 20, 2011

Related U.S. Application Data

(63) Continuation of application No. 12/587,385, filed on Oct. 5, 2009, now abandoned, which is a continuation of application No. 10/268,730, filed on Oct. 9, 2002, now Pat. No. 7,598,031, which is a continuation of application No. 09/477,148, filed on Jan. 4, 2000, now abandoned.

(60) Provisional application No. 60/115,125, filed on Jan. 6, 1999.

(51) Int. Cl.
*C12P 19/34* (2006.01)
*C12Q 1/68* (2006.01)

(52) U.S. Cl. ............... 435/6.1; 435/6.11; 435/6.12
(58) Field of Classification Search ............... None
See application file for complete search history.

(56) References Cited

U.S. PATENT DOCUMENTS

| 6,190,857 B1 * | 2/2001 | Ralph et al. ............... 435/4 |
| 6,607,879 B1 * | 8/2003 | Cocks et al. ............... 435/6 |
| 7,598,031 B2 * | 10/2009 | Liew ............... 435/6 |
| 7,662,558 B2 * | 2/2010 | Liew ............... 435/6 |

FOREIGN PATENT DOCUMENTS

WO       WO 98/49342      * 11/1998

OTHER PUBLICATIONS

Ditkoff et al. Surgery 1996; 120; 959-965.*
Nagai et al. Neurology 1996; 46:791-795.*
Affymetrix. Hu6800 Array Information Sheet. 1998. 2 pages.*

* cited by examiner

*Primary Examiner* — Juliet Switzer
(74) *Attorney, Agent, or Firm* — Edwards Wildman Palmer LLP; Kathleen Williams; Amy DeCloux

(57) ABSTRACT

The present invention is directed to detection and measurement of gene transcripts in blood. Specifically provided is a RT-PCR analysis performed on a drop of blood for detecting, diagnosing and monitoring diseases using tissue-specific primers. The present invention also describes methods by which delineation of the sequence and/or quantitation of the expression levels of disease-associated genes allows for an immediate and accurate diagnostic/prognostic test for disease or to assess the effect of a particular treatment regimen.

10 Claims, 7 Drawing Sheets

SEQUENCE LISTING

```
<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: Forward primer of exon1 of insulin gene

<400> SEQUENCE: 1
gccctctggg gacctgac                                                   18

<210> SEQ ID NO 2
```

```
<211> LENGTH: 18
<212> TYPE: DNA
<213> ORGANISM: Artificial Sequence
<220> FEATURE:
<223> OTHER INFORMATION: Reverse priners of exon 1 and 2 of inslin gene

<400> SEQUENCE: 2
cccacctgca ggtcctct                                              18

<210> SEQ ID NO 3
<211> LENGTH: 24
<212> TYPE: DNA
<213> ORGANISM: Artificial Sequence
<220> FEATURE:
<223> OTHER INFORMATION: Forward primer of MyHC gene

<400> SEQUENCE: 3
gctggaacgt agagactccc tgct                                       24

<210> SEQ ID NO 4
<211> LENGTH: 24
<212> TYPE: DNA
<213> ORGANISM: Artificial Sequence
<220> FEATURE:
<223> OTHER INFORMATION: Reverse primer of MyHC gene

<400> SEQUENCE: 4
ggatccttcc agatcatcca cttg                                       24

<210> SEQ ID NO 5
<211> LENGTH: 20
<212> TYPE: DNA
<213> ORGANISM: Artificial Sequence
<220> FEATURE:
<223> OTHER INFORMATION: Forward primer of ANF gene

<400> SEQUENCE: 5
ggatttcaag aatttgctgg                                            20

<210> SEQ ID NO 6
<211> LENGTH: 20
<212> TYPE: DNA
<213> ORGANISM: Artificial Sequence
<220> FEATURE:
<223> OTHER INFORMATION: Reverse primer of ANF gene

<400> SEQUENCE: 6
gcagatcgat cagaggagtc                                            20

<210> SEQ ID NO 7
<211> LENGTH: 20
<212> TYPE: DNA
<213> ORGANISM: Artificial Sequence
<220> FEATURE:
<223> OTHER INFORMATION: Forward primer of APP gene

<400> SEQUENCE: 7
ggatgcttca tgtgaacgtg                                            20

<210> SEQ ID NO 8
<211> LENGTH: 19
<212> TYPE: DNA
<213> ORGANISM: Artificial Sequence
<220> FEATURE:
<223> OTHER INFORMATION: reverse primer of APP gene

<400> SEQUENCE: 8
```

-continued

```
tcattcacac cagcacatg                                           19

<210> SEQ ID NO 9
<211> LENGTH: 21
<212> TYPE: DNA
<213> ORGANISM: Artificial Sequence
<220> FEATURE:
<223> OTHER INFORMATION: Forward primer of ZFP gene

<400> SEQUENCE: 9
cacargagrc arggtcaacg a                                        21

<210> SEQ ID NO 10
<211> LENGTH: 22
<212> TYPE: DNA
<213> ORGANISM: Artificial Sequence
<220> FEATURE:
<223> OTHER INFORMATION: Reverse primer for ZFP gene

<400> SEQUENCE: 10
ggattaaaat gaagcaccca ga                                       22
```

METHOD OF PROFILING GENE EXPRESSION IN A SUBJECT HAVING AN INFECTIOUS DISEASE

CROSS-REFERENCE TO RELATED APPLICATION

This application is a continuation of U.S. patent application Ser. No. 12/587,385, filed Oct. 5, 2009, which is a continuation of U.S. patent application Ser. No. 10/268,730 filed Oct. 9, 2002 (issued as U.S. Pat. No. 7,598,031), which is a continuation of U.S. application Ser. No. 09/477,148 filed Jan. 4, 2000, now abandoned, which claims the benefit of U.S. Provisional Application No. 60/115,125 filed on Jan. 6, 1999, now abandoned.

BACKGROUND OF THE INVENTION

1. Field of the Invention

The present invention relates generally to the molecular biology of human diseases. More specifically, the present invention relates to a process using the genetic information contained in human peripheral whole blood for the diagnosis, prognosis and monitoring of genetic and infectious disease in the human body.

2. Description of the Related Art

The blood is a vital part of the human circulatory system for the human body. Numerous cell types make up the blood tissue including monocytes, leukocytes, lymphocytes and erythrocytes. Although many blood cell types have been described, there are likely many as yet undiscovered cell types in the human blood. Some of these undiscovered cells may exist transiently, such as those derived from tissues and organs that are constantly interacting with the circulating blood in health and disease. Thus, the blood can provide an immediate picture of what is happening in the human body at any given time.

The turnover of cells in the hematopoietic system is enormous. It was reported that over one trillion cells, including 200 billion erythrocytes and 70 billion neutrophilic leukocytes, turn over each day in the human body (Ogawa 1993). As a consequence of continuous interactions between the blood and the body, genetic changes that occur within the cells or tissues of the body will trigger specific changes in gene expression within blood. It is the goal of the present invention that these genetic alterations be harnessed for diagnostic and prognostic purposes, which may lead to the development of therapeutics for ameliorating disease.

The complete profile of gene expression in the circulating blood remains totally unexplored. It is hypothesized that gene expression in the blood is reflective of body state and, as such, the resultant disruption of homeostasis under conditions of disease can be detected through analysis of transcripts differentially expressed in the blood alone. Thus, the identification of several key transcripts or genetic markers in blood will provide information about the genetic state of the cells, tissues, organ systems of the human body in health and disease.

The prior art is deficient in non-invasive methods of screening for tissue-specific diseases. The present invention fulfills this long-standing need and desire in the art.

SUMMARY OF THE INVENTION

This present invention discloses a process of using the genetic information contained in human peripheral whole blood in the diagnosis, prognosis and monitoring of genetic and infectious disease in the human body. The process described herein requires a simple blood sample and is, therefore, non-invasive compared to conventional practices used to detect tissue specific disease, such as biopsies.

One object of the present invention is to provide a non-invasive method for the diagnosis, prognosis and monitoring of genetic and infectious disease in humans and animals.

In one embodiment of the present invention, there is provided a method for detecting expression of a gene in blood from a subject, comprising the steps of: a) quantifying RNA from a subject blood sample; and b) detecting expression of the gene in the quantified RNA, wherein the expression of the gene in quantified RNA indicates the expression of the gene in the subject blood.

In another embodiment of the present invention, there is provided a method for detecting expression of one or more genes in blood from a subject, comprising the steps of: a) obtaining a subject blood sample; b) extracting RNA from the blood sample; c) amplifying the RNA; d) generating expressed sequence tags (ESTs) from the amplified RNA product; and e) detecting expression of the genes in the ESTs, wherein the expression of the genes in the ESTs indicates the expression of the genes in the subject blood. Preferably, the genes are tissue-specific genes.

In still another embodiment of the present invention, there is provided a method for detecting expression of one or more genes in blood from a subject, comprising the steps of: a) obtaining a subject blood sample; b) extracting DNA fragments from the blood sample; c) amplifying the DNA fragments; and d) detecting expression of the genes in the amplified DNA product, wherein the expression of the genes in the amplified DNA product indicates the expression of the genes in the subject blood.

In yet another embodiment of the present invention, there is provided a method for monitoring a course of a therapeutic treatment in an individual, comprising the steps of: a) obtaining a blood sample from the individual; b) extracting RNA from the blood sample; c) amplifying the RNA; d) generating expressed sequence tags (ESTs) from the amplified RNA product; e) detecting expression of genes in the ESTs, wherein the expression of the genes is associated with the effect of the therapeutic treatment; and f) repeating steps a)-e), wherein the course of the therapeutic treatment is monitored by detecting the change of expression of the genes in the ESTs. Such a method may also be used for monitoring the onset of overt symptoms of a disease, wherein the expression of the genes is associated with the onset of the symptoms.

In still yet another embodiment of the present invention, there is provided a method for diagnosing a disease in a test subject, comprising the steps of: a) generating a cDNA library for the disease from a whole blood sample from a normal subject; b) generating expressed sequence tag (EST) profile from the normal subject cDNA library; c) generating a cDNA library for the disease from a whole blood sample from a test subject; d) generating EST profile from the test subject cDNA library; and e) comparing the test subject EST profile to the normal subject EST profile, wherein if the test subject EST profile differs from the normal subject EST profile, the test subject might be diagnosed with the disease.

In still yet another embodiment of the present invention, there is provided a kit for diagnosing, prognosing or predicting a disease, comprising: a) gene-specific primers; wherein the primers are designed in such a way that their sequences contain the opposing ends of two adjacent exons for the specific gene with the intron sequence excluded; and b) a carrier, wherein the carrier immobilizes the primer(s). Such a kit may be applied to a test subject whole blood sample to diagnose, prognose or predict a disease.

In yet another embodiment of the present invention, there is provided a kit for diagnosing, prognosing or predicting a disease, comprising: a) probes derived from a whole blood sample for a specific disease; and b) a carrier, wherein the carrier immobilizes the probes. Such a kit may be applied to a test subject whole blood sample to diagnose, prognose or predict a disease.

Furthermore, the present invention provides a cDNA library specific for a disease, wherein the cDNA library is generated from whole blood samples.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope. not be considered to limit the scope of the invention.

FIG. 1A: Lane 1, Molecular weight marker; Lane 2, RT-PCR on APP gene; Lane 3, PCR on APP gene; Lane 4, RT-PCR on APC gene; Lane 5, PCR on APC gene; FIG. 1B: Lanes 1 and 2, RT-PCR and PCR of (MyHC, respectively; Lanes 3 and 4, RT-PCR of (MyHC from RNA prepared from human fetal and human adult heart, respectively; Lane 5, Molecular weight marker.

FIG. 5C shows standardized levels of insulin gene expressed in each fractionated cell from whole blood.

FIG. 6A shows blood cell cDNA probes vs. adult heart cDNA probes. FIG. 6B shows blood cell cDNA probes vs. human brain cDNA probes.

DETAILED DESCRIPTION OF THE INVENTION

Figure 1:
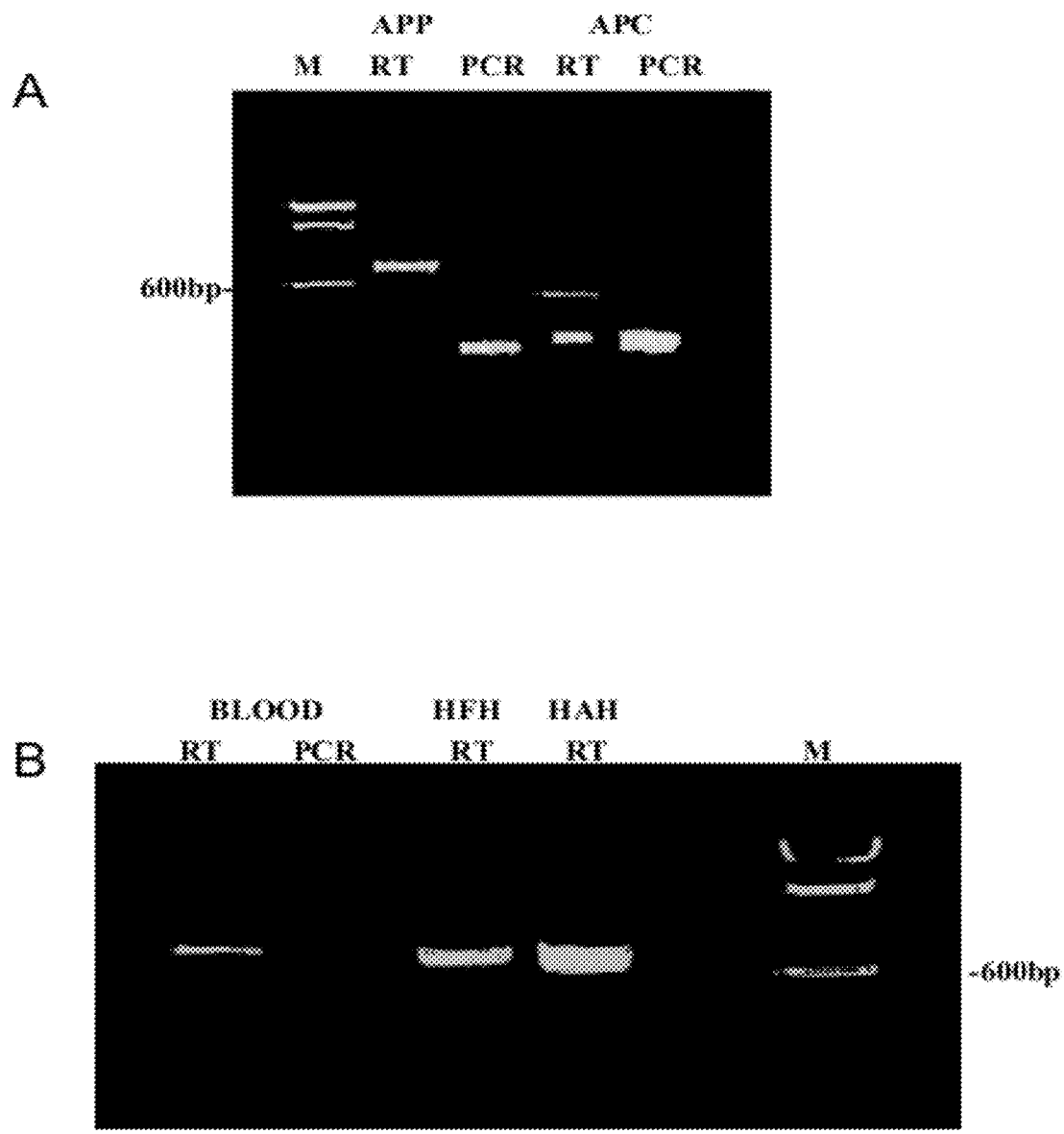
FIG. 1 shows the following RNA samples prepared from human blood.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "cDNA" is defined as copy-DNA or complementary-DNA, and is a product of a reverse transcription reaction from an mRNA transcript. "RT-PCR" refers to reverse transcription polymerase chain reaction and results in production of cDNAs that are complementary to the mRNA template(s).

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-25 or more nucleotides, although it may contain fewer nucleotides. The factors involved in determining the appropriate length of primer are readily known to one of ordinary skill in the art.

As used herein, random sequence primers refer to a composition of primers of random sequence, i.e. not directed towards a specific sequence. These sequences possess sufficient complementary to hybridize with a polynucleotide and the primer sequence need not reflect the exact sequence of the template.

"Restriction fragment length polymorphism" refers to variations in DNA sequence detected by variations in the length of DNA fragments generated by restriction endonuclease digestion.

A standard Northern blot assay can be used to ascertain the relative amounts of mRNA in a cell or tissue obtained from plant or other tissue, in accordance with conventional Northern hybridization techniques known to those persons of ordinary skill in the art. The Northern blot uses a hybridization probe, e.g. radiolabelled cDNA, either containing the full-length, single stranded DNA or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art. The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, (-glucuronidase, (-D-glucosidase, (-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, "individual" refers to human subjects as well as non-human subjects. The examples herein are not meant to limit the methodology of the present invention to human subjects only, as the instant methodology is useful in the fields of veterinary medicine, animal sciences and such.

In one embodiment of the present invention, there is provided a method for detecting expression of a gene in blood from a subject, comprising the steps of: a) quantifying RNA from a subject blood sample; and b) detecting expression of the gene in the quantified RNA, wherein the expression of the gene in quantified RNA indicates the expression of the gene in the subject blood. An example of the quantifying method is by mass spectrometry.

In another embodiment of the present invention, there is provided a method for detecting expression of one or more genes in blood from a subject, comprising the steps of: a) obtaining a subject blood sample; b) extracting RNA from the blood sample; c) amplifying the RNA; d) generating expressed sequence tags (ESTs) from the amplified RNA product; and e) detecting expression of the genes in the ESTs, wherein the expression of the genes in the ESTs indicates the expression of the genes in the subject blood. Preferably, the subject is a fetus, an embryo, a child, an adult or a non-human animal. The genes are non-cancer-associated and tissue-specific genes. Still preferably, the amplification is performed by RT-PCR using random sequence primers or gene-specific primers.

In still another embodiment of the present invention, there is provided a method for detecting expression of one or more genes in blood from a subject, comprising the steps of: a) obtaining a subject blood sample; b) extracting DNA fragments from the blood sample; c) amplifying the DNA fragments; and d) detecting expression of the genes in the amplified DNA product, wherein the expression of the genes in the amplified DNA product indicates the expression of the genes in the subject blood.

In yet another embodiment of the present invention, there is provided a method for monitoring a course of a therapeutic treatment in an individual, comprising the steps of: a) obtaining a blood sample from the individual; b) extracting RNA from the blood sample; c) amplifying the RNA; d) generating expressed sequence tags (ESTs) from the amplified RNA product; e) detecting expression of genes in the ESTs, wherein the expression of the genes is associated with the effect of the therapeutic treatment; and f) repeating steps a)-e), wherein the course of the therapeutic treatment is monitored by detecting the change of expression of the genes in the ESTs. Such a method may also be used for monitoring the onset of overt symptoms of a disease, wherein the expression of the genes is associated with the onset of the symptoms. Preferably, the amplification is performed by RT-PCR, and the change of the expression of the genes in the ESTs is monitored by sequencing the ESTs and comparing the resulting sequences at various time points; or by performing single nucleotide polymorphism analysis and detecting the variation of a single nucleotide in the ESTs at various time points.

In still yet another embodiment of the present invention, there is provided a method for diagnosing a disease in a test subject, comprising the steps of: a) generating a cDNA library for the disease from a whole blood sample from a normal subject; b) generating expressed sequence tag (EST) profile from the normal subject cDNA library; c) generating a cDNA library for the disease from a whole blood sample from a test subject; d) generating EST profile from the test subject cDNA library; and e) comparing the test subject EST profile to the normal subject EST profile, wherein if the test subject EST profile differs from the normal subject EST profile, the test subject might be diagnosed with the disease.

In still yet another embodiment of the present invention, there is provided a kit for diagnosing, prognosing or predicting a disease, comprising: a) gene-specific primers; wherein the primers are designed in such a way that their sequences contain the opposing ends of two adjacent exons for the specific gene with the intron sequence excluded; and b) a carrier, wherein the carrier immobilizes the primer(s). Preferably, the gene-specific primers are selected from the group consisting of insulin-specific primers, atrial natriuretic factor-specific primers, zinc finger protein gene-specific primers, beta-myosin heavy chain gene-specific primers, amyloid precurser protein gene-specific primers, and adenomatous polyposis-coli protein gene-specific primers. Further preferably, the gene-specific primers are selected from the group consisting of SEQ ID Nos. 1 and 2; and SEQ ID Nos. 5 and 6. Such a kit may be applied to a test subject whole blood sample to diagnose, prognose or predict a disease by detecting the quantitative expression levels of specific genes associated with the disease in the test subject and then comparing to the levels of same genes expressed in a normal subject. Such a kit may also be used for monitoring a course of therapeutic treatment or monitoring the onset of overt symptoms of a disease.

In yet another embodiment of the present invention, there is provided a kit for diagnosing, prognosing or predicting a disease, comprising: a) probes derived from a whole blood sample for a specific disease; and b) a carrier, wherein the carrier immobilizes the probes. Such a kit may be applied to a test subject whole blood sample to diagnose, prognose or predict a disease by detecting the quantitative expression levels of specific genes associated with the disease in the test subject and then comparing to the levels of same genes expressed in a normal subject. Such a kit may also be used for monitoring a course of therapeutic treatment or monitoring the onset of overt symptoms of a disease.

Furthermore, the present invention provides a cDNA library specific for a disease, wherein the cDNA library is generated from whole blood samples.

The following examples are given for the purpose of illustrating various embodiments of the invention and are not meant to limit the present invention in any fashion.

Example 1

Construction of a cDNA Library

RNA extracted from human tissues (including fetal heart, adult heart, liver, brain, prostate gland and whole blood) were used to construct unidirectional cDNA libraries. The first mammalian heart cDNA library was constructed as early as 1982. Since then, the methodology has been revised and optimal conditions have been developed for construction of human heart and hematopoietic progenitor cDNA libraries (Liew et al., 1984; Liew 1993, Claudio et al., 1998). Most of the novel genes which were identified by sequence annotation can now be obtained as full length transcripts.

Example 2

Catalogue of Blood Cell ESTs

Random partial sequencing of expressed sequence tags (ESTs) of cDNA clones from the blood cell library was carried out to establish an EST database of blood. The known genes as derived from the ESTs were categorized into seven major cellular functions (Hwang, Dempsey et al., 1997).

Example 3

Differential Screening of cDNA Library cDNA probes generated from transcripts of each tissue were used to hybridize the blood cell cDNA clones (Liew et al., 1997). The "positive" signals which were hybridized with P-labelled cDNA probes were defined as genes which shared identity with blood and respective tissues. The "negative" spots which were not exposed to P-labelled cDNA probes were considered to be blood-cell-enriched or low frequency transcripts.

Example 4

Reverse Transcriptase-Polymerase Chain Reaction (RT-PCR) Assay

RNA extracted from samples of human tissue was used for RT-PCR analysis (Jin et al. 1990). Three pairs of forward and reverse primers were designed for human cardiac beta-myosin heavy chain gene ((MyHC), amyloid precurser protein (APP) gene and adenomatous polyposis-coli protein (APC) gene. The PCR products were also subjected to automated DNA sequencing to verify the sequences as derived from the specific transcripts of blood.

Example 5

Detection of Tissue Specific Gene Expression in Human Blood Using RT-PCR

The beta-myosin heavy chain gene ((MyHC) transcript (mRNA) is known to be highly expressed in ventricles of the human heart. This sarcomeric protein is important for heart muscle contraction and its presence would not be expected in other non-muscle tissues and blood. In 1990, the gene for human cardiac (MyHC was completely sequenced (Liew et al. 1990) and was comprised of 41 exons and 42 introns.

The method of reverse transcription polymerase chain reaction (RT-PCR) was used to determine whether this cardiac specific mRNA is also present in human blood. A pair of primers was designed; the forward primer (SEQ ID No. 3) was on the boundary of exons 21 and 22, and the reverse primer (SEQ ID No. 4) was on the boundary of exons 24 and 25. This region of mRNA is only present in (MyHC and is not found in the alpha-myosin heavy chain gene ((MyHC).

A blood sample was first treated with lysing buffer and then undergone centrifuge. The resulting pellets were further processed with RT-PCR. RT-PCR was performed using the total blood cell RNA as a template. A nested PCR product was generated and used for sequencing. The sequencing results were subjected to BLAST and the identity of exons 21 to 25 was confirmed to be from (MyHC (FIG. 1A).

Using the same method just described, two other tissue specific genes—amyloid precursor protein (APP, forward primer, SEQ ID No. 7; reverse primer, SEQ ID No. 8) found in the brain and associated with Alzheimer's disease, and adenomatous polyposis coli protein (APC) found in the colon and rectum and associated with colorectal cancer (Groden et al. 1991; Santoro and Groden 1997)—were also detected in the RNA extracted from human blood (FIG. 1B).

Example 6

Multiple RT-PCR Analysis on a Drop of Blood from a Normal/Diseased Individual

Figure 2:
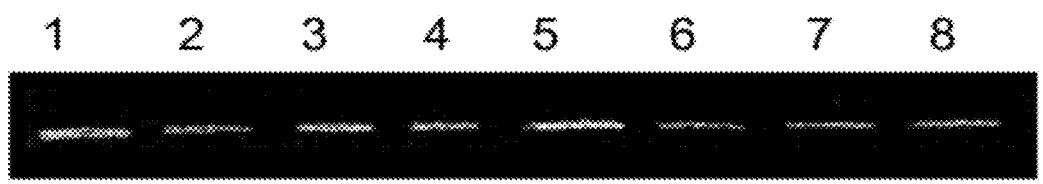
FIG. 2 shows quantitative RT-PCR analysis performed on RNA samples extracted from a drop of blood. Forward primer (5'-GCCCTCTGGGGACCTGAC-3', SEQ ID No. 1) of exon 1 and reverse primer (5'-CCCACCTGCAGGTCCTCT-3", SEQ ID No. 2) of exons 1 and 2 of insulin gene. Blood samples of 4 normal subjects were assayed. Lanes 1, 3, 5 and 7 represent overnight "fasting" blood sample and lanes 2, 4, 6 and 8 represent "non-fasting" samples.

A drop of blood was extracted to obtain RNA to carry out quantitative RT-PCR analysis. Specific primers for the insulin gene were designed: forward primer (5'-GCCCTCTGGG-GACCTGAC-3', SEQ ID No. 1) of exon 1 and reverse primer (5'-CCCACCTGCAGGTCCTCT-3", SEQ ID No. 2) of exons 1 and 2 of insulin gene. Such reverse primer was obtained by deleting the intron between the exons 1 and 2. Blood samples of 4 normal subjects were assayed. It was found that the insulin gene is expressed in the blood and the quantitative expression of the insulin gene in a drop of blood is influenced by fasting and non-fasting states of normal healthy subjects (FIG. 2). This very low level of expression of the insulin gene reflects the phenotypic status of a person and strongly suggests that there is a physiological and pathological role for its expression, contrary to the basal or illegitimate theory of transcription suggested by Chelly et al. (1989) and Kimoto (1998).

Figure 3:
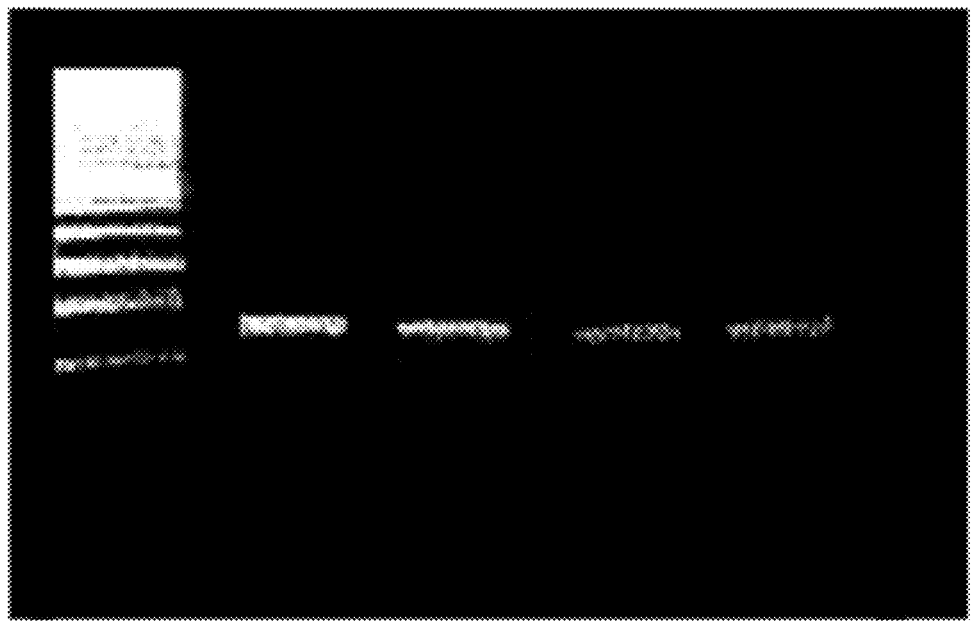
FIG. 3 shows quantitative RT-PCR analysis performed on RNA samples extracted from a drop of blood. Lanes 1 and 2 represent normal healthy person and lane 3 represents late-onset diabetes (Type II) and lane 4 represents asymptomatic diabetes.

Same quantitative RT-PCR analysis was performed using insulin specific primers on RNA samples extracted from a drop of blood from a normal healthy person, a person having late-onset diabetes (Type II) and a person having asymptomatic diabetes. It was found that the insulin gene is expressed differentially amongst subjects that are healthy, diagnosed as type II diabetic, and also in an asymptomatic preclinical patient (FIG. 3).

Similarly, specific primers for the atrial natriuretic factor (ANF) gene were designed (forward primer, SEQ ID No. 5; reverse primer, SEQ ID No. 6) and RT-PCR analysis was performed on a drop of blood. ANF is known to be highly expressed in heart tissue biopsies and in the plasma of heart failure patients. However, atrial natriuretic factor was observed to be expressed in the blood and the expression of the atrial natriuretic factor gene is significantly higher in the blood of patients with heart failure as compared to the blood of a normal control patient.

Specific primers for the zinc finger protein gene (ZFP, forward primer, SEQ ID No. 9; reverse primer, SEQ ID No. 10) were also designed and RT-PCR analysis was performed on a drop of blood. ZFP is known to be high in heart tissue biopsies of cardiac hypertrophy and heart failure patients. In the present study, the expression of ZFP was observed in the blood as well as differential expression levels of ZFP amongst the normal, diabetic and asymptomatic preclinical subjects (FIG. 4); although neither of the non-normal subjects has been specifically diagnosed as suffering from cardiac hypertrophy and/or heart failure, the higher expression levels of the ZFP gene in their blood may indicate that these subjects are headed in that general direction.

Figure 4:
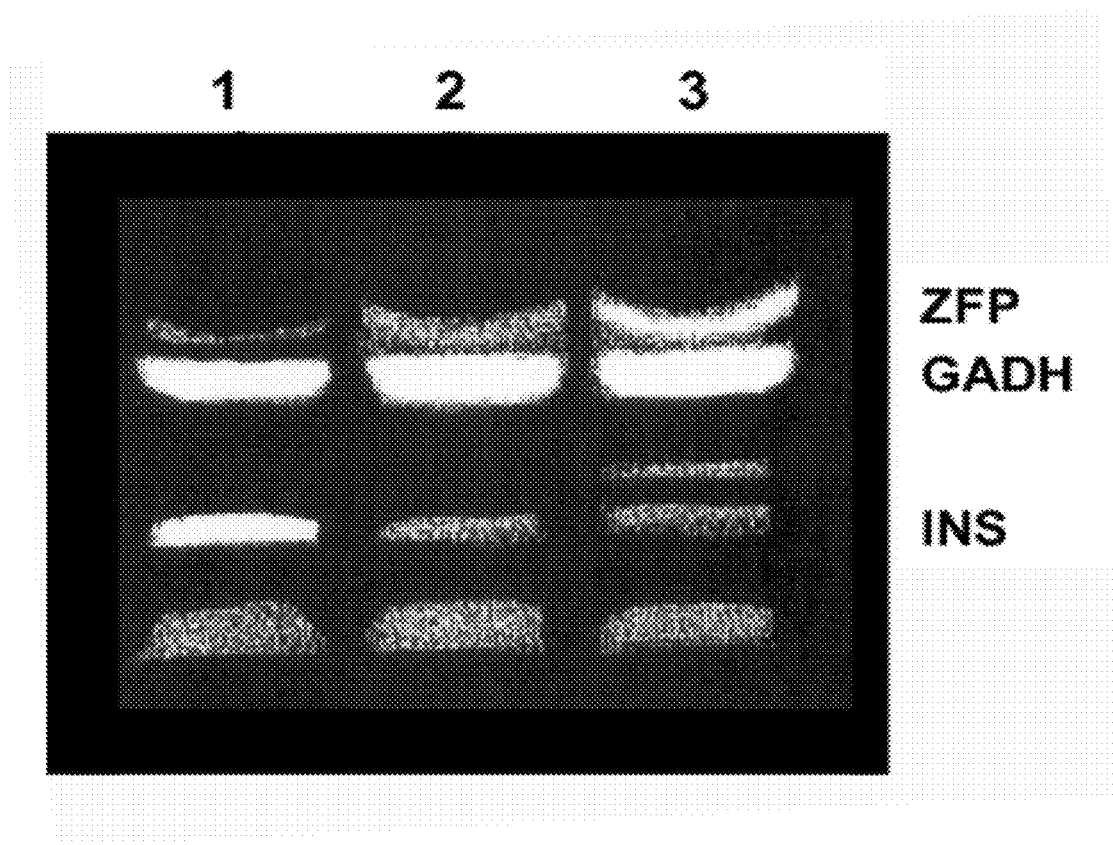
FIG. 4 shows multiple RT-PCR assay in a drop of blood. Primers were derived from insulin gene (INS), zinc-finger protein gene (ZFP) and house-keeping gene (GADH). Lane 1 represents normal person. Lane 2 represents late-onset diabetes and lane 3 represents asymptomatic diabetes.

It was hypothesized that a housekeeping gene such as glyceraldehyde dehydrogenase (GADH) which is required and highly expressed in all cells would not be differentially expressed in the blood of normal vs. disease subjects. This hypothesis was confirmed by RT-PCR using GADH specific primers (FIG. 4). Thus, GADH is useful as an internal control.

Figure 5:
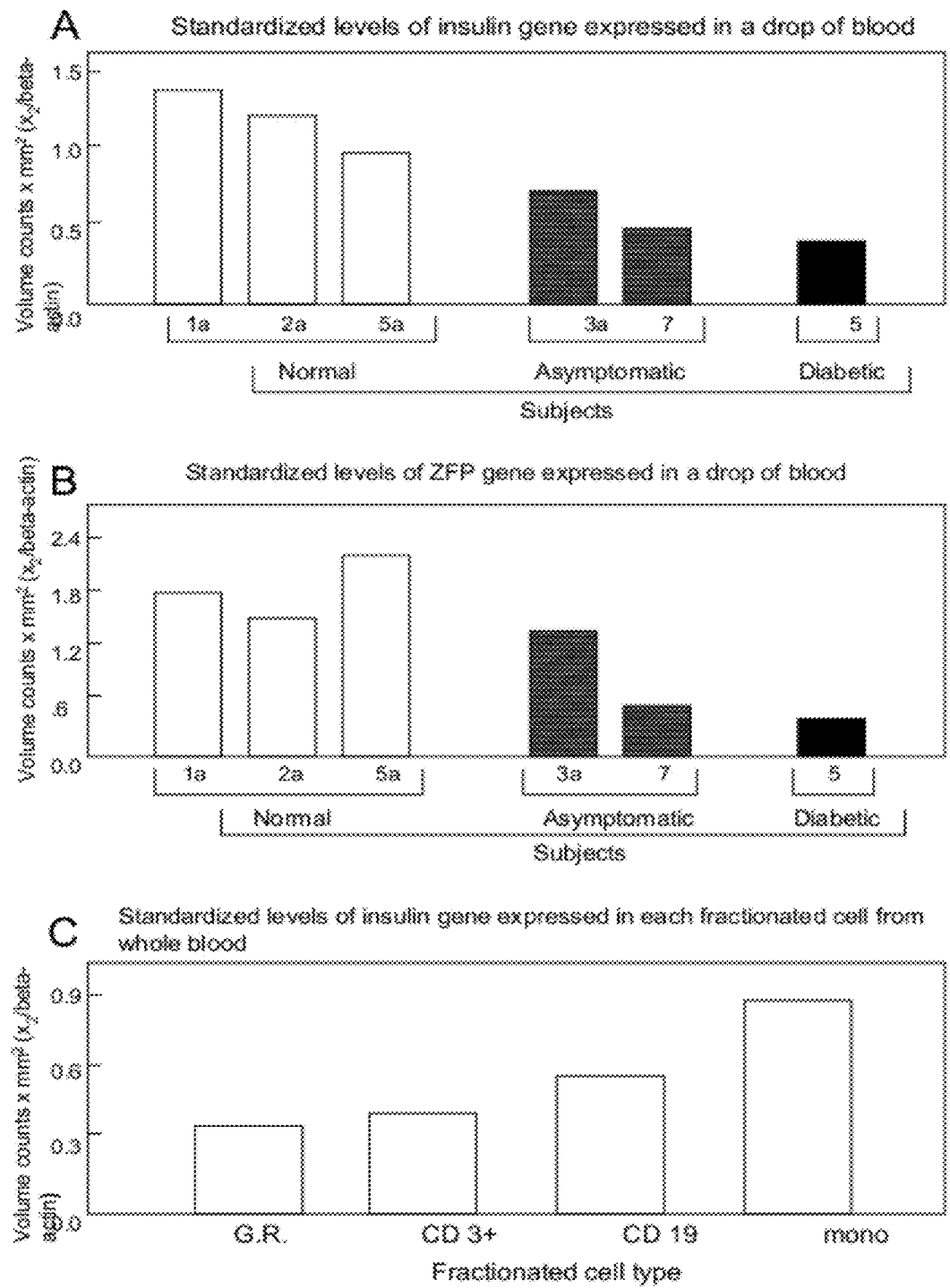
FIG. 5 shows standardized levels of insulin gene (FIG. 5A) and ZFP gene (FIG. 5B) expressed in a drop of blood. The first three subjects were normal, second two subjects showed normal glucose tolerance, and the last subject had late onset diabetes type II.
Figure 6:
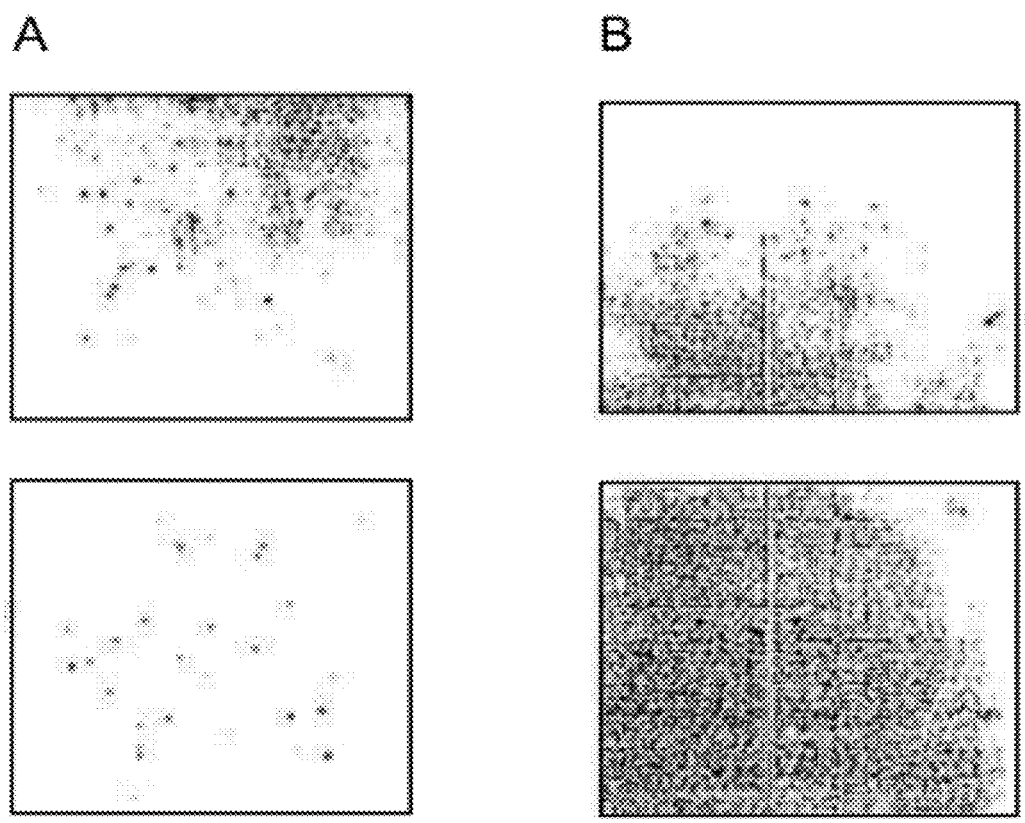
FIG. 6 shows the differential screening of human blood cell cDNA library with different cDNA probes of heart and brain tissue.

Standardized levels of insulin gene or ZFP gene expressed in a drop of blood were estimated using a housekeeping gene as an internal control relative to insulin or ZFP expressed (FIGS. 5A & 5B). The levels of insulin gene expressed in each fractionated cell from whole blood were also standardized and shown in FIG. 5C.

Example 7

Human Blood Cell cDNA Library

Figure 7:
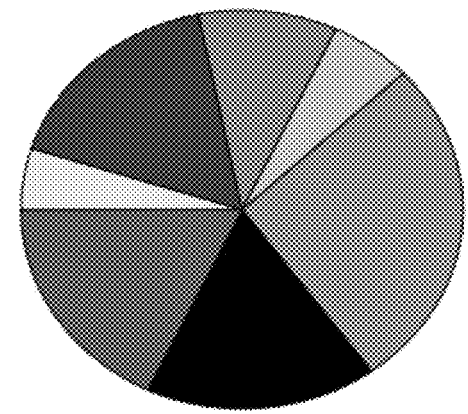
FIG. 7 graphically shows the 1,800 unique genes in human blood and in the human fetal heart grouped into seven cellular functions.
Figure 7:
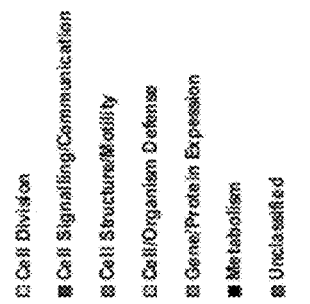
Figure 7:
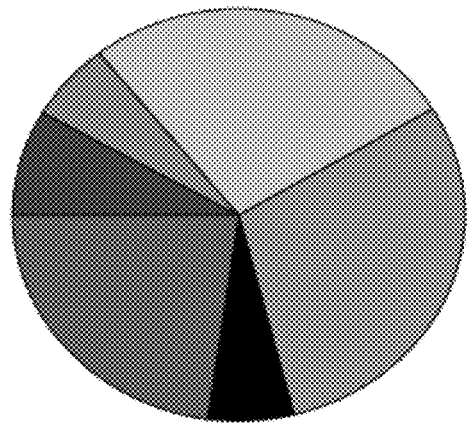

In order to further substantiate the present invention, differential screening of the human blood cell cDNA library was conducted. cDNA probes derived from human blood, adult heart or brain were respectively hybridized to the human blood cDNA library clones. As shown in FIG. 7, more than 95% of the "positively" identified clones are identical between the blood and other tissue samples.

DNA sequencing of randomly selected clones from the human whole blood cell cDNA library was also performed. This allowed information regarding the cellular function of blood to be obtained concurrently with gene identification. More than 20,000 expressed sequence tags (ESTs) have been generated and characterized to date, 17.6% of which did not result in a statistically significant match to entries in the GenBank databases and thus were designated as "Novel" ESTs. These results are summarized in FIG. 7 together with the seven cellular functions related to percent distribution of known genes in blood and in the fetal heart.

From 20,000 ESTs, 1,800 have been identified as known genes which may not all appear in the hemapoietic system. For example, the insulin gene and the atrial natriuretic factor gene have not been detected in these 20,000 ESTs but their transcripts were detected in a drop of blood, strongly suggesting that all transcripts of the human genome can be detected by performing RT-PCR analysis on a drop of blood.

In addition, approximately 400 novel genes have been identified from the 20,000 ESTs characterized to date, and these will be subjected to full length sequencing and open reading frame alignment to reduce the actual number of novel ESTs prior to screening for disease markers.

Analysis of the approximately 6,283 ESTs which have known matches in the GenBank databases revealed that this dataset represents over 1,800 unique genes. These genes have been catalogued into seven cellular functions. Comparisons of this set of unique genes with ESTs derived from human brain, heart, lung and kidney demonstrated a greater than 50% overlap in expression (Table 1).

TABLE 1

Overlap of Genes Expressed in Blood*

| Tissues | ESTs** | Overlap in Blood |
|---------|--------|------------------|
| brain   | 134,000 | 60% |
| heart   | 65,000  | 59% |
| lung    | 60,200  | 58% |
| kidney  | 32,300  | 54% |

*Estimated from limited known genes of about 1,800 as derived from the database of 6,297 ESTs from human blood cell library.
**Obtained from the National Centre of Biotechnology Information (NCBI), U.S.A.

Example 8

Blood Cell ESTs

The results from the differential screening clearly indicate that the transcripts expressed in the whole blood are reflective of genes expressed in all cells and tissues of the body. More than 95% of detectable spots were identical from two different tissues. The remaining 5% of spots may represent cell- or tissue-specific transcripts; however, results obtained from partial sequencing to generate ESTs of these clones revealed most of them not to be cell- or tissue-specific transcripts. Therefore, the negative spots are postulated to be reflective of low abundance transcripts in the tissue from which the cDNA probes were derived.

An alternative approach that was employed to identify transcripts expressed at low levels is the large-scale generation of expressed sequence tags (ESTs). There is substantial evidence regarding the efficiency of this technology to detect previously characterized (known) and uncharacterized (unknown or novel) genes expressed in the cardiovascular system (Hwang & Dempsey et al. 1997). In the present invention, 20,000 ESTs have been produced from a human blood cell cDNA library and resulted in the identification of approximately 1,800 unique known genes (Table 2)

In the most recent GenBank release, analysis of more than 300,000 ESTs in the database (dbESTs) generated more than 48,000 gene clusters which are thought to represent approximately 50% of the genes in the human genome. Only 4,800 of the dbESTs are blood-derived. In the present invention, 20,000 ESTs have been obtained to date from a human blood cDNA library, which provides the world's most informative database with respect to blood cell transcripts. From the limited amount of information generated so far (i.e. 1,800 unique genes), it has already been determined that more than 50% of the transcripts are found in other cells or tissues of the human body (Table 2). Thus, it is expected that by increasing the number of ESTs generated, more genes will be identified that have an overlap in expression between the blood and other tissues. Furthermore, the transcripts for several genes which are known to have tissue-restricted patterns of expression (i.e. (MyHC, APP, APC, ANF, ZFP) have also been demonstrated to be present in blood.

Most recently, a cDNA library of human hematopoietic progenitor stem cells has also been constructed. From the limited set of 1,000 ESTs, there are at least 200 known genes that are shared with other tissue related genes (Claudio et al. 1998).

Table 2 demonstrates the expression of known genes of specific tissues in blood cells. Previously, only the presence of "housekeeping" genes would have been expected. Additionally, the presence of at least 25 of the currently known 500 genes corresponding to molecular drug targets was detected. These molecular drug targets are used in the treatment of a variety of diseases which involve inflammation, renal and cardiovascular function, neoplastic disease, immunomodulation and viral infection (Drews & Ryser, 1997). It is expected that additional novel ESTs will represent future molecular drug targets.

TABLE 2

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| 100 kDa coactivator | 2 | U22055 | | + | | | | + |
| 10 kD protein (BC10) | 2 | AF053470 | | + | + | | + | + |
| 14-3-3 epsilon | 2 | U54778 | | + | + | | | + |
| 14-3-3 protein | 11 | U28964 | | + | + | + | | |
| 15 kDa selenoprotein (SEP15) | 1 | AF051894 | | + | + | | | + |
| 1-phosphatidylinositol-4-phosphate 5-kinase isoform C | 1 | S78798 | | | | | | |
| 23 kD highly basic protein | 21 | X56932 | + | + | + | + | + | + |
| 2-5A-dependent RNase | 1 | L10381 | | | | | | |
| 2'-5'oligoadenylate synthetase 2 (OAS2) | 4 | M87284 | B | | | | | |
| 26S proteasome subunit 11 | 1 | AF086708 | | | | | | |
| 36 kDa phosphothyrosine protein | 2 | AJ223280 | T | | + | | | |
| 3-7 gene product (non-exact 86% aa) | 1 | D64159 | | | | | | |
| 3-phosphoglycerate dehydrogenase (PGAD) | 1 | AF006043 | T | + | + | | | + |
| 3-prime-phosphoadenosine 5-prime-phosphosulfate synthase 1 (PAPSS1) | 2 | U53447 | + | + | + | + | | + |
| 46 kd mannose 6-phosphate receptor (MPR46) (low match) | 1 | X56257 | | | | | | |
| 5-aminoimidazole-4-carboxamide ribonucleotide transformylase | 1 | D89976 | | | | | | |
| 5'-nucleotidase | 3 | D38524 | T | + | | | + | |
| 6-phosphofructo-2-kinase/fructose-2,6-biphosphatase 4 (PFKFB4) | 1 | D49818 | | + | | | | |
| 6-phosphofructo-2-kinase/fructose-2,6-bisphosphatase (PF2K) | 1 | AF041829 | | | | | | |
| 71 kd heat shock cognate protein hsc70 | 23 | Y00371 | | | | | | |
| 76 kDa membrane protein (P76) | 2 | U81006 | | + | + | + | + | + |
| 8-oxoguanine DNA glycosylase (OGG1) | 1 | U96710 | B | | | | + | + |
| a disintegrin and metalloprotease domain 10 (ADAM10) | 1 | AF009615 | T | | | | + | |
| a disintegrin and metalloprotease domain 8 (ADAM8) | 1 | D26579 | B | + | | | | |
| A kinase anchor protein 95 (AKAP95) | 2 | Y11997 | B, T activated | | + | | | + |
| A kinase anchor protein, 149 kD (AKAP149) | 2 | X97335 | | + | + | + | | + |
| A4 differentiation-dependent protein (A4), triple LIM domain protein (LMO6), and synaptophysin (SYP); calcium channel alpha-1 subunit (CACNA1F) | 1 | U93305 | | | | | | |
| ABL and putative M8604 Met protein | 1 | U07561 | | | | | | |
| Absent in melanoma 1 (AIM1) | 1 | U83115 | + | + | | | | + |
| accessory proteins BAP31/BAP29 (DXS1357E) | 2 | Z31696 | | + | + | | | |
| acetyl-Coenzyme A acyltransferase (peroxisomal 3-oxoacyl-Coenzyme A thiolase) (ACAA) | 2 | X12966 | + | + | + | + | + | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| acetyl-Coenzyme A transporter (ACATN) | 1 | D88152 | T lymphoma | + | + | | | | |
| acidic 82 kDa protein | 4 | U15552 | | | | | | | |
| acidic protein rich in leucines (SSP29) | 1 | Y07969 | B | + | + | | + | + | |
| Aconitase 2, mitochondrial (ACO2) | 1 | U80040 | + | + | + | + | | + | |
| actin binding protein MAYVEN | 1 | AF059569 | | | | | | | |
| actin, beta (ACTB) | 158 | X04098 | T, B | + | + | | + | | |
| actin, beta (ACTB) (non-exact, low match 73%) | 1 | M10277 | | | | | | | |
| actin, gamma (low score) | 1 | K00791 | | | | | | | |
| actin, gamma 1 (ACTG1) | 4 | X04098 | + | + | + | + | + | + | high in many libraries |
| actin-binding LIM protein (ABLIM) | 4 | D31883 | | + | + | + | | + | |
| Actinin, alpha 1 (ACTN1) | 8 | M95178 | | + | + | + | | + | |
| actinin, alpha 4 (ACTN4) | 1 | D89980 | | + | + | | + | | |
| activated p21cdc42Hs kinase (ACK) | 1 | L13738 | B | + | | | | + | |
| activated RNA polymerase II transcription cofactor 4 (PC4) | 1 | X79805 | + | + | + | + | | + | |
| activating transcription factor 1 (ATF1) | 1 | X55544 | | | + | | | | |
| activating transcription factor 2 (ATF2) | 1 | X15875 | | + | + | | + | | |
| activating transcription factor 4 (tax-responsive enhancer element B67) (ATF4) | 2 | M86842 | | | | | + | + | |
| active BCR-related gene (ABR) | 1 | U01147 | + | + | + | + | | + | |
| acyl-CoA oxidase (AOX) | 1 | U03254 | | | | | | | |
| acyl-Coenzyme A dehydrogenase, C-4 to C-12 straight chain (ACADM) | 2 | M16827 | | | | | | | |
| acyl-Coenzyme A dehydrogenase, very long chain (ACADVL) | 3 | D43682 | + | + | + | + | + | + | |
| acyloxyacyl hydrolase (neutrophil) (AOAH) | 3 | M62840 | T | | + | | + | | |
| adaptin, delta (ADTD) | 2 | U91930 | | + | + | + | | | |
| adaptin, delta (ADTD) (non-exact 59%) | 1 | AC005328 | | | | | | | |
| adaptin, gamma (ADTG) | 1 | Y12226 | | + | + | + | | + | |
| adaptor complex sigma3B (AP3S3) | 2 | X99459 | | + | | + | | + | |
| adaptor protein p150 | 1 | Y08991 | | | | | | | |
| adducin 1 (alpha) (ADD1) | 2 | L07261 | | + | + | + | | | |
| adducin 1 (alpha) (add1) | 3 | L29296 | + | + | + | + | | + | |
| adducin 3 (gamma) (ADD3) | 3 | U37122 | B, W | + | + | | + | + | |
| adenine nucleotide translocator 2 (fibroblast) (ANT2) | 2 | M57424 | + | + | + | | | | |
| adenine nucleotide translocator 2 (fibroblast) (ANT2) (non-exact 81%) | 1 | J02683 | | | | | | | |
| adenine nucleotide translocator 2 (fibroblast) (ANT2) (non-exact, 79%) | 1 | J02683 | | | | | | | |
| adenine nucleotide translocator 2 (fibroblast) (ANT2) (non-exact, 86%) | 1 | J02683 | | | | | | | |
| adenine nucleotide translocator 3 (liver) (ANT3) | 3 | J03592 | | + | + | | + | + | |
| adenosine deaminase, RNA-specific (ADAR) | 6 | U18121 | | + | + | | + | | |
| adenylate cyclase 3 (ADCY3) | 2 | AF033861 | | + | + | + | + | + | |
| adenylate cyclase 7 (ADCY7) | 1 | D25538 | | | | | | | |
| adenylate kinase 2 (AK2) | 2 | U39945 | | + | + | | + | + | |
| adenylate kinase 3 (AK3) (non-exact, 67%) | 1 | X60673 | | | | | | | |
| adenylyl cyclase-associated protein (CAP) | 28 | M98474 | T | | + | | + | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| adipose differentiation-related protein; adipophilin (ADFP) | 1 | X97324 | | | + | | + | + |
| ADP-ribosylation factor 1 (ARF1) | 13 | M84326 | | + | + | | + | + |
| ADP-ribosylation factor 3 (ARF3) | 2 | M33384 | | + | + | | + | |
| ADP-ribosylation factor 4 (ARF4) | 1 | M36341 | T lymphoma | + | + | | | + |
| ADP-ribosylation factor 5 (ARF5) | 1 | M57567 | | | + | + | + | + |
| ADP-ribosylation factor domain protein 1, 64 kD (ARFD1) | 1 | L04510 | | | + | | | |
| ADP-ribosyltransferase (NAD+; poly (ADP-ribose) polymerase) (ADPRT) | 4 | M32721 | + | | + | + | + | + |
| adrenergic, beta, receptor kinase 1 (ADRBK1) | 2 | X61157 | B | | + | | + | |
| adrenoleukodystrophy-like 1 (ALDL1) | 1 | AJ000327 | | | | | | |
| AE-binding protein 1 (AEBP1) (non-exact, 62%) | 1 | D86479 | | | | | | |
| AF-17 | 1 | U07932 | | | | | | |
| A-gamma-globin | 1 | V00514 | | | | | | |
| A-gamma-globin (chromosome 11 allele) | 1 | J00176 | | | | | | |
| agammaglobulinaemia tyrosine kinase (ATK) | 1 | U78027 | | | | | | |
| AHNAK nucleoprotein (desmoyokin) (AHNAK) | 4 | M80899 | + | | + | + | | + |
| alanyl (membrane) aminopeptidase (aminopeptidase N, aminopeptidase M, microsomal aminopeptidase, CD13, p150) (ANPEP) | 1 | X13276 | | | + | | + | |
| alcohol dehydrogenase 5 (class III), chi polypeptide (ADH5) | 1 | M29872 | | | | | | |
| aldehyde dehydrogenase 1, soluble (ALDH1) | 1 | AF003341 | | | + | | + | + |
| aldehyde dehydrogenase 10 (fatty aldehyde dehydrogenase) (ALDH10) | 2 | U75286 | | | | | | |
| aldehyde reductase 1 (low Km aldose reductase) (ALDR1) | 3 | J04795 | B | | + | + | + | + |
| aldo-keto reductase family 1, member A1 (aldehyde reductase) (AKR1A1) | 2 | J04794 | B | | + | + | + | |
| aldo-keto reductase family 1, member C3 (3-alpha hydroxysteroid dehydrogenase, type II) (AKR1C3) | 1 | D17793 | | | + | + | | + |
| aldo-keto reductase family 7, member A2 (aflatoxin aldehyde reductase) (AKR7A2) | 1 | Y16675 | | | + | + | + | + |
| aldolase A, fructose-bisphosphate (ALDOA) | 7 | X12447 | | | + | + | + | |
| aldolase C, fructose-bisphosphate (ALDOC) | 2 | X05196 | | | + | + | + | |
| alkaline phosphatase, liver/bone/kidney (ALPL) | 1 | 4502062 | | | | | | |
| ALL-1 (=L04731; L04284 HRX) | 4 | Z69780 | | | | | | |
| alpha mannosidase II isozyme | 1 | D55649 | | | + | | + | |
| alpha thalassemia/mental retardation syndrome X-linked (ATRX) | 3 | U75653 | + | | + | + | + | + |
| alpha-2 macroglobulin | 1 | Z11711 | | | | | | |
| alpha-2-globin | 2 | V00516 | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| alpha-2-macroglobulin receptor/lipoprotein receptor protein (A2MR/LRP) | 1 | U06985 | | | | | | | |
| alpha-polypeptide of N-acetyl-alpha-glucosaminidase (HEXA) | 1 | M13520 | | | | | | | |
| alpha-spectrin | 1 | X86901 | | | | | | | |
| alpha-subunit of Gi2 a (GTP-binding signal transduction protein) | 1 | X07854 | | | | | | | |
| aminin receptor 1 (67 kD); Ribosomal protein SA (LAMR1) | 2 | J03799 | T | + | + | | + | + | |
| aminolevulinate, delta-, dehydratase (ALAD) | 1 | X64467 | | + | | | | | |
| amino-terminal enhancer of split (AES) | 2 | X73358 | + | + | + | + | | + | |
| amino-terminal enhancer of split (AES) | 3 | U04241 | B | + | + | | + | + | |
| AMP deaminase isoform L (AMPD2) | 8 | M91029 | | + | | | + | | |
| amphiphysin (Stiff-Mann syndrome with breast cancer 128 kD autoantigen) (AMPH) | 1 | U07616 | B | + | | | + | | |
| amphiphysin (Stiff-Mann syndrome with breast cancer 128 kD autoantigen) (AMPH)(non-exact, 68%) | 1 | U07616 | | | | | | | |
| amphiphysin (Stiff-Mann syndrome with breast cancer 128 kD autoantigen) (AMPH)(non-exact, 68%) | 1 | U07616 | | | | | | | |
| amphiphysin II | 4 | U87558 | | + | + | + | | | |
| amphiphysin II (67% aa amphiphysin?) | 1 | AF068915 | | | | | | | |
| amphiphysin II (non-exact 69% aa) | 1 | AF001383 | | | | | | | |
| amphiphysin-like (AMPHL) | 1 | U68485 | | + | + | | | | |
| amphiphysin-like (AMPHL) (low match) | 1 | AF068918 | | | | | | | |
| AMY-1 | 1 | D50692 | B, T | | | + | | | |
| amyloid beta (A4) precursor protein-binding, family B, member 1 (Fe65) (APBB1) | 1 | L77864 | | + | + | + | | + | |
| amyloid beta (A4) precursor-like protein 2 (APLP2) | 6 | L27631 | T lymphoma | + | + | | + | + | |
| ankyrin 3, node of Ranvier (ankyrin G) (ANK) (non-exact, 50%) | 1 | U43965 | | | | | | | |
| annexin I (lipocortin I) (ANX1) | 1 | X05908 | | + | + | + | | + | |
| annexin II | 1 | D28364 | | | | | | | |
| annexin II (lipocortin II; calpactin I, heavy polypeptide) (ANX2) | 7 | D00017 | + | + | + | + | + | + | high in many libraries |
| annexin IV (placental anticoagulant protein II) (ANX4) | 1 | M19383 | | + | + | + | + | | |
| annexin V (endonexin II) (ANX5) | 2 | M21731 | | + | + | + | | + | |
| annexin V (endonexin II) (ANXV) | 1 | M19384 | | + | + | + | | | |
| annexin VI (p68) (ANX6) | 6 | Y00097 | | + | + | + | | + | |
| annexin VII (synexin) (ANX7) | 1 | J04543 | | + | + | + | | + | |
| antigen identified by monoclonal antibodies 12E7, F21 and O13 (MIC2) | 2 | M16279 | | + | + | + | | | |
| antigen identified by monoclonal antibodies 4F2, TRA1.10, TROP4, and T43 (MDU1) | 3 | J02939 | | + | + | + | + | | |
| antigen TQ1 | 1 | | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| anti-oxidant protein 2 (non-selenium glutathione peroxidase, acidic calcium-independent phospholipase A2) (KIAA0106) | 1 | D14662 | | + | + | + | + | + |
| APEX nuclease (multifunctional DNA repair enzyme) (APEX) | 5 | X66133 | | + | + | | + | + |
| Apolipoprotein L (APOL) (59% aa) | 1 | Z82215 | | | | | | |
| apoptosis inhibitor 1 (API1) | 1 | L49431 | | + | + | + | + | + |
| apoptosis inhibitor 4 (survivin) (API4) | 1 | U75285 | B, W | + | + | | + | |
| apoptosis inhibitor 5 (API5) | 1 | U83857 | T lymphoma | + | | | + | |
| apoptosis specific protein (ASP) | 1 | Y11588 | B | + | | | + | + |
| apoptotic protease activating factor (APAF1) | 1 | AF013263 | B | + | + | | + | |
| aquaporin 3 (AQP3) | 1 | AB001325 | T | | | | + | |
| aquaporin 9 (AQP9) | 7 | AB008775 | T activated | | | | + | |
| arachidonate 12-lipoxygenase (ALOX12) | 1 | M58704 | T | | | | + | + |
| arachidonate 5-lipoxygenase-activating protein (ALOX5AP) | 3 | X52195 | + | + | | + | | + |
| ariadne homolog (ARI) | 1 | AJ009771 | + | + | + | + | | + |
| ariadne-2 (*D. melanogaster*) homolog (all-trans retinoic acid inducible RING finger) (ARI2) | 1 | AF099149 | + | + | + | + | | + |
| ARP1 (actin-related protein 1, yeast) homolog A (centractin alpha) (ACTR1A) | 1 | X82206 | | + | | | + | |
| ARP2 (actin-related protein 2, yeast) homolog (ACTR2) | 9 | AF006082 | | + | + | | + | + |
| ARP2/3 protein compex subunit 34 (ARC34) | 5 | AF006085 | T activated, W | + | + | | + | |
| Arp2/3 protein compex subunit p41 (ARC41) | 6 | AF006084 | monocyte stimulated | + | + | | + | |
| Arp2/3 protein compex subunit p41 (ARC41)) (low match) | 1 | AF006084 | | | | | | |
| Arp2/3 protein complex subunit p16 (ARC16) | 20 | AF017807 | | + | + | | + | + |
| Arp2/3 protein complex subunit p20 (ARC20) | 2 | AF006087 | | + | + | | + | + |
| Arp2/3 protein complex subunit p21(ARC21) | 3 | AF006086 | W | | | | + | + |
| ARP3 (actin-related protein 3, yeast) homolog (ACTR3) | 11 | AF006083 | W | | + | | + | + |
| arrestin, beta 2 (ARRB2) | 1 | AF106941 | B, T, W | + | + | | + | |
| arsA (bacterial) arsenite transporter, ATP-binding, homolog 1 (ASNA1) | 1 | AF047469 | B, T | + | | | + | |
| aryl hydrocarbon receptor nuclear translocator-like (ARNTL) | 2 | AF044288 | B | + | + | | + | |
| aryl hydrocarbon receptor-interacting protein (AIP) | 1 | U31913 | + | + | + | + | | + |
| arylsulfatase A (ARSA) | 1 | X52151 | T activated | + | | | + | |
| asialoglycoprotein receptor 2 (ASGR2) | 1 | M11025 | | | | | + | + |
| asparaginyl-tRNA synthetase (NARS) | 3 | D84273 | | + | + | | + | |
| aspartyl-tRNA synthetase (DARS) | 1 | J05032 | B | + | + | | + | |
| ataxia telangiectasia mutated (includes complementation groups A, C and D) (ATM) | 1 | U82828 | B, T | | + | | + | |
| ataxin-2-like protein A2LP (A2LG) | 1 | AF034373 | B, T activated | + | + | | | + |
| ATF6 | 1 | AF005887 | | + | | | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| ATP binding cassette transporter (ABCR) (non-exact 80%) | 1 | U88667 | | | | | | |
| ATP synthase (F1-ATPase) alpha subunit, mitochondrial | 1 | X59066 | | | | | | |
| ATP synthase beta subunit gene | 1 | M19482 | | | | | | |
| ATP synthase, H+ transporting, mitochondrial F0 complex, subunit b, isoform 1 (ATP5F1) | 1 | X60221 | + | | + | + | + | + |
| ATP synthase, H+ transporting, mitochondrial F0 complex, subunit c (subunit 9), isoform 1 (ATP5G1) | 1 | X69907 | T activated | | + | + | + | + |
| ATP synthase, H+ transporting, mitochondrial F1 complex, alpha subunit, isoform 1, cardiac muscle (ATP5A1) | 3 | D14710 | | | | | | |
| ATP synthase, H+ transporting, mitochondrial F1 complex, alpha subunit, isoform 1, cardiac muscle (ATP5A1) (low match) | 1 | D14710 | | | | | | |
| ATP synthase, H+ transporting, mitochondrial F1 complex, beta polypeptide (ATP5B) | 2 | M27132 | | | | | | |
| ATP synthase, H+ transporting, mitochondrial F1 complex, gamma polypeptide 1 (ATP5C1) | 1 | D16563 | W | | + | + | + | + |
| ATP synthase, H+ transporting, mitochondrial F1F0, subunit g (ATP5JG) | 1 | AF092124 | + | + | + | + | + | + |
| ATP/GTP-binding protein (HEAB) | 2 | U73524 | + | + | + | + | | + |
| ATPase, Ca++ transporting, ubiquitous (ATP2A3) | 5 | Z69881 | | + | | | | |
| ATPase, H+ transporting, lysosomal (vacuolar proton pump) 21 kD (ATP6F) | 2 | D89052 | + | + | + | + | | + |
| ATPase, H+ transporting, lysosomal (vacuolar proton pump) 31 kD (ATP6E) | 1 | X76228 | | + | + | + | | + |
| ATPase, H+ transporting, lysosomal (vacuolar proton pump) 42 kD; Vacuolar proton-ATPase, subunit C; V-ATPase, subunit C (ATP6D) | 5 | X69151 | + | | + | + | | + |
| ATPase, H+ transporting, lysosomal (vacuolar proton pump), alpha polypeptide, 70 kD, isoform 1 (ATP6A1) | 3 | L09235 | | | + | + | | |
| ATPase, H+ transporting, lysosomal (vacuolar proton pump), beta polypeptide, 56/58 kD, isoform 2 (ATP6B2) | 6 | X62949 | + | | + | + | | + |
| ATPase, H+ transporting, lysosomal (vacuolar proton pump), member J (ATP6J) | 2 | AF038954 | + | | + | + | + | high in testis |
| ATPase, H+ transporting, lysosomal (vacuolar proton pump), subunit 1 (ATP6S1) | 1 | D16469 | | | + | + | | + |
| ATP-binding cassette 50 (TNF-alpha stimulated) (ABC50) | 1 | AF027302 | + | | + | + | | + |
| ATP-binding cassette protein M-ABC1 (mitochondrial) | 1 | AF047690 | | | | | | |
| ATP-dependent RNA helicase | 1 | AJ010840 | T lymphoma | | + | + | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| autoantigen (Hs.75528) | 2 | L05425 | T activated | + | | | | | |
| autoantigen (Hs.75528) (non-exact 84%) | 1 | L05425 | | | | | | | |
| autoantigen (Hs.75682) | 1 | U17474 | B | + | | | + | | |
| autoantigen La/SS-B | 1 | Z35127 | | | | | | | |
| axin (AXIN1) | 1 | AF009674 | T | + | | | | | |
| axonemal dynein heavy chain (DNAH17) | 1 | AJ000522 | | | | | + | | |
| BAI1-associated protein 3 (BAIAP3) (non-exact 54%) | 1 | AB017111 | | | | | | | |
| basement membrane-induced gene (ICB1) | 1 | AF044896 | | | | | | | |
| basic leucine zipper nuclear factor 1 (JEM-1) (BLZF1) | 2 | U79751 | | | | | | | |
| basic transcription factor 3 (BTF3) | 5 | X74070 | + | + | + | + | + | + | |
| basigin (BSG) | 1 | L10240 | | + | | + | | | |
| BC-2 | 1 | AF042384 | B | | + | + | | | |
| B-cell CLL/lymphoma 6 (zinc finger protein 51) (BCL6) | 1 | U00115 | | + | + | | | | |
| B-cell translocation gene 1, anti-proliferative (BTG) | 1 | X61123 | | | + | | + | | |
| BCL2/adenovirus E1B 19 kD-interacting protein 2 (BNIP2) | 1 | U15173 | B | + | | | + | + | |
| BCL2/adenovirus E1B 19 kD-interacting protein 3-like (BNIP3L) | 2 | AF067396 | | + | + | + | + | | |
| beclin 1 (coiled-coil, myosin-like BCL2-interacting protein) (BECN1) | 1 | AF077301 | B | + | + | + | | | |
| beta-1,2-N-acetylglucosaminyltransferase II (MGAT2) | 2 | U15128 | | | | | | | |
| beta-2-microglobulin (B2M) | 63 | S82297 | + | + | + | + | + | + | high in invasive prostate tumor |
| beta-hexosaminidase alpha chain (HEXA) | 1 | M16411 | | | | | | | |
| beta-tubulin | 7 | V00599 | + | + | + | + | + | + | high in many libraries |
| beta-tubulin (non-exact, 76%) | 1 | AF070561 | | | | | | | |
| beta-tubulin, pseudogene | 1 | J00315 | | | | | | | |
| BING4 | 1 | Z97184 | | | | | | | |
| biotinidase (BTD) (non-eact 62%) | 1 | U03274 | | | | | | | |
| biotinidase (BTD) (non-exact 70%) | 1 | U03274 | | | | | | | |
| biotinidase (BTD) (non-exact, 56%) | 1 | U03274 | | | | | | | |
| BIOTINIDASE PRECURSOR | 1 | P43251 | | | | | | | |
| biphenyl hydrolase-like (serine hydrolase) (BPHL) | 1 | X81372 | | + | | + | | | |
| bone marrow stromal cell antigen 1 (BST1) | 1 | D21878 | | | | + | | | |
| box-dependent myc-interacting protein isoform BIN1-10 (BIN1) | 1 | AF043900 | | | | | | | |
| box-dependent myc-interacting protein isoform BIN1-10 (BIN1) (non-exact, 64%) | 1 | AF043900 | | | | | | | |
| brain my047 protein | 1 | AF063605 | T | + | + | + | | | |
| branched chain keto acid dehydrogenase E1, alpha polypeptide (maple syrup urine disease) (BCKDHA) | 3 | Z14093 | T | + | + | + | | | |
| BRCA1 associated protein-1 (ubiquitin carboxy-terminal hydrolase) (BAP1) | 1 | D87462 | + | + | + | + | | | |
| BRCA1, Rho7 and vatI genes, and ipf35 | 1 | L78833 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| breakpoint cluster region protein, uterine leiomyoma, 1; barrier to autointegration factor (BCRP1) | 2 | AF044773 | | + | + | | | |
| breakpoint cluster region protein, uterine leiomyoma, 2 (BCRP2) | 2 | AF044774 | | + | + | | + | + |
| breast cancer anti-estrogen resistance 3 (BCAR3) (non-exact 73%) | 1 | U92715 | | | | | | |
| bromodomain-containing protein, 140 kD (peregrin) (BR140) | 2 | M91585 | | + | | | | |
| Bruton's agammaglobulinemia tyrosine kinase (Btk) | 1 | U13424 | | | | | | |
| Bruton's tyrosine kinase (BTK) | 1 | U78027 | | | | | | |
| Bruton's tyrosine kinase (BTK), alpha-D-galactosidase A (GLA), L44-like ribosomal protein (L44L) and FTP3 (FTP3) | 1 | U78027 | | | | | | |
| BS4 | 1 | AF108083 | | | | | | |
| BTG2 (BTG2) | 6 | Y09943 | + | + | + | + | | + |
| BTK region clone ftp | 1 | U78027 | + | + | + | + | | + |
| BTK region clone ftp-3 | 1 | U01923 | | + | + | + | | |
| BUB3 (budding uninhibited by benzimidazoles 3, yeast) homolog (BUB3) | 4 | AF053304 | + | + | + | + | | + |
| butyrate response factor 1 (EGF-response factor 1) (BRF1) | 4 | X79067 | + | + | + | + | | + |
| butyrophilin (BTF1) | 7 | U90543 | | + | + | + | | |
| butyrophilin like receptor | 1 | AB020625.1 | | | | | | |
| CAG repeat containing (CTG4A) | 2 | U80744 | | + | + | | | |
| CAGH32 | 2 | U80743 | | + | + | + | | |
| calcium channel, voltage-dependent, L type, alpha 1D subunit (CACNA1D) (low match) | 1 | M83566 | | | | | | |
| calcium/calmodulin-dependent protein kinase (CaM kinase) II gamma (CAMK2G) | 1 | AF069765 | | + | + | + | | + |
| calcium/calmodulin-dependent protein kinase kinase (KIAA0787) | 1 | AF101264 | B | + | + | + | | |
| calmodulin (=M19311) | 7 | D45887 | | | | | | |
| calmodulin 1 (phosphorylase kinase, delta) (CALM1) | 6 | M27319 | B | + | + | | + | + |
| calnexin (CANX) | 3 | M94859 | T | + | | | + | + |
| calpain, large polypeptide L1 (CAPN1) | 5 | X04366 | | + | + | | + | + |
| calpain, large polypeptide L2 (CANP2) | 5 | M23254 | | + | + | | | |
| calpain, small polypeptide (CAPN4) | 1 | X04106 | | + | + | | + | + |
| calpastatin (CAST) | 3 | D16217 | | | | | + | |
| Calponin 2 | 2 | D83735 | | + | | + | | + |
| calponin 2 (CNN2) | 1 | D83735 | B, T | + | | + | | |
| calponin 2 (CNN2) (low score) | 1 | D83735 | | | | | | |
| calumenin (CALU) | 3 | AF013759 | B | | + | | + | + |
| cAMP response element-binding protein CRE-Bpa (H_GS165L15.1) | 4 | L05912 | | | | | | |
| cAMP-dependent protein kinase type II (Ht31) | 1 | M90360 | | | | | | |
| canicular multispecific organic anion transporter (CMOAT2) | 1 | AF009670 | | | | + | + | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| capping protein (actin filament) muscle Z-line, alpha 1 (CAPZA1) | 6 | U56637 | B, T | | + | | | + |
| capping protein (actin filament) muscle Z-line, alpha 2 (CAPZA2) | 2 | U03269 | B | + | + | | | |
| capping protein (actin filament) muscle Z-line, beta (CAPZB) | 1 | U03271 | + | + | + | + | | + |
| capping protein (actin filament), gelsolin-like (CAPG) | 8 | M94345 | + | + | | + | | + |
| carbamoyl-phosphate synthetase 2, aspartate transcarbamylase, and dihydroorotase (CAD) | 1 | D78586 | + | + | + | + | | + |
| carbonic anhydrase V, mitochondrial (CA5) | 1 | L19297 | | + | | + | | |
| carboxypeptidase D (CPD) | 3 | U65090 | B | + | + | | | |
| carnitine/acylcarnitine translocase (CACT) | 1 | Y10319 | | + | + | + | | |
| Cas-Br-M (murine) ecotropic retroviral transforming sequence (cbl) | 2 | X57110 | | | | + | | |
| casein kinase 1, alpha 1 (CSNK1A1) | 1 | L37042 | + | + | + | + | | + |
| casein kinase 2, alpha 1 polypeptide (CSNK2A1) | 2 | M55265 | B | + | | | + | + |
| casein kinase I gamma 3L (CSNK1G3L) | 1 | AF049090.1 | | | | | | |
| casein kinase II alpha subunit (=S72393) | 1 | X69951 | | | | | | |
| CASP8 and FADD-like apoptosis regulator (CFLAR) | 4 | AF015450 | | + | + | + | + | + |
| caspase 1, apoptosis-related cysteine protease (interleukin 1, beta, convertase) (CASP1) | 7 | U13697 | + | | | + | | |
| caspase 10, apoptosis-related cysteine proteas (CASP10) | 1 | U60519 | B, T activated, T lymphoma | | | | + | |
| caspase 3, apoptosis-related cysteine protease (CASP3) | 3 | U13737 | B, T | + | + | + | + | |
| caspase 4, apoptosis-related cysteine protease (CASP4) | 6 | U25804 | + | | + | + | + | + |
| caspase 5, apoptosis-related cysteine protease (CASP5) | 1 | U28015 | | | | + | | |
| caspase 8, apoptosis-related cysteine protease (CASP8) | 2 | X98173 | | + | | + | | + |
| caspase 9, apoptosis-related cysteine protease (CASP9) | 1 | U56390 | B | | | + | + | |
| catalase (CAT) | 5 | X04076 | B | + | + | + | | |
| catechol-O-methyltransferase (COMT) | 1 | M65213 | | + | + | + | | |
| catenin (cadherin-associated protein), alpha 1 (102 kD) (CTNNA1) | 6 | D14705 | | + | + | | | |
| cathelicidin antimicrobial peptide (CAMP) | 1 | X89658 | B | | | | | |
| cathepsin B (CTSB) | 4 | L16510 | | | + | | + | + |
| cathepsin C (CTSC) | 3 | U79415 | | + | + | + | | + |
| cathepsin D (lysosomal aspartyl protease) (CTSD) | 4 | M11233 | | + | + | + | | |
| cathepsin E (CTSE) | 1 | J05036 | | | | + | | |
| cathepsin G (CTSG) | 1 | M16117 | T, W | | + | | | |
| cathepsin S (CTSS) | 34 | M86553 | B, Monocyte stimulated, T lymphoma | | | | + | + |
| cathepsin W (lymphopain) (CTSW) | 4 | AF013611 | | | | | | + |
| CBF1 interacting corepressor CIR (=U03644 recepin) | 1 | AF098297 | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| CCAAT/enhancer binding protein (C/EBP), alpha (CEBPA) | 3 | X87248 | | + | + | + | | + | |
| CCAAT/enhancer binding protein (C/EBP), delta (CEBPB) | 1 | S63168 | | | + | | + | + | |
| CCAAT-box-binding transcription factor (CBF2) | 2 | M37197 | T lymphoma | | | + | + | | |
| CCR5 receptor (CCR5) (non-exact?) | 1 | AF011504 | | | | | | | |
| CD14 antigen (CD14) | 11 | M86511 | + | | + | + | + | + | |
| CD18 (=M95293) | 4 | X64071 | | | | | | | |
| CD1C antigen, c polypeptide (CD1C) | 2 | M28827 | | | | | | + | |
| CD2 antigen (cytoplasmic tail)-binding protein 2 (CD2BP2) | 1 | AF104222 | | | | | | | |
| CD2 antigen (p50), sheep red blood cell receptor (CD2) | 4 | M14362 | + | | + | + | | + | |
| CD2 cytoplasmic tail-binding protein 1 (CD2BP1) | 2 | AF038602 | | | | + | | | |
| CD20 antigen (CD20) | 1 | X12530 | | | | | | | |
| CD20 receptor (S7) | 1 | X07203 | | | | | | | |
| CD22 antigen (CD22) | 1 | U62631 | B | | | | | | |
| CD24 signal transducer | 1 | M58664 | | | | | | | |
| CD33 antigen (gp67) (CD33) | 1 | M23197 | | | | | + | | |
| CD33 antigen-like 2; OB binding protein-2 (CD33L2) (non-exact, 68%) | 1 | U71383 | | | | | | | |
| CD33L2 (61% aa) | 1 | D86359 | | | | | | | |
| CD36 antigen (collagen type I receptor, thrombospondin receptor) (CD36) | 7 | M98398 | T lymphoma | | + | + | + | | |
| CD37 antigen (CD37) | 5 | X14046 | + | + | | + | | + | |
| CD38 alt | 1 | D84277 | | | | | | | |
| CD39 antigen (CD39) | 1 | U87967 | B | + | | | + | + | |
| CD3D antigen, delta polypeptide (TiT3 complex) (CD3D) | 1 | X03934 | | | + | + | | + | |
| CD3E antigen, epsilon polypeptide (TiT3 complex) (CD3E) | 1 | X03884 | + | | | + | | | |
| CD3G antigen, gamma polypeptide (TiT3 complex) (CD3G) | 2 | X06026 | W | | | | + | | |
| CD3Z antigen, zeta polypeptide (TiT3 complex) (CD3Z) | 2 | J04132 | + | | | + | | | |
| CD3-zeta (clone pBS NK1) | 1 | X55510 | | | | | | | |
| CD4 (low match) | 1 | S68043 | | | | | | | |
| CD4 antigen (p55) (CD4) | 4 | M12807 | | + | + | + | | | |
| CD44 antigen (homing function and Indian blood group system) (CD44) | 6 | X56794 | W | | | + | | + | |
| CD48 antigen (B-cell membrane protein) (CD48) | 3 | X06341 | + | + | + | + | | + | |
| CD53 antigen (CD53) | 10 | L11670 | + | + | | + | | + | |
| CD53 antigen (CD53) (low match) | 1 | M60871 | | | | | | | |
| CD63 antigen (melanoma 1 antigen) (CD63) | 3 | M59907 | | | | | | | |
| CD68 antigen (CD68) | 2 | S57235 | | | + | + | + | + | |
| CD74 antigen (invariant polypeptide of major histocompatibility complex, class II antigen-associated) (CD74) | 72 | K01144 | + | + | + | + | + | + | high in many libraries |
| CD79A antigen (immunoglobulin-associated alpha) (CD79A) | 2 | M80462 | | | + | | | | |
| CD79B antigen (immunoglobulin-associated beta) (CD79B) | 2 | M89957 | + | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| CD8 antigen, alpha polypeptide (p32) (CD8A) | 2 | M27161 | + | | | + | | + | |
| CD8 antigen, beta polypeptide 1 (p37) (CD8B1) | 1 | X13445 | W | | | | | | |
| CD81 antigen (target of antiproliferative antibody 1) (CD81) | 1 | M33680 | | + | + | | | + | |
| CD83 antigen (activated B lymphocytes, mmunoglobulin superfamily) (CD83) | 1 | Q01151 | B | + | + | | | + | |
| CD84 antigen (leukocyte antigen) (CD84) | 1 | U82988 | | + | + | | | + | |
| CD86 antigen | 1 | L25259 | | | + | | | | |
| CD9 antigen (p24) (CD9) | 2 | M38690 | | | + | + | + | | |
| CD97 antigen (CD97) | 12 | X84700 | + | + | | + | | | |
| CD97 antigen (CD97) (noin-exact 59%) | 1 | P48960 | | | | | | | |
| CD97 antigen (CD97) (non-exact 62%) | 1 | X94630 | + | + | | + | | | |
| CDC23 (cell division cycle 23, yeast, homolog) (CDC23) | 1 | AF053977 | | + | | | + | + | |
| CDC37 homolog | 1 | U63131 | B | + | + | + | + | | |
| Cdc42 effector protein 3 (CEP3) | 2 | AF104857 | B | + | + | + | | | |
| CDC-like kinase (CLK) | 1 | L29219 | | + | + | + | | + | |
| CDC-like kinase 2 (CLK2) | 1 | AF023268 | B | + | + | | | | |
| CDW52 antigen (CAMPATH-1 antigen) (CDW52) | 13 | X15183 | T activated | + | + | + | | | |
| cell cycle progression restoration 8 protein(CPR8) | 1 | AF011794 | | | | | | | |
| cell division cycle 10 (homologous to CDC10 of S. cerevisiae) (CDC10) | 4 | S72008 | + | + | + | + | | + | |
| cell division cycle 20, S. cerevisiae homolog (CDC20) | 1 | U05340 | | + | + | + | | | |
| cell division cycle 25B (CDC25B) | 6 | Z68092 | + | + | + | + | | + | |
| cell division cycle 2-like 1 (PITSLRE proteins) (CDC2L1) (non-exact 42%) | 1 | AF067514 | | | | | | | |
| cell division cycle 42 (GTP-binding protein, 25 kD) (CDC42) | 5 | M35543 | + | + | + | + | | + | |
| cell division protein (non-exact 68%) | 1 | AF063015 | | | | | | | |
| CELL-CYCLE NUCLEAR AUTOANTIGEN SG2NA (S/G2 NUCLEAR ANTIGEN) | 1 | Q13033 | | | | | | | |
| centromere protein B (80 kD) (CENPB) | 1 | X55039 | | + | | + | | | |
| cep250 centrosome associated protein | 3 | AF022655 | B | + | | + | | | |
| ceroid-lipofuscinosis, neuronal 2, late infantile (Jansky-Bielschowsky disease) (CLN2) | 7 | AF017456 | + | + | + | + | + | + | high in bone |
| c-fgr (=M63877 nonreceptor protein-tyrosine kinase (fgr)) | 6 | X52206 | | | | | | | |
| CGI-19 protein | 3 | AF132953.1 | | | | | | | |
| chaperonin containing TCP1, subunit 3 (gamma) (CCT3) | 1 | X74801 | | + | + | | | + | |
| chaperonin containing TCP1, subunit 4 (delta) (CCT4) | 1 | AF026291 | | + | + | | + | + | |
| chaperonin containing TCP1, subunit 6A (zeta 1) (CCT6A) | 4 | L27706 | B | + | + | | | | |
| chaperonin containing TCP1, subunit 7 (eta) (CCT7) | 4 | AF026292 | B | + | | | | + | |
| Chediak-Higashi syndrome 1 (CHS1) | 1 | U67615 | B, T lymphoma | + | + | + | | | |
| Chediak-Higashi syndrome 1 (CHS1) (low score) | 1 | U67615 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| chemokine (C-C motif) receptor 2 (CCR2) | 4 | U03905 | | | | | | |
| chemokine (C-C motif) receptor 4 (CCR4) (low match) (may contain repeat) | 1 | X85740 | | | | | | |
| chemokine (C-C motif) receptor 7 (CCR7) | 6 | L31581 | | | | | | |
| chemokine (C—X3—C) receptor 1 (CX3CR1) | 5 | U20350 | | + | | | | |
| chemokine (C—X—C motif), receptor 4 (fusin) (CXCR4) | 5 | M99293 | + | + | + | + | | + |
| chitinase 3-like 1 (cartilage glycoprotein-39) (CHI3L1) | 2 | M80927 | | + | | + | | + |
| chitinase 3-like 2 (CHI3L2) | 2 | U49835 | | + | | + | | + |
| chloride channel 1, skeletal muscle (CLCN1) | 1 | G18280 | | | | | | |
| chloride channel 6 (CLCN6) | 1 | D28475 | | + | + | | | |
| Chloride intracellular channel 1 (CLIC1) | 1 | U93205 | + | + | + | + | | + |
| chondroitin sulfate proteoglycan 2 (versican) (CSPG2) | 5 | X15998 | | + | | | | |
| chondroitin sulfate proteoglycan core protein | 2 | J02814 | | + | | | | + |
| chromatin assembly factor 1 p48 subunit (CAF-1 P48 subunit) (retinoblastoma binding protein p48) (retinoblastoma-binding protein 4) (MSI1 protein homolog) | 1 | Q09028 | | | | | | |
| chromodomain helicase DNA binding protein 1 (CHD1) | 2 | AF006513 | | | | | | |
| chromodomain helicase DNA binding protein 1-like (CHD1L) | 1 | AF054177 | | | | | | |
| chromodomain helicase DNA binding protein 2 (CHD2) | 1 | AF006514 | B | + | + | + | | |
| chromodomain helicase DNA binding protein 3 (CHD3) | 1 | AF006515 | | | | | | |
| chromodomain helicase DNA binding protein 4 (CHD4) | 5 | X86691 | + | + | + | + | | + |
| chromosome 1 open reading frame 7 (C1ORF7) | 1 | AF054176 | | | | | | |
| chromosome 1 specific transcript KIAA0493 | 1 | AB007962 | | | | | | |
| chromosome 17 open reading frame 1B (C17ORF1B) | 1 | AJ008112 | T | + | | | | |
| chromosome 4 open reading frame 1 (C4ORF1) | 1 | AF006621 | | + | + | + | | + |
| chromosome condensation 1-like (CHC1L) | 2 | AF060219 | | + | + | + | | + |
| chromosome X open reading frame 5 (CXORF5) | 1 | Y15164 | B | + | + | + | | |
| chromosome-associated polypeptide C(CAP-C) | 2 | AF092564 | B | + | + | + | | + |
| cig42 | 1 | AF026944 | | | | | | |
| cig5 | 3 | AF026941 | | | | | | |
| citrate synthase (CS) | 2 | AF047042 | B | + | + | + | | + |
| class I major histocompatibility antigen (HLA-Cw3) | 2 | U31372 | | | | | | |
| class I major histocompatibility antigen (HLA-Cw3) (low match) | 1 | U31372 | | | | | | |
| clathrin assembly protein lymphoid myeloid leukemia (CALM) | 3 | U45976 | B | + | + | | | + |
| clathrin heavy chain | 1 | X55878 | | | | | | |
| clathrin, heavy polypeptide-like 2 (CLTCL2) | 1 | D21260 | | | | | | |
| clathrin, light polypeptide (Lca) (CLTA) (low match) | 1 | M20472 | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| clathrin-associated/assembly/adaptor protein, medium 1 (CLAPM1) | 3 | D63475 | | + | + | + | + | + | |
| cleavage stimulation factor, 3' pre-RNA, subunit 2 64 kD (CSTF2) (non-exact 82%) | 1 | M85085 | | | | | | | |
| cleavage stimulation factor, 3' pre-RNA, subunit 3, 77 kD (CSTF3) | 1 | U15782 | B | + | + | | + | | |
| clk3 | 1 | L29220 | B | + | + | | | | |
| clone 23815 (Hs.82845) | 1 | U90916 | | + | + | | | + | |
| clone 24592 mRNA sequence | 1 | D88378 | + | + | + | + | | + | |
| C1q/MBL/SPA receptor C1qR(p) ( ) | 1 | U94333 | | | | | | | |
| clusterin (complement lysis inhibitor, SP-40,40, sulfated glycoprotein 2, testosterone-repressed prostate message 2, apolipoprotein J) (CLU) | 1 | M64722 | + | + | + | + | + | + | |
| CMP-sialic acid transporter (CMPST) | 1 | D87969 | B | + | + | | | | |
| CMRF35 | 3 | X66171 | | | | | | | |
| c-myc oncogene containing coxIII | 1 | X54629 | | | | | | | |
| coagulation factor II (thrombin) receptor (F2R) | 1 | M62424 | | + | + | | | + | |
| coagulation factor V (proaccelerin, labile factor) (F5) | 1 | M14335 | | + | | + | + | | |
| coagulation factor XIII a subunit | 3 | M21998 | | | | | | | |
| coagulation factor XIII, A1 polypeptide (F13A1) | 6 | M14354 | | + | + | + | | + | |
| coated vesicle membrane protein (RNP24) | 1 | X92098 | + | + | + | + | + | + | |
| coatomer protein complex, subunit alpha (COPA) | 5 | U24105 | T | + | | + | | | |
| Cofilin 1 (non-muscle) (CFL1) | 13 | X95404 | + | + | + | + | + | + | high in fetal brain |
| cold inducible RNA-binding protein (CIRBP) | 7 | D78134 | | + | + | | + | | |
| cold shock domain protein A (CSDA) | 3 | X95325 | | + | + | | | | |
| collagen, type IX, alpha 2 (COL9A2) | 3 | AF019406 | B | | | | | | |
| colony stimulating factor 1 receptor, formerly McDonough feline sarcoma viral (v-fms) oncogene homolog (CSF1R) | 3 | X03663 | | + | | + | + | | |
| colony stimulating factor 2 receptor, beta, low-affinity (granulocyte-macrophage) (CSF2RB) | 5 | M59941 | | | | | | | |
| colony stimulating factor 2 receptor, beta, low-affinity (granulocyte-macrophage) (CSF2RB) (low match) | 1 | M59941 | | | | | | | |
| colony stimulating factor 3 receptor (granulocyte) (CSF3R) | 16 | X55720 | | + | | | | | |
| complement component 5 receptor 1 (C5a ligand) (C5R1) | 1 | M62505 | L | | | | | | |
| conserved gene amplified in osteosarcoma (OS4) | 2 | AF000152 | | + | + | + | | + | |
| COP9 (constitutive photomorphogenic, Arabidopsis, homolog) subunit 3 (COPS3) | 2 | AF031647 | | + | + | | + | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| COP9 homolog (HCOP9) | 2 | U51205 | B | + | + | + | + | + |
| COPII protein, homolog of *s. cerevisiae* SEC23p (SEC23A) | 4 | X97064 | | + | + | | | |
| copine I (CPNE1) | 2 | U83246 | B | + | + | | + | |
| copine I (CPNE1) (low score) | 1 | U83246 | | | | | | |
| coproporphyrinogen oxidase (coproporphyria, harderoporphyria) (CPO) | 1 | D16611 | | | + | | + | + |
| core-binding factor, beta subunit (CBFB) | 1 | L20298 | | | + | | | |
| coronin | 22 | X89109 | T, W | + | + | | + | |
| coronin (low match) | 1 | U34690 | | | | | | |
| coronin (non-exact, 71%) | 1 | X89109 | | | | | | |
| cot (cancer Osaka thyroid) oncogene (COT) | 1 | D14497 | + | + | + | + | | + |
| cryptochrome 1 (photolyase-like) (CRY1) | 1 | D84657 | | + | + | | | + |
| CTD (carboxy-terminal domain, RNA polymerase II, polypeptide A) phosphatase, subunit 1 (CTDP1) | 1 | AF081287 | | + | + | | | + |
| C-terminal binding protein 1 (CTBP1) | 1 | U37408 | B | + | + | | + | |
| C-terminal binding protein 2 (CTBP2) | 2 | AF016507 | | + | + | | + | |
| CUG triplet repeat, RNA-binding protein 1 (CUGBP1) | 3 | U63289 | | + | + | + | | + |
| cullin 1 (CUL1) | 3 | U58087 | | + | + | + | | + |
| cullin 3 (CUL3) | 2 | U58089 | | + | + | + | | + |
| cut (*Drosophila*)-like 1 (CCAAT displacement protein) (CUTL1) | 1 | M74099 | B | + | | | | |
| cyclin D2 (CCND2) | 2 | D13639 | | + | + | + | | + |
| cyclin D3 (CCND3) | 5 | M92287 | B, T lymphoma | | + | | + | |
| cyclin G1 (CNNG1) | 1 | D78341 | B | + | + | | | + |
| cyclin I | 3 | D50310 | B | + | | + | | |
| cyclin T2 (CNNT2) | 1 | AF048732 | B, T lymphoma | B | | | | |
| cyclin-dependent kinase 2 (CDK2) | 1 | X62071 | | | | | | |
| cyclin-dependent kinase inhibitor (p27Kip1) | 1 | S76986 | | | | | | |
| cyclin-dependent kinase inhibitor 1A (p21, Cip1) (CDKN1A) | 2 | S67388 | + | + | + | + | + | + |
| CYP2D7-CYP2D6 intergenic region (partial) | 1 | X90926 | | | | | | |
| cystatin B (stefin B) (CSTB) | 1 | L03558 | | | + | | + | + |
| cysteine and glycine-rich protein 3 (cardiac LIM protein) (CSRP3) | 5 | L54057 | | | + | | | |
| cytidine deaminase (CDA) | 2 | L27943 | | | | | + | |
| cytochrome b | 1 | AF042500 | | | | | | |
| cytochrome b (CYTB) (isolate Aus5) | 1 | AF042518 | | | | | | |
| cytochrome b(-245) beta chain N-terminal region (X-linked granulomatous disease gene) | 2 | X05895 | | | | | | |
| cytochrome b-245, beta polypeptide (chronic granulomatous disease) (CYBB) | 2 | X04011 | + | | | + | | + |
| cytochrome C | 1 | P00001 | | | | | | |
| cytochrome c oxidase subunit IV (COX4) | 1 | U90915 | T | + | + | | + | + |
| cytochrome c oxidase subunit Vb (COX5B) | 2 | M59250 | | | | | + | |
| cytochrome c oxidase subunit VII-related protein (COX7RP) | 6 | AB007618 | + | + | + | + | | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| cytokine suppressive anti-inflammatory drug binding protein 1 (p38 MAP kinase) (CSBP1) | 1 | L35263 | lymphocyte | + | + | | + | |
| Cytoplasmic antiproteinase = 38 kda intracellular serine proteinase inhibitor | 1 | S69272 | | | | + | | |
| cytotoxic granule-associated RNA-binding protein p40-TIA-1 | 1 | S70114 | | | | | | |
| D123 (D123) | 1 | D14878 | + | + | | + | | + |
| D2-2 | 1 | AF019226 | | | | | | |
| D38 | 1 | X74802 | | | | | | |
| damage-specific DNA binding protein 1 (127 kD) (DDB1) | 2 | AJ002955 | + | + | + | + | + | + |
| DCHT (low match) | 1 | AF017635 | | | | | | |
| DEAD/H (Asp-Glu-Ala-Asp/His) box binding protein 1 (DDXBP1) | 1 | U78524 | | + | + | + | + | + |
| DEAD/H (Asp-Glu-Ala-Asp/His) box polypeptide (72 KD) (P72) | 2 | U59321 | T | + | + | | + | + |
| DEAD/H (Asp-Glu-Ala-Asp/His) box polypeptide 1 (DDX1) | 1 | X70649 | | + | + | | | + |
| DEAD/H (Asp-Glu-Ala-Asp/His) box polypeptide 15 (DDX15) | 2 | AB001636 | | | | | | |
| DEAD/H (Asp-Glu-Ala-Asp/His) box polypeptide 16 (DDX16) | 2 | AB011149 | + | + | + | + | | + |
| DEAD/H (Asp-Glu-Ala-Asp/His) box polypeptide 3 (DDX3) | 3 | U50553 | + | + | + | + | | + |
| DEAD/H (Asp-Glu-Ala-Asp/His) box polypeptide 5 (RNA helicase, 68 kD) (DDX5) | 37 | X15729 | + | + | + | + | | + |
| DEAD/H (Asp-Glu-Ala-Asp/His) box polypeptide 5 (RNA helicase, 68 kD) (DDX5) (low match) | 1 | AF015812 | | | | | | |
| DEAD/H (Asp-Glu-Ala-Asp/His) box polypeptide 6 (RNA helicase, 54 kD) (DDX6) | 2 | D17532 | + | + | | | | |
| DEAD/H (Asp-Glu-Ala-Asp/His) box polypeptide 8 (RNA helicase, 54 kD) (DDX8) | 1 | D50487 | | + | + | + | | + |
| DEAD/H (Asp-Glu-Ala-Asp/His) box polypeptide 9 (RNA helicase A, nuclear DNA helicase II; leukophysin) (DDX9) | 3 | L13848 | + | + | + | + | | + |
| DEAD/H (Asp-Glu-Ala-Asp/His) box polypeptide, Y chromosome (DBY) | 1 | AF000985 | | + | + | | + | |
| Death associated protein 3 (DAP3) | 2 | X83544 | + | + | + | + | + | + |
| death effector domain-containing protein (DEDD) | 1 | AF083236 | | + | + | + | | + |
| death-associated protein 6 (DAXX) | 2 | AF039136 | | + | + | + | | + |
| dedicator of cyto-kinesis 2 (DOCK2) | 4 | D86964 | + | + | | + | | + |
| defender against cell death 1 (DAD1) | 1 | D15057 | | | + | | + | + |
| Defensin, alpha 1, myeloid-related sequence (DEFA1) | 4 | L12690 | | | | + | + | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| DEK gene (D6S231E) | 1 | X64229 | B | | + | + | | | |
| delta sleep inducing peptide, immunoreactor (DSIPI) | 4 | Z50781 | + | + | + | + | | + | |
| dendritic cell protein (GA17) | 3 | AF064603 | + | + | + | + | | + | |
| deoxycytidine kinase (DCK) | 1 | M60527 | | | | | | | |
| deoxyribonuclease II, lysosomal (DNASE2) | 3 | AB004574 | | | | | | | |
| DGS-I | 2 | L77566 | | + | | | | | |
| diacylglycerol kinase | 3 | D16440 | | | | | | | |
| diacylglycerol kinase alpha (DAGK1) (clone 24) | 3 | AF064771 | | + | | | | | |
| diacylglycerol kinase alpha (DAGK1) (clone 24) (low match) | 1 | AF064771 | | | | | | | |
| diaphanous (*Drosophila*, homolog) 1 (DIAPH1) | 1 | AF051782 | B, monocyte stimulated | + | + | | + | + | |
| diaphorase (NADH) (cytochrome b-5 reductase) (DIA1) | 1 | Y09501 | + | + | + | + | + | + | |
| differentiated Embryo Chondrocyte expressed gene 1 (DEC1) | 1 | AB004066 | | + | | | + | + | |
| differentiated Embryo Chondrocyte expressed gene 1 (DEC1) (low match) | 1 | AB004066 | | | | | | | |
| differentiation antigen CD20 | 1 | L23415 | | | | | | | |
| DiGeorge syndrome critical region gene 2 (DGCR2) | 1 | X84076 | | + | + | | | + | |
| dihydrolipoamide dehydrogenase (E3 component of pyruvate dehydrogenase complex, 2-oxo-glutarate complex, branched chain keto acid dehydrogenase complex) (DLD) | 2 | J03620 | | + | | | + | + | |
| dihydrolipoamide S-acetyltransferase (E2 component of pyruvate dehydrogenase complex) (DLAT) | 1 | Y00978 | B | + | | | + | | |
| dihydropyrimidinase-like 2 (DPYSL2) | 1 | D78013 | | + | + | | + | + | |
| dinG gene | 1 | Y10571 | | | | | | | |
| diptheria toxin resistance protein required for diphthamide biosynthesis (*Saccharomyces*)-like 2 (DPH2L2) | 3 | AF053003 | B | + | + | | + | + | |
| disintegrin-protease (non-exact 72%) | 1 | Y13323 | | | | | | | |
| DJ-1 protein | 2 | AF021819 | + | + | + | + | | + | |
| Dmx-like 1 (DMXL1) | 1 | AJ005821 | + | | + | + | | | |
| DNA (cytosine-5-)-methyltransferase 1 (DNMT1) | 3 | X63692 | T activated, lymphoma | + | | | + | + | |
| DNA fragmentation factor, 40 kD, beta subunit (DFFB) | 1 | AF064019 | | | | | | | |
| DNA fragmentation factor, 45 kD, alpha subunit (DFFA) | 2 | U91985 | T | + | + | | | + | |
| DNA mismatch repair protein (hMLH1) | 1 | U17840 | | | | | | | |
| DNA segment on chromosome X (unique) 648 expressed sequence | 3 | M64241 | + | + | + | + | + | + | high in many libraries |
| DNA segment, single copy probe LNS-CAI/LNS-CAII (deleted in polyposis (D5S346) | 3 | M73547 | | + | + | + | | + | |
| DNA-damage-inducible transcript 1 (DDIT1) (low match) | 1 | L24498 | | | | | | | |
| DnaJ protein | 1 | AJ001309 | | | | | | | |
| DnaJ protein | 1 | AJ001309 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| docking protein 2, 56 kD (DOK2) | 1 | AF034970 | | | | | | | |
| dolichyl-diphosphooligosaccharide-protein glycosyltransferase (DDOST) | 1 | D89060 | + | + | + | + | + | + | activated T cell |
| dolichyl-phosphate mannosyltransferase polypeptide 1, catalytic subunit (DPM1) | 1 | D86198 | T activated | + | + | | + | | |
| down-regulated by activation (immunoglobulin superfamily) (DORA) | 1 | AJ223183 | | | | | + | | |
| down-regulated in adenoma DRA (low match) | 1 | P40879 | | | | | | | |
| D-type cyclin-interacting protein 1 (DIP1) | 1 | AF082569 | B | | | | + | + | |
| dual specificity phosphatase 1 (DUSP1) | 4 | X68277 | + | + | + | + | + | + | |
| dual specificity phosphatase 11 (RNA/RNP complex 1-interacting) (dusp11) | 1 | AF023917 | + | + | + | + | | + | |
| dual specificity phosphatase 3 (vaccinia virus phosphatase VH1-related) (DUSP3) | 1 | L05147 | | + | + | | + | + | |
| dual specificity phosphatase 6 (DUSP6) | 6 | X93920 | + | + | + | + | + | + | |
| dynactin 1 (p150, Glued (*Drosophila*) homolog) (DYTN1) | 3 | X98801 | | | | | | | |
| dynactin 1 (p150, Glued (*Drosophila*) homolog) (DYTN1) (low match) | 1 | X98801 | B | + | + | | | | |
| dynamin 2 (DNM2) | 1 | L36983 | | | | | | | |
| dynamitin (dynactin complex 50 kD subunit) (DCTN-50) (non-exact 88%) | 1 | U50733 | | | | | | | |
| dynein, axonemal, heavy polypeptide 17-like (non-exact, 57% aa) | 1 | X99947 | | | | | | | |
| dynein, cytoplasmic, light intermediate polypeptide 2 (DNCLI2) | 1 | AF035812 | B | + | + | | | + | |
| dynein, cytoplasmic, light intermediate polypeptide 2 (DNCLI2) (non-exact, 69%) | 1 | AF035812 | | | | | | | |
| dyskeratosis congenita 1, dyskerin (DKC1) | 1 | U59151 | B | + | | | + | + | |
| dystonia 1, torsion (autosomal dominant) (DYT1) | 1 | AF007871 | | + | + | + | | + | |
| dystrobrevin, beta (DTNB) | 1 | AF022728 | | + | | | | | |
| dystrophia myotonica-containing WD repeat motif (DMWD) | 1 | L19267 | | + | + | | + | + | |
| dystrophia myotonica-protein kinase (DMPK) | 1 | L08835 | + | + | + | | | + | |
| dystrophin (muscular dystrophy, Duchenne and Becker types) (DMD) (low match, 59% aa) | 1 | X14298 | | | | | | | |
| E1B-55 kDa-associated protein | 1 | AJ007509 | W | + | + | | + | + | |
| E2F transcription factor 3 (E2F3) | 2 | D38550 | | + | + | + | + | + | |
| E2F transcription factor 4, p107/p130-binding (E2F4) | 1 | X86096 | B | + | | | + | | |
| E2F transcription factor 5, p130-binding (E2F5) | 2 | U15642 | + | + | | + | | + | |
| E74-like factor 1 (ets domain transcription factor) (ELF1) | 1 | M82882 | B | | + | | + | + | |
| E74-like factor 4 (ets domain transcription factor) (ELF4) | 3 | U32645 | | + | + | | | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| E74-like factor 4 (ets domain transcription factor) (ELF4) (non-exact, 71%) | 1 | U32645 | | | | | | |
| early development regulator 2 (homolog of polyhomeotic 2) (EDR2) | 4 | U89278 | + | + | + | + | | + |
| EBV induced G-protein coupled receptor (EBI2) | 1 | L08177 | W | | | | | |
| ecotropic viral integration site 2B (EVI2B) | 3 | M60830 | | + | | + | | |
| ectin, galactoside-binding, soluble, 1 (galectin 1) (LGALS1) | 1 | J04456 | | | | | | + |
| EGF-like-domain, multiple 4 (EGFL4) | 1 | AB011541 | | | | | | |
| eIF-2-associated p67 homolog | 3 | U13261 | B | + | | | | + |
| elastin (supravalvular aortic stenosis, Williams-Beuren syndrome) (ELN) (low match) | 1 | M24782 | | + | + | | | |
| elav-type RNA-binding protein (ETR-3) | 3 | U69546 | | | | | | |
| electron-transfer-flavoprotein, alpha polypeptide (glutaric aciduria II) (ETFA) | 2 | J04058 | | + | | | | |
| ELK3, ETS-domain protein (SRF accessory protein 2) (ELK3) | 2 | Z36715 | | | + | | | + |
| elongation factor 1-beta | 1 | L26404 | | | | | | |
| elongation factor Ts (mitochondrial protein) | 1 | AF110399 | | | | | | |
| elongation factor Tu-nuclear encoded mitochondrial | 1 | X84694 | | | | | | |
| eMDC II protein | 1 | AJ242015.1 | | | | | | |
| ems1 sequence (mammary tumor and squamous cell carcinoma-associated (p80/85 src substrate) (EMS1) | 1 | M98343 | | + | + | + | | + |
| endogenous retroviral element HC2 | 1 | Z70664 | | | | | | |
| endosulfine alpha (ENSA) | 1 | X99906 | T | + | | | | |
| endothelial differentiation, sphingolipid G-protein-coupled receptor, 1 (EDG1) | 2 | M31210 | | + | + | + | | + |
| endothelial differentiation, sphingolipid G-protein-coupled receptor, 1 (EDG1) (low match 66%) | 1 | M31210 | | | | | | |
| endothelial monocyte-activating polypeptide (EMAPII) | 1 | U10117 | + | + | + | + | | + |
| enolase 1, (alpha) (ENO1) | 12 | M14328 | + | + | + | + | + | + |
| enolase 2, (gamma, neuronal) (ENO2) | 1 | X51956 | | + | | | | |
| enolase-alpha | 1 | D28437 | | | | | | |
| enoyl Coenzyme A hydratase 1, peroxisomal (ECH1) | 2 | U16660 | | | | | | |
| enoyl Coenzyme A hydratase, short chain, 1, mitochondrial (ECHS1) | 1 | D13900 | + | + | + | + | + | + |
| ENOYL-COA HYDRATASE, MITOCHONDRIAL PRECURSOR (SHORT CHAIN ENOYL-COA HYDRATASE) (SCEH) (ENOYL-COA HYDRATASE 1) (low match, non-exact 56%) | 1 | P30084 | | | | | | |
| epidermal growth factor receptor pathway substrate 15 (EPS15) | 2 | U07707 | | + | | + | | + |

TABLE 2-continued

Comparison of 1,800 Unique Genes Identified in the Blood Cell cDNA Library to Genes
Previously Identified in Specific Tissues

| Gene Identification | No. of ESTs | Accession No. | Bl | Br | H | K | Li | Lu | |
|---|---|---|---|---|---|---|---|---|---|
| EPIDIDYMAL SECRETORY PROTEIN E1 PRECURSOR (EPI-1) (HE1) (EPIDIDYMAL SECRETORY PROTEIN 14.6) (ESP14.6) | 2 | Q15668 | | | | | | | |
| epithelial membrane protein 3 (EM[P3) | 1 | U87947 | + | + | + | + | | + | |
| Epoxide hydrolase 1, microsomal (xenobiotic) (EPHX1) | 1 | L29766 | | | | | + only | | |
| ERCC2 (=L47234) | 1 | X52221 | | | | | | | |
| ERF-2 | 3 | U07802 | + | + | + | + | | + | high in gall bladder |
| ERp28 protein | 1 | X94910 | + | + | + | + | | + | |
| erythrocyte membrane protein | 2 | M81635 | | | | | | | |
| erythroleukemic cells K562 | 2 | L25343 | | | | | | | |
| EST (Hs.189509) | 2 | U24166 | | | | | | | |
| estrogen receptor-related protein (hERRa1) | 1 | L38487 | | | | | | | |
| ESTs, Highly similar to ADENYLOSUCCINATE SYNTHETASE | 1 | X66503 | B, T | + | + | | | | |
| ESTs, Moderately similar to cysteine-rich fibroblast growth factor receptor | 1 | U28811 | + | + | + | + | | + | |
| ET binding factor 1 (SBF1) | 1 | U93181 | + | + | | | | + | |
| ets domain protein ERF | 1 | U15655 | + | + | + | + | | + | |
| eukaryotic translation elongation factor 1 alpha 1 (EEF1A1) | 326 | X03558 | T | + | + | | | + | |
| eukaryotic translation elongation factor 1 alpha 1 (EEF1A1) (low match) | 1 | X03558 | | | | | | | |
| eukaryotic translation elongation factor 1 alpha 1 (EEF1A1) (low match) | 1 | X03558 | | | | | | | |
| eukaryotic translation elongation factor 1 beta 2 (EEF1B2) | 5 | X60489 | + | + | + | + | | + | |
| eukaryotic translation elongation factor 1 delta (guanine nucleotide exchange protein) (EEF1D) | 1 | Z21507 | + | + | + | + | + | + | |
| eukaryotic translation elongation factor 1 gamma (EEF1G) | 31 | Z11531 | | | | | | | |
| eukaryotic translation elongation factor 2 (EEF2) | 2 | X51466 | | + | | | | + | |
| eukaryotic translation initiation factor 2, subunit 1 (alpha, 35 kD) (EIF2S1) | 1 | J02645 | | | | | | | |
| eukaryotic translation initiation factor 2, subunit 2 (beta, 38 kD) (EIF2S2) | 1 | M29536 | | | | | | | |
| eukaryotic translation initiation factor 2, subunit 3 (gamma, 52 kD) (EIF2S3) | 3 | L19161 | | + | + | | | | |
| eukaryotic translation initiation factor 3, subunit 10 (theta, 150/170 kD) (EIF3S10) | 2 | U78311 | | | | | | | |
| eukaryotic translation initiation factor 3, subunit 2 (beta, 36 kD) (EIF3S2) | 3 | U36764 | + | + | + | + | + | + | high in white blood cells |
| eukaryotic translation initiation factor 3, subunit 3 (gamma, 40 kD) (EIF3S3) | 6 | U54559 | + | + | + | + | | + | high in spleen |
| eukaryotic translation initiation factor 3, subunit 4 (delta, 44 kD) (EIF3S4) | 9 | AF020833 | | + | + | + | | + | |
| eukaryotic translation initiation factor 3, subunit 6 (48 kD) (EIF3S6) | 4 | U94175 | + | + | + | + | | + | high in bladder |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| eukaryotic translation initiation factor 3, subunit 6 (EIF3S6) | 1 | U62962 | | + | + | + | | + | Highly represented (1.4833 pct) in library 36 human gall bladder |
| eukaryotic translation initiation factor 3, subunit 7 (zeta, 66/67 kD) (EIF3S7) | 3 | U54558 | + | + | + | + | | + | |
| eukaryotic translation initiation factor 3, subunit 8, 110 KD (EIF3S8) | 5 | U46025 | + | + | + | + | + | + | high in testis |
| eukaryotic translation initiation factor 4 gamma, 1 (EIF4G) | 1 | AF012088 | | | | | | | |
| eukaryotic translation initiation factor 4 gamma, 1 (EIF4G) (low match) | 1 | AF012088 | | | | | | | |
| eukaryotic translation initiation factor 4 gamma, 1 (EIF4G1) | 2 | D12686 | | | | | | | |
| eukaryotic translation initiation factor 4 gamma, 2 (EIF4G2) | 6 | U73824 | + | + | + | + | + | + | |
| eukaryotic translation initiation factor 4 gamma, 2 (EIFG2) | 2 | U76111 | + | + | + | + | + | + | |
| eukaryotic translation initiation factor 4A, isoform 1 (EIF4A1) | 29 | D13748 | | | | | | | |
| eukaryotic translation initiation factor 4A, isoform 2 (EIF4A2) | 11 | D30655 | + | + | + | + | + | + | |
| eukaryotic translation initiation factor 4B (EIF4B) | 18 | X55733 | + | + | + | + | | + | |
| eukaryotic translation initiation factor 4E (EIF4E) | 1 | P06730 | | | | | | | |
| Eukaryotic translation initiation factor 4E binding protein 2 (EIF4EBP2) | 3 | L36056 | T, B | + | | | + | + | |
| eukaryotic translation initiation factor 4H (EIF4H) | 2 | Q15056 | | | | | | | |
| eukaryotic translation initiation factor 5 (EIF5) | 2 | U49436 | + | + | + | + | + | + | |
| eukaryotic translation termination factor 1 (ETF1) | 2 | U90176 | + | + | + | + | | + | |
| EV12 protein | 1 | M55266 | | + | | | | | |
| Ewing sarcoma breakpoint region 1 (EWSR1) | 1 | X66899 | + | + | + | + | | + | |
| EWS/FLI1 activated transcript 2 homolog (EAT-2) | 2 | AF020264 | | | | | | | |
| EWS-EIA-F chimeric protein | 1 | U35622 | | | | | | | |
| excision repair cross-complementing rodent repair deficiency, complementation group 1 (includes overlapping antisense sequence) (ERCC1) | 1 | M28650 | + | + | + | + | | + | |
| excision repair cross-complementing rodent repair deficiency, complementation group 5 (xeroderma pigmentosum, complementation group G (Cockayne syndrome)) (ERCC5) | 1 | X69978 | | + | + | + | | + | |
| exostoses (multiple)-like 3 (EXTL3) | 1 | AF001690 | | + | + | + | | + | |
| F11 | 1 | X77744 | | | | + | | | |
| F1-ATPase beta subunit (F-1 beta) | 2 | X03559 | | | | | | | |
| Fanconi anaemia group A | 2 | Z83095 | | | | | | | |
| Fanconi anemia, complementation group A (FANCA) | 1 | X99226 | + | + | + | | | | |
| far upstream element (FUSE) binding protein 1 (FUBP1) | 2 | U05040 | + | | + | | | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| farnesyl diphosphate synthase (farnesyl pyrophosphate synthetase, dimethylallyltranstransferase, geranyltranstransferase) (FDPS) | 1 | J05262 | + | + | + | + | | + | |
| farnesyl-diphosphate farnesyltransferase 1 (FDFT1) | 2 | X69141 | + | + | + | + | + | + | |
| farnesyltransferase, CAAX box, beta (FNTB) | 2 | L00635 | | + | + | | | | |
| Fas ligand (gene and promoter region) | 1 | AF044583 | | | | | | | |
| Fas-ligand associated factor 1 | 1 | U70667 | | | | | | | |
| fatty-acid-Coenzyme A ligase, long-chain 1 (FACL1) | 4 | D10040 | + | + | + | + | + | + | |
| Fc fragment of IgA, receptor for (FCAR) | 1 | X54150 | | | | | | | |
| Fc fragment of IgE, high affinity I, receptor for; gamma polypeptide (FCER1G) | 1 | M33195 | + | + | + | + | | + | |
| Fc fragment of IgE, low affinity II, receptor for (CD23A) (FCER2) | 2 | X04772 | + | + | | | | | |
| Fc fragment of IgG, low affinity IIa, receptor for (CD32) | 6 | M31932 | + | + | + | + | | + | |
| Fc fragment of IgG, low affinity IIa, receptor for (CD32) (FCGR2A) | 1 | X62572 | + | + | + | + | + | + | |
| Fc fragment of IgG, low affinity IIIa, receptor for (CD16) (FCGR3A) | 34 | X07934 | + | + | + | + | | + | |
| Fc fragment of IgG, receptor, transporter, alpha (FCGRT) | 3 | U12255 | | + | + | + | + | + | high in many libraries |
| fc-fgr | 1 | Z13983 | | | | | | | |
| Fc-gamma-receptorIIIB (FCGR3B) | 2 | M90746 | | | | | | | |
| feline sarcoma (Snyder-Theilen) viral (v-fes)/Fujinamiavian sarcoma (PRCII) viral (v-fps) oncogene homolog(FES) c-fes/fps | 3 | X06292 | | | | | | | |
| female sterile homeotic-related gene 1 (mouse homolog) (FSRG1) | 2 | X96670 | + | + | + | + | | + | |
| ferritin L-chain | 9 | Y09188 | | | | | | | |
| ferritin, heavy polypeptide 1 (FTH1) | 4 | M11146 | + | + | + | + | + | + | |
| fertilin alpha pseudogene | 1 | Y09232 | | | | | | | |
| fetal Alzheimer antigen (FALZ) | 2 | U05237 | | + | | | | | |
| fetal Ig heavy chain variable region | 1 | M34024 | | | | | | | |
| fibrillarin (FBL) | 1 | X56597 | + | + | + | + | + | + | |
| fibrinogen-like protein 2 (T49) | 3 | Z36531 | | | | | + | | |
| fibroblast growth factor receptor 2 (bacteria-expressed kinase, keratinocyte growth factor receptor, craniofacial dysostosis 1, Crouzon syndrome) syndrome, Pfeiffer syndrome, Jackson-Weiss (FGFR2) | 1 | M35718 | + | + | + | + | + | + | |
| ficolin (collagen/fibrinogen domain-containing) 1 (FCN1) | 19 | D83920 | | | | | + | + | |
| filamin A, alpha (actin-binding protein-280) (FLNA) | 2 | X53416 | | | | | | | |
| filamin B, beta (actin-binding protein-278) (FLNB) | 1 | AF043045 | | + | + | | + | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| Finkel-Biskis-Reilly murine sarcoma virus (FBR-MuSV) ubiquitously expressed (fox derived); ribosomal protein S30 (FAU) | 2 | X65923 | + | + | + | + | + | + | Highly represented in intraepithelial neoplasia and invasive prostate tumor |
| FK-506 binding protein | 1 | M80199 | + | + | + | + | | + | |
| FK506-binding protein 1A (12 kD) (FKBP1A) | 2 | M34539 | | | | | | | |
| FK506-binding protein 1B (12.6 kD) (FKBP1B) | 1 | M92423 | | + | | + | | + | |
| FK506-binding protein 5 (FKBP5) | 4 | U71321 | + | + | + | | | + | |
| Flightless I (*Drosophila*) homolog (FLII) | 3 | U80184 | + | | | | | | |
| Flightless I (*Drosophila*) homolog (FLII) (low match) | 1 | U80184 | | | | | | | |
| FLN29 (FLN29) | 2 | AB007447 | | + | | + | | + | |
| flotillin 2 (FLOT2) | 5 | M60922 | + | + | + | + | + | + | |
| folate receptor 2 (fetal) (FOLR2) | 1 | AF000380 | | + | + | + | | + | |
| forkhead (*Drosophila*) homolog (rhabdomyosarcoma) like 1 (FKHRL1) | 1 | AF032886 | + | + | | + | | + | |
| Formyl peptide receptor 1 (FPR1) | 9 | M60627 | + | + | + | + | | + | |
| formyl peptide receptor-like 1 (FPRL1) | 1 | M84562 | | | | | | | Found only in libraries from placenta |
| formyl peptide receptor-like 1 (FPRL1) (low score) | 1 | M84562 | | | | | | | |
| fragile X mental retardation 1 (FMR1) | 1 | L29074 | + | + | | + | | + | |
| fragile X mental retardation, autosomal homolog 1 (FXR1) | 1 | U25165 | + | + | + | + | | | |
| Friend leukemia virus integration 1 (FLI1) | 3 | M93255 | + | + | | | | | |
| fructose-bisphosphatase 1 (FBP1) | 1 | D26054 | | | | + | | + | |
| FSHD-associated repeat DNA, proximal region | 1 | U85056 | | | | | | | |
| fucose-1-phosphate guanylyltransferase (FPGT) | 1 | AF017445 | + | + | + | | | | |
| full length insert cDNA clone ZA78A09 | 1 | AF086122 | | | | | | | |
| full length insert cDNA YP07G10 | 1 | AF075061 | | | | | | | |
| fumarate hydratase (FH) | 1 | U59309 | | + | + | + | | + | |
| FUS (low match) | 1 | X99006 | | | | | | | |
| FYN-binding protein (FYB-120/130) (FYB) | 16 | U93049 | + | + | | | | | |
| G alpha interacting protein (GAIP) (low score) | 1 | X91809 | | | | | | | |
| G protein beta subunit-like protein 12.3 | 2 | D28398 | | | | | | | |
| G protein-coupled receptor 64 (HE6) (non-exact 59%) | 1 | X81892 | | | | + | | | |
| G protein-coupled receptor kinase 6 (GPRK6) | 2 | L16862 | + | + | + | | | + | |
| G1 to S phase transition 1 (GSPT1) | 2 | X17644 | + | + | + | + | | + | |
| GA-binding protein transcription factor, beta subunit 2 (47 kD) (GABPB2) | 1 | D13316 | | + | + | + | + | + | |
| galactose-1-phosphate uridylyltransferase (GALT) | 2 | M60091 | | | | | | | |
| galactosidase, beta 1 (GLB1) | 3 | M27508 | | + | | + | | + | |
| galactosyltransferase (=X13223 N-acetylglucosamide-(beta 1-4)-galactosyltransferase) | 1 | M13701 | | | | | | | |
| galectin-9 isoform | 1 | AB006782 | + | | | + | | + | |
| gamma2-adaptin (G2AD) | 1 | AF068706 | + | + | | + | | + | |
| gamma-actin | 2 | M37130 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| gamma-aminobutyric acid (GABA) B receptor 1 (GABBR1) | 2 | AJ012187 | | + | + | | + | | |
| GATA-binding protein 2 (GATA2) | 1 | M68891 | | | | + | | + | |
| GATA-binding protein 3 (GATA3) | 1 | M69106 | | | + | + | | + | |
| GCN5 (general control of amino-acid synthesis, yeast, homolog)-like 1 (GCN5L1) | 3 | D64007 | + | | + | + | | + | |
| GDP dissociation inhibitor 1 (GDI1) | 1 | D45021 | + | + | + | + | | + | high in adult brain |
| GDP dissociation inhibitor 2 (GCI2) | 4 | Y13286 | | | | | | | |
| GDS-related protein (HKE1.5) | 4 | U68142 | + | + | + | + | | + | |
| gelsolin (amyloidosis, Finnish type) (GSN) | 3 | X04412 | | + | + | + | + | + | |
| general transcription factor II, I (GTF2I) | 4 | Y14946 | + | + | + | + | + | | |
| general transcription factor II, i, pseudogene 1 (GTF2IP1) | 1 | AF038968 | + | + | + | + | + | + | high in fetal brain |
| general transcription factor IIF, polypeptide 1 (74 kD subunit) (GTF2F1) | 4 | X64037 | + | + | + | | + | | |
| general transcription factor IIH, polypeptide 3 (34 kD subunit) (GTF2H3) | 2 | Z30093 | B, T | | | | | | |
| general transcription factor IIH, polypeptide 4 (52 kD subunit) (GTF2H4) | 3 | Y07595 | | | + | | + | + | |
| general transcription factor IIIA (GTF3A) | 1 | U14134 | + | + | | + | | + | |
| general transcription factor IIIC, polypeptide 1 (alpha subunit, 220 kD) (GTF3C1) | 1 | U02619 | | + | | + | | | |
| general transcription factor IIIC, polypeptide 2 (beta subunit, 110 kD) (GTF3C2) | 3 | D13636 | + | + | + | + | + | + | |
| germline immunoglobulin heavy chain (IGHV@) | 1 | L06612 | | | | | | | |
| germline immunoglobulin heavy chain, variabl region | 1 | X92236 | | | | | | | |
| germline immunoglobulin heavy chain, variable region, (21-2) | 1 | X92343 | | | | | | | |
| GLE1 (yeast homolog)-like, RNA export mediator (GLE1L) | 1 | AF058922 | | + | + | | | | |
| glia maturation factor, beta (GMFB) | 1 | AB001106 | + | + | | + | | + | |
| glioma-associated oncogene homolog (zinc finger protein) (GLI) | 1 | X07384 | | | | | | | |
| glioma-associated oncogene homolog (zinc finger protein) (GLI) (low score) | 1 | X07384 | | | | | | | |
| globin, alpha 2 | 1 | V00516 | | | | | | | |
| glucocorticoid receptor (=M69104) | 1 | M32284 | | | | | | | |
| glucocorticoid receptor (GRL) | 2 | U80947 | + | + | + | + | | + | |
| glucos phosphate isomerase (CONTAINS LARGE REPEAT) | 1 | L09105 | | | | | | | |
| glucosamine (N-acetyl)-6-sulfatase (Sanfilippo disease IIID) (GNS) | 1 | Z12173 | + | | | | | | |
| glucosamine (N-acetyl)-6-sulfatase (Sanfilippo disease IIID) (GNS) (non-exact 56%) | 1 | Z12173 | | | | | | | |
| glucose transporter-like protein-III (GLUT3) | 1 | M20681 | | + | + | + | + | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| glucose transporter-like protein-III (GLUT3) (low match) | 1 | M20681 | | | | | | |
| glucosidase, alpha; acid (Pompe disease, glycogen storage disease type II) (GAA) | 1 | Y00839 | + | + | | + | | + |
| glucosidase, beta; acid (includes glucosylceramidase) (GBA) | 1 | K02920 | + | + | + | + | | + |
| glutamate dehydrogenase 1 (GLUD1) | 1 | M20867 | | + | + | + | + | + |
| glutamate-ammonia ligase (glutamine synthase) (GLUL) | 12 | X59834 | + | + | + | + | | + |
| glutamate-ammonia ligase (glutamine synthase) (GLUL) (low score) | 1 | Y00387 | | | | | | |
| glutamate-cysteine ligase (gamma-glutamylcysteine synthetase), catalytic (72.8 kD) (GLCLC) | 1 | M90656 | | | | + | | |
| glutamine cyclotransferase | 1 | X71125 | | + | + | | | |
| glutamine-fructose-6-phosphate transaminase 1 (GFPT1) | 1 | M90516 | | + | | + | | |
| glutaminyl-tRNA synthetase | 1 | X72396 | | | | | | |
| glutaminyl-tRNA synthetase (QARS) | 6 | X76013 | + | + | + | + | | + |
| glutamyl-prolyl-tRNA synthetase (EPRS) | 1 | X54326 | | | | | | |
| glutathione peroxidase 1 (GPX1) | 2 | M21304 | + | + | + | + | + | + |
| glutathione peroxidase 4 (phospholipid hydroperoxidase) (GPX4) | 1 | X71973 | + | + | + | + | | + |
| glutathione S-transferase pi (GSTP1) | 1 | U30897 | + | + | + | + | + | |
| glutathione S-transferase subunit 13 homolog | 1 | AF070657 | | | | | | |
| glyceraldehyde-3-phosphate dehydrogenase (GAPD) | 12 | J02642 | | | | | + | |
| glycogenin (GYG) | 1 | U31525 | | + | + | + | | + |
| glycophorin C (Gerbich blood group) (GYPC) | 1 | X12496 | | + | + | + | | + |
| glycoprotein M6B (GPM6B) | 1 | U45955 | | + | + | | | |
| glycyl-tRNA synthetase (GARS) | 1 | U09587 | | + | + | + | | + |
| glyoxalase I (lactoyl glutathione lyase) (GLYI) | 1 | L07837 | + | + | + | + | | + |
| golgi autoantigen, golgin subfamily a, 1 (GOLGA1) | 1 | U51587 | | + | + | | | |
| golgi autoantigen, golgin subfamily a, 2 (GOLGA2) (non-exact, 70%) | 1 | L06147 | | | | | | |
| golgi autoantigen, golgin subfamily a, 4 (GOLGA4) | 1 | U31906 | | | | | | |
| golgi autoantigen, golgin subfamily b, macrogolgin (with transmembrane signal), 1 (GOLGB1) | 1 | X75304 | | + | + | + | | + |
| gp25L2 protein | 4 | X90872 | | | | | | |
| grancalcin | 8 | M81637 | | + | + | + | | |
| granulin (GRN) | 16 | X62320 | + | + | + | + | | + |
| granulin (GRN) (low match) | 1 | X62320 | | | | | | |
| Granulysin (NKG5) | 5 | M85276 | + | | | | | + |
| granzyme A (granzyme 1, cytotoxic T-lymphocyte-associated serine esterase 3) (GZMA) | 1 | M18737 | + | + | + | + | | + |
| GRB2-related adaptor protein (GRAP) | 1 | U52518 | T only | | | | | |
| Grb2-related adaptor protein 2 (GRAP2) | 1 | AF090456 | T | | | + | | |

TABLE 2-continued

Comparison of 1,800 Unique Genes Identified in the Blood Cell cDNA Library to Genes
Previously Identified in Specific Tissues

| Gene Identification | No. of ESTs | Accession No. | Bl | Br | H | K | Li | Lu | |
|---|---|---|---|---|---|---|---|---|---|
| GRO1 oncogene (melanoma growth stimulating activity, alpha) (GRO1) | 1 | X54489 | | | | + | | + | |
| growth arrest and DNA-damage-inducible gene (GADD153) | 1 | S40706 | | | | | | | |
| growth arrest-specific 7 (GAS7) | 4 | AB007854 | | + | + | | | | |
| growth factor receptor-bound protein 2 (GRB2) | 1 | X62852 | B | + | | + | + | | |
| GS1 (protein of unknown function) | 1 | M86934 | | + | + | + | | | |
| GS3955 | 4 | D87119 | | + | + | + | | + | |
| GTP binding protein 1 (GTPBP1) | 1 | U87964 | | + | + | + | | | |
| GTP binding protein similar to S. cerevisiae HBS1 (HBS1) | 1 | U87791 | | + | + | + | | + | |
| GTPase activating protein-like (GAPL) | 1 | AB011110 | | + | + | + | | + | high fetal brain |
| GTP-binding protein (low match) | 1 | Z49068 | | | | | | | |
| GTP-binding protein G(K), alpha subunit (=G(I) ALPHA-3)(=GTP-binding regulatory protein Gi alpha-3 chain) | 1 | P08754 | | | | | | | |
| Gu protein (GURDB) | 2 | U41387 | + | | + | + | | + | |
| guanine nucleotide binding protein | 1 | | | | | | | | |
| guanine nucleotide binding protein (G protein), alpha inhibiting activity polypeptide 2 (GNAI2) | 4 | J03004 | + | + | + | + | | + | |
| guanine nucleotide binding protein (G protein), alpha inhibiting activity polypeptide 3 (GNAI3) | 7 | M20597 | + | + | + | + | | + | |
| guanine nucleotide binding protein (G protein), alpha stimulating activity polypeptide 1 (GNAS1) | 2 | X04409 | B, T | + | | + | + | | |
| guanine nucleotide binding protein (G protein), alpha transducing activity polypeptide 2 (GNAT2) | 1 | Z18859 | | | | | | | |
| guanine nucleotide binding protein (G protein), beta 5 (GNB5) | 2 | AF017656 | | + | + | + | | + | |
| guanine nucleotide binding protein (G protein), beta polypeptide 1 (GNB1) | 5 | M36430 | + | + | + | + | + | + | |
| guanine nucleotide binding protein (G protein), q polypeptide (GNAQ) | 2 | AF011496 | | + | + | + | | | |
| guanine nucleotide binding protein-like 1 (GNL1) | 1 | L25665 | + | + | + | + | | + | |
| guanine nucleotide exchange factor | 1 | L13857 | + | + | + | + | | | |
| guanine nucleotide regulatory factor (LFP40) | 1 | X15610 | + | + | + | + | | + | |
| guanine nucleotide regulatory factor (LFP40) | 1 | U72206 | + | + | + | + | | + | |
| GUANINE NUCLEOTIDE-BINDING PROTEIN BETA SUBUNIT-LIKE PROTEIN 12.3 (P205) (RECEPTOR OF ACTIVATED PROTEIN KINASE C 1) (RACK1) | 1 | P25388 | | | | | | | |
| GUANINE-MONOPHOSPHATE SYNTHETASE (GMPS) | 1 | U10860 | | | + | | | | |
| guanosine monophosphate reductase (GMPR) (non-exact, 72%) | 1 | M24470 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | Tissue Distribution |
|---|---|---|---|---|---|---|---|---|---|
| guanosine-diphosphatase like protein | 1 | AF016032 | | | | | | | |
| guanylate binding protein 1, interferon-inducible, 67 kD (GBP1) | 2 | M55542 | | + | + | + | + | + | |
| guanylate binding protein 2, interferon-inducible (GBP2) | 6 | M55543 | + | + | + | + | | + | |
| H2A histone family, member C (H2AFC) | 1 | Z83742 | | | | | | | |
| H2A histone family, member Y (H2AY) | 2 | AF041483 | + | + | + | + | | + | |
| H2B histone family, member L (H2BFL) | 2 | Z80783 | + | | + | + | + | + | high in adrenal gland tumor |
| h2-calponin | 1 | D86059 | | | | | | | |
| H-2K binding factor-2 | 1 | L08904 | | + | + | + | | + | |
| H3 histone family, member K (H3FK) | 1 | Z83735 | | | | | | | |
| H3 histone, family 3A (H3F3A) | 7 | M11353 | + | + | + | + | | + | high in ovary |
| H3 histone, family 3B (H3.3B) (H3F3B) | 15 | Z48950 | + | + | + | + | | + | high in endothelial cells |
| hbc647 | 1 | U68494 | | + | + | + | + | | |
| heat shock 27 kD protein 1 (HSPB1) | 1 | U12404 | | + | + | | + | + | |
| heat shock 40 kD protein 1 (HSPF1) | 4 | D85429 | + | + | + | + | + | + | high in testis |
| heat shock 60 kD protein 1 (chaperonin) (HSPD1) | 3 | M22382 | + | + | + | + | + | + | |
| heat shock 70 kD protein 1 (HSPA1A) | 7 | M59828 | + | + | + | + | + | + | high in activated T cells |
| heat shock 70 kD protein 5 (glucose-regulated protein, 78 kD) (HSPA5) | 13 | X87949 | | + | + | | + | | |
| heat shock 70 kD protein 6 (HSP70B') (HSPA6) | 4 | X51757 | + | | + | + | | | |
| heat shock 70 kD protein 9B (mortalin-2) (HSPA9B) | 2 | L15189 | + | | + | + | + | + | |
| HEAT SHOCK COGNATE 71 KD PROTEIN | 1 | P11142 | | | | | | | |
| heat shock factor binding protein 1 (HSBP1) | 2 | AF068754 | | | | | | | |
| heat shock protein 90 | 13 | M27024 | + | + | + | + | + | + | high in many libraries |
| heat shock protein, DNAJ-like 2 (HSJ2) | 1 | D13388 | | + | + | + | + | | |
| Hect (homologous to the E6-AP (UBE3A) carboxyl terminus) domain and RCC1 (CHC1)-like domain (RLD) 1 (HERC1) | 1 | U50078 | | + | + | + | | | |
| hect domain and RLD 2 (HERC2) | 1 | AB002391 | + | + | + | + | | + | |
| helicase-like protein (HLP) | 1 | X98378 | + | + | | + | | + | |
| helix-loop-helix protein HE47 (E2A) | 1 | M65214 | | | | | | + | |
| hematopoietic cell-specific Lyn substrate 1 (HCLS1) | 18 | X16663 | + | | + | + | | + | |
| heme oxygenase (decycling) 1 (HMOX1) | 1 | X06985 | + | | + | + | | + | |
| HEMOGLOBIN ALPHA CHAIN | 1 | P19015 | | | | | | | |
| hemoglobin beta (beta globin) | 5 | AF117710 | | | | | | | |
| hemoglobin, alpha 1 (HBA1) | 301 | V00491 | | | | + | | + | + |
| hemoglobin, alpha 1 (HBA1) (low match) | 1 | V00491 | | | | | | | |
| hemoglobin, alpha 1 (low match) | 1 | V00493 | | | | | | | |
| hemoglobin, alpha 1 (non-exact, 76%) | 1 | J00153 | | | | | | | |
| hemoglobin, alpha 1 (non-exact, 82%) | 1 | V00493 | | | | | | | |
| hemoglobin, beta (HBB) | 129 | V00497 | + | + | + | + | + | + | high in many libraries |
| hemoglobin, beta (HBB) (low match) | 1 | V00497 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| hemoglobin, beta (HBB) (low match) | 1 | L48220 | | | | | | | |
| hemokine (C—X—C motif), receptor 4 (fusin) (CXCR4) | 1 | D10924 | + | + | + | + | | + | |
| hemopoietic cell kinase (HCK) | 5 | M16591 | | | | + | | + | |
| hepatitis C-associated microtubular aggregate protein p44 | 2 | D28908 | | | | | | | |
| hepatoma-derived growth factor | 1 | D16431 | + | + | + | + | | + | |
| Hermansky-Pudlak syndrome (HPS) | 2 | U65676 | | | | | | | |
| HERV-E integrase (non-exact 76% aa) | 1 | AF026246 | | | | | | | |
| heterogeneous nuclear protein similar to rat helix destabilizing protein (FBRNP) | 2 | S63912 | | + | + | + | | + | |
| heterogeneous nuclear ribonucleoprotein (C1/C2) (HNRPC) | 4 | M16342 | | | | | | | |
| heterogeneous nuclear ribonucleoprotein A/B (HNRPAB) | 1 | M65028 | + | + | + | + | + | + | |
| heterogeneous nuclear ribonucleoprotein A1 (HNRPA1) | 20 | X12671 | + | + | + | + | + | + | High in alveolar rhabdomyosarcoma |
| heterogeneous nuclear ribonucleoprotein A2/B1 (HNRPA2B1) | 3 | M29064 | + | + | + | + | + | + | High in activated T cell, fetal brain |
| heterogeneous nuclear ribonucleoprotein D (hnRNP D) | 2 | D55673 | + | + | + | + | + | + | |
| heterogeneous nuclear ribonucleoprotein D-like (HNRPDL) | 5 | D89092 | + | + | + | + | + | + | |
| heterogeneous nuclear ribonucleoprotein F (HNRPF) | 1 | L28010 | + | + | + | + | | + | |
| heterogeneous nuclear ribonucleoprotein F (HNRPF) (83%) | 1 | L28010 | | | | | | | |
| heterogeneous nuclear ribonucleoprotein G (HNRPG) | 2 | Z23064 | | + | + | + | | + | |
| heterogeneous nuclear ribonucleoprotein H (HNRPH) (FTP-3) | 3 | P55795 | | | | | | | |
| heterogeneous nuclear ribonucleoprotein H (HNRPH) (low match) | 1 | P31943 | | | | | | | |
| heterogeneous nuclear ribonucleoprotein H1 (H) (HNRPH1) | 2 | L22009 | + | + | + | + | | + | |
| heterogeneous nuclear ribonucleoprotein K (HNRPK) | 21 | S74678 | + | + | + | + | + | + | |
| heterogeneous nuclear ribonucleoprotein R (HNRPR) | 1 | AF000364 | | + | + | + | | + | |
| heterogeneous nuclear ribonucleoprotein U (scaffold attachment factor A) (HNRPU) | 3 | X65488 | + | + | + | + | + | + | |
| hexokinase 1 (HK1) | 2 | X66957 | | + | + | + | | + | |
| hexokinase 2 (HK2) | 3 | Z46376 | + | + | + | + | | + | |
| hexokinase 3 (HK3) | 2 | U51333 | | | | | | | |
| hexosaminidase A (alpha polypeptide) (HEXA | 1 | S62047 | | | | | | | |
| HGMP07I gene for olfactory receptor | 2 | U76377 | | | | | | | |
| High density lipoprotein binding protein (HDLBP) | 2 | M64098 | + | + | + | + | + | + | |

TABLE 2-continued

Comparison of 1,800 Unique Genes Identified in the Blood Cell cDNA Library to Genes
Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| high-mobility group (nonhistone chromosomal) protein 1 (HMG1) | 5 | X12597 | + | + | + | + | + | + | |
| high-mobility group (nonhistone chromosomal) protein 1 (HMG1) (non-exact 60%) | 1 | D63874 | | | | | | | |
| High-mobility group (nonhistone chromosomal) protein 17 (HMG17) | 2 | M12623 | + | + | + | + | | + | |
| high-mobility group (nonhistone chromosomal) protein 2 (HMG2) | 2 | M83665 | + | + | + | + | + | + | |
| high-mobility group (nonhistone chromosomal) protein isoforms I and Y | 2 | L17131 | + | + | + | | + | + | |
| high-risk humanpapilloma viruses E6 oncoproteins targeted protein E6TP1 beta (=AB007900 KIAA0440) | 1 | AF090990.1 | | | | | | | |
| histidine ammonia-lyase (HAL) | 1 | D16626 | | | +, only | | | | |
| histidyl-tRNA synthetase (HARS) | 2 | Z11518 | + | + | + | + | + | + | |
| histocompatibility antigen (HLA-Cw3), class I | 1 | U31372 | | | | | | | |
| histone deacetylase 1 (HDAC) | 4 | U50079 | + | + | + | + | | + | |
| histone deacetylase 1 (HDAC1) | 2 | D50405 | + | + | + | + | | + | |
| histone deacetylase 5 (NY-CO-9) | 1 | AF039691 | | + | + | | | | |
| HK2 gene for hexokinase II | 1 | Z46362 | | | | | | | |
| HL9 monocyte inhibitory receptor precursor | 2 | U91928 | | | | + | | | |
| HLA class I heavy chain (HLA-Cw*1701) | 1 | | | | | | | | |
| HLA class I locus C heavy chain | 1 | X58536 | | | | | | | |
| HLA class II SB 4-beta chain | 1 | X03022 | | | | | | | |
| HLA class III region containing NOTCH4 gene | 1 | U89335 | + | + | + | + | | + | |
| HLA-A | 1 | Z72423 | | | | | | | |
| HLA-A | 2 | AJ006020 | | | | | | | |
| HLA-A*7402 | 1 | AJ223060 | | | | | | | |
| HLA-A11 | 1 | U02934 | | | | | | | |
| HLA-B | 2 | X75953 | | | | | | | |
| HLA-B | 1 | X83401 | | | | | | | |
| HLA-B | 1 | X78426 | | | | | | | |
| HLA-B associated transcript-1 (D6S81E) | 1 | Z37166 | + | + | + | + | + | + | |
| HLA-B associated transcript-2 (D6S51E) | 2 | M33509 | + | + | + | + | | | |
| HLA-B*1529 | 4 | D44501 | | | | | | | |
| HLA-Bw72 antigen | 119 | L09736 | + | + | + | + | + | + | high in many libraries |
| HLA-C gene (HLA-Cw*0701 allele) | 1 | D83957 | | | | | | | |
| HLA-Cw*0701 | 9 | Z46810 | | | | | | | |
| HLA-Cw*0801 | 1 | D64151 | | | | | | | |
| HLA-Cw*1203 | 1 | D64146 | | | | | | | |
| HLA-DC classII histocompatibility antigens alpha-chain (=K01160) | 2 | X00370 | | | | | | | |
| HLA-DR alpha-chain | 17 | M60333 | + | + | + | + | + | + | high in spleen |
| HLA-F (leukocyte antigen F) | 3 | X17093 | | | + | + | | + | |
| HMG box containing protein 1 | 3 | AF019214 | | | | | | | |
| hMLH1 (=U83845) | 1 | AB017806.1 | | | | | | | |
| Hmob33 | 3 | Y14155 | | | | | | | |
| HMT1 (hnRNP methyltransferase, S. cerevisiae)-like 1 (HRMT1L1) | 2 | U80213 | + | + | + | + | | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| hnRNP C1/C2 | 2 | D28382 | | | | | | |
| homeobox (=X58250 Mouse homeo box protein, put. transcription factor involved in embryogenesis and hematopoiesis) | 1 | M60721 | | | | | | |
| homeobox protein (HLX1) (=M60721) | 1 | U14326 | | | | | | |
| homeodomain-interacting protein kinase 3 (HIPK3) | 1 | AF004849 | + | | + | + | | + |
| homolog of *Drosophila* past (PAST) | 2 | AF001434 | + | + | + | + | | + |
| homolog of yeast (*S. cerevisiae*) ufd2 (UFD2) | 3 | D50916 | | + | + | + | | + |
| HPV16 E1 protein binding protein | 1 | U96131 | + | + | | | | + |
| HRIHFB2157 | 1 | AB015344 | + | + | | | | + |
| HRX-like protein (=AF010403 ALR) | 1 | Y08836 | | | | | | |
| hsc70 gene for 71 kd heat shock cognate protein | 3 | Y00371 | | | | | | |
| HSPC012 | 1 | AF077036.1 | | | | | | |
| HSPC021 | 1 | AF077207.1 | | | | | | |
| HsPex13p | 1 | U71374 | | | | | | |
| htra2-beta-2 | 1 | U87836 | + | + | + | + | | + |
| HU-K4 | 1 | U60644 | | | | | | |
| hunc18b2 | 1 | U63533 | | + | + | + | | + |
| HUNKI | 1 | Y12059 | + | + | | + | + | + |
| huntingtin-interacting protein HYPA/FBP11 (HYPA) | 1 | AF049528 | | | | | | |
| hVps41p (HVPS41) | 1 | U87309 | | | | | | |
| hydroxyacyl-Coenzyme A dehydrogenase/3-ketoacyl-Coenzyme A thiolase/enoyl-Coenzyme A hydratase (trifunctional protein), alpha subunit (HADHA) | 1 | U04627 | | + | + | + | | |
| hydroxyacyl-Coenzyme A dehydrogenase/3-ketoacyl-Coenzyme A thiolase/enoyl-Coenzyme A hydratase (trifunctional protein), beta subunit (HADHB) | 1 | D16481 | + | + | + | + | | + |
| hydroxysteroid (17-beta) dehydrogenase 1 (HSD17B1) | 1 | U34879 | | + | | + | | |
| hypothetical protein | 1 | | | | | | | |
| hypothetical protein (AL008729) (dJ257A7.2) | 1 | | | | | | | |
| hypothetical protein (CIT987SK_2A8_1 chromosome 8) | 1 | U96629 | | | | | | |
| hypothetical protein (clone 24640) | 1 | AF055004 | | | | | | |
| hypothetical protein (clone ICRFp507G2490). | 1 | Z70222 | | | | | | |
| hypothetical protein (dJ1042K10.4) (non-exact 76%) | 1 | AL022238 | | | | | | |
| hypothetical protein (dJ465N24.1 similar to predicted yeast and worm proteins) | 2 | AL031432 | | | | | | |
| hypothetical protein (dJ487J7.1.1) | 2 | AL008730 | | | | | | |
| hypothetical protein (dJ753P9.2) | 2 | AL023653 | | | | | | |
| hypothetical protein (DKFZp586I111) | 1 | AL050131.1 | | | | | | |
| hypothetical protein (J257A7.2) | 1 | AL008729 | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| hypothetical protein (KIAA0440) (=AF026504 *R. norvegicus* SPA-1 like protein) | 1 | AB007900 | | | | | | |
| hypothetical protein (L1H 3' region) | 1 | | | | | | | |
| hypothetical protein (S164) | 1 | P49756 | | | | | | |
| hypothetical protein (similar to thrombospondin) (non-exact 56%) | 1 | AF109907 | | | | | | |
| hypothetical protein 3 | 1 | | | | | | | |
| hypothetical protein B (HSU47926) (non-exact, 56%) | 1 | U47926 | | | | | | |
| hypothetical protein from BCRA2 region (CG005) | 3 | U50532 | + | + | + | + | | + |
| hypoxia-inducible factor 1, alpha subunit (basic helix-loop-helix transcription factor) (HIF1A) | 1 | AF050115 | | | | | | |
| Ia-associated invariant gamma-chain (clones lambda-y (1,2,3)) | 1 | M13555 | | | | | | |
| iduronate 2-sulfatase (Hunter syndrome) (IDS) | 2 | M58342 | + | + | + | + | | + |
| Ig heavy chain V region (=D11016) | 1 | L20779 | | | | | | |
| Ig heavy chain variable region | 2 | M34024 | | | | | | |
| Ig heavy chain variable region (VH4DJ) (clone T14.4) | 1 | Z75378 | | | | | | |
| Ig heavy chain variable region (VH4DJ) (clone T22.18) | 1 | Z75392 | | | | | | |
| Ig J chain | 1 | M12378 | | | | | | |
| Ig kappa | 1 | S49007 | | | | | | |
| IG kappa light chain variable region A20 | 1 | X63398 | | | | | | |
| Ig kappa light chain, V- and J-region (=X59315) | 1 | D90158 | | | | | | |
| Ig lambda light chain variable region (26-34ITIIIF120) | 1 | Z85052 | | | | | | |
| Ig mu-chain VDJ4-region | 1 | M16949 | | | | | | |
| Ig rearranged anti-myelin kappa-chain (V-J4-region, hybridoma AE6-5) | 1 | M29469 | | | | | | |
| Ig rearranged H-chain mRNA V-region | 2 | M97920 | | | | | | |
| Ig rearranged light-chain V region (=D90158) | 1 | M74020 | | | | | | |
| IGF-II mRNA-binding protein 3 (KOC1) (non-exact, 75%) | 1 | U97188 | + | + | + | | | |
| IgG Fc binding protein (FC(GAMMA)BP) | 1 | D84239 | + | + | | + | | + |
| IgG heavy chain variable region (vH26) | 1 | M83136 | | | | | | |
| IgM heavy chain (C mu, membrane exons) | 1 | X14939 | | | | | | |
| IkB kinase-beta (IKK-beta) | 1 | AF029684 | | | | | | |
| IL-1 receptor type II | 1 | U14177 | | | | | | |
| IL2-inducible T-cell kinase (ITK) | 2 | S65186 | | | | | | |
| immediate early protein (ETR101) | 1 | M62831 | + | | | + | + | + |
| immunogloblin light chain (lambda) | 1 | D87018 | | | | | | |
| Immunoglobulin (CD79A) binding protein 1 (IGBP1) | 1 | Y08915 | B, T | + | + | | + | |
| immunoglobulin C (mu) and C (delta) heavy chain (=K02878) | 2 | X57331 | | | | | | |
| immunoglobulin G Fc receptor IIIB | 1 | Z46223 | | | | | | |
| immunoglobulin gamma 3 (Gm marker) (IGHG3) | 3 | Y14737 | + | | | + | + | high in many libraries |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| immunoglobulin gamma heavy chain variable region (=X61011) | 1 | Z66542 | | | | | | |
| immunoglobulin heavy chain (VI-3B) | 1 | X62109 | | | | | | |
| immunoglobulin heavy chain J region | 1 | X86356 | | | | | | |
| immunoglobulin heavy chain J region, B1 haplotype | 2 | X86355 | | | | | | |
| immunoglobulin heavy chain variable region (IGH) (clone 21u-48) | 1 | AF062126 | | | | | | |
| immunoglobulin heavy chain variable region (IGH) (clone 23u-1) | 1 | AF062212 | | | | | | |
| immunoglobulin heavy chain variable region V1-18 (IGHV@) (=X60503) | 2 | M99641 | | | | | | |
| immunoglobulin heavy chain variable region V3-43 (IGHV@) | 2 | M99672 | | | | | | |
| immunoglobulin heavy chain variable region V3-7 (IGHV@) | 3 | M99649 | | | | | | |
| immunoglobulin IgH heavy chain Fd fragment | 1 | U07986 | | | | | | |
| immunoglobulin kappa light chain | 1 | X58081 | | | | | | |
| immunoglobulin kappa light chain V-segment A27 | 1 | X12686 | | | | | | |
| immunoglobulin light chain | 1 | D86990 | | | | | | |
| immunoglobulin light chain (low match) | 1 | D86996 | | | | | | |
| immunoglobulin light chain variable region (lambda IIIb subgroup) from IgM rheumatoid factor | 1 | L29157 | | | | | | |
| immunoglobulin M heavy chain V region = anti-lipid A antibody | 1 | S50735 | | | | | | |
| immunoglobulin mu (IGHM) | 9 | X57086 | + | + | | + | + | |
| immunoglobulin mu binding protein 2 (IGHMBP2) | 1 | L24544 | T | + | | + | | |
| immunoglobulin superfamily, member 2 (IGSF2) | 1 | Z33642 | | | | | | |
| Immunoglobulin VH mRNA (487 bp) (=M99652 immunoglobulin heavy chain variable region V3-11 (IGHV@)) | 1 | X61013 | | | | | | |
| imogen 38 (IMOGEN38) | 1 | Z68747 | | + | + | + | + | |
| IMP (inosine monophosphate) dehydrogenase 1 (IMPDH1) | 1 | J05272 | + | + | + | + | | |
| IMP (inosine monophosphate) dehydrogenase 2 (IMPDH2) | 2 | L39210 | + | + | + | + | + | |
| inc finger protein 151 (pHZ-67) (ZNF151) | 1 | Y09723 | + | + | + | + | + | |
| inc finger protein, C2H2, rapidly turned over (ZNF20) | 1 | AF011573 | | + | + | | | |
| inducible poly(A)-binding protein (IPABP) | 1 | U33818 | + | + | + | + | + | |
| inducible poly(A)-binding protein (IPABP) (low match) | 1 | U33818 | | | | | | |
| inducible protein (Hs.80313) | 2 | L47738 | + | + | + | + | + | |
| inhibitor of DNA binding 2, dominant negative helix-loop-helix protein (ID2) | 4 | M97796 | + | + | + | + | + | + |
| inhibitor of kappa light polypeptide gene enhancer in B-cells, kinase complex-associated protein (IKBKAP) | 2 | AF044195 | | | | | | |
| inositol 1,3,4-trisphosphate 5/6-kinase | 1 | U51336 | + | + | + | + | + | + |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| inositol 1,4,5 trisphosphate receptor type 1 (ITPR1) | 1 | U23850 | | + | + | + | | |
| inositol 1,4,5-trisphosphate 3-kinase B (ITPKB) | 2 | X57206 | B | + | + | | + | |
| inositol monophosphatase | 1 | S38980 | | | | | | |
| inositol polyphosphate-5-phosphatase, 145 kD (INPP5D) | 2 | U84400 | + | + | + | + | | + |
| Ins(1,3,4,5)P4-binding protein | 1 | X89399 | | + | | | | + |
| insulin-like growth factor 2 receptor (IGF2R) | 5 | Y00285 | + | + | + | + | | + |
| integral membrane protein 1 (ITM1) | 1 | L38961 | | | + | + | | + |
| integral membrane protein 2C (ITM2C) | 1 | AF038953 | T | + | | + | | + |
| integral membrane protein Tmp21-I (p23) | 3 | U61734 | + | + | + | + | + | + |
| integrin beta 4 binding protein (ITGB4BP) | 2 | AF047433 | | | + | | | + |
| integrin, alpha 2b (platelet glycoprotein IIb of IIb/IIIa complex, antigen CD41B) (ITGA2B) | 3 | M34480 | | + | | + | | |
| integrin, alpha 5 (fibronectin receptor, alpha polypeptide) (ITGA5) | 4 | X06256 | + | + | + | | + | + |
| integrin, alpha L (antigen CD11A (p180), lymphocyte function-associated antigen 1; alpha polypeptide) (ITGAL) | 6 | Y00796 | | | | | | |
| integrin, alpha M (complement componentreceptor 3, alpha; also known as CD11b (p170), macrophage antigen alpha polypeptide) (ITGAM) | 1 | M18044 | | | | | | |
| integrin, alpha X (antigen CD11C (p150), alpha polypeptide) (ITGAX) | 1 | M81695 | + | + | | | | + |
| integrin, beta 1 (fibronectin receptor, beta polypeptide, antigen CD29 includes MDF2 MSK12) (ITGB1) | 2 | X07979 | | | | | | |
| integrin, beta 2 (antigen CD18 (p95), lymphocyte function-associated antigen 1; macrophage antigen 1 (mac-1) beta subunit) (ITGB2) | 32 | M15395 | + | + | | + | | + |
| integrin, beta 7 (ITGB7) | 1 | M68892 | + | | | | | |
| Integrin-linked kinase (ILK) | 1 | U40282 | + | + | + | + | | + |
| intercellular adhesion molecule 1 (CD54), human rhinovirus receptor (ICAM1) | 1 | J03132 | + | | | + | + | + |
| intercellular adhesion molecule 2 (ICAM2) | 1 | X15606 | + | + | + | + | | + |
| intercellular adhesion molecule 3 (ICAM3) | 6 | X69819 | + | | | | | + |
| intercellular adhesion molecule 4, Landsteiner-Wiener blood group (ICAM4) | 1 | L27670 | | | | | | + |
| Interferon consensus sequence binding protein 1 (ICSBP1) | 1 | M91196 | W, T lymphoma | | | | | |
| Interferon consensus sequence binding protein 1 (ICSBP1) (low match) | 1 | M91196 | | | | | | |
| interferon regulatory factor 2 (IRF2) | 4 | X15949 | + | + | + | + | | |
| interferon regulatory factor1 (IRF1) | 4 | L05072 | + | + | + | + | | + |
| interferon regulatory factor5 (IRF5) | 1 | U51127 | + | + | | + | | |
| interferon, gamma-inducible protein 16 (IFI16) | 2 | M63838 | + | + | + | + | | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| interferon, gamma-inducible protein 30 (IFI30) | 9 | J03909 | + | + | | + | | + |
| INTERFERON-INDUCED GUANYLATE-BINDING PROTEIN 1 (GUANINE NUCLEOTIDE-BINDING PROTEIN 1) (non-exact 62%) | 1 | P32455 | | | | | | |
| interferon-induced protein 17 (IFI17) | 3 | X84958 | | + | + | + | | + |
| interferon-induced protein 54 (IFI54) | 5 | M14660 | | | | | | |
| interferon-inducible (1-8D) | 5 | X57351 | T | | + | + | + | |
| interferon-inducible (1-8U) | 1 | X57352 | | | + | + | + | |
| interferon-related developmental regulator 1 (IFRD1) | 5 | Y10313 | | + | + | | | + |
| interferon-stimulated transcription factor 3, gamma (48 kD) (ISGF3G) | 2 | M87503 | | + | | + | + | |
| interleukin 1 receptor, type II (IL1R2) | 1 | U64094 | | | | + | | |
| Interleukin 10 receptor, beta (I.10RB) | 1 | U08988 | T activated | | + | | + | |
| interleukin 12 receptor, beta 1 (IL12RB1) | 2 | U03187 | + | | | | | only found in T cell |
| interleukin 13 receptor, alpha 1 (IL13RA1) | 2 | Y09328 | | + | + | + | + | + |
| interleukin 16 (lymphocyte chemoattractant factor) (IL16) | 6 | U82972 | | + | | | | |
| interleukin 18 receptor 1 (IL18R1) | 1 | U43672 | | | | | | |
| interleukin 2 receptor, beta (IL2RB) | 9 | M26062 | | | | | | |
| interleukin 2 receptor, gamma (severe combined immunodeficiency) (IL2RG) | 6 | D11086 | + | | + | | + | |
| interleukin 4 receptor (IL4R) | 3 | X52425 | + | + | | + | | + |
| interleukin 6 receptor (IL6R) | 5 | X12830 | | + | | | | + |
| interleukin 6 signal transducer (gp130, oncostatin M receptor) (IL6ST) | 1 | M57230 | | | | | | |
| interleukin 7 receptor (IL7R) | 14 | M29696 | + | | | | + | |
| interleukin 7 receptor (IL7R) (low match) | 1 | AF043123 | | | | | | |
| interleukin 8 (IL8) | 8 | Y00787 | + | | + | | + | High in activated T cells, bone and pancreatic islets |
| interleukin 8 receptor alpha (IL8RA) | 11 | L19591 | | | | | | |
| interleukin 8 receptor, beta (IL8RB) | 14 | M94582 | | | | | | |
| interleukin enhancer binding factor 2, 45 kD (ILF2) | 3 | U10323 | + | + | + | + | + | + high in uterus |
| interleukin enhancer binding factor 3, 90 kD (ILF3) | 2 | U10324 | | | | | | |
| interleukin-1 receptor-associated kinase 1 (IRAK1) | 2 | L76191 | | + | + | + | + | |
| interleukin-1 receptor-associated kinase 1 (low match) | 1 | U52112 | | | | | | |
| interleukin-10 receptor, alpha (IL10RA) | 5 | U00672 | + | + | + | + | | |
| interleukin-11 receptor, alpha (IL11RA) | 7 | Z38102 | | + | + | | | |
| INTERLEUKIN-14 PRECURSOR (IL-14) (HIGH MOLECULAR WEIGHT B-CELL GROWTH FACTOR) (HMW-BCGF) (non-exact 46%) | 1 | P40222 | | | | | | |
| intestinal carboxylesterase; liver carboxylesterase-2 (ICE) | 1 | U60553 | | + | | | + | |

TABLE 2-continued

Comparison of 1,800 Unique Genes Identified in the Blood Cell cDNA Library to Genes
Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| inversin protein (non-exact 52%) | 1 | AF084367 | | | | | | |
| IQ motif containing GTPase activating protein 1 (IQGAP1) | 6 | L33075 | | | | | | |
| IQ motif containing GTPase activating protein 2 (IQGAP2) | 1 | U51903 | | + | | + | | |
| isocitrate dehydrogenase 1 (NADP+), soluble (IDH1) | 1 | AF020038 | + | + | + | + | + | + |
| isocitrate dehydrogenase 2 (NADP+), mitochondrial (IDH2) | 2 | X69433 | + | + | + | + | + | + |
| isocitrate dehydrogenase 3 (NAD+) alpha (IDH3A) | 2 | U07681 | | | | + | | |
| isocitrate dehydrogenase 3 (NAD+) gamma (IDH3G) | 1 | Z68907 | + | + | + | + | | + |
| isolate Aus3 cytochrome b (CYTB) | 1 | AF042516 | | | | | | |
| isolate TzCCR5-179 CCR5 receptor (CCR5) | 1 | AF011524 | | | | | | |
| isopentenyl-diphosphate delta isomerase (IDI1) | 5 | X17025 | + | + | + | + | | + |
| Janus kinase 1 (a protein tyrosine kinase) (JAK1) | 4 | M64174 | + | + | + | + | | + |
| Janus kinase 2 (a protein tyrosine kinase) (JAK2) | 1 | AF005216 | | | | | | |
| Jk-recombination signal binding protein (RBPJK) | 2 | L07876 | | | | | | |
| JM1 protein | 1 | AJ005890 | | + | | + | | |
| jumonji (mouse) homolog (JMJ) | 1 | U57592 | | + | + | + | | + |
| jun D proto-oncogene (JUND) | 1 | X51346 | + | + | + | + | | + |
| jun dimerization protein | 1 | AF111167 | | | | | | only found in germ |
| junction plakoglobin (JUP) | 1 | M23410 | | + | + | + | | + |
| kangai 1 (suppression of tumorigenicity 6, prostate; CD82 antigen (R2 leukocyte antigen, antigen detected by monoclonal and antibody IA4)) (KAI1) | 1 | U20770 | + | + | + | + | + | + |
| karyopherin (importin) beta 1 (KPNB1) | 2 | L39793 | + | + | + | + | + | + |
| karyopherin (importin) beta 2 (KPNB2) | 1 | U72395 | + | + | + | + | | |
| karyopherin alpha 1 (importin alpha 5) (KPNA1) | 1 | S75295 | + | + | + | | | + |
| karyopherin alpha 2 (RAG cohort 1, importin alpha 1) (DPNA2) | 1 | U09559 | | | | | | |
| karyopherin alpha 3 (importin alpha 4) (KPNA3) | 1 | D89618 | | + | | | + | |
| karyopherin alpha 4 (KPNA4) | 1 | M17887 | | + | + | | | |
| Katanin (80 kDa) (KAT) | 1 | AF052432 | | + | + | + | | + |
| KE03 protein | 2 | AF064604 | | | | | | |
| Kelch-like ECH-associated protein 1 (KIAA0132) (66% aa) | 1 | D50922 | | | | | | |
| Keratin 8 (KRT8) | 1 | X74929 | | + | + | + | + | |
| ketohexokinase (fructokinase) (KHK) | 1 | X78678 | + | | | + | + | |
| KIAA0001 (KIAA0001) (72% aa) | 1 | Q15391 | | | | | | |
| KIAA0001 (KIAA0001) (76% aa) | 1 | Q15391 | | | | | | |
| KIAA0001 (KIAA0001) (non-exact 72%) | 1 | Q15391 | | | | | | |
| KIAA0002 (KIAA0002) | 5 | D13627 | | + | + | + | | + |
| KIAA0005 (KIAA0005) | 4 | D13630 | | + | + | + | | + |
| KIAA0010 (KIAA0010) | 1 | D13635 | | + | | | | + |
| KIAA0016 (KIAA0016) | 1 | D13641 | + | + | + | + | | + |
| KIAA0017 (KIAA0017) | 2 | D87686 | | | | | | |
| KIAA0022 (KIAA0022) | 2 | D14664 | | + | + | + | | |
| KIAA0023 (KIAA0023) | 1 | D14689 | | + | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| KIAA0024 (KIAA0024) | 1 | D14694 | + | + | + | + | | + |
| KIAA0025 (KIAA0025) | 1 | D14695 | | + | + | + | + | + |
| KIAA0026 (KIAA0026) | 2 | D14812 | | + | + | + | | + |
| KIAA0027 | 1 | D25217 | | + | | | | |
| KIAA0032 (KIAA0032) | 2 | D25215 | | + | + | + | | |
| KIAA0040 (KIAA0040) | 1 | D25539 | + | + | + | + | | + |
| KIAA0050 (KIAA0050) | 4 | D26069 | | | | | | |
| KIAA0053 (KIAA0053) | 17 | D29642 | + | | + | + | | |
| KIAA0057 (KIAA0057) | 1 | D31762 | + | + | + | + | + | + | high in fetal lung |
| KIAA0058 (KIAA0058) | 11 | D31767 | + | + | + | + | | + |
| KIAA0063 (KIAA0063) | 3 | D31884 | + | + | + | + | | + |
| KIAA0064 (KIAA0064) | 1 | D31764 | + | + | + | + | | + |
| KIAA0066 | 1 | D31886 | + | + | + | + | | + |
| KIAA0068 | 1 | D38549 | | + | + | + | + | |
| KIAA0073 | 3 | D38552 | | + | + | | | + |
| KIAA0081 | 2 | D42039 | | + | | + | | + |
| KIAA0084 | 2 | D42043 | + | + | + | + | | + |
| KIAA0085 | 26 | U30498 | + | + | + | + | + | + |
| KIAA0088 | 3 | D42041 | + | + | + | + | + | + |
| KIAA0090 | 2 | D42044 | + | + | + | + | + | + |
| KIAA0092 (KIAA0092) | 1 | D42054 | | + | + | + | | + |
| KIAA0094 | 3 | D42084 | | | + | + | | |
| KIAA0095 (KIAA0095) | 1 | D42085 | | | | | | |
| KIAA0096 | 1 | D43636 | + | + | + | + | | + |
| KIAA0097 (KIAA0097) | 1 | X92474 | T | + | + | | + | |
| KIAA0099 (KIAA0099) | 3 | D43951 | + | + | + | + | + | + |
| KIAA0102 (KIAA0102) | 2 | D14658 | | + | | + | + | + |
| KIAA0105 | 1 | D14661 | B | + | | | + | + |
| KIAA0120 | 2 | P37802 | | | | | | |
| KIAA0120 (non-exact, 65%) | 1 | M83106 | | | | | | |
| KIAA0121 (KIAA0121) | 1 | D50911 | + | | + | + | + | + |
| KIAA0123 | 1 | D21064 | | + | + | + | | + |
| KIAA0128 | 1 | D50918 | + | + | + | + | | + |
| KIAA0129 (KIAA0129) | 1 | D50919 | + | + | + | + | | |
| KIAA0130 (KIAA0130) | 1 | AF055995 | | + | + | + | | |
| KIAA0136 | 2 | D50926 | | | | | | |
| KIAA0137 (KIAA0137) | 1 | AB004885 | | + | + | + | | + |
| KIAA0140 (KIAA0140) | 1 | D50930 | + | + | | + | | + |
| KIAA0141 | 3 | D50931 | | | | | | |
| KIAA0144 (KIAA0144) | 3 | D63478 | + | + | + | + | | + |
| KIAA0144 (KIAA0144) (low match) | 1 | D63478 | | | | | | |
| KIAA0144 (non-exact 61%) | 1 | Q14157 | | | | | | |
| KIAA0144 (non-exact 65%) | 1 | Q14157 | | | | | | |
| KIAA0146 | 2 | D63480 | | + | + | + | | + |
| KIAA0148 (KIAA0148) | 1 | D63482 | | + | | | | + |
| KIAA0154 | 2 | D63876 | + | + | + | + | | + |
| KIAA0156 | 1 | D63879 | | + | + | + | | + |
| KIAA0160 | 2 | D63881 | | | | | | |
| KIAA0161 (KIAA0161) | 1 | D79983 | + | + | | + | | |
| KIAA0164 (KIAA0164) | 3 | D79986 | | | | | | |
| KIAA0167 (KIAA0167) | 1 | D79989 | | + | | | | |
| KIAA0168 (KIAA0168) | 3 | D79990 | | + | + | + | | + |
| KIAA0169 | 3 | D79991 | | | | | | |
| KIAA0171 (KIAA0171) | 3 | D79993 | | + | + | + | | + |
| KIAA0174 (KIAA0174) | 7 | D79996 | + | + | + | + | | + |
| KIAA0179 | 2 | D80001 | | + | + | + | | + |
| KIAA0181 | 1 | D80003 | | + | + | + | | + |
| KIAA0183 | 4 | D80005 | + | + | + | + | + | + |
| KIAA0184 | 1 | D80006 | + | + | + | + | | + |
| KIAA0191 (72% aa) | 1 | D83776 | | | | | | |
| KIAA0191 (non-exact 77%) | 1 | | | | | | | |
| KIAA0193 (KIAA0193) | 1 | D83777 | + | + | + | + | | + |
| KIAA0200 (KIAA0200) | 1 | D83785 | + | + | + | + | | |
| KIAA0210 (KIAA0210) | 3 | D86965 | | | | | | |
| KIAA0217 | 2 | D86971 | + | + | + | + | | + |
| KIAA0219 | 2 | U77700 | + | + | + | + | | |
| KIAA0222 (KIAA0222) | 1 | D86975 | | | | | | |
| KIAA0223 | 2 | D86976 | | | | | | |
| KIAA0229 | 1 | D86982 | + | + | | | | |
| KIAA0232 (KIAA0232) | 1 | D86985 | | + | + | + | | + |
| KIAA0233 (KIAA0233) | 1 | D87071 | | | | | | |
| KIAA0235 | 2 | D87078 | + | + | + | + | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| KIAA0239 | 1 | D87076 | + | + | | | | |
| KIAA0239 (non-exact 80%) | 1 | D87076 | | | | | | |
| KIAA0240 | 1 | D87077 | | | | | | |
| KIAA0242 | 4 | D87684 | + | + | + | + | + | + |
| KIAA0248 | 2 | D87435 | | + | + | + | | + |
| KIAA0249 (KIAA0249) | 3 | D87436 | + | + | + | + | | + |
| KIAA0253 | 5 | D87442 | + | + | + | + | + | + |
| KIAA0254 (KIAA0254) | 1 | D87443 | | + | + | + | | |
| KIAA0255(KIAA0255) | 4 | D87444 | | + | + | + | | + |
| KIAA0262 (KIAA0262) | 3 | D87451 | + | + | + | + | | + |
| KIAA0263 (KIAA0263) | 1 | D87452 | + | + | + | + | | + |
| KIAA0264 | 3 | D87453 | + | + | + | | | + |
| KIAA0268 | 1 | D87742 | + | + | | + | | + |
| KIAA0269 | 1 | Q92558 | | | | | | |
| KIAA0275 (KIAA0275) | 13 | D87465 | + | + | | + | | + |
| KIAA0304 (KIAA0304) | 2 | AB002302 | + | + | + | + | + | + |
| KIAA0308 | 2 | AB002306 | | + | + | | | + |
| KIAA0310 (KIAA0310) | 1 | AB002308 | + | + | + | | | + |
| KIAA0314 (=U96635 M. musculus ubiquitin protein ligase Nedd-4) | 3 | AB002312 | | | | | | |
| KIAA0315 (KIAA0315) | 4 | AB002313 | | + | + | + | + | + |
| KIAA0325 (=L08505 R. norvegicus cytoplasmic dynein heavy chain (MAP1C)) | 2 | AB002323 | | | | | | |
| KIAA0329 (KIAA0329) | 1 | AB002327 | | + | + | + | | + |
| KIAA0330 | 1 | AB002328 | + | + | + | | | + |
| KIAA0332 | 1 | AB002330 | | + | + | + | | + |
| KIAA0333 | 2 | AB002331 | | + | + | + | + | + |
| KIAA0336 (KIAA0336) | 3 | AB002334 | + | + | + | + | | + |
| KIAA0336 (KIAA0336) (low match) | 1 | AB002334 | | | | | | |
| KIAA0342 (KIAA0342) | 1 | AB002340 | | + | + | | | + |
| KIAA0344 (KIAA0344) | 2 | AB002342 | | | | + | | + |
| KIAA0354 (KIAA0354) | 1 | AB002352 | + | + | + | + | | + |
| KIAA0365 (KIAA0365) | 3 | AB002363 | + | + | + | + | + | + |
| KIAA0370 | 6 | AB002368 | | + | + | + | + | + |
| KIAA0372 (KIAA0372) | 1 | AB002370 | | | | | | |
| KIAA0373 (KIAA0373) | 1 | AB002371 | | + | | + | | |
| KIAA0375 (KIAA0375) | 1 | AB002373 | | + | | + | | |
| KIAA0377 (KIAA0377) | 1 | AB002375 | | + | | + | + | |
| KIAA0379 | 1 | AB002377 | | | | + | | |
| KIAA0379 (non-exact, 65%) | 1 | AB002377 | | | | | | |
| KIAA0380 (KIAA0380) | 1 | AB002378 | + | + | | + | | + |
| KIAA0380 (KIAA0380) (60% aa) | 1 | AB002378 | | | | | | |
| KIAA0382 (KIAA0382) | 2 | AB002380 | | + | + | + | | + |
| KIAA0383 | 1 | AB002381 | | | | | | |
| KIAA0386 (KIAA0386) | 5 | AB002384 | | | | | | |
| KIAA0392 | 1 | AB002390 | | | | | | |
| KIAA0397 (KIAA0397) | 4 | AB007857 | | + | + | + | + | + |
| KIAA0403 | 3 | AB007863 | | | | | | |
| KIAA0404 | 1 | AB007864 | | + | | + | | |
| KIAA0409 | 1 | AB007869 | | + | | + | | |
| KIAA0421 | 1 | AB007881 | + | + | + | | | + |
| KIAA0424 (non-exact 82%) | 1 | AB007884 | | | | | | |
| KIAA0428 (KIAA0428) | 9 | Y13829 | | | | | | |
| KIAA0429 (KIAA0429) | 2 | AB007889 | + | + | + | + | | + |
| KIAA0430 (KIAA0430) | 2 | AB007890 | | | | | | only in ovary |
| KIAA0432 (KIAA0432) | 2 | U86753 | T | + | + | | | |
| KIAA0435 (KIAA0435) | 1 | AB007895 | | | | | | |
| KIAA0438 (KIAA0438) | 1 | AB007898 | | + | + | + | | + |
| KIAA0447 (KIAA0447) | 3 | AB007916 | + | + | + | + | | + |
| KIAA0449 | 1 | AB007918 | | + | | | | + |
| KIAA0456 | 1 | AB007925 | | + | + | + | | |
| KIAA0458 (KIAA0458) | 1 | AB007927 | | | | | | |
| KIAA0462 | 1 | AB007931 | + | + | + | + | | + |
| KIAA0465 | 1 | AB007934 | | + | + | + | + | + |
| KIAA0476 (KIAA0476) | 1 | AB007945 | | + | + | | | |
| KIAA0489 | 1 | AB007958 | | | | | | |
| KIAA0494 (KIAA0494) | 1 | AB007963 | + | + | + | + | | + |
| KIAA0515 | 1 | AB011087 | + | + | + | + | | + |
| KIAA0521 | 3 | AB011093 | + | + | | | | + |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| KIAA0525 | 1 | AB011097 | | + | | + | | |
| KIAA0530 | 1 | AB011102 | | + | + | | | |
| KIAA0532 | 1 | AB011104 | + | + | + | + | | + |
| KIAA0537 (KIAA0537) | 1 | AB011109 | | | | | | |
| KIAA0540 | 1 | AB011112 | + | + | + | + | | + |
| KIAA0543 | 1 | AB011115 | | | + | + | | + |
| KIAA0544 | 1 | AB011116 | | + | + | + | | + |
| KIAA0549 | 2 | AB011121 | | + | + | + | | + |
| KIAA0551 | 2 | AB011123 | | + | | | | + |
| KIAA0554 | 8 | AB011126 | | + | + | + | | + |
| KIAA0561 | 1 | AB011133 | | + | | + | | |
| KIAA0562 (KIAA0562) | 1 | AB011134 | | | | | | |
| KIAA0563 (KIAA0563) | 1 | AB011135 | | | | | | |
| KIAA0569 (KIAA0569) | 2 | AB011141 | | + | + | + | | + |
| KIAA0571 (KIAA0571) | 2 | AB011143 | | + | + | + | | |
| KIAA0573 | 1 | AB011145 | | + | | + | | + |
| KIAA0576 | 1 | AB011148 | | | | | | |
| KIAA0580 | 1 | AB011152 | | | | | | |
| KIAA0584 | 1 | AB011156 | | + | | | | |
| KIAA0592 | 3 | AB011164 | + | + | + | + | | + |
| KIAA0596 | 1 | AB011168 | | + | + | | | |
| KIAA0598 (KIAA0598) | 1 | AB011170 | | + | + | + | | |
| KIAA0608 | 1 | AB011180 | | | + | + | | |
| KIAA0614 | 2 | AB014514 | + | + | + | + | | + |
| KIAA0615 (KIAA0615) | 1 | AB014515 | | | | | | |
| KIAA0621 | 1 | AB014521 | | + | + | | | + |
| KIAA0648 | 1 | AB014548 | | + | + | + | | + |
| KIAA0652 (KIAA0652) | 1 | AB014552 | + | + | + | + | | + |
| KIAA0668 | 1 | AB014568 | | | | | | |
| KIAA0669 | 1 | AB014569 | | | | | | |
| KIAA0671 (KIAA0671) | 1 | AB014571 | | | + | + | | + |
| KIAA0675 (KIAA0675) | 1 | AB014575 | | + | | + | + | |
| KIAA0676 | 1 | AB014576 | | + | + | + | | + |
| KIAA0677 (KIAA0677) | 2 | AB014577 | | + | + | + | + | + |
| KIAA0678 | 1 | AB014578 | + | + | + | + | | + |
| KIAA0679 | 6 | AB014579 | | + | + | + | | + |
| KIAA0680 (KIAA0680) | 1 | AB014580 | | | | | | |
| KIAA0692 | 1 | AB014592 | + | + | + | + | | + |
| KIAA0697 | 1 | AB014597 | | | | | | |
| KIAA0699 | 1 | AB014599 | + | + | + | + | | + |
| KIAA0700 | 1 | AB014600 | | + | + | + | | + |
| KIAA0737 (KIAA0737) | 3 | AF014837 | + | + | + | + | | + |
| KIAA0748 (KIAA0748) | 2 | AB018291 | | + | | | | |
| KIAA0763 (KIAA0763) | 2 | AB018306 | + | + | + | + | | + |
| KIAA0769 (KIAA0769) | 2 | AB018312 | | + | + | + | | + |
| KIAA0782 | 1 | AB018325 | + | + | | + | | high in BPH stroma |
| KIAA0796 | 1 | AB018339 | | + | + | + | | + |
| KIAA0798 (KIAA0798) | 1 | AB018341 | | | | | | |
| KIAA0823 | 1 | AB020630 | | | | | | |
| KIAA0854 | 1 | AB020661 | + | + | + | + | | + |
| KIAA0856 | 1 | AB020663 | | + | + | + | | + |
| KIAA0860 | 1 | AB020667 | | + | | + | | |
| KIAA0862 | 1 | AF054828 | + | + | + | | | |
| KIAA0871 (non-exact 88%) | 1 | AB020678 | | | | | | |
| KIAA0873 | 1 | AB020680 | | + | + | + | | + |
| KIAA0892 | 1 | AB020699 | | + | + | + | | + |
| KIAA0906 | 1 | AB020713 | + | + | + | + | | + |
| KIAA0991 | 1 | AB023208.1 | | | | | | |
| killer cell lectin-like receptor subfamily B, member 1 (KLRB1) | 1 | U11276 | | | + | + | | + |
| killer cell lectin-like receptor subfamily C, member 4 (KLRC4) | 1 | U96846 | | | | | | |
| kinectin 1 (kinesin receptor) (KTN1) | 1 | D13629 | | | | | | |
| kinesin family member 5B (KIF5B) | 2 | X65873 | | + | + | + | | |
| kinesin-like DNA binding protein | 1 | AB017430 | + | + | + | + | | + |
| Krueppel-related DNA-binding protein (TF6) (low match) | 1 | M61869 | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| Kruppel related gene (clone pHKR1RS) | 1 | M20675 | | | | | | | |
| Kruppel-like zinc finger protein Zf9 | 3 | U51869 | + | + | + | + | + | + | |
| Kruppel-like zinc finger protein Zf9 (non-exact 76%) | 1 | U44975 | + | + | | + | + | | |
| kruppel-type zinc finger protein, ZK1 | 1 | AB011414.1 | | | | | | | |
| L apoferritin | 3 | X03742 | | | | | | | |
| lactate dehydrogenase A (LDHA) | 3 | X02152 | + | + | + | + | + | | |
| lactate dehydrogenase A (LDHA) (non-exact, 81%) | 1 | X02152 | | | | | | | |
| lactate dehydrogenase B (LDHB) | 6 | X13794 | + | + | + | + | + | + | high in fetal lung fibrablast |
| lactotransferrin (LTF) | 1 | U07643 | + | | | + | | + | high in bone marrow |
| laminin binding protein (low score) | 1 | D28372 | | | | | | | |
| laminin receptor 1 (67 kD); Ribosomal protein SA (LAMR1) | 20 | X15005 | + | + | + | + | + | + | high in many libraries |
| laminin receptor homolog {3' region} | 1 | S35960 | | | | | | | |
| laminin, gamma 1 (formerly LAMB2) (LAMC1) | 2 | J03202 | + | + | + | | + | | |
| latent transforming growth factor beta binding protein 1 (LTBP1) | 2 | M34057 | + | + | + | | + | | |
| LAZ3/BCL6 (=Z79582; D28522/4) | 1 | Z79581 | | | | | | | |
| LDLC | 2 | Z34975 | + | + | + | + | + | | |
| lecithin-cholesterol acyltransferase (LCAT) (non-exact, 66%) | 1 | M17959 | | | | | | | |
| lectin, galactoside-binding, soluble, 2 (galectin 2) (LGALS2) | 1 | M87842 | | | | + | | | |
| lectin, galactoside-binding, soluble, 3 binding protein (galectin 6 binding protein) (LGALS3BP) | 1 | L13210 | + | + | + | + | | + | |
| leucine rich repeat (in FLII) interacting protein 1 (LRRFIP1) | 5 | AJ223075 | + | + | + | + | + | + | |
| leucocyte immunoglobulin-like receptor-5 (LIR-5) | 2 | AF072099 | | | | + | | | |
| leucocyte immunoglobulin-like receptor-6a (LIR-6) | 7 | AF025530 | | | | | | | |
| leucocyte immunoglobulin-like receptor-7 (LIR-7) | 2 | U82275 | | + | | | | | only found in CNS |
| leukemia virus receptor 1 (GLVR1) | 1 | L20859 | + | + | + | + | + | | |
| leukocyte adhesion protein p150,95 alpha subunit | 1 | M29484 | | | | | | | |
| leukocyte antigen, HLA-A2 | 3 | Y13267 | | | | | | | |
| leukocyte immunoglobulin-like receptor (MIR-10) | 3 | AF025528 | | + | | | | | |
| leukocyte tyrosine kinase (LTK) | 1 | X60702 | + | | | | | | found only in blood |
| leukocyte-associated Ig-like receptor 1 (LIAR1) | 3 | AF013249 | | | | + | | | |
| leukotriene A4 hydrolase (LTA4H) | 6 | J03459 | + | + | + | + | + | + | |
| leupaxin (LDPL) | 2 | AF062075 | + | | | + | | + | |
| ligase I, DNA, ATP-dependent (LIG1) | 1 | M36067 | B, T | + | + | | + | + | |
| LIM and SH3 protein 1 (LASP1) | 2 | X82456 | + | + | + | + | + | + | |
| LIM domain kinase 2 (LIMK2) | 2 | AC002073 | + | + | + | | + | | |
| line-1 protein | 1 | | | | | | | | |
| Line-1 repeat mRNA with 2 open reading frames | 1 | U93566 | + | + | + | + | + | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| Line-1 repeat with 2 open reading frames | 1 | M22332 | + | + | + | + | + | + | high in gastric tumor |
| LINE-1 REVERSE TRANSCRIPTASE HOMOLOG | 1 | P08547 | | | | | | | |
| lipase A, lysosomal acid, cholesterol esterase (Wolman disease) (LIPA) | 4 | X76488 | + | + | + | + | | + | |
| lipase, hormone-sensitive (LIPE) | 1 | L11706 | + | + | | | | + | |
| LMP7 | 1 | L11045 | | | | | | | |
| Lon protease-like protein (LONP) | 2 | X74215 | + | + | + | + | | + | |
| low density lipoprotein-related protein 1 (alpha-2-macroglobulin receptor) (LRP1) | 2 | AF058414 | | | | | + | | only in liver |
| low density lipoprotein-related protein-associated protein 1 (alpha-2-macroglobulin receptor-associated protein 1) (LRPAP1) | 1 | M63959 | | + | + | | + | + | |
| low density lipoprotein-related protein-associated protein 1 (alpha-2-macroglobulin receptor-associated protein 1) (LRPAP1) (non-exact, 75%) | 1 | M63959 | | | | | | | |
| low-affinity Fc-gamma receptor IIA | 1 | L08107 | | | | | | | |
| LPS-induced TNF-alpha factor (PIG7) | 9 | AF010312 | + | + | + | + | + | + | |
| Lst-1 | 1 | U00921 | + | + | + | + | | + | |
| L-type amino acid transporter subunit LAT1 | 1 | AF104032 | | | | | | | |
| lung resistance-related protein (LRP) | 1 | X79882 | + | + | + | + | | + | |
| Lymphocyte antigen 75 (LY75) | 1 | AF011333 | B | | | | | | |
| lymphocyte antigen 9 (LY9) | 2 | L42621 | | | | | | | |
| lymphocyte antigen HLA-B*4402 and HLA-B*5101 | 2 | L42345 | | | | | | | |
| lymphocyte cytosolic protein 1 (L-plastin) (LCP1) | 42 | J02923 | | | | | | | |
| lymphocyte cytosolic protein 2 (SH2 domain-containing leukocyte protein of 76 kD) (LCP2) | 4 | U20158 | T lymphoma, T activated | | | | | | |
| lymphocyte glycoprotein T1/Leu-1 | 2 | X04391 | + | | | + | | | |
| lymphocyte-specific protein 1 (LSP1) | 16 | M33552 | + | + | + | + | | + | |
| lymphocyte-specific protein tyrosine kinase (LCK) | 7 | M36881 | | + | | | | + | |
| lymphoid phosphatase LyP1 | 1 | AF001847 | | | | | | | |
| lymphoid-restricted membrane protein (LRMP) | 4 | U10485 | + | | + | + | | | |
| lymphoid-specific SP100 homolog (LYSP100-A) | 1 | U36500 | | | | | | + | |
| lymphoma proprotein convertase (LPC) | 2 | U33849 | + | + | + | + | | + | |
| LYSOSOMAL PROTECTIVE PROTEIN PRECURSOR (CATHEPSIN A) (CARBOXYPEPTIDASE C) | 1 | P10619 | | | | | | | |
| lysosomal-associated membrane protein 1 (LAMP1) | 1 | J04182 | + | + | + | + | + | + | |
| Lysosomal-associated membrane protein 2 (LAMP2) | 1 | J04183 | | + | + | + | + | + | |
| lysozyme (renal amyloidosis) (LYZ) | 39 | M19045 | + | + | + | + | | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| lysyl-tRNA synthetase (KARS) | 2 | D32053 | + | + | + | + | | + | |
| M phase phosphoprotein 10 (U3 small nucleolar ribonucleoprotein) (MPP-10) | 1 | X98494 | | | | | | | |
| M1-type and M2-type pyruvate kinase | 2 | X56494 | | | | | | | |
| m6A methyltransferase (MT-A70) | 7 | AF014837 | + | + | | + | | | |
| mab-21 (*C. elegans*)-like 1 (MAB21L1) | 1 | U38810 | | + | + | + | | + | |
| MacMarcks | 1 | X70326 | + | + | + | + | + | + | |
| macrophage-associated antigen (MM130) | 1 | Z22968 | | + | + | + | | + | |
| MADS box transcription enhancer factor 2, polypeptide A (myocyte enhancer factor 2A) (MEF2A) | 1 | U49020 | | + | + | + | | + | |
| MADS box transcription enhancer factor 2, polypeptide C (myocyte enhancer factor 2C) (MEF2C) | 1 | L08895 | | + | + | + | | + | |
| major cytoplasmic tRNA-Val(IAC) (=M33940) | 1 | X17516 | | | | | | | |
| major histocompatibility complex class I beta chain (HLA-B) | 1 | M95531 | | | | | | | |
| major histocompatibility complex, class I, A (HLA-A) | 41 | Z93949 | + | + | + | + | | + | high in villous adenoma |
| major histocompatibility complex, class I, A (HLA-A) (low match) | 1 | Z72422 | | | | | | | |
| major histocompatibility complex, class I, C (HAL-C) | 82 | M24097 | + | + | + | + | + | + | |
| major histocompatibility complex, class I, E (HLA-E) | 77 | M20022 | + | + | + | + | | + | |
| major histocompatibility complex, class II, DM BETA (HLA-DMB) | 2 | U15085 | + | + | + | + | | + | |
| major histocompatibility complex, class II, DP beta 1 (HLA-DPB1) | 10 | M57466 | + | + | + | + | | + | |
| major histocompatibility complex, class II, DR beta 1 (HLA-DRB1) | 9 | V00522 | + | + | + | + | | + | |
| Major histocompatibility complex, class II, Y box-binding protein I; DNA-binding protein B (YB1) | 2 | M24070 | | + | + | | + | + | |
| malate dehydrogenase 1, NAD (soluble) (mdh1) | 1 | D55654 | + | + | + | + | + | + | |
| malate dehydrogenase 1, NAD (soluble) (MDH1) | 3 | D55654 | | + | + | | + | + | |
| malonyl-CoA decarboxylase precursor | 2 | AF097832 | | | | | | | |
| maltase-glucoamylase (mg) | 1 | AF016833 | | | | + | | | |
| manic fringe (*Drosophila*) homolog (MFNG) | 1 | U94352 | + | + | + | + | | + | |
| mannose phosphate isomerase (MPI) | 1 | X76057 | | + | + | + | | + | |
| mannose phosphate isomerase (mpi) | 2 | X76057 | | + | + | + | | | |
| mannose-6-phosphate receptor (cation dependent) (M6PR) | 3 | X56253 | | + | + | | + | + | |
| mannose-P-dolichol utilitzation defect 1 (MPDU1) | 1 | AF038961 | | + | + | + | | + | |
| mannosidase, alpha B, lysosomal (MANB) | 1 | U60885 | | + | | + | | + | |
| mannosyl (alpha-1,3-)-glycoprotein beta-1,2-N-acetylglucosaminyltransferase (MGAT1) | 1 | M55621 | + | + | + | + | + | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| map 4q35 repeat region | 1 | AF064849 | | | | | | |
| MAP kinase-interacting serine/threonine kinase 1 (MKNK1) | 2 | AB000409 | | + | + | + | + | + |
| MAP/ERK kinase kinase 3 (MEKK3) | 5 | U78876 | | + | | | | |
| MAP/ERK kinase kinase 5 (MEKK5) | 1 | D84476 | | + | + | | + | |
| MAP/microtubule affinity-regulating kinase 3 (MARK3) | 4 | M80359 | | + | + | | | + |
| Marenostrin protein | 1 | Y14441 | | | | | | |
| MASL1 | 1 | AB016816 | | | | | | |
| MAX dimerization protein (MAD) | 3 | L06895 | | | | | | + |
| MaxiK potassium channel beta subunit | 1 | AF035046 | | | | | | |
| MBP-2 for MHC binding protein 2 | 1 | X65644 | | + | + | + | | + |
| Meis (mouse) homolog 3 (MEIS3) | 1 | U68385 | | + | + | + | | + |
| melanoma-associated antigen p97 (melanotransferrin) | 1 | M12154 | | | | | | |
| membrane cofactor protein (CD46, trophoblast-lymphocyte cross-reactive antigen) (MCP) | 4 | X59405 | | + | + | + | | + |
| membrane component, chromosome 17, surface marker 2 (ovarian carcinoma antigen CA125) (M17S2) | 4 | D14696 | | + | + | + | + | |
| membrane metallo-endopeptidase (neutral endopeptidase, enkephalinase, CALLA, CD10) (MME) | 2 | J03779 | B | | + | + | + | + |
| membrane protein, palmitoylated 1 (55 kD) (MPP1) | 2 | M64925 | | + | + | + | + | + |
| meningioma expressed antigen (MGEA) | 1 | U94780 | | | | + | | |
| meningioma-expressed antigen 11 (MEA11) | 1 | U73682 | + | + | | + | + | |
| Menkes Disease (ATP7A) putative Cu++-transporting P-type ATPase | 1 | L06133 | | + | | | | |
| metallothionein 2A (MT2A) | 1 | V00594 | | + | + | + | + | + |
| metaxin 1 (MTX1) | 1 | U46920 | | + | | + | | + |
| methionine adenosyltransferase II, alpha (MAT2A) | 2 | X68836 | + | + | + | + | | + |
| methyl-CpG binding domain protein 1 (MBD1) (non-exact 59% aa) | 1 | Y10746 | | | | | | |
| methylene tetrahydrofolate dehydrogenase (NAD+ dependent), methenyltetrahydrofolate cyclohydrolase (MTHFD2) | 2 | X16396 | + | | + | + | + | |
| methylenetetrahydrofolate dehydrogenase (NADP+ dependent), methenyltetrahydrofolate cyclohydrolase, formyltetrahydrofolate synthetase (MTHFD1) | 1 | J04031 | | + | + | + | + | + |
| methyltransferase, putative | 2 | AJ224442 | | | | | | |
| MHC antigen (HLA-B) (=L42024) | 1 | U14943 | | | | | | |
| MHC class 1 region | 2 | AF055066 | | | | | | |
| MHC class I antigen (HLA-A2) | 1 | U70863 | | | | | | |
| MHC class I antigen (HLA-A33) | 1 | U19736 | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| MHC class I antigen (HLA-C) | 1 | U38975 | | | | | | |
| MHC class I antigen B*5801 (HLA-B) | 1 | U52813 | | | | | | |
| MHC class I antigen HLA-A (HLA-A) | 2 | AF015930 | | | | | | |
| MHC class I antigen HLA-A (HLA-A-2402 allele) | 1 | U36687 | | | | | | |
| MHC class I antigen HLA-A11K | 2 | X13112 | | | | | | |
| MHC class I antigen HLA-B (B*0801 variant) (=AF028596) | 1 | U67331 | | | | | | |
| MHC class I antigen HLA-B (B*0801 variant) (=U88254) | 1 | U67330 | | | | | | |
| MHC class I antigen HLA-B (B*48 allele) | 1 | AF017328 | | | | | | |
| MHC class I antigen HLA-B (HLA-B*1502 allele) | 1 | AF014770 | | | | | | |
| MHC class I antigen HLA-B (HLA-B*40MD) | 1 | U58643 | | | | | | |
| MHC class I antigen HLA-B (HLA-B*4103 allele) | 1 | AF028596 | | | | | | |
| MHC class I antigen HLA-B gene (HLA-B*4402 variant allele) | 1 | AF035648 | | | | | | |
| MHC class I antigen HLA-B GN00110-B*3910 | 1 | U52175 | | | | | | |
| MHC class I antigen HLA-Cw*04011 | 1 | D83030 | | | | | | |
| MHC class I antigen R69772 HLA-A (A*0302) | 1 | U56434 | | | | | | |
| MHC class I antigen SHCHA (HLA-B*4403 variant) | 1 | U58469 | | | | | | |
| MHC class I histocompatibility antigen (HLA-B) (clone C21/14) | 1 | U06697 | | | | | | |
| MHC class I HLA B71 | 2 | L07950 | | | | | | |
| MHC class I HLA-A (Aw33.1) | 1 | Flp | | | | | | |
| MHC class I HLA-B | 1 | U18660 | | | | | | |
| MHC class I HLA-B (HLA-B-07ZEL allele) (=X86704) | 1 | U18661 | | | | | | |
| MHC class I HLA-B (HLA-B-08NR allele) | 1 | U28759 | | | | | | |
| MHC class I HLA-B*3512 | 1 | L76094 | | | | | | |
| MHC class I HLA-B41 variant (=U17572) | 3 | U17572 | | | | | | |
| MHC class I HLA-B44.2 chain | 1 | M24038 | | | | | | |
| MHC class I HLA-B51-cd3.3 | 1 | L41086 | | | | | | |
| MHC class I HLA-C allele | 2 | Z33459 | | | | | | |
| MHC class I HLA-Cw*0304 (=M84172; M99389) | 1 | D64150 | | | | | | |
| MHC class I HLA-Cw*0803 | 3 | Z15144 | | | | | | |
| MHC class I HLA-Cw6 | 1 | M28206 | | | | | | |
| MHC class I HLA-J antigen | 1 | L56139 | | | | | | |
| MHC class I lymphocyte antigen A2 (A2.1) variant DK1 | 1 | M19670 | | | | | | |
| MHC class I mic-B antigen | 1 | X91625 | | | | | | |
| MHC class I polypeptide-related sequence A (MICA) | 1 | L14848 | | | | | + | |
| MHC class I protein HLA-C heavy chain (C*0701new allele) (=AF017331) | 1 | U61274 | | | | | | |
| MHC class II DNA Sequence (clone A37G7-1C11) | 1 | L18885 | | | | | | |
| MHC class II DQ-alpha associated with DRw6, DQw1 protein | 1 | M16995 | + | | | + | + | + |
| MHC class II DQ-beta associated with DR2, DQw1 protein | 2 | M17564 | | | + | | + | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| MHC class II HAL-DQ-LTR5 (DQ, w8) DNA fragment, long terminal repeat region | 1 | M33842 | | | | | | |
| MHC class II hla-dr alpha-chain (=J00197; M60334; K011171; J00194; M60333; X00274) | 1 | J00195 | | | | | | |
| MHC class II HLA-DRB1 | 1 | AF007883 | | | | | | |
| MHC class II HLA-DRw11-beta-I chain (DRw11.3) | 1 | M21966 | | | | | | |
| MHC class II lymphocyte antigen (DPw4-beta-1) | 1 | M23907 | | | | | | |
| MHC CLASS II TRANSACTIVATOR CIITA (non-exact 57%) | 1 | P33076 | | | | | | |
| MHC HLA-E2.1 (=X87679) | 1 | M32507 | | | | | | |
| MHC HLA-E2.1 (alpha-2 domain) (low match) | 1 | M32507 | | | | | | |
| Mi-2 autoantigen 240 kDa protein (non-exact 84%) | 1 | U08379 | | | | | | |
| microsomal stress 70 protein ATPase core (stch) | 1 | U04735 | | | | | | |
| microtubule-associated protein 4 (MAP4) | 1 | U19727 | + | | + | + | + | |
| microtubule-associated protein 7 (MAP7) | 1 | X73882 | | | | | | |
| mineralocorticoid receptor (aldosterone receptor) (MLR) | 2 | M16801 | | + | | + | + | |
| minichromosome maintenance deficient (*S. cerevisiae*) 3 (MCM31) | 1 | X62153 | | + | + | + | + | |
| minichromosome maintenance deficient (*S. cerevisiae*) 3-associated protein (MCM3AP) | 1 | AB011144 | | + | + | + | + | |
| minichromosome maintenance deficient (*S. cerevisiae*) 5 (cell division cycle 46) (MCM5) | 2 | X74795 | + | | + | + | + | + |
| mitochondiral cytochrome b (CYTB) | 1 | AF042517 | | | | | | |
| mitochondrial 16S rRNA | 11 | Z70759 | | | | | | |
| mitochondrial ATP synthase (F1-ATPase) alpha subunit | 2 | X59066 | | | | | | |
| mitochondrial ATP synthase c subunit (P1 form) | 1 | X69907 | | | | | | |
| mitochondrial cytochrome b (CYTB) | 6 | AF042508 | | | | | | |
| mitochondrial cytochrome b small subunit of complex II | 1 | AB006202 | | | | | | |
| mitochondrial CYTOCHROME C OXIDASE POLYPEPTIDE I | 1 | P00395 | | | | | | |
| mitochondrial CYTOCHROME C OXIDASE POLYPEPTIDE II | 1 | P00403 | | | | | | |
| mitochondrial cytochrome C oxidase subunit II | 2 | P00403 | | | | | | |
| mitochondrial cytochrome oxidase subunit II (COII) (=U12692 Hsa4 mitochondrion cytochrome oxidase subunit II) | 5 | U12691 | | | | | | |
| mitochondrial DNA loop attachment sequences (clone LAS34) | 1 | X89763 | | | | | | |
| mitochondrial DNA polymerase accessory subunit precursor (MtPolB) nuclear gene encoding mitochondrial protein, | 1 | U94703 | | + | | | | |
| mitochondrial DNA, complete genome | 1 | X93334 | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| mitochondrial genes for several tRNAs (Phe, Val, Leu) and 12S and 16S ribosomal RNAs. | 8 | V00710 | | | | | | |
| mitochondrial genes for tRNA (Phe) and 12S rRNA (fragment) | 3 | V00660 | | | | | | |
| mitochondrial inner membrane preprotein translocase Tim17a | 1 | AF106622 | | | | | | |
| mitochondrial isolate Afr7 cytochrome b(CYTB) | 1 | AF042503 | | | | | | |
| mitochondrial loop attachment sequence (clone LAS88) | 1 | X89843 | | | | | | |
| mitochondrial NADH dehydrogenase subunit 2 (ND2) | 14 | AF014893 | | | | | | |
| mitochondrial translational initiation factor 2 (MTIF2) | 1 | L34600 | | + | + | + | | + |
| mitochondrion cytochrome b | 1 | U09500 | | | | | | |
| mitogen inducible gene mig-2 | 1 | Z24725 | | + | + | + | | + |
| mitogen inducible gene mig-2 (non-exact, 71%) | 1 | Z24725 | | | | | | |
| mitogen-activated protein kinase-activated protein kinase 3 (MAPKAPK3) | 2 | U43784 | | + | + | + | | + |
| MLN51 | 2 | X80199 | | + | + | + | + | + |
| MLN64 (=D38255 CAB1) | 1 | X80198 | + | + | + | + | | |
| moesin (MSN) | 14 | M69066 | + | + | + | + | | + |
| monocytic leukaemia zinc finger protein (MOZ) | 2 | U47742 | | + | + | + | | + |
| MOP1 ( ) | 2 | U29165 | | | | | | |
| motor protein (Hs.78504) | 2 | D21094 | + | + | + | + | | + |
| mouse double minute 2, human homolog of; p53-binding protein (MDM2) | 1 | U39736 | | | + | + | | |
| M-phase phosphoprotein 6 (MPP-6) | 1 | X98263 | | + | + | + | | + |
| M-phase phosphoprotein, mpp11 | 1 | X98260 | | | | | | |
| MPS1 | 1 | L20314 | | | | | | |
| Mr 110,000 antigen | 2 | D64154 | | + | | + | + | + |
| MRC OX-2, V-like region (=M17227) | 1 | X05324 | | | | | | |
| mu-adaptin-related protein-2; mu subunit of AP-4 (MU-ARP2) | 1 | Y08387 | | | | | | |
| multifunctional polypeptide similar to SAICAR synthetase and AIR carboxylase (ADE2H1) | 1 | X53793 | | + | + | + | | + |
| murine leukemia viral (bmi-1) oncogene homolog (BMI1) | 1 | L13689 | | + | | + | | + |
| mutant (Daudi) beta2 - microglobulin | 44 | X07621 | | | | | | |
| mutated in colorectal cancers (MCC) | 1 | M62397 | | + | + | | | + |
| myeloid cell leukemia sequence 1 (BCL2-related) (MCL1) | 9 | L08246 | + | + | + | + | + | + |
| myeloid cell nuclear differentiation antigeN (MNDA) | 11 | M81750 | + | | | | | + |
| myeloid differentiation primary response gene (88) (MYD88) | 4 | U70451 | | + | + | + | | + |
| myeloid leukemia factor 2 (MLF2) | 3 | U57342 | | + | | + | | + |
| myeloid/lymphoid or mixed-lineage leukemia (trithorax (Drosophila) homolog); translocated to, 7 (MLLT7) | 8 | U89867 | | + | + | + | | + |

TABLE 2-continued

Comparison of 1,800 Unique Genes Identified in the Blood Cell cDNA Library to Genes
Previously Identified in Specific Tissues

| Gene Identification | No. of ESTs | Accession No. | Bl | Br | H | K | Li | Lu |
|---|---|---|---|---|---|---|---|---|
| MYH9 (cellular myosin heavy chain) | 1 | M81105 | | | | | | |
| myomesin (M-protein) 2 (165 kD) (MYOM2) | 1 | X69089 | | | | | | |
| myosin IE (MYO1E) | 11 | X98411 | | + | | + | | |
| myosin light chain kinase (MLCK) | 1 | U48959 | + | | + | + | | + |
| myosin phosphatase, target subunit 1 (MYPT1) | 2 | D87930 | | + | + | + | | + |
| myosin regulatory light chain (=U26162) | 2 | D50372 | | | | | | |
| myosin VIIa (low match 71) | 1 | U55208 | | | | | | |
| myosin, heavy polypeptide 9, non-muscle (MYH9) | 3 | M81105 | + | + | + | + | | + |
| myosin, light polypeptide, regulatory, non-sarcomeric (20 kD) (MLCB) | 6 | X54304 | + | + | + | + | + | + |
| myosin-I beta | 1 | X98507 | + | + | + | + | | + |
| myristoylated alanine-rich protein kinase C substrate (MARCKS, 80K-L) (MACS) | 1 | D10522 | | + | + | | | |
| myxovirus (influenza) resistance 1, homolog of murine (interferon-inducible protein p78) (MX1) | 1 | M30817 | + | + | + | + | | + |
| myxovirus (influenza) resistance 2, homolog of murine (MX2) | 3 | M30818 | | | + | | | |
| N-acetylgalactosaminidase, alpha-(NAGA) | 2 | M62783 | | + | + | | + | + |
| N-acetylglucosamine receptor 1 (thyroid) (NAGR1) | 1 | L03532 | | + | + | + | | + |
| NACP/alpha-synuclein | 2 | U46896 | | | | | | |
| N-acylaminoacyl-peptide hydrolase (APEH) | 1 | D38441 | | + | + | | + | + |
| N-acylsphingosine amidohydrolase (acid ceramidase) (ASAH) | 11 | U47674 | + | + | + | + | | + |
| NAD+-specific isocitrate dehydrogenase beta subunit precursor (encoding mitochondrial protein) | 1 | U49283 | + | + | + | + | + | + |
| NADH dehydrogenase (ubiquinone) 1 alpha subcomplex, 5 (13 kD, B13) (NDUFA5) | 1 | U53468.1 | + | + | + | + | + | + |
| NADH dehydrogenase (ubiquinone) 1 beta subcomplex, 5 (16 kD, SGDH) (NDUFB5) | 1 | AF047181 | | + | + | + | + | + |
| NADH dehydrogenase (ubiquinone) Fe—S protein 2 (49 kD) (NADH-coenzyme Q eductase) (NDUFS2) | 1 | AF050640 | | + | + | + | + | + |
| NADH dehydrogenase (ubiquinone) flavoprotein 2 (24 kD) (NDUFV2) | 1 | M22538 | | | + | + | + | + |
| NADH: ubiquinone dehydrogenase 51 kDa subunit (NDUFV1) | 2 | AF053070 | + | + | + | + | + | + |
| NADH-CYTOCHROME B5 REDUCTASE (B5R) (50% aa) | 1 | P00387 | | | | | | |
| NADH-UBIQUINONE OXIDOREDUCTASE CHAIN 1 | 1 | P03886 | | | | | | |
| Nardilysin (N-arginine dibasic convertase) (NRD1) | 2 | U64898 | + | + | + | + | | + |
| nascent-polypeptide-associated complex alpha polypeptide (NACA) | 5 | X80909 | | + | + | | + | + |
| natural killer cell group 7 sequence (NKG7) | 8 | S69115 | | | | | + | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| natural killer cell transcript 4 (NK4) | 19 | M32011 | + | | | | | | |
| natural killer-associated transcript 3 (NKAT3) | 1 | U30274 | + | | | | | | blood only |
| natural killer-associated transcript 5 (NKAT5) | 1 | AF022045 | + | | | | | | blood only |
| natural killer-tumor recognition sequence (NKTR) | 1 | L04288 | B | | + | + | + | | |
| N-deacetylase/N-sulfotransferase (heparan glucosaminyl) 2 (NDST2) | 2 | AF042084 | + | + | | + | + | | |
| Ndr protein kinase | 3 | Z35102 | | + | | | | | |
| Nedd-4-like ubiquitin-protein ligase WWP1 | 1 | U96113 | | | | | | | |
| nel (chicken)-like 2 (NELL2) | 3 | D83018 | + | + | | | | | |
| N-ethylmaleimide-sensitive factor attachment protein, alpha (NAPA) | 1 | U39412 | | + | | + | | | |
| N-ethylmaleimide-sensitive factor attachment protein, gamma (NAPG) | 1 | U78107 | | + | + | | | | |
| neural precursor cell expressed, developmentally down-regulated 5 (NEDD5) | 3 | X92544 | + | + | + | + | | + | high in testis |
| neural precursor cell expressed, developmentally down-regulated 8 (NEDD8) | 1 | D23662 | + | + | + | + | + | + | |
| neuregulin 1 (NRG1) | 1 | U02330 | | + | | + | + | | |
| neuroblastoma RAS viral (v-ras) oncogene homolog (NRAS) | 4 | AB020692 | + | + | + | + | | + | |
| Neuroblastoma RAS viral (v-ras) oncogene homolog (NRAS) (low match) | 1 | X68286 | | | | | | | |
| Neurofibromin 2 (bilateral acoustic neuroma) (NF2) | 1 | S73853 | | + | | | | + | |
| neuronal apoptosis inhibitory protein (NAIP) | 2 | U19251 | + | + | + | | | + | |
| neuronal cell adhesion molecule (NRCAM) | 1 | AB002341 | | + | + | + | | + | |
| neuropathy target esterase (NTE) | 1 | AJ004832 | + | + | + | | | + | |
| neuropeptide Y3 receptor, 5'UTR (low score) | 1 | D28433 | | | | | | | |
| neurotrophic tyrosine kinase, receptor, type 1 (NTRK1) | 14 | X03541 | + | | + | + | + | + | |
| neutrophil cytosolic factor 4 (40 kD) | 2 | U50720 | | | | | | | |
| NG31 | 1 | AF129756 | | | | | | | |
| NGAL (=X83006) | 1 | X99133 | | | | | | | |
| nibrin (NBS) | 1 | AF051334 | | | | | | | |
| NIK | 1 | AB014587 | | + | + | + | | + | |
| Ninjurin 1; nerve injury-induced protein-1 | 1 | U72661 | | + | + | + | | + | |
| nitrilase 1 (NIT1) (=AF069984) | 1 | AF069987 | | | | | | | |
| NKG2-D (low match) (non-exact, 58%) | 1 | X54870 | | | | | | | |
| Nmi | 1 | U32849 | | | | | | | |
| N-myristoyltransferase 1 (NMT1) | 1 | AF043324 | + | + | + | + | + | | |
| No arches-like (zebrafish) zinc finger protein (NAR) | 1 | U79569 | | + | + | + | | + | |
| non-histone chromosome protein 2 (S. cerevisiae)-like 1 (NHP2L1) | 1 | D50420 | + | + | + | + | + | | |
| non-muscle (fibroblast) tropomyosin | 1 | | | | | | | | |
| non-muscle alpha-actinin | 1 | U48734 | | | | | | | |
| non-muscle myosin alkali light chain (Hs.77385) | 3 | M22918 | + | + | + | + | + | + | High in fetal adrenal gland and BPH stroma |
| non-neuronal enolase (EC 4.2.1.11) | 1 | X16289 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| non-receptor tyrosine phosphatase 1 | 1 | M33689 | | | | | | | |
| normal keratinocyte substraction library mRNA, clone H22a | 3 | X53778 | + | + | + | + | + | + | high in many libraries |
| notch group protein (N) | 3 | M99437 | | | | | | | |
| novel protein | 1 | X99961 | | | | | | | |
| novel T-cell activation protein | 1 | X94232 | | + | + | + | | + | |
| N-ras protein NRU | 1 | A60196 | | | | | | | |
| N-sulfoglucosamine sulfohydrolase (sulfamidase) (SGSH) | 1 | U60111 | | + | | | | + | |
| nsulin induced gene 1 (INSIG1) | 1 | U96876 | + | + | + | + | + | + | |
| ntegrin, alpha 4 (antigen CD49D, alpha 4 subunit of VLA-4 receptor) (ITGA14) | 3 | L12002 | + | | | + | | | |
| nterferon, gamma-inducible protein 16 (IFI16) | 1 | M63838 | + | + | + | + | | + | |
| nterleukin 1, beta (IL1RB) | 1 | M15330 | | | | | | | |
| nuclear antigen H731-like protein | 2 | U83908 | | + | + | + | | + | |
| nuclear antigen Sp100 (SP100) | 4 | U36501 | + | | | + | + | + | |
| Nuclear antigen Sp100 (SP100) (85% aa) | 1 | P23497 | | | | | | | |
| Nuclear antigen Sp100 (SP100) (89% aa) | 1 | P23497 | | | | | | | |
| nuclear autoantigenic sperm protein (histone-binding) (NASP) | 1 | M97856 | + | | + | | | | |
| nuclear corepressor KAP-1 (KAP-1) (=U95040; X97548 TIF1beta zinc finger protein) | 1 | U78773 | | | | | | | |
| Nuclear domain 10 protein (NDP52) | 4 | U22897 | + | + | + | + | + | + | |
| Nuclear factor (erythroid-derived 2)-like 2 (NFE2L2) | 1 | S74017 | | + | + | + | + | + | |
| Nuclear factor of kappa light polypeptide gene enhancer in B-cells 1 (p105) (NFKB1) | 2 | M58603 | | + | + | | + | + | |
| nuclear factor of kappa light polypeptide gene enhancer in B-cells inhibitor, alpha (NFKBIA) | 3 | M69043 | | + | + | + | | + | |
| nuclear factor related to kappa B binding protein (NFRKB) | 1 | U08191 | | + | + | + | | + | |
| nuclear mitotic apparatus protein 1 (NUMA1) | 3 | Z11583 | + | + | + | + | + | + | |
| nuclear receptor coactivator 2 (GRIP1) | 1 | X97674 | | | | | | | |
| nuclear receptor coactivator 3 (AIB3) | 2 | AF010227 | + | + | + | | | + | |
| nuclear receptor coactivator 4 (ELE1) | 22 | X77548 | | + | + | + | + | + | |
| nuclear receptor interacting protein 1 (NRIP1) | 1 | X84373 | | + | | + | | + | |
| nuclear respiratory factor 1 (NRF1) | 1 | U02683 | B | + | + | | | | |
| nuclear RNA helicase, DECD variant of DEAD box family (DDXL) | 4 | U90426 | + | + | + | + | | + | |
| nuclear transcription factor Y, alpha (NFYA) | 1 | X59711 | B | | | | | | |
| nuclear transcription factor, X-box binding 1 (NFX1) | 3 | U15306 | | + | + | + | | | |
| nuclear transport factor 2 (placental protein 15) (PP15) | 1 | X07315 | + | + | + | + | | + | |
| nucleobindin (=M96824) | 1 | U31336 | | | | | | | |
| nucleobindin 1 (NUCB1) | 2 | M96824 | + | + | + | + | | + | |
| nucleolar phosphoprotein p130 (P130) | 1 | Z34289 | | + | + | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| nucleolar protein (KKE/D repeat) (NOP56) | 1 | Y12065 | + | + | + | + | | + | |
| nucleolar protein (MSP58) | 1 | AF015308 | | | | | | | |
| nucleolar protein 1 (120 kD) (NOL1) | 1 | M32110 | + | + | | | | | |
| nucleolar protein p40 | 1 | U86602 | + | + | + | + | | + | |
| nucleolin (NCL) | 2 | M60858 | + | + | + | + | | + | |
| nucleophosmin (nucleolar phosphoprotein B23, numatrin) (NPM1) | 14 | M28699 | + | + | + | + | | + | |
| nucleophosmin-retinoic acid receptor alpha fusion protein NPM-RAR long form | 1 | U41742 | | | | | | | |
| nucleoporin (NUP358) (=D42063 RanBP2 (Ran-binding protein 2)) | 2 | L41840 | | | | | | | |
| nucleoporin 153 kD (NUP153) | 1 | Z25535 | | | | | | | |
| nucleoporin 98 kD (NUP98) | 1 | U41815 | | | | | | | |
| nucleosome assembly protein | 1 | D28430 | | | | | | | |
| nucleosome assembly protein 1-like 1 (NAP1L1) | 1 | M86667 | | + | + | + | | + | |
| nucleosome assembly protein 1-like 4 (NAP1L4) | 2 | U77456 | + | + | + | + | | + | |
| nucleosome assembly protein, 5'UTR | 1 | D28430 | | | | | | | |
| olfactory receptor (OR7-141) | 1 | U86281 | | | | | | | |
| OLFACTORY RECEPTOR-LIKE PROTEIN HGMP07E (OR17-4) (non-exact 65%) | 1 | P34982 | | | | | | | |
| oligodendrocyte myelin glycoprotein (OMG) | 7 | L05367 | | + | | | | | |
| O-linked N-acetylglucosamine (GlcNAc) transferase (UDP-N-acetylglucosamine: polypeptide-N-acetylglucosaminyl transferase) (OGT) | 1 | U77413 | + | + | | + | + | + | |
| oncofetal trophoblast glycoprotein 5T4 precursor (non-exact 55%) | 1 | A53531 | | | | | | | |
| Oncogene TIM (TIM) (non-exact 84%) | 1 | U02082 | | | | | | | |
| ORF (Hs.77868) | 1 | M68864 | + | + | + | + | + | + | |
| ORF1; MER37; putative transposase similar to pogo element Length = 454 | 1 | U49973 | | | | | | | |
| origin recognition complex, subunit 2 (yeast homolog)-like (ORC2L) | 2 | U27459 | | | | + | | | |
| origin recognition complex, subunit 4 (yeast homolog)-like (ORC4L) (low match) | 1 | AF022108 | | | | | | | |
| ornithine aminotransferase (gyrate atrophy) (OAT) | 2 | M23204 | | + | + | + | | | |
| ornithine decarboxylase (ODC) | 1 | M20372 | | | | | | | |
| ornithine decarboxylase antizyme, ORF 1 and ORF 2 | 11 | D78361 | + | + | + | + | + | + | High in pancreas, and activated T cells |
| orphan receptor (Hs.100221) | 2 | U07132 | + | + | + | + | | + | |
| OS-9 precurosor | 6 | AB002806 | + | + | + | + | + | + | |
| osteonectin (=X82259 BM-40) | 1 | D28381 | | | | | | | |
| ovel centrosomal protein RanBPM (RANBPM) | 1 | AB008515 | | + | + | + | | + | |
| over-expressed breast tumor protein | 1 | L34839 | | | | | | | |
| oviductal glycoprotein 1, 120 kD (OVGP1) | 1 | U09550 | | | + | + | + | | |
| oxidase (cytochrome c) assembly 1-like (OXA1L) | 1 | X80695 | | + | + | + | + | + | |
| oxoglutarate dehydrogenase (lipoamide) (OGDH) | 4 | D10523 | T | + | + | | + | + | |

TABLE 2-continued

Comparison of 1,800 Unique Genes Identified in the Blood Cell cDNA Library to Genes
Previously Identified in Specific Tissues

| Gene Identification | No. of ESTs | Accession No. | Bl | Br | H | K | Li | Lu | |
|---|---|---|---|---|---|---|---|---|---|
| oxysterol binding protein (OSBP) | 1 | M86917 | + | + | | + | | | |
| OZF | 1 | X70394 | | + | + | + | | + | |
| OZF (non-exact zinc finger) | 1 | X70394 | | | | | | | |
| p21/Cdc42/Rac1-activated kinase 1 (yeast Ste20-related) (PAK1) | 2 | U51120 | + | + | | + | | | |
| P35-related protein (= S80990 ficolin) | 1 | D63392 | | | | | | | |
| p40 | 1 | U93569 | | | | | | | |
| p40phox (=U50720) | 1 | X77094 | | | | | | | |
| P47 LBC oncogene | 4 | U03634 | | | | | | | |
| p53-induced protein (PIG11) | 1 | AF010315 | + | + | + | + | | | |
| p54nrb (low match) | 1 | Y11287 | | | | | | | |
| p62 nucleoporin | 1 | X58521 | | | | | | | |
| p63 mRNA for transmembrane protein | 1 | X69910 | + | + | + | + | | + | |
| PAC clone DJ0701O16 from 7q33-q36 (non-exact 54%) | 1 | Q07108 | | | | | | | |
| palmitoyl-protein thioesterase (ceroid-lipofuscinosis, neuronal 1, infantile; Haltia-Santavuori disease) (PPT) | 10 | U44772 | | + | + | + | | + | |
| papillary renal cell carcinoma (translocation-associated) (PRCC) | 1 | X99720 | + | + | + | + | + | + | |
| PAR protein | 1 | AF115850 | | + | | + | | | |
| partial EST (clone c-1gh04) | 1 | Z43627 | | | | | | | |
| PAX3/forkhead transcription factor gene fusion | 1 | U02368 | | | | | | | |
| paxillin (PXN) | 4 | D86862 | | + | + | + | | + | |
| PBK1 protein | 2 | AJ007398 | + | + | + | + | | + | |
| PBS-EST (nz92e01.s1 NCI_CGAP_GCB1 clone IMAGE: 1302936) (low score) | 1 | AA732534 | | | | | | | |
| PDZ domain protein (Drosophila inaD-like) (INALD) | 1 | AJ224747 | + | | | + | | + | |
| PEBP2aC Runt domain encoding gene (=Z35728) | 1 | Z38108 | | | | | | | |
| peptidase D (PEPD) | 1 | J04605 | | | | | | | |
| peptidylprolyl isomerase A (cyclophilin A) (PPIA) | 3 | Y00052 | | + | + | + | + | + | high in many libraries |
| peptidylprolyl isomerase D (cyclophilin D) (PPID) | 2 | L11667 | T | + | + | | + | + | |
| peptidylprolyl isomerase E (cyclophilin E) (PPIE) | 1 | AF042386 | | + | + | | + | + | |
| PERB11.1 (=U56942 MHC class I chain-related protein A) | 1 | U69630 | | | | | | | |
| perforin 1 (preforming protein) (PRF1) | 14 | M28393 | | | | | | | |
| peroxisomal acyl-CoA thioesterase (PTE1) | 2 | X86032 | | | | | | | |
| Peroxisomal acyl-coenzyme A oxidase | 1 | X71440 | | + | + | + | + | + | |
| peroxisomal farnesylated protein (PXF) | 1 | X75535 | | + | + | + | + | + | |
| phorbol-12-myristate-13-acetate-induced protein (PMAIP1) | 1 | D90070 | B, W | | | | | | |
| phosphate carrier (mitochondrial gene?) | 1 | X77337 | | | | | | | |
| Phosphate carrier, mitochondrial (PHC) | 3 | X60036 | + | + | + | + | | + | |
| phosphate cytidylyltransferase 1, choline, alpha isoform (PCYT1A) | 1 | L28957 | T | | + | | + | | |
| PHOSPHATIDATE CYTIDYLYLTRANSFERASE (CDP-DIGLYCERIDE) | 1 | Q92903 | | | | | | | |
| phosphatidylinositol 3-kinase delta catalytic subunit | 2 | U57843 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| phosphatidylinositol 4-kinase, catalytic, beta polypeptide (PIK4CB) | 3 | AB005910 | + | + | + | + | | + |
| phosphatidylinositol glycan, class H (PIGH) | 1 | L19783 | | + | + | + | + | + |
| phosphatidylinositol transfer protein (PI-TPbeta) | 2 | D30037 | | | | | | |
| phosphatidylinositol transfer protein, membrane-associated (PITPNM) | 2 | X98654 | B, T lymphoma | + | | | | |
| phosphatidylinositol transfer protein, membrane-associated (PITPNM) (non-exact 64%) | 1 | X98654 | | | | | | |
| phosphatidylinositol-4-phosphate 5-kinase, type II, alpha (PIP5K2A) | 1 | U14957 | | | + | | + | |
| phosphatidylinositol-4-phosphate 5-kinase, type II, beta (PIP5K2B) | 1 | U85245 | | | + | + | + | + |
| phosphodiesterase 7A (PDE7A) | 1 | L12052 | B, W | + | + | | + | |
| phosphodiesterase IB (PDES1B) | 1 | U56976 | | ONLY | | | | |
| phosphoglucomutase 1 (PGM1) | 2 | M83088 | | | + | + | + | + |
| phosphogluconate dehydrogenase (PGD) | 1 | U30255 | | | + | | | |
| phosphoglycerate kinase 1 (PGK1) | 12 | V00572 | | | | | | |
| phosphoglycerate mutase 1 (brain) (PGAM1) | 3 | J04173 | + | + | + | + | + | + |
| phosphoglycerate mutase 2 (muscle) (PGAM2) | 1 | M55673 | | + | + | | | + |
| phosphoinositide-3-kinase, catalytic, alpha polypeptide (PIK3CA) | 1 | Z29090 | | + | + | + | | |
| phosphoinositide-3-kinase, catalytic, delta polypeptide (PIK3CD) | 4 | U86453 | | + | + | + | | + |
| phosphoinositide-3-kinase, catalytic, gamma polypeptide (PIK3CG) | 1 | X83368 | | | | | | |
| phospholipase C | 1 | X14034 | | | | | | |
| phospholipase C, delta 1 (PLCD1) | 2 | U09117 | | + | + | + | | + |
| phospholipase C, gamma 1 (formerly subtype 148) (PLCG1) | 1 | M34667 | + | + | + | + | | + |
| phospholipid scramblase | 1 | AF008445 | | | | | | |
| phosphoribosyl pyrophosphate synthetase-associated protein 1 (PRPSAP1) | 1 | D61391 | | + | + | | | + |
| phosphoribosylglycinamide formyltransferase, phosphoribosylglycinamide synthetase, phosphoribosylaminoimidazole synthetase (GART) | 3 | X54199 | | + | + | + | + | + |
| phosphorylase kinase, alpha 2 (liver), glycogen storage disease IX (PHKA2) | 3 | D38616 | | + | + | + | + | + |
| phosphorylase, glycogen; brain (PYGB) | 1 | U47025 | + | + | + | | | + |
| phosphorylase, glycogen; brain (PYGB) (low match, non-exact, 75%) | 1 | U47025 | | | | | | |
| phosphorylase, glycogen; liver (Hers disease, lycogen storage disease type VI) (PYGL) | 1 | Y15233 | | + | + | + | | + |
| phosphorylation regulatory protein HP-10 | 2 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
| --- | --- | --- | --- | --- | --- | --- | --- | --- |
| | | | Bl | Br | H | K | Li | Lu |
| phosphotidylinositol transfer protein (PITPN) | 1 | D30036 | + | + | + | + | | + |
| pigment epithelium-derived factor (PEDF) | 1 | U29953 | + | + | + | + | + | + |
| pim-1 oncogene (PIM1) | 1 | M24779 | + | + | + | | | + |
| pinin, desmosome associated protein (PNN) | 1 | U77718 | B, monocyte, T lymphoma | | | | | |
| placenta (Diff33) | 5 | U49188 | | + | + | + | | + |
| placenta (Diff33) (non-exact, 69%) | 1 | U49188 | | | | | | |
| placenta (Diff48) | 18 | U49187 | + | | | | | |
| placenta (Diff48) (low match) | 1 | U49187 | | | | | | |
| placenta(Diff48) (low match) | 1 | U49187 | | | | | | |
| plasminogen activator, urokinase receptor (PLAUR) | 1 | X74039 | | + | | + | | + |
| platelet factor 4 (PF4) | 1 | M25897 | | | + | | | + |
| platelet/endothelial cell adhesion molecule (CD31 ntigen) (PECAM1) | 8 | M37780 | | + | + | + | + | + |
| platelet-activating factor acetylhydrolase 2 (40 kD) (PAFAH2) | 4 | U89386 | | + | + | + | | |
| platelet-activating factor acetylhydrolase, isoform Ib, alpha subunit (45 kD) (PAFAH1B1) | 1 | U72342 | + | + | + | + | + | + |
| platelet-activating factor receptor (PTAFR) | 1 | D10202 | | + | | | | + |
| pleckstrin (PLEK) | 10 | X07743 | | | + | + | | + |
| pleckstrin (PLEK) (low match) | 1 | X07743 | | | | | | |
| pleckstrin homology, Sec7 and coiled/coil domains 1(cytohesin 1) (PSCD1) | 4 | M85169 | + | + | | + | | + |
| pleckstrin homology, Sec7 and coiled/coil domains, binding protein (PSCDBP) | 4 | L06633 | + | | | + | | |
| pM5 protein | 1 | X57398 | + | + | + | + | | + |
| PMP69 | 2 | Y14322 | | | | | | |
| poly (ADP-ribose) polymerase (NAD (+) ADP-ribosyltransferase) (=X16674) | 1 | X56140 | | | | | | |
| poly(A) polymerase (PAP) | 1 | X76770 | + | + | + | + | | + |
| poly(A)-binding protein-like 1 (PABPL1) | 19 | Y00345 | + | + | + | + | + | + |
| poly(rC)-binding protein 1 (PCBP1) | 3 | X78137 | + | + | + | + | + | + |
| polyadenylate binding protein | 1 | U75686 | | | | | | |
| polycystic kidney disease 1 (autosomal dominant) (PKD1) | 5 | U24498 | | | | | | |
| polymerase (DNA directed), beta (POLB) | 1 | D29013 | | + | | + | | + |
| polymerase (DNA directed), gamma (POLG) | 6 | D84103 | | | | | | |
| polymerase (RNA) II (DNA directed) polypeptide A (220 kD) (POLR2A) | 1 | X63564 | + | + | + | + | + | + |
| polymyositis/scleroderma autoantigen 2 (100 kD) (PMSCL2) | 1 | L01457 | + | + | + | + | + | + |
| polypyrimidine tract binding protein (heterogeneous nuclear ribonucleoprotein I) (PTB) | 1 | X65372 | + | + | + | + | + | + |
| positive regulator of programmed cell death ICH-1L (Ich-1) | 3 | U13021 | | | + | | | |
| postmeiotic segregation increased 2-like 12 (PMS2L12) | 1 | M16514 | + | + | + | + | | + |
| postmeiotic segregation increased 2-like 8 (PMS2L8) | 1 | U38964 | + | + | + | + | | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| potassium inwardly-rectifying channel, subfamily J, member 15 (KCNJ15) | 1 | D87291 | | | | + | | + |
| potassium voltage-gated channel, KQT-like subfamily, member 1 (KCNQ1) | 1 | AF051426 | | + | + | + | | + |
| POU domain, class 2, associating factor 1 (POU2AF1) | 1 | Z49194 | | | | + | | |
| POU domain, class 2, transcription factor 1 (POU2F1) | 2 | X13403 | | + | | + | | |
| PPAR binding protein (PPARBP) | 1 | Y13467 | + | | + | + | | + |
| PPAR gamma2 | 1 | D83233 | | | | | | |
| pre-B-cell colony-enhancing factor (PBEF) | 8 | U02020 | | | | | | |
| prefoldin 1 (PFDN1) | 1 | Y17392 | + | + | + | + | + | + |
| prefoldin 5 (PRFLD5) | 3 | D89667 | B | + | + | + | | |
| prefoldin subunit 3 (=U96759 von Hippel-Lindau binding protein (VBP-1)) | 1 | Y17394 | | | | | | |
| pregnancy-associated plasma protein A (PAPPA) | 1 | U28727 | | + | | + | | high in placenta |
| pre-mRNA splicing factor SF3a (60 kD), similar to *S. cerevisiae* PRP9 (spliceosome-associated protein 61) (SF3A60) | 1 | U08815 | + | + | + | + | | + |
| pre-mRNA splicing factor SF3a (60 kD), similar to *S. cerevisiae* PRP9 (spliceosome-associated protein 61) (SF3A60) (low score) | 1 | U08815 | | | | | | |
| pre-mRNA splicing factor SRp20, 5'UTR | 2 | D28423 | | | | | | |
| preprotein translocase (TIM17) | 3 | X97544 | + | + | + | + | | + |
| prion protein | 1 | X82545 | | | | | | |
| prion protein (p27-30) (Creutzfeld-Jakob disease, Gerstmann-Strausler-Scheinker syndrome, fatal familial insomnia) (PRNP) | 1 | M13899 | | + | + | + | | + |
| pristanoyl-CoA oxidase (low match) | 1 | Y11411 | | | | | | |
| pristanoyl-CoA oxidase (low score) | 1 | Y11411 | | | | | | |
| procollagen-lysine, 2-oxoglutarate 5-dioxygenase (lysine hydroxylase, Ehlers-Danlos syndrome type VI) (PLOD) | 1 | M98252 | | + | + | + | | + |
| procollagen-proline, 2-oxoglutarate 4-dioxygenase (proline 4-hydroxylase), alpha polypeptide 1 (P4HA1) | 1 | M24486 | + | + | + | + | + | + |
| procollagen-proline, 2-oxoglutarate 4-dioxygenase (proline 4-hydroxylase), beta polypeptide (protein disulfide isomerase; thyroid hormone binding protein p55) (P4HB) | 4 | X05130 | + | + | + | + | + | + |
| profilin 1 (PFN1) | 1 | J03191 | + | + | + | + | + | + |
| progesterone receptor-associated p48 protein (P48) | 2 | U28918 | | + | | | | |
| prohibitin (PHB) | 1 | S85655 | | + | + | + | + | + |
| proliferating cell nuclear antigen (PCNA) | 3 | J04718 | + | + | + | + | | + |
| proliferation-associated gene A (natural iller-enhancing factor A) (PAGA) | 4 | L19184 | + | + | + | + | + | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| proline-rich protein B stNI subfamily 2 (PRB2) (non-exact, 43% aa) | 1 | S62936 | | | | | | |
| proline-serine-threonine phosphatase interacting protein 1 (PSTPIP1) | 1 | U94778 | | | | | | |
| prolyl endopeptidase (PREP) | 2 | X74496 | | + | | + | | + |
| prolylcarboxypeptidase (angiotensinase C) (PRCP) | 5 | L13977 | | + | + | + | + | + |
| promyelocytic leukemia (PML) | 1 | M80185 | + | + | + | + | | + |
| properdin P factor, complement (PFC) | 4 | X57748 | + | | | | | |
| pro-platelet basic protein (includes platelet basic protein, beta-thromboglobulin, connective tissue-activating peptide III, neutrophil-activating peptide-2) (PPBP) | 1 | M54995 | | | | + | + | + |
| pro-platelet basic protein (includes platelet basic protein, beta-thromboglobulin, connective tissue-activating peptide III, neutrophil-activating peptide-2) (PPBP) | 7 | M54995 | + | | | + | + | |
| proprotein convertase subtilisin/kexin type 7 (PCSK7) | 4 | U40623 | | | | | | |
| prosaposin (variant Gaucher disease and variant metachromatic leukodystrophy) (PSAP) | 89 | D00422 | + | + | + | + | + | + |
| prostaglandin-endoperoxide synthase 1 (prostaglandin G/H synthase and cyclooxygenase) (PTGS1) | 1 | U63846 | B | + | | | + | + |
| prostaglandin-endoperoxide synthase 2 (prostaglandin G/H synthase and cyclooxygenase) (PTGS2) | 2 | L15326 | | | | | | |
| prostaglandin-endoperoxide synthase-1 (=L08404; U84208) (all promoters) | 1 | D64068 | | | | | | |
| prostate carcinoma tumor antigen (pcta-1) | 2 | L78132 | | | | | | |
| protease inhibitor 1 (anti-elastase), alpha-1-antitrypsin (PI) | 17 | K02212 | | + | + | + | + | + high in many libraries |
| protease inhibitor 2 (anti-elastase), monocyte/neutrophil (ELANH2) (low match) | 1 | M93056 | | | | + | | + |
| proteasome (prosome, macropain) 26S subunit, ATPase, 1 (PSMC1) | 3 | L02426 | B | + | + | | | + |
| proteasome (prosome, macropain) 26S subunit, ATPase, 3 (PSMC3) | 1 | M34079 | + | + | + | + | | + |
| proteasome (prosome, macropain) 26S subunit, ATPase, 4 (PSMC4) | 2 | AF020736 | | | | | | |
| proteasome (prosome, macropain) 26S subunit, ATPase, 5 (PSMC5) | 5 | L38810 | + | + | + | + | + | + |
| proteasome (prosome, macropain) 26S subunit, ATPase, 6 (PMSC6) | 2 | D78275 | + | + | + | + | | + |
| proteasome (prosome, macropain) 26S subunit, non-ATPase, 11 (PSMD11) | 1 | AF001212 | T | + | | + | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| proteasome (prosome, macropain) 26S subunit, non-ATPase, 2 (PSMD2) | 2 | D78151 | | + | + | | + | | |
| proteasome (prosome, macropain) 26S subunit, non-ATPase, 5 (PSMD5) | 1 | S79862 | T | + | + | + | | | |
| proteasome (prosome, macropain) 26S subunit, non-ATPase, 7 (Mov34 homolog) (PMSD7) | 1 | D50063 | | + | + | + | | + | high in many libraries |
| proteasome (prosome, macropain) 26S subunit, on-ATPase, 12 (PMSD12) | 1 | AB003103 | | + | + | + | | + | |
| proteasome (prosome, macropain) activator subunit 1 (PA28 alpha) (PSME1) | 3 | L07633 | + | + | + | + | | + | |
| proteasome (prosome, macropain) subunit, alpha type, 3 (PSMA3) | 2 | D00762 | | + | + | + | | + | |
| proteasome (prosome, macropain) subunit, alpha type, 5 (PSMA5) | 3 | X61970 | + | + | + | + | | + | |
| proteasome (prosome, macropain) subunit, alpha type, 7 (PSMA7) | 3 | AF054185 | | + | + | + | + | + | |
| proteasome (prosome, macropain) subunit, alpha type, 7 (PSMA7) (low match) | 1 | AF022815 | | | | | | | |
| proteasome (prosome, macropain) subunit, beta type, 1 (PSMB1) | 1 | D00761 | + | + | + | + | + | + | |
| proteasome (prosome, macropain) subunit, beta type, 10 (PSMB10) | 1 | X71874 | + | + | | + | + | + | |
| proteasome (prosome, macropain) subunit, beta type, 6 (PMSB6) | 1 | D29012 | | + | + | + | | + | |
| proteasome (prosome, macropain) subunit, beta type, 8 (large multifunctional protease 7) (PSMB8) | 1 | U17497 | + | + | + | + | | + | |
| proteasome (prosome, macropain) subunit, beta type, 9 (large multifunctional protease 2) (PSMB9) | 3 | Z14977 | + | | | + | | + | |
| proteasome (prosome, macropain) subunit, beta ype, 7 (PSMB7) | 1 | D38048 | + | + | + | + | + | + | |
| protective protein for beta-galactosidase (galactosialidosis) (PPGB) | 3 | M22960 | + | + | + | + | + | + | |
| protein A alternatively spliced form 2 (A-2) | 1 | U47925 | | + | | | | | |
| protein activator of the interferon-induced protein kinase (PACT) | 1 | AF072860 | | + | + | + | | + | high in testis |
| protein disulfide isomerase-related protein (P5) | 2 | D49489 | + | + | + | + | + | + | |
| protein geranylgeranyltransferase type I, beta subunit (PGGT1B) | 1 | L25441 | + | + | + | | | | |
| protein homologous to chicken B complex protein, guanine nucleotide binding (H12.3) | 20 | M24194 | + | + | + | + | + | + | high in many libraries |
| protein kinase A anchoring protein | 1 | AF037439 | | + | | | | | |
| protein kinase C substrate 80K-H (PRKCSH) | 2 | U50317 | + | + | + | + | | + | |
| protein kinase C, beta 1 (PRKCB1) | 6 | X06318 | + | + | + | + | | + | |
| protein kinase C, delta (PRKCD) | 1 | D10495 | + | + | + | + | | + | |

TABLE 2-continued

Comparison of 1,800 Unique Genes Identified in the Blood Cell cDNA Library to Genes
Previously Identified in Specific Tissues

| Gene Identification | No. of ESTs | Accession No. | Tissue Distribution | | | | | |
| --- | --- | --- | --- | --- | --- | --- | --- | --- |
| | | | Bl | Br | H | K | Li | Lu |
| protein kinase C, eta (PRKCH) | 1 | M55284 | | | + | | | + |
| protein kinase C, mu (PRKCM) (non-exact 78%) | 1 | X75756 | | | | | | |
| Protein kinase C-like 1 (PRKCL1) | 2 | D26181 | + | + | + | + | | + |
| protein kinase, AMP-activated, gamma 1 non-catalytic subunit (PRKAG1) | 1 | U42412 | B, T lymphoma | + | + | | | |
| protein kinase, cAMP-dependent, regulatory, type I, alpha (tissue specific extinguisher 1) (PRKAR1A) | 4 | M18468 | | + | + | + | + | + |
| protein kinase, DNA-activated, catalytic polypeptide (PRKDC) | 1 | U47077 | | + | + | | + | + |
| protein kinase, mitogen-activated 1 (MAP kinase 1; p40, p41) (PRKM1) | 1 | Z11695 | B | + | | | + | |
| protein kinase, mitogen-activated 6 (extracellular signal-regulated kinase, p97) (PRKM6) | 1 | L77964 | | + | | + | + | + |
| protein kinase, mitogen-activated, kinase 3 (MAP kinase kinase 3) (PRKMK3) | 1 | U66839 | + | + | + | + | + | |
| protein phosphatase 1, catalytic subunit, alpha isoform (PPP1CA) | 5 | M63960 | + | + | + | + | + | + |
| protein phosphatase 1, regulatory subunit 10 (PPPR10) | 3 | Y13247 | | + | + | + | | + |
| protein phosphatase 1, regulatory subunit 7 (PPP1R7) | 2 | Z50749 | + | + | + | + | + | + |
| protein phosphatase 2 (formerly 2A), catalytic subunit, beta isoform (PPP2CB) | 1 | X12656 | + | + | + | + | + | + |
| protein phosphatase 2 (formerly 2A), regulatory subunit B'' (PR 72), alpha isoform and (PR 130), beta isoform (PPP2R3) | 1 | L07590 | | | + | + | | + |
| protein phosphatase 2, regulatory subunit B (B56), alpha isoform (PPP2R5A) | 2 | L42373 | + | + | + | + | | + |
| protein phosphatase 2, regulatory subunit B (B56), delta isoform (PPP2R5D) | 3 | D78360 | | + | + | + | | + |
| protein phosphatase 2, regulatory subunit B (B56), gamma isoform (PPP2R5C) | 1 | D26445 | + | + | + | + | | + |
| protein phosphatase 2A regulatory subunit alpha-isotype (alpha-PR65) | 5 | J02902 | + | + | + | + | | + |
| protein phosphatase 4 (formerly X), catalytic subunit (PPP4C) | 2 | AF097996 | + | + | + | + | | + |
| protein tyrosine kinase 2 beta (PTK2B) | 4 | L49207 | | + | | + | | + |
| protein tyrosine phosphatase epsilon | 1 | X54134 | | | | | | |
| protein tyrosine phosphatase type IVA, member 2 (PTP4A2) | 2 | L48723 | + | + | + | + | | + |
| protein tyrosine phosphatase, non-receptor type 1 (PTPN1) | 1 | M31724 | + | + | + | | | |
| protein tyrosine phosphatase, non-receptor type 12 (PTPN12) | 1 | M93425 | | + | + | + | + | high in testis |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| protein tyrosine phosphatase, non-receptor type 12 (PTPN12) (non-exact, 70%) | 1 | M93425 | | | | | | |
| protein tyrosine phosphatase, non-receptor type 2 (PTPN2) | 2 | M25393 | | + | + | + | | + |
| protein tyrosine phosphatase, non-receptor type 4 (megakaryocyte) (PTPN4) | 1 | M68941 | | | + | + | | + |
| protein tyrosine phosphatase, non-receptor type 6 (PTPN6) | 7 | M74903 | + | + | + | + | | + |
| protein tyrosine phosphatase, non-receptor type 7 (PTPN7) | 1 | D11327 | + | | | + | | + |
| protein tyrosine phosphatase, receptor type, alpha polypeptide (PTPRA) | 1 | M34668 | + | + | + | + | | + |
| protein tyrosine phosphatase, receptor type, c polypeptide (PTPRC) | 44 | Y00638 | + | + | | + | | + |
| protein tyrosine phosphatase, receptor type, M (PTPRM) | 1 | X58288 | + | + | + | | | + |
| protein tyrosine phosphatase, receptor type, N polypeptide 2 (PTPRN2) | 2 | U81561 | + | | + | | | + |
| protein with polyglutamine repeat (ERPROT213-21) | 1 | U94836 | + | + | + | + | | + |
| protein-kinase, interferon-inducible double stranded RNA dependent inhibitor (PRKRI) | 1 | U28424 | + | + | + | + | + |
| protein-L-isoaspartate (D-aspartate) O-methyltransferase (PCMT1) | 4 | D13892 | + | + | | | | |
| proteoglycan 1, secretory granule (PRG1) | 7 | J03223 | + | | | + | | + |
| prothymosin, alpha (gene sequence 28) (PTMA) | 12 | M14483 | + | + | + | + | + | + |
| prp28, U5 snRNP 100 kd protein (U5-100K) | 7 | AF026402 | + | + | + | + | | + |
| PRP4/STK/WD splicing factor (HPRP4P) | 1 | AF001687 | | + | + | + | | + |
| PTK7 protein tyrosine kinase 7 (PTK7) | 1 | U40271 | | + | + | + | | + |
| purinergic receptor P2X, ligand-gated ion channel, 4 (P2RX4) | 3 | AF000234 | | + | + | + | | + |
| purinergic receptor P2X, ligand-gated ion channel, 7 (P2RX7) | 1 | Y12851 | + | | | | | macrophage only |
| puromycin-sensitive aminopeptidase (PSA) | 1 | Y07701 | | + | + | | | + |
| putative ATP(GTP)-binding protein | 2 | AJ010842 | | + | | | | + |
| putative brain nuclearly-targeted protein (KIAA0765) | 1 | AB018308 | + | + | + | + | | + |
| putative chemokine receptor; GTP-binding protein (HM74) | 1 | D10923 | + | | | | | |
| putative dienoyl-CoA isomerase (ECH1) | 1 | AF030249 | | | | | | |
| putative G-binding protein | 1 | AF065393 | | | | | | |
| Putative human HLA class II associated protein I (PHAP1) | 1 | U73477 | B | + | | + | | |
| Putative L-type neutral amino acid transporter (KIAA0436) | 1 | AB007896 | | | | | | |
| putative mitochondrial space protein 32.1 | 1 | AF050198 | | | | | | |
| PUTATIVE MUCIN CORE PROTEIN PRECURSOR 24 (MULTI-GLYCOSYLATED CORE PROTEIN 24) (MGC-24) (MUC-24) | 1 | Q04900 | | | | | | |
| putative nucleic acid binding protein | 2 | X76302 | + | + | + | + | | + |

TABLE 2-continued

Comparison of 1,800 Unique Genes Identified in the Blood Cell cDNA Library to Genes
Previously Identified in Specific Tissues

| Gene Identification | No. of ESTs | Accession No. | Bl | Br | H | K | Li | Lu | |
|---|---|---|---|---|---|---|---|---|---|
| putative outer mitochondrial membrane 34 kDa translocase Htom34 | 1 | U58970 | | + | + | + | | + | |
| putative p150 (non-exact 88%) | 1 | U93568 | | | | | | | |
| putative translation initiation factor (SUI1) | 1 | L26247 | + | + | + | + | + | + | High in moderately differentiated colon adenocarcinoma |
| putative tumor suppressor protein (123F2) | 1 | AF061836 | | + | + | + | | + | |
| pyrroline 5-carboxylate reductase | 1 | M77836 | + | + | + | + | | + | |
| pyruvate dehydrogenase (lipoamide) alpha 1 (PDHA1) | 1 | D90084 | | + | + | + | + | + | |
| pyruvate dehydrogenase (lipoamide) beta (PDHB) | 2 | J03576 | + | + | + | | | + | |
| Pyruvate dehydrogenase complex, lipoyl-containing component X; E3-binding protein (PDX1) | 3 | Y13145 | | + | + | | | | |
| pyruvate kinase, muscle (PKM2) | 11 | M23725 | | | | | + | | |
| RAB, member of RAS oncogene family-like (RABL) | 1 | U18420 | | + | + | + | | + | |
| RAB1, member RAS oncogene family (RAB1) | 3 | M28209 | | + | + | + | | + | |
| RAB11A, member RAS oncogene family (RAB11A) | 2 | X56740 | + | + | + | + | | + | high in spleen |
| RAB11B, member RAS oncogene family (Rab11B) | 1 | D45418 | | + | | | | + | |
| RAB27A, member RAS oncogene family (RAB27A) | 3 | U38654 | | | | + | | | |
| RAB5B, member RAS oncogene family (RAB5B) | 1 | X54871 | | + | + | + | | + | |
| RAB6, member RAS oncogene family (RAB6) | 1 | M28212 | | + | | | | + | |
| RAB7, member RAS oncogene family (RAB7) | 1 | X93499 | + | + | + | + | | + | |
| RAB7, member RAS oncogene family-like 1 (RAB7L1) | 2 | D84488 | | + | + | + | | + | |
| RAB9, member RAS oncogene family (RAB9) | 1 | U44103 | | | | | | | |
| RAD50 (S. cerevisiae) homolog (RAD50) | 2 | U63139 | | + | + | + | | | |
| RAD51 (S. cerevisiae) homolog C (RAD51C) | 1 | AF029669 | | + | + | + | | + | |
| Radin blood group (RD) | 2 | L03411 | | + | + | + | | + | |
| RAE1 (RNA export 1, S. pombe) homolog (RAE1) | 3 | U84720 | + | + | + | + | | + | |
| ralA-binding protein (RLIP76) | 2 | L42542 | + | + | + | + | | | |
| RAN binding protein 2-like 1 (RANBP2L1) | 2 | AF012086 | | | | | | | |
| Ran GTPase activating protein 1 (RANGAP1) | 3 | X82260 | + | + | + | + | | + | |
| RAN, member RAS oncogene family (RAN) (low match) | 1 | M31469 | | | | | | | |
| RanBP2 (Ran-binding protein 2) (=U19248; L41840 sapiens nucleoporin (NUP358)) | 1 | D42063 | | | | | | | |
| ransforming growth factor, beta receptor II (70-80 kD) (TGFBR2) | 4 | D50683 | + | + | + | + | | + | |
| RAP1A, member of RAS oncogene family (RAP1A) | 10 | M22995 | + | + | + | + | + | + | |
| RAR-related orphan receptor C (RORC) | 1 | U16997 | | | | | | + | |
| RAS guanyl releasing protein 2 (calcium and DAG-regulated) | 1 | Y12336 | + | + | | | | | |
| ras homolog gene family, member A (ARHA) | 12 | X05026 | + | + | + | + | + | + | high in ovary |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| ras homolog gene family, member G (rho G) (ARHG) | 1 | X61587 | + | + | + | + | | |
| ras homolog gene family, member H (ARHH) | 2 | Z35227 | + | + | + | | | + |
| ras inhibitor (RIN1) | 2 | M37191 | | + | | | | |
| Ras-GTPase activating protein SH3 domain-binding protein 2 (KIAA0660) | 2 | AF053535 | + | + | + | + | | + |
| Ras-GTPase-activating protein SH3-domain-binding protein (G3BP) | 3 | U32519 | + | + | + | + | | + |
| ras-related C3 botulinum toxin substrate 2 (rho family, small GTP binding protein Rac2) (RAC2) | 11 | M29871 | | | + | | | + |
| RAS-RELATED PROTEIN RAP-1B (GTP-BINDING PROTEIN SMG P21B) | 1 | P09526 | | | | | | |
| RBQ-1 | 1 | X85133 | + | + | + | | | |
| rearranged T cell receptor beta variable region (TCRB) (=X58810) | 1 | L06891 | | | | | | |
| regulator of Fas-induced apoptosis (TOSO) | 1 | AF057557 | B | | | + | | |
| regulator of G protein signalling 6 (RGS6) | 1 | AF073920 | | + | | | | |
| regulator of G-protein signalling 14 (RGS14) | 2 | AF037195 | + | + | + | + | | |
| regulator of G-protein signalling 2, 24 kD (RGS2) | 6 | L13391 | + | + | + | + | | + |
| regulator of G-protein signalling 5 (RGS5) (49% aa) | 1 | O15539 | | | | | | |
| regulatory factor X, 4 (influences HLA class II expression) (RFX4) | 1 | M69297 | | | + | + | | |
| regulatory factor X, 5 (influences HLA class II expression (RFX5) | 2 | X85786 | T | + | + | | | + |
| replication protein A1 (RPA1) | 1 | M63488 | + | + | + | + | | + |
| replication protein A3 (14 kD) (RPA3) (low match) | 1 | L07493 | | | | | | |
| reproduction 8 (D8S2298E) | 1 | D83767 | | + | + | + | | |
| requiem, apoptosis response zinc finger gene (REQ) | 2 | U94585 | + | + | + | + | | + |
| requiem, apoptosis response zinc finger gene (REQ) (=AF001433) (low match) | 1 | U94585 | | | | | | |
| restin (Reed-Steinberg cell-expressed intermediate filament-associated protein) (RSN) | 1 | M97501 | B, T | + | + | | | |
| retinoblastoma 1 (including osteosarcoma) (RB1) | 3 | L11910 | + | + | + | + | | |
| retinoblastoma binding protein 2 homolog 1 (RBBP2H1) | 1 | AF087481 | | | | | | |
| retinoblastoma-binding protein 1 (RBBP1) | 1 | S66427 | + | + | | | | |
| retinoblastoma-binding protein 2 (RBBP2) | 5 | S66431 | + | + | + | + | | + |
| retinoblastoma-binding protein 4 (RBBP4) | 1 | X71810 | | + | + | + | | |
| retinoblastoma-binding protein 4 (RBBP4) | 1 | X74262 | | + | + | + | | |
| retinoblastoma-binding protein 7 (RBBP7) | 1 | U35143 | | | | | | |
| retinoblastoma-like 2 (p130) (RBL2) | 1 | X76061 | | + | + | + | | |
| retinoic acid receptor responder (tazarotene nduced) 3 (RARRES3) | 1 | AF060228 | | + | | + | + | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| retinoic acid receptor, alpha (RARA) | 1 | X06538 | + | + | | + | | | |
| retinoic acid responsive (NN8-4AG) | 1 | U50383 | | + | | + | | + | |
| retinoid X receptor beta (RXR-beta) | 2 | X66424 | | + | + | + | | + | |
| REV3 (yeast homolog)-like, catalytic subunit of DNA polymerase zeta (REV3L) | 1 | AF035537 | | | | | | | |
| Rho GDP dissociation inhibitor (GDI) beta (ARHGDIB) | 23 | L07916 | + | + | + | + | + | + | |
| Rho GTPase activating protein 4 (ARHGAP4) | 2 | X78817 | + | + | | | | | |
| Rho GTPase activating protein 4 (ARHGAP4) (low match) | 1 | P98171 | | | | | | | |
| Rho-associated, coiled-coil containing protein kinase 2 (ROCK2) | 1 | AB014519 | | | | | | | |
| ribonuclease 6 precursor (RNASE6PL) | 2 | U85625 | + | + | + | + | + | + | |
| ribonuclease 6 precursor (RNASE6PL) (low match) | 1 | U85625 | | | | | | | |
| ribonuclease, RNase A family, 2 (liver, eosinophil-derived neurotoxin) (RNASE2) | 1 | X55988 | | | | + | | | |
| ribonuclease/angiogenin inhibitor (RNH) | 3 | M36717 | + | + | + | + | | + | |
| ribonucleoside diphosphate reductase M1 subunit | 1 | X65708 | | | | | | | |
| ribonucleotide reductase M2 polypeptide (non-exact 91%) | 1 | P31350 | | | | | | | |
| ribophorin I (RPN1) | 1 | Y00281 | + | + | + | + | | + | |
| ribophorin II (RPN2) | 1 | Y00282 | + | + | + | + | + | + | |
| ribosomal 18S rRNA | 3 | M10098 | | | | | | | |
| ribosomal 28S RNA | 1 | M11167 | | | | | | | |
| ribosomal phosphoprotein P0, 5'UTR (low match) | 1 | D28418 | | | | | | | |
| Ribosomal protein | 1 | | | | | | | | |
| ribosomal protein L10 (RPL10) | 30 | L25899 | + | + | + | + | + | + | high in many libraries |
| RIBOSOMAL PROTEIN L10A (CSA-19) | 2 | P53025 | | | | | | | |
| ribosomal protein L11 (RPL11) | 4 | X79234 | + | + | + | + | + | + | Alveolar rhabdomyosarcoma |
| ribosomal protein L12 (RPL19) | 2 | L06505 | + | + | + | + | + | + | |
| ribosomal protein L13 (PRL13) | 1 | P26373 | + | + | + | + | + | + | high in many libraries |
| ribosomal protein L14 (RPL14) | 4 | D87735 | + | + | + | + | + | + | high in many libraries |
| ribosomal protein L17 (RPL17) | 4 | X53777 | + | | | | | | blood only |
| ribosomal protein L18 (RPL18) | 10 | L11566 | + | + | + | + | | + | |
| ribosomal protein L18a (RPL18A) | 5 | L05093 | | + | + | + | | + | High in fetal adrenal gland and skin |
| ribosomal protein L18a homologue | 2 | X80821 | | | | + | | | |
| ribosomal protein L19 (RPL19) | 15 | X63527 | + | + | + | + | + | + | |
| ribosomal protein L21 (RPL21) | 6 | U14967 | + | + | + | + | + | + | |
| ribosomal protein L22 (RPL22) | 3 | D17652 | + | + | + | | | + | |
| ribosomal protein L23 (RPL23) | 2 | X55954 | + | + | + | + | | + | high in many libraries |
| ribosomal protein L23a (RPL23A) | 5 | U37230 | + | + | + | + | | + | high in many libraries |
| ribosomal protein L26 (RPL26) | 8 | X69392 | + | + | + | + | + | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| ribosomal protein L27 (RPL27) | 6 | L05094 | + | + | + | + | | + | |
| ribosomal protein L27a (RPL27A) | 10 | U14968 | + | + | + | + | + | + | |
| ribosomal protein L28 (RPL28) | 6 | U14969 | + | + | + | + | | + | |
| ribosomal protein L29 (RPL29) | 6 | U10248 | + | + | + | + | + | + | |
| ribosomal protein L3 (RPL3) | 81 | | + | + | + | + | + | + | high in many libraries |
| ribosomal protein L3 homologue | 81 | X06323 | | | | | | | |
| ribosomal protein L30 (RPL30) | 6 | X79238 | + | + | + | + | + | + | high in lymphoma |
| ribosomal protein L30 (RPL30) (low score) | 1 | X79238 | | | | | | | |
| ribosomal protein L31 (RPL31) | 10 | X15940 | + | + | + | + | + | + | High in alveolar rhabdomyosarcoma |
| ribosomal protein L32 (RPL32) | 3 | X03342 | + | + | + | + | + | + | |
| ribosomal protein L33-like (RPL33L) | 1 | AF047440 | | + | + | + | | + | |
| ribosomal protein L34 (RPL34) | 5 | L38941 | + | + | + | + | + | | |
| ribosomal protein L34 (RPL34) (low match) | 1 | L38941 | | | | | | | |
| ribosomal protein L37 (RPL37) | 5 | D23661 | + | + | + | + | + | + | high in barstead prostate |
| ribosomal protein L37a | 4 | X66699 | + | + | + | + | + | + | high in many libraries |
| ribosomal protein L38 (PRL38) | 1 | Z26876 | + | + | + | + | + | + | high in many libraries |
| ribosomal protein L4 (RPL4) | 27 | D23660 | + | + | + | + | + | + | high in many libraries |
| ribosomal protein L41 (RPL41) | 4 | AF026844 | + | + | + | + | + | + | high in many libraries |
| ribosomal protein L5 (RPL5) | 14 | U14966 | + | + | + | + | + | + | High in alveolar rhabdomyosarcoma |
| ribosomal protein L5 (RPL5) (low match) | 1 | U14966 | | | | | | | |
| ribosomal protein L6 (RPL6) | 7 | X69391 | + | + | + | + | + | + | high in many libraries |
| ribosomal protein L7 (RPL7) | 14 | X52967 | + | + | + | + | + | + | high in conorm |
| ribosomal protein L7a (RPL7A) | 15 | M36072 | + | + | + | + | + | + | High in uterus, and seminoma |
| ribosomal protein L8 (RPL8) | 5 | Z28407 | + | + | + | + | + | + | high in ovary |
| ribosomal protein L9 (RPL9) | 10 | U09953 | | + | + | + | + | + | |
| ribosomal protein S10 (RPS10) | 5 | U14972 | + | + | + | + | + | + | high in many libraries |
| ribosomal protein S11 (RPS11) | 4 | X06617 | + | + | + | + | + | + | high in many libraries |
| ribosomal protein S11 (RPS11) (low match) | 1 | AB007152 | | | | | | | |
| ribosomal protein S12 (RPS12) | 3 | X53505 | + | + | + | + | + | + | high in many libraries |
| ribosomal protein S13 (RPS13) | 2 | L01124 | + | + | + | + | + | | |
| ribosomal protein S14 (RPS14) | 12 | M13934 | + | + | + | + | + | | |
| ribosomal protein S15 (RPS15) | 2 | M32405 | + | + | + | + | + | | |
| ribosomal protein S16 (RPS16) | 3 | M60854 | + | + | + | + | + | + | High in prostate invasive tumor |
| ribosomal protein S17 (RPS17) | 2 | M13932 | + | + | + | + | + | + | high in many libraries |
| ribosomal protein S18 | 8 | X69150 | | | | | | | |
| ribosomal protein S19 (RPS19) | 7 | M81757 | + | + | + | + | + | + | high in many libraries |
| ribosomal protein S2 (RPS2) | 4 | X17206 | + | + | + | + | + | + | high in many libraries |
| RIBOSOMAL PROTEIN S2 (RPS4) | 2 | P15880 | | | | | | | |
| ribosomal protein S20 (RPS20) | 7 | L06498 | + | + | + | + | + | + | high in many libraries |
| ribosomal protein S21 (RPS21) | 3 | L04483 | + | + | + | + | + | + | high in CD34+/CD38− hematopoietic cells and skin tumor |

TABLE 2-continued

Comparison of 1,800 Unique Genes Identified in the Blood Cell cDNA Library to Genes
Previously Identified in Specific Tissues

| Gene Identification | No. of ESTs | Accession No. | Bl | Br | H | K | Li | Lu | Tissue Distribution |
|---|---|---|---|---|---|---|---|---|---|
| ribosomal protein S23 (RPS23) | 3 | D14530 | | + | + | + | | + | |
| ribosomal protein S24 (RPS24) | 7 | M31520 | + | + | + | + | + | + | high in uterus |
| ribosomal protein S25 (RPS25) | 3 | M64716 | + | + | + | + | + | + | high in barstead prostate |
| ribosomal protein S26 (RPS26) | 2 | X69654 | | + | + | + | + | + | |
| ribosomal protein S27 ((metallopanstimulin 1) (RPS27) | 5 | U57847 | + | + | + | + | + | + | |
| ribosomal protein S28 (RPS28) | 3 | U58682 | + | + | + | + | | + | |
| ribosomal protein S29 (RPS29) | 2 | U14973 | + | + | + | + | + | | |
| ribosomal protein S3 (RPS3) | 9 | X55715 | + | + | + | + | + | + | high in many libraries |
| ribosomal protein S3 (RPS3) (low match) | 1 | U14990 | | | | | | | |
| ribosomal protein S3A (RPS3A) | 21 | Z83334 | | + | + | + | + | + | high in many libraries |
| ribosomal protein S3A (RPS3A) (low score) | 1 | M77234 | | | | | | | |
| ribosomal protein S4, X-linked (RPS4X) | 9 | M58458 | + | + | + | + | | + | high in ovary and Synovial sarcoma |
| ribosomal protein S4, Y-linked (RPS4Y) | 2 | M58459 | + | + | + | + | + | + | |
| ribosomal protein S5 (RPS5) | 4 | U14970 | + | + | + | + | + | + | high in lymphoma |
| RIBOSOMAL PROTEIN S6 (PHOSPHOPROTEIN NP33) | 1 | P10660 | | | | | | | |
| ribosomal protein S6 (RPS6) | 22 | M20020 | + | + | + | + | + | + | |
| ribosomal protein S6 (RPS6) (non-exact 86%) | 1 | M77232 | | | | | | | |
| ribosomal protein S6 kinase, 90 kD, polypeptide 1 (RPS6KA1) | 3 | L07597 | + | + | + | + | | + | |
| ribosomal protein S6 kinase, 90 kD, polypeptide 2 (RPS6KA2) | 1 | X85106 | | | | | | | |
| ribosomal protein S7 (RPS7) | 4 | Z25749 | | + | + | + | + | + | |
| ribosomal protein S8 (RPS8) | 6 | X67247 | | + | + | + | + | + | |
| ribosomal protein S9 (RPS9) | 8 | U14971 | | | | | | | colon tumor |
| ribosomal protein, large, P0 (RPLP0) | 18 | M17885 | T | | + | | | + | |
| ribosomal protein, large, P1 (RPLP1) | 12 | M17886 | T | + | + | | + | | |
| ribosomal RNA 18S (=M10098; K03432) (=polyadenylating sequence) | 11 | X03205 | | | | | | | |
| ribosomal RNA 28S | 2 | M11167 | | | | | | | |
| ribosomal RNA, 16S | 1 | U25123 | | | | | | | |
| ring finger protein (non-exact 58%) | 1 | AJ001019 | | | | | | | |
| ring finger protein 3 (RNF3) | 1 | AJ001019 | | | | | | | |
| ring finger protein 4 (RNF4) | 3 | AB000468 | | + | + | + | | + | |
| ring zinc-finger protein (ZNF127-Xp) | 3 | U41315 | | + | + | + | | + | |
| RNA (guanine-7-) methyltransferase (RNMT) | 1 | AB007858 | | + | + | + | | + | |
| RNA binding motif protein 5 (RBM5) | 4 | U23946 | + | + | + | + | | + | |
| RNA binding motif, single stranded interacting protein 2 (RBMS2) | 1 | D28483 | | + | | + | | + | |
| RNA helicase (putative), (Myc-regulated DEAD box protein) (MRD8) | 1 | X98743 | + | + | + | + | | + | |
| RNA helicase-related protein | 1 | AF083255 | | + | + | + | | + | |
| RNA pol II largest subunit | 2 | X74872 | | | | | | | |
| RNA polymerase I subunit (RPA40) | 1 | AF008442 | | + | + | | | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| RTVP-1 protein | 2 | X91911 | + | + | + | + | + | |
| S100 calcium-binding protein A10 (annexin II ligand, calpactin I, light polypeptide (p11)) (S100A10) | 2 | M81457 | | | + | | + | + |
| S100 calcium-binding protein A11 (calgizzarin) (S100A11) | 1 | X80201 | | + | + | + | | + |
| S100 calcium-binding protein A4 (calcium protein, calvasculin, metastasin, murine placental homolog)(S100A4) | 3 | M80563 | B | | + | | + | |
| S100 calcium-binding protein A8 (calgranulin A) (S100A8) | 7 | M21005 | | | + | + | | + high in bone marrow |
| S100 calcium-binding protein A9 (calgranulin B) (S100A9) | 14 | X06233 | | | + | + | | high in invasive larynx squamous cell carcinoma |
| S164 gene | 1 | AF109907 | | | | | | |
| S-adenosylmethionine decarboxylase 1 (AMD1) | 3 | M88003 | + | + | + | + | | + |
| SB classII histocompatibility antigen alpha-chain | 5 | M27487 | + | + | + | + | | + |
| SC35-interacting protein 1 (SRRP129) | 5 | AF030234 | + | + | + | + | + | + |
| scaffold attachment factor B (SAFB) | 1 | U72355 | + | + | + | + | | + |
| scaffold attachment factor B (SAFB) (non-exact 78%) | 1 | U72355 | | | | | | |
| scRNA molecule, transcribed from Alu repeat | 1 | L13713 | | | | | | |
| SEC14 (S. cerevisiae)-like (SEC14L) | 4 | D67029 | | + | + | + | | + |
| SEC23-like protein B (SEC23B) | 2 | X97065 | + | + | + | + | | + |
| SEC63 (SEC63) | 1 | AF100141 | | + | + | | | + |
| secreted protein, acidic, cysteine-rich (osteonectin) (SPARC) | 7 | M25746 | | + | + | + | + | + high in bone marrow stroma |
| secretory carrier membrane protein 1 (SCAMP1) | 1 | AF038966 | | + | | + | | |
| secretory carrier membrane protein 2 (SCAMP2) | 1 | AF005038 | + | + | + | + | + | + |
| secretory carrier membrane protein 3 (SCAMP3) | 1 | AF005039 | | | | | | |
| secretory granule proteoglycan core (clones lambda-PG[6,7,8]) | 1 | M33649 | | | | | | |
| selectin L (lymphocyte adhesion molecule 1) (SELL) | 43 | X17519 | + | | | + | | + |
| selectin P ligand (SELPLG) | 13 | U02297 | + | + | | | | |
| sema domain, immunoglobulin domain (Ig), transmembrane domain (TM) and short cytoplasmic domain, (semaphorin) 4D (SEMA4D) | 2 | U60800 | | + | | + | | + |
| Ser/Arg-related nuclear matrix protein (plenty of prolines 101-like) (SRM160) | 4 | AF048977 | | + | + | + | | + |
| serine palmitoyltransferase subunit I (SPTI) | 1 | Y08685 | | | + | + | | + |
| serine palmitoyltransferase, subunit II (LCB2) | 1 | AB011098 | + | + | + | + | | + |
| serine protease | 1 | J02907 | | | | | | |
| serine protease inhibitor, Kunitz type, 2 (SPINT2) | 1 | U78095 | + | + | + | + | | + |
| serine/threonine kinase 10 (STK10) | 1 | AB015718 | + | + | + | + | | |
| serine/threonine kinase 19 (STK19) | 1 | L26260 | + | + | + | | | |
| serine/threonine kinase 4 (STK4) | 1 | U18297 | | | + | | | + |

TABLE 2-continued

Comparison of 1,800 Unique Genes Identified in the Blood Cell cDNA Library to Genes
Previously Identified in Specific Tissues

| Gene Identification | No. of ESTs | Accession No. | Bl | Br | H | K | Li | Lu |
|---|---|---|---|---|---|---|---|---|
| serine/threonine protein kinase KKIALRE (KKIALRE) | 1 | X66358 | | + | + | + | | + |
| serine/threonine protein-kinase (NIK) | 1 | Y10256 | | + | + | + | | |
| SERINE/THREONINE-PROTEIN KINASE RECEPTOR R3 PRECURSOR (SKR3) | 1 | P37023 | | | | | | |
| serologically defined colon cancer antigen 16 (NY-CO-16) | 2 | AF039694 | | | | | | |
| serologically defined colon cancer antigen 33 (SDCCAG33) | 1 | AF039698 | B, T | + | + | | + | |
| serologically defined colon cancer antigen 33 (SDCCAG33) (low score) | 1 | AF039698 | | | | | | |
| serologically defined colon cancer antigen 33 (SDCCAG33) (low score) | 1 | AF039698 | | | | | | |
| serum deprivation response (phosphatidylserine-binding protein) (SDPR) (=S67386) | 1 | AF085481.1 | | | | | | |
| serum/glucocorticoid regulated kinase (SGK) | 2 | Y10032 | + | + | + | + | | + |
| SET domain, bifurcated 1 (SETDB1) | 2 | D31891 | + | + | + | | | + |
| SH2 domain protein 1A, Duncan's disease lymphoproliferative syndrome) (SH2D1A) | 1 | AF073019 | T | | | | | + |
| SH3 binding protein (SAB) | 2 | AB005047 | + | + | + | + | | + |
| SH3 domain protein 1B (SH3D1B) | 4 | U61167 | + | | | + | | + |
| SH3BGR PROTEIN (=21-GLUTAMIC ACID-RICH PROTEIN; 21-GARP) (non-exact 82% aa) | 1 | P55822 | | | | | | |
| SH3-binding domain glutamic acid-rich protein like (SH3BGRL) | 1 | AF042081 | + | + | + | + | | + |
| SH3-domain GRB2-like 1 (SH3GL1) | 1 | U65999 | + | + | + | + | | + |
| SHC (Src homology 2 domain-containing) transforming protein 1 (SHC1) | 2 | X68148 | | + | + | + | | + |
| siah binding protein 1 (SiahBP1) | 2 | U51586 | | + | + | + | | + |
| siah binding protein 1 (SiahBP1) (non-exact, 69%) | 1 | U51586 | | | | | | |
| Sialomucin CD164 (CD164) | 9 | D14043 | | | | | | |
| sialophorin (gpL115, leukosialin, CD43) (SNP) | 2 | J04536 | | | | | | |
| sialyltransferase (STHM) | 1 | U14550 | | | + | + | | + |
| sialyltransferase 1 (beta-galactoside alpha-2,6-sialyltransferase) (SIAT1) | 2 | X17247 | + | + | + | + | + | + |
| sialyltransferase 4A (beta-galactosidase alpha-2,3-sialyltransferase) (SIAT4A) | 1 | AF059321 | B | + | + | | + | + |
| sialyltransferase 8 (alpha-2,8-polysialyltransferase) D (SIAT8D) | 1 | L41680 | | + | | | | |
| signal peptidase 25 kDa subunit | 1 | L38950 | | | | | | |
| signal recognition particle 14 kD (homologous Alu RNA-binding protein) (SRP14) | 1 | X73459 | + | + | + | + | + | + |
| signal recognition particle 54 kD (SRP54) | 1 | U51920 | | | + | + | | + |

TABLE 2-continued

Comparison of 1,800 Unique Genes Identified in the Blood Cell cDNA Library to Genes Previously Identified in Specific Tissues

| | | | Tissue Distribution | | | | | |
|---|---|---|---|---|---|---|---|---|
| Gene Identification | No. of ESTs | Accession No. | Bl | Br | H | K | Li | Lu |
| signal recognition particle 9 kD (SRP9) | 2 | U20998 | | + | + | + | + | + |
| signal recognition particle receptor ('docking protein') SRPR | 5 | X06272 | | | | | | |
| signal regulatory protein, beta, 1 (SIRP-BETA-1) | 5 | Y10376 | | + | | | | + |
| signal sequence receptor, alpha (translocon-associated protein alpha) (SSR1) | 2 | Z12830 | | | | + | | + |
| signal sequence receptor, beta (translocon-associated protein beta) (SSR2) | 2 | X74104 | + | + | + | + | | + |
| signal transducer and activator of transcription (STAT5A) | 4 | L41142 | + | + | + | + | + | + |
| signal transducer and activator of transcription 2, 113 KD (STAT2) | 1 | U18671 | | | | | | + |
| signal transducer and activator of transcription 3 (acute-phase response factor) (STAT3) | 3 | L29277 | | | | | | |
| signal transducer and activator of transcription 5A (STAT5A) | 2 | U48730 | + | + | + | + | + | + |
| signal transducing adaptor molecule (SH3 domain and ITAM motif) 1 (STAM) | 1 | U43899 | | | | | | |
| silencing mediator of retinoid and thyroid hormone action (SMRT) | 1 | U37146 | | | | | | |
| similar to beta-transducin superfamily proteins (SAZD) | 1 | U02609 | + | + | + | | | + |
| similar to S. cerevisiae SSM4 (TEB4) | 1 | AB011169 | + | + | + | | | + |
| similar to yeast pre-mRNA splicing factors, Prp1/Zer1 and Prp6 | 1 | AF026031 | + | + | + | + | | + |
| SIT protein | 1 | AJ010059.1 | | | | | | |
| Sjogren syndrome antigen A1 (52 kD, ribonucleoprotein autoantigen SS-A/Ro) (SSA1) | 2 | M62800 | | | | | + | |
| Sjogren syndrome antigen A1 (52 kD, ribonucleoprotein autoantigen SS-A/Ro) (SSA1) (non-exact 63%) (match to zinc finger) | 1 | M62800 | | | | | | |
| SKAP55 homologue (SKAP-HOM) | 1 | AJ004886 | | + | + | + | | + |
| skb1 (S. pombe) homolog (SKB1) | 2 | AF015913 | + | + | + | + | | + |
| skeletal muscle abundant protein | 1 | X87613 | + | + | + | + | | + |
| SMA3 (SMA3) | 1 | X83300 | + | + | | + | | + |
| small acidic protein | 3 | U51678 | + | + | + | + | | + |
| small EDRK-rich factor 2 (SERF2) | 2 | Y10351 | + | + | + | + | + | + | high in fetal lung |
| small inducible cytokine A5 (RANTES) (SCYA5) | 2 | M21121 | + | + | + | + | + | + | high in many libraries |
| small inducible cytokine subfamily C, member 2 (SCYC2) | 1 | D63789 | | | | | | |
| small nuclear ribonucleoprotein polypeptide B" (SNRPB2) | 2 | M15841 | | + | + | | | + |
| small nuclear ribonucleoprotein polypeptide N (SNRPN) | 4 | J04615 | + | + | + | + | + | + |
| small nuclear ribonucleoprotein polypeptides B and B1 (SNRPB) | 2 | J04564 | + | + | + | | | + |
| small nuclear RNA activating complex, polypeptide 5, 19 kD (SNAPC5) | 1 | AF093593 | + | + | + | + | | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| smallest subunit of ubiquinol-cytochrome c reductase | 1 | D55636 | + | + | + | + | + | + | high in fetal lung |
| SMC (mouse) homolog, X chromosome (SMCX) | 1 | L25270 | + | + | + | + | | + | |
| SMT3B protein (2) | 2 | X99585 | + | + | + | + | + | + | |
| SNARE protein (YKT6) (low match) | 1 | U95735 | | | | | | | |
| SNC19 | 1 | U20428 | | | | | | | |
| SNC73 protein (SNC73) | 2 | J00220 | + | + | | + | + | + | high in many libraries |
| solute carrier family 1 (neutral amino acid transporter), member 5 (SLC1A5) | 2 | U53347 | | + | | + | | + | |
| Solute carrier family 11 (proton-coupled divalent metal ion transporters), member 1 (SLC11A1) | 7 | D50403 | + | | | | | | |
| solute carrier family 17 (sodium phosphate), member 3 (SLC17A3) | 1 | U90545 | | | | + | | | |
| solute carrier family 19 (folate transporter), member 1 (SLC19A1) | 1 | U17566 | B, lymphoma | + | | + | | | |
| solute carrier family 2 (facilitated glucose transporter), member 1 (SLC2A1) | 1 | K03195 | + | + | + | + | + | + | |
| solute carrier family 23 (nucleobase transporters), member 2 (SLC23A2) | 3 | D87075 | | + | + | + | | + | |
| solute carrier family 25 (mitochondrial carrier; oxoglutarate carrier), member 11 (SLC25A11) | 1 | AF070548 | B, T | + | + | | + | + | |
| solute carrier family 31 (copper transporters), member 2 (SLC31A2) | 3 | U83461 | | + | | + | | | |
| solute carrier family 4, anion exchanger, member 2 (erythrocyte membrane protein band 3-like 1) (SLC4A2) | 1 | X62137 | | + | + | | | + | |
| solute carrier family 4, sodium bicarbonate cotransporter, member 8 (SLC4A8) | 1 | AB018282 | | + | | | | | |
| solute carrier family 7 (cationic amino acid transporter, y+ system), member 5 (SLC7A5) | 2 | M80244 | T, W | + | + | + | | | |
| solute carrier family 7 (cationic amino acid transporter, y+ system), member 6 (SLC7A6) | 3 | D87432 | + | + | + | | | + | |
| solute carrier family 7 (cationic amino acid transporter, y+ system), member 6 (SLC7A6) (non-exact 77%) | 1 | D87432 | | | | | | | |
| solute carrier family 9 (sodium/hydrogen exchanger), isoform 6 (SLC9A6) | 1 | AF030409 | | + | + | + | | + | |
| somatic cytochrome c (HCS) | 2 | M22877 | | | | | | | |
| SON DNA binding protein (SON) | 2 | X63753 | | + | + | + | | + | |
| son of sevenless (Drosophila) homolog 1 (SOS1) | 1 | L13858 | + | + | | + | | | |
| sorcin (SRI) | 1 | M32886 | | | | | | | |
| sortilin 1 (SORT1) | 2 | X98248 | | + | | + | | + | |
| sortilin-related receptor, L(DLR class) A repeats-containing (SORL1) | 6 | Y08110 | | | | | | | |
| sorting nexin 1 (SNX1) | 3 | U53225 | + | + | + | + | | + | |
| sorting nexin 2 (SNX2) | 2 | AF043453 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| sorting nexin 6 (SNX6) (=U83194.1 TRAF4-associated factor 2) | 1 | AF121856.1 | | | | | | |
| Sp3 transcription factor (SP3) | 1 | X68560 | + | + | + | + | | + |
| Sp3 transcription factor (SP3) | 4 | M97191 | + | + | + | + | | + |
| special AT-rich sequence binding protein 1 (binds to nuclear matrix/scaffold-associating DNA's) (SATB1) | 1 | M97287 | | | | | | |
| speckle-type POZ protein (SPOP) | 4 | AJ000644 | | | | | | |
| speckle-type POZ protein (SPOP) (non-exact) | 1 | AJ000644 | | | | | | |
| spectrin SH3 domain binding protein 1 (SSH3BP1) | 6 | U87166 | + | + | + | + | | |
| Spectrin, alpha, non-erythrocytic 1 (alpha-fodrin) (SPTAN1) | 2 | J05243 | | + | + | | | + |
| spermidine/spermine N1-acetyltransferase (SAT) | 11 | M55580 | | | | | | |
| spermidine/spermine N1-acetyltransferase (SAT) (non-exact, 84%) | 1 | U40369 | | | | | | |
| spermine synthase (SMS) | 1 | AD001528 | + | + | + | + | | + |
| SPF31 (SPF31) | 1 | AF083190 | + | + | + | + | | + |
| sphingomyelin phosphodiesterase 1, acid lysosomal (acid sphingomyelinase) (SMPD1) | 1 | X52679 | | + | + | + | | |
| SPINDLIN HOMOLOG (PROTEIN DXF34) | 1 | Q99865 | | | | | | |
| spinocerebellar ataxia 1 (olivopontocerebellar ataxia 1, autosomal dominant, ataxin 1) (SCA1) | 3 | X79204 | B | + | | + | | |
| spinocerebellar ataxia 2 (olivopontocerebellar ataxia 2, autosomal dominant, ataxin 2) (SCA2) | 1 | U70323 | B | | | + | | |
| spinocerebellar ataxia 7 (olivopontocerebellar atrophy with retinal degeneration) (SCA7) | 2 | AJ000517 | | + | | | | |
| spliceosome associated protein (SAP 145) | 3 | U41371 | | + | + | + | + | + |
| splicing factor (CC1.3) (CC1.3) | 2 | L10910 | + | + | + | + | + | + |
| splicing factor SRp40-1 (SRp40) | 7 | U30826 | + | + | + | + | + | + |
| splicing factor, arginine/serine-rich 11 (SFRS11) | 3 | M74002 | B | + | + | | + | + |
| splicing factor, arginine/serine-rich 7 (35 kD) (SFRS7) | 4 | L41887 | | + | + | + | | + |
| Src-like adapter protein (non-exact, 76% aa) | 1 | U30473 | | | | | | |
| Src-like-adapter (SLA) | 6 | D89077 | | + | + | + | | + |
| Src-like-adapter (SLA) (low match) | 1 | D89077 | | | | | | |
| Src-like-adapter (SLA) (low score) | 1 | U44403 | | | | | | |
| stannin (SNN) | 2 | AF030196 | + | + | + | + | | + |
| STAT induced STAT inhibitor 3 (SSI-3) | 1 | AB004904 | | | | + | | |
| STE20-like kinase 3 (MST-3) | 2 | AF024636 | + | + | + | + | | + |
| step II splicing factor SLU7 (SLU7) | 1 | AF101074 | | + | | + | + | + |
| steroid sulfatase | 1 | M17591 | | | | | | |
| steroid sulfatase (microsomal), arylsulfatase C, isozyme S (STS) | 1 | J04964 | | + | + | + | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| sterol carrier protein 2 (SCP2) | 1 | M55421 | | + | + | + | + | + |
| sterol O-acyltransferase (acyl-Coenzyme A: cholesterol acyltransferase) 1 (SOAT1) | 1 | AF059202 | | | | + | | |
| stimulated trans-acting factor (50 kDa) (STAF50) | 6 | X82200 | + | + | | + | | |
| Striatin, calmodulin-binding protein (STRN) (low match, 71% aa) | 1 | U17989 | | | | | | |
| Stromal antigen 2 (STAG2) | 2 | Z75331 | | | + | + | + | + |
| stromal interaction molecule 1 (STIM1) | 3 | U52426 | + | | + | + | + | + |
| structure specific recognition protein 1 (SSRP1) | 1 | M86737 | | + | + | + | | + |
| succinate dehydrogenase complex, subunit A, flavoprotein (Fp) (SDHA) | 5 | L21936 | | | | + | | |
| succinate dehydrogenase complex, subunit B, iron sulfur (Ip) (SDHB) | 1 | U17248 | + | + | + | + | | + |
| succinate dehydrogenase complex, subunit C, integral membrane protein, 15 kD (SDHC) | 1 | U57877 | + | + | + | + | | + |
| succinate dehydrogenase complex, subunit D, Integral membrane protein (SDHD) | 3 | AB006202 | | + | + | | + | |
| succinate-CoA ligase, GDP-forming, beta subunit (SUCLG2) | 1 | AF058954 | | + | + | + | + | + |
| succinyl CoA synthetase | 1 | Z68204 | | | | | | |
| sudD (suppressor of bimD6, *Aspergillus nidulans*) homolog (SUDD) | 2 | AF013591 | | + | | | + | + |
| sulfotransferase family 1A, phenol-preferring, member 1 (SULT1A1) | 1 | L19999 | | + | | | + | + |
| sulfotransferase family 1A, phenol-preferring, member 3 (SULT1A3) (non-exact 67%) | 1 | U37686 | | | | | | |
| superoxide dismutase 1, soluble (amyotrophic lateral sclerosis 1 (adult)) (SOD1) | 4 | X02317 | | + | + | | + | + |
| superoxide dismutase 2, mitochondrial (SOD2) | 5 | Y00985 | | + | + | + | + | + |
| supervillin (SVIL) | 2 | AF051851 | | | + | + | | + |
| suppression of tumorigenicity 5 (ST5) | 2 | U15131 | | + | | + | | + |
| suppression of tumorigenicity 5 (ST5) (non-exact 82%) | 1 | U15779 | | | | | | |
| suppressor of K+ transport defect 1 (SKD1) | 1 | AF038960 | | | + | + | | |
| suppressor of Ty (*S. cerevisiae*) 3 homolog (SUPT3H) | 1 | AF064804 | + | + | + | + | | + |
| suppressor of Ty (*S. cerevisiae*) 4 homolog 1 (SUPT4H1) | 2 | U38817 | + | + | + | + | | + |
| suppressor of Ty (*S. cerevisiae*) 5 homolog (SUPT5H) | 2 | U56402 | | + | | | | + |
| suppressor of Ty (*S. cerevisiae*) 6 homolog (SUPT6H) | 2 | U46691 | + | + | + | + | + | + |
| suppressor of variegation 3-9 (*Drosophila*) homolog 1 (SUV39H1) | 1 | AF019968 | | + | + | + | | |
| survival of motor neuron 1, telomeric (SMN1) | 1 | U18423 | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| SWI/SNF related, matrix associated, actin dependent regulator of chromatin, subfamily a, member 1 (SMARCA1) (non-exact, 75%) | 1 | M88163 | | | + | + | | + |
| SWI/SNF related, matrix associated, actin dependent regulator of chromatin, subfamily a, member 2 (SMARCA2) | 2 | D26155 | | + | | | | |
| SWI/SNF related, matrix associated, actin dependent regulator of chromatin, subfamily a, member 4 (SMARCA4) | 1 | D26156 | + | + | + | + | + | + |
| SWI/SNF related, matrix associated, actin dependent regulator of chromatin, subfamily c, member 2 (SMARCC2) | 4 | U66616 | + | + | + | + | + | + |
| SWI/SNF related, matrix associated, actin dependent regulator of chromatin, subfamily e, member 1 (SMARCE1) | 2 | AF035262 | B, W | + | + | | + | + |
| synaptobrevin-like 1 (SYBL1) | 1 | X95803 | | + | + | + | | + |
| synaptosomal-associated protein, 23 kD (SNAP23) | 2 | AJ011915 | | + | + | + | | + |
| syndecan binding protein (syntenin) (SDCBP) | 15 | AF006636 | + | + | + | + | | + |
| synovial sarcoma, translocated to X chromosome (SSXT) | 2 | X79201 | | + | | | | |
| syntaxin 16 | 1 | AF038897 | | | | | | |
| syntaxin 3A (STX3A) | 2 | U32315 | | + | | + | | + |
| syntaxin 6 (STX6) | 1 | AJ002078.1 | | | | | | |
| SYNTAXIN BINDING PROTEIN 3 (UNC-18 HOMOLOG 3) (UNC-18C) | 1 | O00186 | | | | | | |
| syntaxin-16C | 1 | AF008937 | | | | | | |
| SYT interacting protein (SIP) | 1 | AF080561 | | + | + | + | | + |
| T cell activation, increased late expression (TACTILE) | 4 | M88282 | | | | + | | |
| T cell receptor V alpha gene segment V-alpha-7 (clone IGRa11) | 2 | X58744 | | | | | | |
| T cell receptor V alpha gene segment V-alpha-w27 | 1 | X58740 | | | | | | |
| T3 receptor-associating cofactor-1 | 5 | S83390 | + | + | + | + | + | + |
| tafazzin (cardiomyopathy, dilated 3A (X-linked); endocardial fibroelastosis 2; Barth syndrome) (TAZ) | 1 | X92763 | + | + | | + | | + |
| TAFII100 protein (non-exact 53%) | 1 | U80191 | | | | | | |
| tankyrase, TRF1-interacting ankyrin-related ADP-ribose polymerase (TNKS) | 1 | AF082556 | | + | + | + | | + |
| TAP1, TAP2, LMP2, LMP7 and DOB | 1 | X66401 | | | | | | |
| TAR DNA-binding protein-43 | 6 | U23731 | + | + | + | + | | + |
| Tat interactive protein (60 kD) (TIP60) | 2 | U40989 | + | + | + | + | | + |
| TATA box binding protein (TBP)-associated factor, RNA polymerase II, C1, 130 kD (TAF2C1) (non-exact, 55%) | 1 | O00268 | | | | | | |
| TATA box binding protein (TBP)-associated factor, RNA polymerase II, F, 55 kD (TAF2F) | 4 | X97999 | | + | + | + | + | + |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| TATA box binding protein (TBP)-associated factor, RNA polymerase II, G, 32 kD (TAF2G) | 2 | U21858 | | + | + | + | + | + | |
| TATA box binding protein (TBP)-associated factor, RNA polymerase II, I, 28 kD (TAF2I) | 1 | D63705 | + | + | + | + | | + | |
| Tax1 (human T-cell leukemia virus type I) binding protein 1 (TAX1BP1) | 1 | U33821 | | + | + | + | + | + | |
| T-box 2 (TBX2) (non-exact 77%) | 1 | U28049 | | | | + | + | | + |
| TBP-associated factor 172 (TAF-172) | 1 | AJ001017 | + | | | + | | + | |
| T-cell death-associated gene 8 (TDAG8) | 1 | U95218 | | | | + | | | |
| T-cell leukemia/lymphoma 1A (TCL1A) | 1 | X82240 | + | | | | | | |
| T-cell leukemia/lymphoma 1A (TCL1A) (low match) | 1 | X82240 | | | | | | | |
| T-cell receptor (delta D2-J1-region) (clone K3B) | 1 | M22197 | | | | | | | |
| T-cell receptor (V beta 5.1, J beta 1.5, C beta 1) (low match) | 1 | M97705 | | | | | | | |
| T-cell receptor alpha delta (=M94081) | 2 | AE000662 | | | | | | | |
| T-cell receptor alpha enhancer-binding protein, short form (=X58636 Mouse LEF1 lymphoid enhancer binding factor 1 (=D16503)) | 1 | B39625 | | | | | | | |
| T-cell receptor delta gene D2-J1-region, clone K3B | 1 | M22197 | | | | | | | |
| T-cell receptor germline beta chain gene V-region (V) V-beta-MT1-1 | 1 | M11955 | | | | | | | |
| T-cell receptor germline beta-chain gene J2.1 exon | 1 | M14159 | + | | | | | | only in blood |
| T-cell receptor germline delta-chain D-J region | 2 | M22152 | | | | | | | |
| T-cell receptor interacting molecule (TRIM) protein | 2 | AJ224878 | | | | | | + | |
| T-cell receptor rearranged delta-chain, V-region (V-delta 3-J) | 1 | M21784 | | | | | | | |
| T-cell receptor, alpha (V, D, J, C) (TCRA) | 3 | AE000660 | + | | + | + | + | + | |
| T-cell receptor, beta cluster (TCRB) | 3 | L34740 | + | | + | + | + | + | high in pancreas |
| T-cell receptor, delta (V, D, J, C) (TCRD) | 2 | X73617 | | | + | + | | + | |
| T-cell, immune regulator 1 (TCIRG1) | 3 | U45285 | | | | | | | only found in tumor |
| TCF-1 mRNA for T cell factor 1 | 1 | X59870 | | | | | | | |
| TCF-1 mRNA for T cell factor 1 (splice form B) (low match) | 1 | X59870 | | | | | | | |
| T-COMPLEX PROTEIN 1, ETA SUBUNIT (TCP-1-ETA) (CCT-ETA) (HIV-1 NEF INTERACTING PROTEIN) | 1 | Q99832 | | | | | | | |
| T-COMPLEX PROTEIN 1, THETA SUBUNIT (TCP-1-THETA) (CCT-THETA) (KIAA0002) | 1 | P50990 | | | | | | | |
| TCR eta = T cell receptor(eta-exon) | 1 | S94421 | | | | | | | |
| TCR V Beta 13.2 | 1 | X75419 | | | | | | | |
| TERA | 1 | AC004472 | | | | | | | |
| testis enhanced gene transcript (TEGT) | 33 | X75861 | + | + | + | + | + | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| tetracycline transporter-like protein (TETRAN) | 2 | L11669 | | + | + | + | | + | |
| tetratricopeptide repeat domain 1 (TTC1) | 1 | U46570 | + | + | + | + | | + | |
| tetratricopeptide repeat domain 2 (TTC2) | 1 | U46571 | | + | | + | | + | |
| tetratricopeptide repeat domain 3 (TTC3) | 1 | D84296 | + | + | + | + | | + | |
| TGFB1-induced anti-apoptotic factor 1 (TIAF1) | 1 | D86970 | + | + | + | + | | + | |
| thioredoxin reductase 1 (TXNRD1) | 3 | S79851 | | + | + | + | | + | |
| THIOREDOXIN-DEPENDENT PEROXIDE REDUCTASE PRECURSOR, mitochondrial (ANTI-OXIDANT PROTEIN 1) (AOP-1) | 1 | P30048 | | | | | | | |
| threonyl-tRNA synthetase (TARS) | 1 | M63180 | | + | + | + | | + | |
| thrombin inhibitor | 1 | Z22658 | | | | | | | |
| thrombospondin 1 (THBS1) | 2 | X04665 | | + | + | + | + | + | |
| thromboxane A synthase 1 (platelet, cytochrome P450, subfamily V) (TBXAZ1) | 1 | M80647 | | + | | + | + | + | |
| thymidine kinase 2, mitochondrial (TK2) | 2 | X76104 | | + | + | | + | | |
| thymidylate kinase (CDC8) | 1 | L16991 | | + | + | + | | + | |
| thymine-DNA glycosylase (TDG) | 2 | U51166 | + | + | + | + | | + | |
| Thymosin, beta 10 (TMSB10) | 2 | M20259 | + | + | + | + | + | + | |
| thymosin, beta 4, X chromosome (TMSB4X) | 29 | M17733 | | + | + | + | | + | |
| thyroid autoantigen 70 kD (Ku antigen) (G22P1) | 7 | J04611 | | | | | | | |
| thyroid hormone receptor coactivating protein (SMAP) | 1 | AF016270 | | + | | + | | + | |
| thyroid hormone receptor interactor 7 (TRIP7) | 2 | L40357 | | + | + | + | | + | |
| thyroid hormone receptor interactor 8r (TRIP8) | 4 | L40411 | | + | | | | | |
| thyroid hormone receptor-associated protein, 230 kDa subunit (TRAP230) | 1 | D83783 | | | | | | | |
| thyroid receptor interacting protein 15 (TRIP15) | 2 | L40388 | + | + | + | + | | | |
| TI-227H | 1 | D50525 | | | | | | | |
| TIA1 cytotoxic granule-associated RNA-binding protein (TIA1) | 1 | M77142 | | + | + | + | | + | |
| tissue inhibitor of metalloproteinase 1 (erythroid potentiating activity, collagenase inhibitor) (TIMP1) | 1 | X02598 | + | + | + | + | + | + | |
| tissue inhibitor of metalloproteinase 2 (TIMP2) | 1 | M32304 | + | + | + | + | | + | high in placenta |
| tissue specific transplantation antigen P35B (TSTA3) | 1 | U58766 | + | + | + | + | | + | |
| titin (TTN) | 1 | X64697 | + | + | + | + | | + | high in muscle |
| TNF receptor-associated factor 2 (TRAF2) | 1 | U12597 | | + | + | + | | + | |
| TNF receptor-associated factor 3 (TRAF3) | 1 | AF110908.1 | | + | | | | | |
| TNF receptor-associated factor 6 (TRAF6) (low match) | 1 | U78798 | | | | | | | |
| toll-like receptor 1 (TLR1) | 1 | U88540 | | | | + | | | |
| toll-like receptor 2 (TLR2) | 1 | U88878 | + | + | | + | | + | |
| toll-like receptor 4 (TLR4) | 1 | U88880 | | + | | + | | | |
| toll-like receptor 5 (TILR5) | 1 | AF051151 | | + | | + | | | |
| topoisomerase (DNA) I (TOP1) | 1 | J03250 | | + | + | + | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | |
|---|---|---|---|---|---|---|---|---|
| | | | Bl | Br | H | K | Li | Lu |
| topoisomerase (DNA) II beta (180 kD) (TOP2B) | 2 | X68060 | + | + | + | + | | + |
| topoisomerase (DNA) III beta (TOP3B) | 3 | D87012 | + | | | | | |
| TR3beta | 1 | D85245 | | + | | | | |
| TRAF family member-associated NF-kB activator (TANK) | 3 | U63830 | + | + | + | + | + | + |
| TRANSALDOLASE | 1 | P37837 | | | | | | |
| transaldolase 1 (TALDO1) | 4 | L19437 | | + | + | + | + | + |
| transaldolase-related protein | 1 | AF010398 | | | | | | |
| transcobalamin II (TCII) | 1 | AF047576 | | | | | | |
| transcription elongation factor B (SIII), polypeptide 1-like (TCEB1L) | 2 | Z47087 | + | + | + | + | | + |
| transcription elongation factor B (SIII), polypeptide 3 (110 kD, elongin A) (TCEB3) | 1 | L47345 | + | + | + | + | + | + |
| transcription factor 12 (HTF4, helix-loop-helix transcription factors 4) (TCF12) | 1 | M83233 | + | + | + | + | | + |
| transcription factor 17 (TCF17) | 2 | D89928 | | + | | + | | |
| transcription factor 4 (TCR4) | 2 | X52079 | | + | + | + | | + |
| transcription factor 6-like 1 (mitochondrial transcription factor 1-like) (TCF6L1) | 2 | M62810 | + | + | + | + | | |
| transcription factor 7-like 2 (T-cell specific, HMG-box) (TCF7L2) | 1 | Y11306 | | + | + | + | | + |
| transcription factor binding to IGHM enhancer 3 (TFE3 | 1 | X96717 | + | + | + | + | | + |
| transcription factor IL-4 Stat | 7 | AF067575 | + | + | + | + | + | + |
| transcription factor IL-4 Stat (low match) | 1 | U16031 | | | | | | |
| transcription factor ISGF-3 (=M97936) | 4 | M97935 | | | | | | |
| transcription factor REST | 1 | A56138 | | | | | | |
| transcription factor TFIID | 1 | Z22828 | | | | | | |
| transcriptional adaptor 2 (ADA2, yeast, homolog)-like (TADA2L) | 1 | AF064094 | | | | | | |
| transcriptional intermediary factor 1 (TIF1) (non-exact 72%) | 1 | AF009353 | | | | | | |
| transducin (beta)-like 1 (TBL1) | 1 | Y12781 | + | + | + | + | | + |
| transducin-like enhancer of split 3, homolog of *Drosophila* E(sp1) (TLE3) | 1 | M99438 | + | + | | | | |
| Transformation/transcription domain-associated protein (TRRAP) | 1 | AF076974 | + | + | + | + | | + |
| transformation-sensitive, similar to *Saccharomyces cerevisiae* STI1 (STI1L) | 2 | M86752 | | + | + | + | | + |
| transforming growth factor beta-activated kinase 1 (TAK1) (non-exact 78%) | 1 | AB009356 | | | | | | |
| transforming growth factor beta-stimulated protein TSC-22 (TSC22) | 3 | AJ222700 | + | + | + | + | | + |
| transforming growth factor, beta receptor III (betaglycan, 300 kD) (TGFBR3) | 1 | L07594 | | + | + | + | | + |
| transforming growth factor, beta-induced, 68 kD (TGFBI) | 2 | 4507466 | + | + | + | + | + | + |
| TRANSFORMING GROWTH FACTOR-BETA INDUCED PROTEIN IG-H3 PRECURSOR (BETA IG-H3) | 2 | Q15582 | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| transforming, acidic coiled-coil containing protein 1 (TACC1) (non-exact 70%) | 1 | AF049910 | | | | | | | |
| transgelin 2 (TAGLN2) | 14 | D21261 | + | + | + | + | + | + | |
| transgelin 2 (TAGLN2) (non-exact) | 1 | D21261 | | | | | | | |
| trans-Golgi network protein (46, 48, 51 kD isoforms) (TGN51) | 2 | AF029316 | | + | | + | | | |
| transient receptor potential channel 1 (TRPC1) | 1 | X89066 | | + | + | + | | + | |
| transketolase (Wernicke-Korsakoff syndrome) (TKT) | 7 | L12711 | | + | + | + | | + | |
| translation factor sui1 homolog (GC20) | 1 | AF064607 | | + | + | + | + | + | |
| translin (TSN) | 3 | X78627 | + | + | + | + | | + | |
| translin-associated factor X (TSNAX) | 1 | X95073 | | + | + | + | | + | |
| transmembrane glycoprotein (A33) | 1 | U79725 | | | | | | | |
| transmembrane protein (63 kD), endoplasmic reticulum/Golgi intermediate compartment (P63) | 1 | X69910 | + | + | + | + | | + | |
| transmembrane protein 1 (TMEM2) | 1 | AB001523 | | + | | + | | + | |
| TRANSMEMBRANE PROTEIN SEX PRECURSOR (non-exact 65%) | 1 | P51805 | | | | | | | |
| transmembrane trafficking protein (TMP21) | 2 | X97442 | + | + | + | + | + | + | |
| transporter 1, ABC (ATP binding cassette) (TAP1) | 3 | L21208 | + | + | + | + | | + | |
| Treacher Collins-Franceschetti syndrome 1 (TCOF1) | 2 | U40847 | + | + | + | + | | + | high in many libraries |
| triosephosphate isomerase 1 (TPI1) | 2 | X69723 | + | + | + | + | + | + | |
| tropomyosin | 2 | X04201 | | + | + | + | | + | |
| tropomyosin 4 (TPM4) | 2 | X05276 | + | + | + | + | | + | |
| TRPM-2 protein | 2 | M63376 | | | | | | | |
| tryptase I precursor (non-exact 64%)(=P20231) | 1 | A35863 | | | | | | | |
| tryptophan rich basic protein (WRB) | 1 | Y12478 | | | | | | | |
| tryptophanyl-tRNA synthetase (WARS) | 1 | X59892 | + | + | + | + | + | + | |
| Ts translation elongation factor, mitochondrial (TSFM) | 1 | L37936 | + | + | | + | | + | |
| ttopoisomerase (DNA) II beta (180 kD) | 1 | Z15115 | | + | + | | | + | |
| Tu translation elongation factor, mitochondrial (TUFM) | 4 | L38995 | | | | | | | |
| tuberous sclerosis 1 (TSC1) | 1 | AF013168 | | + | + | + | | + | |
| tuberous sclerosis 2 (TSC2) | 1 | X75621 | | + | + | + | | + | |
| tubulin, alpha 1 (testis specific) (TUBA1) | 1 | X06956 | | + | | + | | | |
| tubulin, alpha, ubiquitous (K-ALPHA-1) | 11 | K00558 | + | + | + | + | + | + | high in many libraries |
| tubulin, alpha, ubiquitous (K-ALPHA-1) (low match) | 1 | K00558 | | | | | | | |
| tubulin-specific chaperone c (TBCC) | 1 | U61234 | | + | + | + | | + | |
| tumor necrosis factor (ligand) superfamily, member 10 (TNFSF10) | 7 | U37518 | | + | + | + | | + | |
| tumor necrosis factor (ligand) superfamily, member 13 (TNFSF13) | 1 | AF046888 | + | + | | + | | + | |
| tumor necrosis factor (ligand) superfamily, member 14 (TNFSF14) | 1 | AF036581 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| tumor necrosis factor (ligand) superfamily, member 6 (TNFSF6) | 1 | D38122 | + | | | | | | Found only in library 386: T-cell lymphoma |
| tumor necrosis factor (ligand) superfamily, member 8 (TNFSF8) | 1 | L09753 | B only | | | | | | |
| tumor necrosis factor alpha-inducible cellular protein containing leucine zipper domains (FIP2) | 1 | AF061034 | | + | + | + | | + | |
| Tumor necrosis factor receptor superfamily member 7 (TNFRSF7) | 2 | M63928 | | + | | + | | | |
| tumor necrosis factor receptor superfamily, member 10b (TNFRSF10B) | 1 | AF016266 | | + | + | + | + | + | |
| tumor necrosis factor receptor superfamily, member 10c, decoy without an intracellular domain (TNFRSF10C) | 3 | AF012629 | | | | | + | | |
| tumor necrosis factor receptor superfamily, member 10d, decoy with truncated death domain (TNFRSF10D) (non-exact 84%) | 1 | AF023849 | | | | | | | found only in prostate |
| tumor necrosis factor receptor superfamily, member 12 (translocating chain-association membrane protein) (TNFRSF12) | 1 | U94508 | + | + | + | + | | + | |
| tumor necrosis factor receptor superfamily, member 14 (herpesvirus entry mediator) (TNFRSF14) | 1 | U70321 | + | + | + | + | | + | |
| tumor necrosis factor receptor superfamily, member 1B (TNFRSF1B) | 5 | U52165 | + | + | + | + | | + | |
| tumor necrosis factor receptor superfamily, member 6 (TNFRSF6) | 1 | X63717 | B, W | | | | | + | |
| tumor necrosis factor receptor superfamily, member 7 (TNFRSF7) | 1 | M63928 | + | + | | | | | |
| tumor necrosis factor, alpha-induced protein 2 (TNFAIP2) | 8 | M92357 | | + | + | + | | | |
| tumor necrosis factor, alpha-induced protein 3 (TNFAIP3) | 2 | M59465 | | | | | | | |
| tumor protein 53-binding protein, 1 (TP53BP1) | 1 | AF078776 | | + | + | + | | + | |
| tumor protein p53 (Li-Fraumeni syndrome) (TP53) | 1 | M14695 | + | + | | | | + | |
| Tumor protein p53-binding protein (TP53BPL) | 1 | U82939 | + | | | + | | + | |
| tumor protein, translationally-controlled 1 (TPT1) | 35 | X16064 | | | | | | | |
| tumor protein, translationally-controlled 1 (TPT1) (low score) | 1 | X16064 | | | | | | | |
| tumor rejection antigen (gp96) 1 (TRA1) | 9 | X15187 | + | + | + | + | + | + | |
| tumorous imaginal discs (Drosophila) homolog (TID1) | 2 | AF061749 | | + | | | | | |
| TXK tyrosine kinase (TXK) | 2 | L27071 | | | | | | | |
| type II integral membrane protein (NKG2-E) | 1 | AJ001685 | | | | + | | | found only in fetal liver/spleen |
| TYRO protein tyrosine kinase binding protein (TYROBP) | 3 | AF019562 | | | + | | | | |
| tyrosine 3-monooxygenase/tryptophan 5-monooxygenase activation protein, beta polypeptide (YWHAB) | 1 | X57346 | + | + | + | + | | + | high in ecnorm |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| tyrosine 3-monooxygenase/tryptophan 5-monooxygenase activation protein, zeta polypeptide (YWHAZ) | 1 | M86400 | | | | | | | |
| tyrosine 3-monooxygenase/tryptophan 5-monooxygenase activation protein, zeta polypeptide (YWHAZ) | 1 | M86400 | | | | | | | |
| Tyrosine kinase 2 (TYK2) | 3 | X54637 | | + | + | + | | + | |
| TYROSINE-PROTEIN KINASE ZAP-70 (70 KD ZETA-ASSOCIATED PROTEIN) (SYK-RELATED TYROSINE KINASE) | 2 | P43403 | | | | | | | |
| tyrosyl-tRNA synthetase (YARS) | 1 | U89436 | + | + | + | + | | + | |
| U1 small nuclear RNA | 1 | M14387 | | | | | | | |
| U19H snoRNA (=M63485 R. norvegicus matrin 3) | 1 | AJ224166 | | | | | | | |
| U2(RNU2) small nuclear RNA auxillary factor 1 (non-standard symbol) (U2AF1) | 1 | M96982 | + | + | + | | | + | |
| U22 snoRNA host gene (UHG) | 2 | U40580 | | | | | | | |
| U4/U6-associated RNA splicing factor (HPRP3P) | 4 | AF016370 | | + | + | + | | + | |
| U49 small nuclear RNA | 1 | X96649 | | | | | | | |
| U5 snRNP-specific protein (220 kD), ortholog of S. cerevisiae Prp8p (PRP8) | 1 | AB007510 | + | + | + | + | | + | |
| U5 snRNP-specific protein, 116 kD (U5-116 KD) | 4 | D21163 | + | + | + | + | | + | |
| U5 snRNP-specific protein, 200 kDa (DEXH RNA helicase family) (U5-200-KD) | 3 | Z70200 | | | | | | | |
| Uba80 mRNA for ubiquitin | 4 | S79522 | + | + | + | + | + | + | high in ovary |
| ubiquinol-cytochrome c reductase (6.4 kD) subunit (UQCR) | 1 | D55636 | + | + | + | + | + | + | high in fetal lung |
| UBIQUINOL-CYTOCHROME C REDUCTASE IRON-SULFUR SUBUNIT PRECURSOR (RIESKE IRON-SULFUR PROTEIN) (RISP) (low match) | 1 | P47985 | | | | | | | |
| ubiquitin A-52 residue ribosomal protein fusion product 1 (UBA52) | 2 | X56999 | | | | | | | |
| ubiquitin activating enzyme E1-like protein (GSA7) | 1 | AF094516 | | + | + | | | + | |
| ubiquitin C (UBC) | 5 | AB009010 | | + | + | + | + | + | high in ovary |
| ubiquitin carboxyl-terminal esterase L3 (ubiquitin thiolesterase) (UCHL3) | 1 | M30496 | + | + | + | + | | + | |
| ubiquitin fusion degradation 1-like (UFD1L) | 1 | U64444 | + | + | + | | | + | |
| ubiquitin protein ligase E3A (human papilloma virus E6-associated protein, Angelman syndrome) (UBE3A) | 1 | U84404 | B | + | + | | | + | |
| ubiquitin specific protease 10 (USP10) | 4 | D80012 | + | + | + | + | | + | |
| ubiquitin specific protease 11 (USP11) | 1 | U44839 | + | + | + | + | + | + | |
| ubiquitin specific protease 15 (USP15) | 3 | AB011101 | + | + | + | + | | + | |
| ubiquitin specific protease 19 (USP19) | 1 | AB020698 | | + | | | | | |
| ubiquitin specific protease 4 (proto-oncogene) (USP4) | 1 | AF017305 | B | + | + | | + | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu |
|---|---|---|---|---|---|---|---|---|
| ubiquitin specific protease 4 (proto-oncogene) (USP4) (non-exact, 66%) | 1 | AF017306 | | | | | | |
| ubiquitin specific protease 7 (herpes virus-associated) (USP7) | 1 | Z72499 | | + | + | + | | + |
| ubiquitin specific protease 8 (USP8) | 5 | D29956 | | + | + | + | | + |
| UBIQUITIN-ACTIVATING ENZYME E1 (A1S9 PROTEIN) (56%) | 1 | P22314 | | | | | | |
| ubiquitin-activating enzyme E1 (A1S9T and BN75 temperature sensitivity complementing) (UBE1) | 1 | M58028 | + | + | + | + | | + |
| ubiquitin-activating enzyme E1, like (UBE1L) | 1 | L34170 | + | + | | + | | + |
| UBIQUITIN-BINDING PROTEIN P62; phosphotyrosine independent ligand for the Lck SH2 domain p62 (P62) | 1 | U41806 | | | + | | + | |
| ubiquitin-conjugating enzyme E2 variant 1 (UBE2V1) | 2 | U49278 | + | + | + | + | + | + |
| ubiquitin-conjugating enzyme E2 variant 2 (UBE2V2) | 1 | X98091 | | | | | | |
| UBIQUITIN-CONJUGATING ENZYME E2-17 KD (UBIQUITIN-PROTEIN LIGASE) | 1 | Q16781 | | | | | | |
| ubiquitin-conjugating enzyme E2B (RAD6 homolog) (UBE2B) | 1 | M74525 | + | + | + | + | | + |
| ubiquitin-conjugating enzyme E2G 2 (homologous to yeast UBC7) (UBE2G2) | 1 | AF032456 | + | + | + | + | | + |
| ubiquitin-conjugating enzyme E2H (homologous to yeast UBC8) (UBE2H) | 1 | Z29328 | + | + | + | + | | + |
| ubiquitin-conjugating enzyme E2L 1 (UBE2L1) | 1 | X92962 | | + | + | | | + |
| ubiquitin-conjugating enzyme E2L 3 (UBE2L3) | 3 | AJ000519 | | + | + | + | | + |
| ubiquitin-conjugating enzyme E2L 6 (UBE2L6) | 4 | AF031141 | | + | + | + | + | + |
| ubiquitin-like 1 (sentrin) (UBL1) | 2 | U61397 | + | + | + | + | | + |
| UDP-N-acetyl-alpha-D-galactosamine:polypeptide N-acetylgalactosaminyltransferase 2 (GalNAc-T2) (GALNT2) | 2 | X85019 | | | | | | |
| UDP-N-acetyl-alpha-D-galactosamine:polypeptide N-acetylgalactosaminyltransferase 3 (GalNAc-T3) (GALNT3) (non-exact 65%) | 1 | X92689 | | | | | | |
| unactive progesterone receptor, 23 Kd (P23) | 2 | L24804 | | + | + | + | | + |
| unconventional myosin-ID (MYO1F) | 3 | U57053 | | | | | | |
| uncoupling protein homolog (UCPH) | 1 | U94592 | | | | | | |
| uncoupling protein homolog (UCPH) (low match 67%) | 1 | U94592 | | | | | | |
| Unknown gene product | 1 | AC002310 | | | | | | |
| unknown mRNA (clone 24514) | 1 | AF070542 | | | | | | |
| unknown protein (clone ICRFp507L0677) | 2 | Z70223 | | | | | | |
| unknown protein (Hs.93832) | 1 | AF070626 | + | + | + | + | + | + |
| unknown protein IT14 | 1 | AF040966 | | | | | | |
| uppressor of Ty (S. cerevisiae) 6 homolog | 1 | D79984 | + | + | + | + | + | + |

TABLE 2-continued

Comparison of 1,800 Unique Genes Identified in the Blood Cell cDNA Library to Genes Previously Identified in Specific Tissues

| Gene Identification | No. of ESTs | Accession No. | Tissue Distribution | | | | | | |
|---|---|---|---|---|---|---|---|---|---|
| | | | Bl | Br | H | K | Li | Lu | |
| upregulated by 1,25-dihydroxyvitamin D-3 (VDUP1) | 74 | S73591 | + | + | + | + | | + | high in heart |
| upregulated by 1,25-dihydroxyvitamin D-3 (VDUP1) (low match) | 1 | S73591 | | | | | | | |
| upregulated by 1,25-dihydroxyvitamin D-3 (VDUP1) (low match) | 1 | S73591 | | | | | | | |
| upregulated by 1,25-dihydroxyvitamin D-3 (VDUP1) (low score) | 1 | S73591 | | | | | | | |
| upstream binding factor (hUBF) | 1 | X53461 | + | + | | + | | + | |
| UV radiation resistance associated gene (UVRAG) | 2 | X99050 | | + | + | + | | + | |
| vacuolar proton-ATPase, subunit D; V-ATPase, subunit D (ATP6DV) | 4 | X71490 | | + | + | + | + | + | |
| v-akt murine thymoma viral oncogene homolog 1 (AKT1) | 1 | M63167 | + | + | + | + | | + | |
| Vanin 2 (VNN2) | 3 | AJ132100 | | | | | | | |
| vasodilator-stimulated phosphoprotein (VASP) | 3 | Z46389 | + | | + | + | | + | |
| vav 1 oncogene (VAV1) | 1 | M59834 | | | | | | + | |
| vav 2 oncogene (VAV2) | 1 | S76992 | + | + | | | | | |
| v-crk avian sarcoma virus CT10 oncogene homolog (CRK) | 1 | D10656 | W | + | + | + | | | |
| v-erb-b2 avian erythroblastic leukemia viral oncogene homolog 3 (ERBB3) | 1 | M29366 | | | | | | + | |
| VERSICAN CORE PROTEIN PRECURSOR | 1 | P13611 | | | | | | | |
| Vesicle-associated membrane protein 1 (synaptobrevin 1) (VAMP1) | 1 | M36196 | | + | + | + | | + | |
| vesicle-associated membrane protein 3 (cellubrevin) (VAMP3) | 1 | U64520 | | | | | | | |
| v-fos FBJ murine osteosarcoma viral oncogene homolog (FOS) | 26 | K00650 | | + | + | + | + | + | high in aorta |
| v-fos FBJ murine osteosarcoma viral oncogene homolog (FOS) (low match) | 1 | K00650 | | | | | | | |
| villin 2 (ezrin) (VIL2) | 1 | X51521 | + | + | + | + | | + | |
| villin-like protein | 1 | D88154 | | | | | | | |
| vimentin (VIM) | 12 | X56134 | | + | + | + | + | + | high in many libraries |
| vinculin (VCL) | 4 | M33308 | | + | + | + | | + | |
| vitamin A responsive; cytoskeleton related (JWA) | 6 | AF070523 | + | + | + | + | | | |
| v-jun avian sarcoma virus 17 oncogene homolog (JUN) | 2 | U65928 | + | + | + | + | | + | |
| v-myb avian myeloblastosis viral oncogene homolog (MYB) | 1 | M15024 | | | | + | | + | |
| voltage-dependent anion channel 1 (VDAC1) | 1 | L06132 | + | + | + | + | | + | |
| voltage-dependent anion channel 3 (VDAC3) | 4 | U90943 | | + | + | + | | + | |
| von Hippel-Lindau syndrome (VHL) | 1 | L15409 | | + | + | + | | + | |
| von Willebrand factor (vWF) (low matched) | 1 | X06828 | | | | | | | |
| v-raf murine sarcoma 3611 viral oncogene homolog 1 (ARAF1) | 2 | L24038 | + | + | + | + | | | |
| v-raf-1 murine leukemia viral oncogene homolog 1 (RAF1) | 1 | X03484 | + | + | + | + | | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| v-ral simian leukemia viral oncogene homolog B (ras related; GTP binding protein) (RALB) | 3 | M35416 | | | | | | | |
| V-rel avian reticuloendotheliosis viral oncogene homolog A (nuclear factor of kappa light polypeptide gene enhancer in B-cells 3 (p65)) (RELA) | 1 | L19067 | | + | + | + | | + | |
| v-yes-1 Yamaguchi sarcoma viral related oncogene homolog (LYN) | 2 | M16038 | + | + | | + | | + | |
| WD repeat domain 1 (WDR1) | 1 | AB010427 | + | + | + | + | + | + | |
| WDR1 (=AF020260) | 1 | AF020056 | | | | | | | |
| WD-repeat protein (HAN11) | 2 | U94747 | | + | + | | | + | |
| Williams-Beuren syndrome chromosome region 1 (WBSCR1) | 12 | AF045555 | + | + | + | + | + | + | |
| Wiskott-Aldrich syndrome protein interacting protein (WASPIP) | 4 | X86019 | + | + | + | | | + | |
| X (inactive)-specific transcript (XIST) | 2 | M97168 | | | | | | | |
| xeroderma pigmentosum, complementation group C (XPC) | 3 | D21089 | + | + | + | + | | | |
| XIAP associated factor-1 | 2 | X99699 | | | | + | | | |
| XIB | 1 | X90392 | | + | + | | + | + | |
| X-linked anhidroitic ectodermal dysplasia | 1 | AF003528 | | | | | | | |
| X-ray repair complementing defective repair in Chinese hamster cells 5 (double-strand-break rejoining; Ku autoantigen, 80 kD) (XRCC5) | 1 | M30938 | + | + | + | + | | + | high in spleen |
| XRP2 protein | 1 | AJ007590 | | | | | | | |
| yeloid differentiation primary response gene (88) (MYD88) | 1 | U84408 | | + | + | + | | + | |
| zeta-chain (TCR) associated protein kinase (70 kD) (ZAP70) | 1 | L05148 | + | | | + | | | |
| zeta-chain (TCR) associated protein kinase (70 kD) (ZAP70) (low match) | 1 | L05148 | | | | | | | |
| zinc finger protein (Hs.47371) | 2 | U69274 | + | + | + | + | | + | |
| zinc finger protein (Hs.78765) | 1 | U69645 | + | + | + | + | | + | |
| zinc finger protein 10 (KOX1) (ZNF10) | 1 | X78933 | | | | | | + only | |
| ZINC FINGER PROTEIN 124 (HZF-16) (non-exact 51%) | 1 | Q15973 | | | | | | | |
| zinc finger protein 124 (HZF-16) (ZNF124) (non-exact, 78%) | 1 | S54641 | | | | | | | |
| ZINC FINGER PROTEIN 133 | 1 | P52736 | | | | | | | |
| zinc finger protein 136 (clone pHZ-20) (ZNF136) | 1 | U09367 | | | + | + | | | |
| zinc finger protein 140 (clone pHZ-39) (ZNF140) | 1 | U09368 | | + | | + | | + | |
| zinc finger protein 140 (clone pHZ-39) (ZNF140) (non-exact 59%) | 1 | AF060865 | | | | | | | |
| zinc finger protein 140 (clone pHZ-39) (ZNF140) (non-exact 73%) | 1 | U09368 | | | | | | | |
| zinc finger protein 140 (clone pHZ-39) (ZNF140) (non-exact 73% aa) | 1 | S66508 | | | | | | | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | Tissue Distribution |
|---|---|---|---|---|---|---|---|---|---|
| zinc finger protein 140 (clone pHZ-39) (ZNF140) (non-exact, 80%) | 1 | U09368 | | | | | | | |
| zinc finger protein 143 (clone pHZ-1) (ZNF143) | 2 | U09850 | + | + | + | + | + | + | |
| zinc finger protein 143 (clone pHZ-1) (ZNF143) (low match) | 1 | U09850 | | | | | | | |
| zinc finger protein 148 (pHZ-52) (ZNF148) | 1 | AF039019 | + | | | | | | |
| ZINC FINGER PROTEIN 151 (MIZ-1 PROTEIN) (low match) | 1 | Q13105 | | | | | | | |
| zinc finger protein 173 (ZNF173) | 1 | U09825 | B, T | + | + | | + | | |
| zinc finger protein 192 (ZNF192) (non-exact, 66%) | 1 | U57796 | | | | | | | |
| zinc finger protein 198 (ZNF198) | 1 | AJ224901 | | + | + | + | | | |
| zinc finger protein 2 (ZNF2) (low match) | 1 | X60152 | | | | | | | |
| zinc finger protein 200 (ZNF200) | 1 | AF060866 | | + | | + | | | |
| zinc finger protein 207 (ZNF207) | 6 | AF046001 | + | + | + | + | + | + | high in prostate |
| zinc finger protein 216 (ZNF216) | 2 | AF062072 | + | + | + | + | | + | |
| zinc finger protein 217 (ZNF217) | 1 | AF041259 | T activated | | | | | + | |
| ZINC FINGER PROTEIN 22 (ZINC FINGER PROTEIN KOX15) (non-exact 58%) | 1 | P17026 | | | | | | | |
| zinc finger protein 230 (ZNF230) | 1 | U95044 | | + | | | | | |
| Zinc finger protein 239 (ANF239) | 1 | L26914 | | + | | + | | | |
| zinc finger protein 261 (ZNF261) | 1 | AB002383 | | + | + | + | | + | |
| zinc finger protein 262 (ANF262) | 1 | AB007885 | | + | + | + | | + | |
| zinc finger protein 263 (ZNF263) | 1 | D88827 | | | | | | | |
| zinc finger protein 264 (ZNF264) | 1 | AB007872 | | + | + | + | | | |
| ZINC FINGER PROTEIN 33A (ZINC FINGER PROTEIN KOX31) (KIAA0065) (HA0946) | 1 | Q06730 | | | | | | | |
| zinc finger protein 42 (myeloid-specific retinoic cid-responsive) (ZNF42) | 1 | M58297 | + | + | + | + | | + | |
| zinc finger protein 43 (HTF6) (ZNF43) (low match) | 1 | X59244 | | | | | | | |
| zinc finger protein 43 (HTF6) (ZNF43) (non-exact, 54%) | 1 | X59244 | | | | | | | |
| zinc finger protein 43 (HTF6) (ZNF43) (non-exact, 71%) | 1 | X59244 | | | | | | | |
| ZINC FINGER PROTEIN 43 (ZINC PROTEIN HTF6) (non-exact 67%) | 1 | P28160 | | | | | | | |
| zinc finger protein 45 (a Kruppel-associated box (KRAB) domain polypeptide) (ZNF45) | 1 | L75847 | | | | | | | only found in testis |
| ZINC FINGER PROTEIN 46 (ZINC FINGER PROTEIN KUP) (non-exact 62%) | 1 | P24278 | | | | | | | |
| zinc finger protein 6 (CMPX1) (ZNF6) | 1 | X56465 | | + | + | + | | + | |
| zinc finger protein 74 (Cos52) (ZNF74) (non-exact, 67%) | 1 | X71623 | | | | | | | |
| zinc finger protein 76 (expressed in testis) (ZNF76) | 1 | M91592 | | + | + | + | | + | |

TABLE 2-continued

Comparison of 1,800 Unique Genes Identified in the Blood Cell cDNA Library to Genes Previously Identified in Specific Tissues

| Gene Identification | No. of ESTs | Accession No. | Bl | Br | H | K | Li | Lu | |
|---|---|---|---|---|---|---|---|---|---|
| ZINC FINGER PROTEIN 83 (ZINC FINGER PROTEIN HPF1) (non-exact 65%) | 1 | P51522 | | | | | | | |
| zinc finger protein 84 (HPF2) (ZNF84) | 1 | M27878 | T activated | + | + | | + | | |
| zinc finger protein 85 (ZNF85)) | 2 | U35376 | | + | + | + | | | |
| zinc finger protein 9 (ZNF9) | 5 | M28372 | | + | + | + | + | + | |
| ZINC FINGER PROTEIN 93 (=ZINC FINGER PROTEIN HTF34) (non-exact 70%) | 1 | P35789 | | | | | | | |
| zinc finger protein C2H2-25 (ZNF25) | 3 | U38904 | | + | + | + | | | |
| zinc finger protein clone L3-4 | 1 | AF024706 | | | | | | | |
| zinc finger protein homologous to Zfp-36 in mouse (ZFP36) | 4 | M92843 | + | | | | | | blood only |
| ZINC FINGER PROTEIN HRX (ALL-1) (71% a.a.) | 1 | Q03164 | | | | | | | |
| zinc finger protein HZF4 | 1 | X78927 | | | | | | | |
| zinc finger protein RIZ | 1 | D45132 | + | + | + | + | | + | |
| zinc finger protein, subfamily 1A, 1 (Ikaros) (LYF1) | 1 | U40462 | + | | | | | | |
| zinc finger protein, subfamily 1A, 1 (Ikaros) (LYF1) (low match) | 1 | U40462 | | | | | | | |
| zinc finger transcriptional regulator (GOS24) | 1 | M92844 | | | | | | | |
| zinc-finger helicase (hZFH) | 2 | U91543 | + | + | + | + | | + | |
| Zn-15 related zinc finger protein (rlf) | 1 | U22377 | | + | + | + | | | |
| Zn-15 related zinc finger protein (rlf) (non-exact 56%) | 1 | U22377 | | | | | | | |
| ZNF80-linked ERV9 long terminal repeat | 1 | X83497 | | | | | | | |
| ZW10 (*Drosophila*) homolog, centromere/kinetochore protein (ZW10) | 2 | U54996 | | + | | | | | |
| zyxin (ZYX) | 4 | X95735 | | | | | | | |

Column 1: List of unique genes derived from 6,283 known ESTs from blood cells.
Column 2: Number of genes found in randomly sequenced ESTs from blood cells.
Column 3: Accession number.
Column 4: "+" indicates the presence of the unique gene in publicly available cDNA libraries of blood (Bl), brain (Br), heart (H), kidney (K), liver (Li) and lung (Lu).
**Comparison to previously identified tissue-specific genes was determined using the GenBank of the National Centre of Biotechnology Information (NCBI) Database.

DISCUSSION

Every cell and tissue comprising the human body share the necessary genetic information required to maintain cellular homeostasis. These "housekeeping" genes function in basic cellular maintenance, including energy metabolism and cellular structure in all cell types. However, in certain situations, even the housekeeping genes show altered expression. Thus, it is necessary to define the use of these genes as internal controls from one investigation to another. Current results from the human blood cell EST database indicate that over 50% of the transcripts are widely expressed throughout the human body. Most of the cell or tissue specific genes are also detectable in blood cells by RT-PCR analysis.

For example, isoformic myosin heavy chain genes are known to be generally expressed in cardiac muscle tissue. In the rodent, the (MyHC gene is only highly expressed in the fetus and in diseased states such as overt cardiac hypertrophy, heart failure and diabetes; the (MyHC gene is highly expressed shortly after birth and continues to be expressed in the adult heart. In the human, however, (MyHC is highly expressed in the ventricles from the fetal stage through adulthood. This highly expressed (MyHC, which harbours several mutations, has been demonstrated to be involved in familial hypertrophic cardiomyopathy (Geisterfer-Lowrance et al. 1990). It was reported that mutations of (MyHC can be detected by PCR using blood lymphocyte DNA (Ferrie et al., 1992). Most recently, it was also demonstrated that mutations of the myosin-binding protein C in familial hypertrophic cardiomyopathy can be detected in the DNA extracted from lymphocytes (Niimura et al., 1998).

Similarly, APP and APC, which are known to be tissue specific and predominantly expressed in the brain and intestinal tract, are also detectable in the transcripts of blood. These cell- or tissue-specific transcripts are not detectable by Northern blot analysis. However, the low number of transcript copies can be detected by RT-PCR analysis. These findings strongly demonstrate that genes preferentially expressed in specific tissues can be detected by a highly sensitive RT-PCR assay. In recent years, evidence has been obtained to indicate that expression of cell or tissue-restricted genes can be detected in the peripheral blood of patients with metastatic transitional cell carcinoma (Yuasa et al. 1998) and patients with prostate cancer (Gala et al. 1998).

Atrial natriuretic factor (ANF) and zinc finger protein (ZFP), which are known to be highly expressed in heart tissue biopsies and in the plasma of heart failure patients, are also detectable in the transcripts of blood. Differential expression of zinc finger protein among the normal, diabetic and asymptomatic preclinical subjects may have additional value as a prophylactic "early warning system". On a related note, there is now more attention/discussion in the cardiovascular disease field being focused on Syndrome X, loosely defined as a continuum of hypertension, increasing sugar levels, diabetes, kidney failure, culminating in heart failure, with the possibility of stroke and heart attack at any time in the continuum. The early identification of patients at risk of organ failure has been a challenge to the medical community for some time and the present method has the potential of resolving or, at least, ameliorating this challenge.

The present invention demonstrates that a simple drop of blood may be used to determine the quantitative expression of various mRNAs that reflect the health/disease state of the subject through the use of RT-PCR analysis. This entire process takes about three hours or less. The single drop of blood may also be used for multiple RT-PCR analyses. There is no need for large samples and/or costly and time-consuming separation of cell types within the blood for this method as compared to the methods described by Kimoto (1998) and Chelly et al. (1989; 1988). It is believed that the present finding can potentially revolutionize the way that diseases are detected, diagnosed and monitored because it provides a non-invasive, simple, highly sensitive and quick screening for tissue-specific transcripts. The transcripts detected in whole blood have potential as prognostic or diagnostic markers of disease, as they reflect disturbances in homeostasis in the human body. Delineation of the sequences and/or quantitation of the expression levels of these marker genes by RT-PCR will allow for an immediate and accurate diagnostic/prognostic test for disease or to assess the efficacy and monitor a particular therapeutic.

In addition to RT-PCR, other methods of amplifying may also be used for the purpose of measuring/quantitating tissue-specific transcripts in human blood. For example, mass spectrometry may be used to quantify the transcripts (Koster et al., 1996; Fu et al., 1998). The application of presently disclosed method for detecting tissue-specific transcripts in blood does not restrict to subjects undergoing course of therapy or treatment, it may also be used for monitoring a patient for the onset of overt symptoms of a disease. Furthermore, the present method may be used for detecting any gene transcripts in blood. A kit for diagnosing, prognosing or even predicting a disease may be designed using gene-specific primers or probes derived from a whole blood sample for a specific disease and applied directly to a drop of blood. A cDNA library specific for a disease may be generated from whole blood samples and used for diagnosis, prognosis or even predicting a disease.

The following references were cited herein:
Claudio J O et al. (1998). *Genomics* 50:44-52.
Chelly J et al. (1989). *Proc. Nat. Acad. Sci. USA*. 86:2617-2621.
Chelly J et al. (1988). *Nature* 333:858-860.
Drews J & Ryser S (1997). *Nature Biotech.* 15:1318-9.
Ferrie R M et al. (1992). *Am. J. Hum. Genet.* 51:251-62.
Fu D-J et al. (1998). *Nat. Biotech* 16: 381-4.
Gala J L et al. (1998). *Clin. Chem.* 44(3):472-81.
Geisterfer-Lowrance A A T et al. (1990). *Cell* 62:999-1006.
Groden J et al. (1991). *Cell* 66:589-600.
Hwang D M et al. (1997). *Circulation* 96:4146-4203.
Jandreski M A & Liew C C (1987). *Hum. Genet.* 76:47-53.
Jin O et al. (1990). *Circulation* 82:8-16
Kimoto Y (1998). *Mol. Gen. Genet.* 258:233-239.
Koster M et al. (1996). *Nat. Biotech* 14: 1123-8.
Liew & Jandreski (1986). *Proc. Nat. Acad. Sci. USA*. 83:3175-3179
Liew C C et al. (1990). *Nucleic Acids Res.* 18:3647-3651.
Liew C C (1993). *J Mol. Cell. Cardiol.* 25:891-894
Liew C C et al. (1994). *Proc. Natl. Acad. Sci. USA*. 91:10645-10649.
Liew et al. (1997). *Mol. and Cell. Biochem.* 172:81-87.
Niimura H et al. (1998). *New Eng. J. Med.* 338:1248-1257.
Ogawa M (1993). *Blood* 81:2844-2853.
Santoro I M & Groden J (1997). *Cancer Res.* 57:488-494.
Yuasa T et al. (1998). *Japanese J. Cancer Res.* 89:879-882.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The invention claimed is:

1. A method of profiling gene expression in a human subject having an infectious disease, the method comprising:
   determining, for each gene of a set of genes, a level of RNA encoded by the gene in a blood sample of the subject, wherein the set comprises the genes identified as:
   100 kDa coactivator; 10 kD protein (BC10); 14-3-3 epsilon; 14-3-3 protein; 15 kDa selenoprotein (SEP15); 1-phosphatidylinositol-4-phosphate 5-kinase isoform C; 23 kD highly basic protein; 2-5A-dependent RNase; 2′-5′ oligoadenylate synthetase 2 (OAS2); 26S proteasome subunit 11; 36 kDa phosphothyrosine protein; 3-phosphoglycerate dehydrogenase (PGAD); 3-prime-phosphoadenosine 5-prime-phosphosulfate synthase 1 (PAPSS1); 5-aminoimidazole-4-carboxamide ribonucleotide transformylase; 5′-nucleotidase; 6-phosphofructo-2-kinase/fructose-2,6-biphosphatase 4 (PFKFB4); 6-phosphofructo-2-kinase/fructose-2,6-bisphosphatase (PF2K); 71 kd heat shock cognate protein hsc70; 76 kDa membrane protein (P76); 8-oxoguanine DNA glycosylase (OGG1); a disintegrin and metalloprotease domain 10 (ADAM10); a disintegrin and metalloprotease domain 8 (ADAM8); A kinase anchor protein 95 (AKAP95); A kinase anchor protein, 149 kD (AKAP149); Absent in melanoma 1 (AIM1); accessory proteins BAP31/BAP29 (DXS1357E); acetyl-Coenzyme A acyltransferase (peroxisomal 3-oxoacyl-Coenzyme A thiolase) (ACAA); acetyl-Coenzyme A transporter (ACATN); acidic 82 kDa protein; acidic protein rich in leucines (SSP29); Aconitase 2, mitochondrial (ACO2); actin binding protein MAYVEN; actin, beta (ACTB); actin, gamma 1 (ACTG1); actin-binding LIM protein (ABLIM); Actinin, alpha 1 (ACTN1); actinin, alpha 4 (ACTN4); activated p21cdc42Hs kinase (ACK); activated RNA polymerase II transcription cofactor 4 (PC4); activating transcription factor 1 (ATF1); activating transcription factor 2 (ATF2); activating transcription factor 4 (tax-responsive enhancer element B67) (ATF4); active BCR-related gene (ABR); acyl-CoA oxidase (AOX); acyl-Coenzyme A dehydrogenase, C-4 to C-12 straight chain (ACADM); acyl-Coenzyme A dehydrogenase, very long chain (ACADVL); acyloxyacyl hydrolase (neutrophil) (AOAH); adaptin, delta (ADTD); adaptin, gamma (ADTG); adaptor complex sigma3B (AP3S3); adaptor protein p150; adducin 1 (alpha) (ADD1); adducin 1 (alpha) (add1); adducin 3 (gamma) (ADD3); adenine nucleotide translocator 2 (fibroblast) (ANT2); adenine nucleotide translocator 3 (liver) (ANT3); adenomatous polyposis-coli protein (APC); adenosine deaminase, RNA-specific (ADAR); adenylate cyclase 3 (ADCY3); adenylate cyclase 7 (ADCY7); adenylate kinase 2 (AK2); adenylyl cyclase-associated protein (CAP); adipose differentiation-related protein; adipophilin (ADFP); ADP-ribosylation factor 1 (ARF1); ADP-ribosylation factor 3 (ARF3); ADP-ribosylation factor 4 (ARF4); ADP-ribosylation factor 5 (ARF5); ADP-ribosylation factor domain protein 1, 64 kD (ARFD1); ADP-ribosyltransferase (NAD+; poly (ADP-ribose) polymerase) (ADPRT); adrenergic, beta, receptor kinase 1 (ADRBK1); adrenoleukodystrophy-like 1 (ALDL1); AF-17; A-gamma-globin; A-gamma-globin (chromosome 11 allele); agamma-globulinaemia tyrosine kinase (ATK); AHNAK nucleoprotein (desmoyokin) (AHNAK); alanyl (membrane) aminopeptidase (aminopeptidase N, aminopeptidase M, microsomal aminopeptidase, CD13, p150) (ANPEP); alcohol dehydrogenase 5 (class III), chi polypeptide (ADH5); aldehyde dehydrogenase 1, soluble (ALDH1); aldehyde dehydrogenase 10 (fatty aldehyde dehydrogenase) (ALDH10); aldehyde reductase 1 (low Km aldose reductase) (ALDR1); aldo-keto reductase family 1, member A1 (aldehyde reductase) (AKR1A1); aldo-keto reductase family 1, member C3 (3-alpha hydroxysteroid dehydrogenase, type II) (AKR1C3); aldo-keto reductase family 7, member A2 (aflatoxin aldehyde reductase) (AKR7A2); aldolase A, fructose-bisphosphate (ALDOA); aldolase C, fructose-bisphosphate (ALDOC); alkaline phosphatase, liver/bone/kidney (ALPL); alpha mannosidase II isozyme; alpha thalassemia/mental retardation syndrome X-linked (ATRX); alpha-2-macroglobulin; alpha-2-globin; alpha-2-macroglobulin receptor/lipoprotein receptor protein (A2MR/LRP); alpha-polypeptide of N-acetyl-alpha-glucosaminidase (HEXA); alpha-spectrin; alpha-subunit of Gi2 a (GTP-binding signal transduction protein); aminin receptor 1 (67 kD); Ribosomal protein SA (LAMR1); aminolevulinate, delta-, dehydratase (ALAD); amino-terminal enhancer of split (AES); amino-terminal enhancer of split (AES); AMP deaminase isoform L (AMPD2); amphiphysin (Stiff-Mann syndrome with breast cancer 128 kD autoantigen) (AMPH); amphiphysin II; amphiphysin-like (AMPHL); AMY-1; amyloid beta (A4) precursor protein-binding, family B, member 1 (Fe65) (APBB1); amyloid beta (A4) precursor-like protein 2 (APLP2); amyloid precursor protein (APP); annexin I (lipocortin I) (ANX1); annexin II; annexin II (lipocortin II; calpactin I, heavy polypeptide) (ANX2); annexin IV (placental anticoagulant protein II) (ANX4); annexin V (endonexin II) (ANX5); annexin V (endonexin II) (ANXV); annexin VI (p68) (ANX6); annexin VII (synexin) (ANX7); antigen identified by monoclonal antibodies 12E7, F21 and O13 (MIC2); antigen identified by monoclonal antibodies 4F2, TRA1.10, TROP4, and T43 (MDU1); anti-oxidant protein 2 (non-selenium glutathione peroxidase, acidic calcium-independent phospholipase A2) (KIAA0106); APEX nuclease (multifunctional DNA repair enzyme) (APEX); apoptosis inhibitor 1 (API1); apoptosis inhibitor 4 (survivin) (API4); apoptosis inhibitor 5 (API5); apoptosis specific protein (ASP); apoptotic protease activating factor (APAF1); aquaporin 3 (AQP3); aquaporin 9 (AQP9); arachidonate 12-lipoxygenase (ALOX12); arachidonate 5-lipoxygenase-activating protein (ALOX5AP); ariadne homolog (ARI); ariadne-2 (*D. melanogaster*) homolog (all-trans retinoic acid inducible RING finger) (ARI2); ARP1 (actin-related protein 1, yeast) homolog A (centractin alpha) (ACTR1A); ARP2 (actin-related protein 2, yeast) homolog (ACTR2); ARP2/3 protein complex subunit 34 (ARC34); Arp2/3 protein complex subunit p41 (ARC41); Arp2/3 protein complex subunit p16 (ARC16); Arp2/3 protein complex subunit p20 (ARC20); Arp2/3 protein complex subunit p21 (ARC21); ARP3 (actin-related protein 3, yeast) homolog (ACTR3); arrestin, beta 2 (ARRB2); arsA (bacterial) arsenite transporter, ATP-binding, homolog 1 (ASNA1); aryl hydrocarbon receptor nuclear translocator-like (ARNTL); aryl hydrocarbon receptor-interacting protein (AIP); arylsulfatase A (ARSA); asialoglycoprotein receptor 2 (ASGR2); asparaginyl-tRNA synthetase (NARS); aspartyl-tRNA synthetase (DARS); ataxia telangiectasia mutated (includes complementation groups A, C and D) (ATM); ataxin-2-like protein A2LP (A2LG); ATF6; ATP synthase (F1-ATPase) alpha subunit, mitochondrial; ATP synthase beta subunit gene; ATP synthase, H+ transporting, mitochondrial F0 complex, subunit b, isoform 1 (ATP5F1); ATP synthase, H+ transporting, mitochondrial F0 complex, subunit c (subunit 9), isoform 1 (ATP5G1); ATP synthase, H+ transporting, mitochondrial F1 complex, alpha subunit, isoform 1, cardiac muscle (ATP5A1); ATP synthase, H+ transporting, mitochondrial F1 complex, beta polypeptide (ATP5B); ATP synthase, H+ transporting, mitochondrial F1 complex, gamma polypeptide 1 (ATP5C1); ATP synthase, H+ transporting, mitochondrial F1F0, subunit g (ATP5JG); ATP/GTP-binding protein (HEAB); ATPase, Ca++ transporting, ubiquitous (ATP2A3); ATPase, H+ transporting, lysosomal (vacuolar proton pump) 21 kD (ATP6F); ATPase, H+ transporting, lysosomal (vacuolar proton pump) 31 kD (ATP6E); ATPase, H+ transporting, lysosomal (vacuolar proton pump) 42 kD; Vacuolar proton-ATPase, subunit C; V-ATPase, subunit C (ATP6D); ATPase, H+ transporting, lysosomal (vacuolar proton pump), alpha polypeptide, 70 kD, isoform 1 (ATP6A1); ATPase, H+ transporting, lysosomal (vacuolar proton pump), beta polypeptide, 56/58 kD, isoform 2 (ATP6B2); ATPase, H+ transporting, lysosomal (vacuolar proton pump), member J (ATP6J); ATPase, H+ transporting, lysosomal (vacuolar proton pump), subunit 1 (ATP6S1); ATP-binding cassette 50 (TNF-alpha stimulated) (ABC50); ATP-binding cassette protein M-ABC1 (mitochondrial); ATP-dependent RNA helicase; atrial natriuretic factor (ANF); autoantigen (Hs.75528); autoantigen (Hs.75682); autoantigen La/SS-B; axin (AXIN1); axonemal dynein heavy chain (DNAH17); basement membrane-induced gene (ICB1); basic leucine zipper nuclear factor 1 (JEM-1) (BLZF1); basic transcription factor 3 (BTF3); basigin (BSG); BC-2; B-cell CLL/lymphoma 6 (zinc finger protein 51) (BCL6); B-cell translocation gene 1, anti-proliferative (BTG); BCL2/adenovirus E1B 19 kD-interacting protein 2 (BNIP2); BCL2/adenovirus E1B 19 kD-interacting protein 3-like (BNIP3L); beclin 1 (coiled-coil, myosin-like BCL2-interacting protein) (BECN1); beta-1,2-N-acetylglucosaminyltransferase II (MGAT2); beta-2-microglobulin (B2M); beta-hexosaminidase alpha chain (HEXA); beta-tubulin; BING4; biphenyl hydrolase-like (serine hydrolase) (BPHL); bone marrow stromal cell antigen 1 (BST1); box-dependent myc-interacting protein isoform BIN1-10 (BIN1); brain my047 protein; branched chain keto acid dehydrogenase E1, alpha polypeptide (maple syrup urine disease) (BCKDHA); BRCA1 associated protein-1 (ubiquitin carboxy-terminal hydrolase) (BAP1); breakpoint cluster region protein, uterine leiomyoma, 1; barrier to autointegration factor (BCRP1); breakpoint cluster region protein, uterine leiomyoma, 2 (BCRP2); bromodomain-containing protein, 140 kD (peregrin) (BR140); Bruton's agammaglobulinemia tyrosine kinase (Btk); Bruton's tyrosine kinase (BTK); BS4; BTG2 (BTG2); BTK region clone ftp; BTK region clone ftp-3; BUB3 (budding uninhibited by benzimidazoles 3, yeast) homolog (BUB3); butyrate response factor 1 (EGF-response factor 1) (BRF1); butyrophilin (BTF1); butyrophilin like receptor; CAG repeat containing (CTG4A); CAGH32; calcium/calmodulin-dependent protein kinase (CaM kinase) II gamma (CAMK2G); calcium/calmodulin-dependent protein kinase kinase (KIAA0787); calmodulin 1 (phosphorylase kinase, delta) (CALM1); calnexin (CANX); calpain, large polypeptide L1 (CAPN1); calpain, large polypeptide L2 (CANP2); calpain, small polypeptide (CAPN4); calpastatin (CAST); Calponin 2; calponin 2 (CNN2); calumenin (CALU); cAMP response element-binding protein CRE-Bpa (H_GS165L15.1); cAMP-dependent protein kinase type II (Ht31); canicular multi-specific organic anion transporter (CMOAT2); capping protein (actin filament) muscle Z-line, alpha 1 (CAPZA1); capping protein (actin filament) muscle Z-line, alpha 2 (CAPZA2); capping protein (actin filament) muscle Z-line, beta (CAPZB); capping protein (actin filament), gelsolin-like (CAPG); carbamoyl-phosphate synthetase 2, aspartate transcarbamylase, and dihydroorotase (CAD); carbonic anhydrase V, mitochondrial (CA5); carboxypeptidase D (CPD); cardiac beta-myosin heavy chain; carnitine/acylcarnitine translocase (CACT); Cas-Br-M (murine) ecotropic retroviral transforming sequence (cbl); casein kinase 1, alpha 1 (CSNK1A1); casein kinase 2, alpha 1 polypeptide (CSNK2A1); casein kinase I gamma 3L (CSNK1G3L); CASP8 and FADD-like apoptosis regulator (CFLAR); caspase 1, apoptosis-related cysteine protease (interleukin 1, beta, convertase) (CASP1); caspase 10, apoptosis-related cysteine protease (CASP10); caspase 3, apoptosis-related cysteine protease (CASP3); caspase 4, apoptosis-related cysteine protease (CASP4); caspase 5, apoptosis-related cysteine protease (CASP5); caspase 8, apoptosis-related cysteine protease (CASP8); caspase 9, apoptosis-related cysteine protease (CASP9); catalase (CAT); catechol-O-methyltransferase (COMT); catenin (cadherin-associated protein), alpha 1 (102 kD) (CTNNA1); cathelicidin antimicrobial peptide (CAMP); cathepsin B (CTSB); cathepsin C(CTSC); cathepsin D (lysosomal aspartyl protease) (CTSD); cathepsin E (CTSE); cathepsin G (CTSG); cathepsin S (CTSS); cathepsin W (lymphopain) (CTSW); CCAAT/enhancer binding protein (C/EBP), alpha (CEBPA); CCAAT/enhancer binding protein (C/EBP), delta (CEBPB); CCAAT-box-binding transcription factor (CBF2); CD14 antigen (CD14); CD1C antigen, c polypeptide (CD1C); CD2 antigen (cytoplasmic tail)-binding protein 2 (CD2BP2); CD2 antigen (p50), sheep red blood cell receptor (CD2); CD2 cytoplasmic tail-binding protein 1 (CD2BP1); CD20 antigen (CD20); CD20 receptor (S7); CD22 antigen (CD22); CD24 signal transducer; CD33 antigen (gp67) (CD33); CD33 antigen-like 2; CD36 antigen (collagen type I receptor, thrombospondin receptor) (CD36); CD37 antigen (CD37); CD38 alt; CD39 antigen (CD39); CD3D antigen, delta polypeptide (TiT3 complex) (CD3D); CD3E antigen, epsilon polypeptide (TiT3 complex) (CD3E); CD3G antigen, gamma polypeptide (TiT3 complex) (CD3G); CD3Z antigen, zeta polypeptide (TiT3 complex) (CD3Z); CD3-zeta (clone pBS NK1); CD4 antigen (p55) (CD4); CD44 antigen (homing function and Indian blood group system (CD44); CD48 antigen (B-cell membrane protein) (CD48); CD53 antigen (CD53); CD63 antigen (melanoma 1 antigen) (CD63); CD68 antigen (CD68); CD74 antigen (invariant polypeptide of major histocompatibility complex, class II antigen-associated) (CD74); CD79A antigen (immunoglobulin-associated alpha) (CD79A); CD79B antigen (immunoglobulin-associated beta) (CD79B); CD8 antigen, alpha polypeptide (p32) (CD8A); CD8 antigen, beta polypeptide 1 (p37) (CD8B1); CD81 antigen (target of antiproliferative antibody 1 (CD81); CD84 antigen (leukocyte antigen) (CD84); CD86 antigen; CD9 antigen (p24) (CD9); CD97 antigen (CD97); CDC23 (cell division cycle 23, yeast, homolog) (CDC23); CDC37 homolog; Cdc42 effector protein 3 (CEP3); CDC-like kinase (CLK); CDC-like kinase 2 (CLK2); CDW52 antigen (CAMPATH-1 antigen) (CDW52); cell cycle progression restoration 8 protein (CPR8); cell division cycle 10 (homologous to CDC10 of *S. cerevisiae*) (CDC10); cell division cycle 20, *S. cerevisiae* homolog (CDC20); cell division cycle 25B (CDC25B); cell division cycle 42 (GTP-binding protein, 25 kD) (CDC42); centromere protein B (80 kD) (CENPB); cep250 centrosome associated protein; ceroid-lipofuscinosis, neuronal 2, late infantile (Jansky-Bielschowsky disease) (CLN2); CGI-19 protein; chaperonin containing TCP1, subunit 3 (gamma) (CCT3); chaperonin containing TCP1, subunit 4 (delta) (CCT4); chaperonin containing TCP1, subunit 6A (zeta 1) (CCT6A); chaperonin containing TCP1, subunit 7 (eta) (CCT7); Chediak-Higashi syndrome 1 (CHS1); chemokine (C-C motif) receptor 2 (CCR2); chemokine (C-C motif) receptor 7 (CCR7); chemokine (C-X3-C) receptor 1 (CX3CR1); chemokine (C-X-C motif), receptor 4 (fusin) (CXCR4); chitinase 3-like 1 (cartilage glycoprotein-39) (CHI3L1); chitinase 3-like 2 (CHI3L2); chloride channel 6 (CLCN6); Chloride intracellular channel 1 (CLIC1); chondroitin sulfate proteoglycan 2 (versican) (CSPG2); chondroitin sulfate proteoglycan core protein; chromodomain helicase DNA binding protein 1 (CHD1); chromodomain helicase DNA binding protein 1-like (CHD1L); chromodomain helicase DNA binding protein 2 (CHD2); chromodomain helicase DNA binding protein 3 (CHD3); chromodomain helicase DNA binding protein 4 (CHD4); chromosome 1 open reading frame 7 (C1ORF7); chromosome 1 specific transcript KIAA0493; chromosome 17 open reading frame 1B (C17ORF1B); chromosome 4 open reading frame 1 (C4ORF1); chromosome condensation 1-like (CHC1L); chromosome X open reading frame 5 (CXORF5); chromosome-associated polypeptide C(CAP-C); cig42; cig5; citrate synthase (CS); class I major histocompatibility antigen (HLA-Cw3); clathrin assembly protein lymphoid myeloid leukemia (CALM); clathrin heavy chain; clathrin, heavy polypeptide-like 2 (CLTCL2); clathrin-associated/assembly/adaptor protein, medium 1 (CLAPM1); cleavage stimulation factor, 3' pre-RNA, subunit 3, 77 kD (CSTF3); clk3; clone 23815 (Hs.82845); clone 24592 mRNA sequence; Clq/MBUSPA receptor ClqR(p); clusterin (complement lysis inhibitor, SP-40,40, sulfated glycoprotein 2, testosterone-repressed prostate message 2, apolipoprotein J) (CLU); CMP-sialic acid transporter (CMPST); CMRF35; c-myc oncogene containing coxIII; coagulation factor II (thrombin) receptor (F2R); coagulation factor V (proaccelerin, labile factor) (F5); coagulation factor XIII a subunit; coagulation factor XIII, A1 polypeptide (F13A1); coated vesicle membrane protein (RNP24); coatomer protein complex, subunit alpha (COPA); Cofilin 1 (non-muscle) (CFL1); cold inducible RNA-binding protein (CIRBP); cold shock domain protein A (CSDA); collagen, type IX, alpha 2 (COL9A2); colony stimulating factor 1 receptor, formerly McDonough feline sarcoma viral (v-fms) oncogene homolog (CSF1R); colony stimulating factor 2 receptor, beta, low-affinity (granulocyte-macrophage) (CSF2RB); colony stimulating factor 3 receptor (granulocyte) (CSF3R); complement component 5 receptor 1 (C5a ligand) (C5R1); conserved gene amplified in osteosarcoma (OS4); COP9 (constitutive photomorphogenic, *Arabidopsis*, homolog) subunit 3 (COPS3); COP9 homolog (HCOP9); COPII protein, homolog of *s. cerevisiae* SEC23p (SEC23A); copine I (CPNE1); coproporphyrinogen oxidase (coproporphyria, harderoporphyria) (CPO); core-binding factor, beta subunit (CBFB); coronin; cot (cancer Osaka thyroid) oncogene (COT); cryptochrome 1 (photolyase-like) (CRY1); CTD (carboxy-terminal domain, RNA polymerase II, polypeptide A) phosphatase, subunit 1 (CTDP1); C-terminal binding protein 1 (CTBP1); C-terminal binding protein 2 (CTBP2); CUG triplet repeat, RNA-binding protein 1 (CUGBP1); cullin 1 (CUL1); cullin 3 (CUL3); cut (*Drosophila*)-like 1 (CCAAT displacement protein) (CUTL1); cyclin D2 (CCND2); cyclin D3 (CCND3); cyclin G1 (CNNG1); cyclin I; cyclin T2 (CNNT2); cyclin-dependent kinase 2 (CDK2); cyclin-dependent kinase inhibitor (p27Kip1); cyclin-dependent kinase inhibitor 1A (p21, Cip1) (CDKN1A); cystatin B (stefin B) (CSTB); cysteine and glycine-rich protein 3 (cardiac LIM protein) (CSRP3); cytidine deaminase (CDA); cytochrome b(-245) beta chain N-terminal region (X-linked granulomatous disease gene); cytochrome b-245, beta polypeptide (chronic granulomatous disease) (CYBB); cytochrome c oxidase subunit IV (COX4); cytochrome c oxidase subunit Vb (COX5B); cytochrome c oxidase subunit VII-related protein (COX7RP); cytokine suppressive anti-inflammatory drug binding protein 1 (p38 MAP kinase) (CSBP1); Cytoplasmic antiproteinase=38 kda intracellular serine proteinase inhibitor; cytotoxic granule-associated RNA-binding protein p40-TIA-1; D123 (D123); D2-2; D38; damage-specific DNA binding protein 1 (127 kD) (DDB1); DEAD/H (Asp-Glu-Ala-Asp/His) box binding protein 1 (DDXBP1); DEAD/H (Asp-Glu-Ala-Asp/His) box polypeptide (72 KD) (P72); DEAD/H (Asp-Glu-Ala-Asp/His) box polypeptide 1 (DDX1); DEAD/H (Asp-Glu-Ala-Asp/His) box polypeptide 15 (DDX15); DEAD/H (Asp-Glu-Ala-Asp/His) box polypeptide 16 (DDX16); DEAD/H (Asp-Glu-Ala-Asp/His) box polypeptide 3 (DDX3); DEAD/H (Asp-Glu-Ala-Asp/His) box polypeptide 5 (RNA helicase, 68 kD) (DDX5); DEAD/H (Asp-Glu-Ala-Asp/His) box polypeptide 6 (RNA helicase, 54 kD) (DDX6); DEAD/H (Asp-Glu-Ala-Asp/His) box polypeptide 8 (RNA helicase, 54 kD) (DDX8); DEAD/H (Asp-Glu-Ala-Asp/His) box polypeptide 9 (RNA helicase A, nuclear DNA helicase II; leukophysin) (DDX9); DEAD/H (Asp-Glu-Ala-Asp/His) box polypeptide, Y chromosome (DBY); Death associated protein 3 (DAP3); death effector domain-containing protein (DEDD); death-associated protein 6 (DAXX); dedicator of cyto-kinesis 2 (DOCK2); defender against cell death 1 (DAD1); Defensin, alpha 1, myeloid-related sequence (DEFA1); DEK gene (D6S231E); delta sleep inducing peptide, immunoreactor (DSIPI); dendritic cell protein (GA17); deoxycytidine kinase (DCK); deoxyribonuclease II, lysosomal (DNASE2); DGS-I; diacylglycerol kinase; diacylglycerol kinase alpha (DAGK1) (clone 24); diaphanous (*Drosophila*, homolog) 1 (DIAPH1); diaphorase (NADH) (cytochrome b-5 reductase) (DIA1); differentiated Embryo Chondrocyte expressed gene 1 (DEC1); differentiation antigen CD20; DiGeorge syndrome critical region gene 2 (DGCR2); dihydrolipoamide dehydrogenase (E3 component of pyruvate dehydrogenase complex, 2-oxo-glutarate complex, branched chain keto acid dehydrogenase complex) (DLD); dihydrolipoamide S-acetyltransferase (E2 component of pyruvate dehydrogenase complex) (DLAT); dihydropyrimidinase-like 2 (DPYSL2); dinG gene; diptheria toxin resistance protein required for diphthamide biosynthesis (Saccharomyces)-like 2 (DPH2L2); DJ-1 protein; Dmx-like 1 (DMXL1); DNA (cytosine-5-)-methyltransferase 1 (DNMT1); DNA fragmentation factor, 40 kD, beta subunit (DFFB); DNA fragmentation factor, 45 kD, alpha subunit (DFFA); DNA mismatch repair protein (hMLH1); DNA segment on chromosome X (unique) 648 expressed sequence; DNA segment, single copy probe LNS-CAI/LNS-CAII (deleted in polyposis (D5S346); DnaJ protein; docking protein 2, 56 kD (DOK2); dolichyl-diphosphooligosaccharide-protein glycosyltransferase (DDOST); dolichyl-phosphate mannosyltransferase polypeptide 1, catalytic subunit (DPM1); down-regulated by activation (immunoglobulin superfamily) (DORA); D-type cyclin-interacting protein 1 (DIP1); dual specificity phosphatase 1 (DUSP1); dual specificity phosphatase 11 (RNA/RNP complex 1-interacting) (dusp11); dual specificity phosphatase 3 (vaccinia virus phosphatase VH1-related) (DUSP3); dual specificity phosphatase 6 (DUSP6); dynactin 1 (p150, Glued (*Drosophila*) homolog) (DYTN1); dynamin 2 (DNM2); dynein, cytoplasmic, light intermediate polypeptide 2 (DNCLI2); dyskeratosis congenita 1, dyskerin (DKC1); dystonia 1, torsion (autosomal dominant) (DYT1); dystrobrevin, beta (DTNB); dystrophia myotonica-containing WD repeat motif (DMWD); dystrophia myotonica-protein kinase (DMPK); E1B-55 kDa-associated protein; E2F transcription factor 3 (E2F3); E2F transcription factor 4, p107/p130-binding (E2F4); E2F transcription factor 5, p130-binding (E2F5); E74-like factor 1 (ets domain transcription factor) (ELF1); E74-like factor 4 (ets domain transcription factor) (ELF4); early development regulator 2 (homolog of polyhomeotic 2) (EDR2); EBV induced G-protein coupled receptor (EBI2); ecotropic viral integration site 2B (EVI2B); ectin, galactoside-binding, soluble, 1 (galectin 1) (LGALS1); EGF-like-domain, multiple 4 (EGFL4); eIF-2-associated p67 homolog; elav-type RNA-binding protein (ETR-3); electron-transfer-flavoprotein, alpha polypeptide (glutaric aciduria II) (ETFA); ELK3, ETS-domain protein (SRF accessory protein 2) (ELK3); elongation factor 1-beta; elongation factor Ts (mitochondrial protein); elongation factor Tu-nuclear encoded mitochondrial; eMDC II protein; ems1 sequence (mammary tumor and squamous cell carcinoma-associated (p80/85 src substrate) (EMS1); endogenous retroviral element HC2; endosulfine alpha (ENSA); endothelial differentiation, sphingolipid G-protein-coupled receptor, 1 (EDG1); endothelial monocyte-activating polypeptide (EMAPII); enolase 1, (alpha) (ENO1); enolase 2, (gamma, neuronal) (ENO2); enolase-alpha; enoyl Coenzyme A hydratase 1, peroxisomal (ECH1); enoyl Coenzyme A hydratase, short chain, 1, mitochondrial (ECHS1); epidermal growth factor receptor pathway substrate 15 (EPS15); epithelial membrane protein 3 (EM[P3); Epoxide hydrolase 1, microsomal (xenobiotic) (EPHX1); ERF-2; ERp28 protein; erythrocyte membrane protein; erythroleukemic cells K562; EST (Hs.189509); estrogen receptor-related protein (hERRa1); ET binding factor 1 (SBF1); ets domain protein ERF; eukaryotic translation elongation factor 1 alpha 1 (EEF1A1); eukaryotic translation elongation factor 1 beta 2 (EEF1B2); eukaryotic translation elongation factor 1 delta (guanine nucleotide exchange protein) (EEF1D); eukaryotic translation elongation factor 1 gamma (EEF1G); eukaryotic translation elongation factor 2 (EEF2); eukaryotic translation initiation factor 2, subunit 1 (alpha, 35 kD) (EIF2S1); eukaryotic translation initiation factor 2, subunit 2 (beta, 38 kD) (EIF2S2); eukaryotic translation initiation factor 2, subunit 3 (gamma, 52 kD) (EIF2S3); eukaryotic translation initiation factor 3, subunit 10 (theta, 150/170 kD) (EIF3S10); eukaryotic translation initiation factor 3, subunit 2 (beta, 36 kD) (EIF3S2); eukaryotic translation initiation factor 3, subunit 3 (gamma, 40 kD) (EIF3S3); eukaryotic translation initiation factor 3, subunit 4 (delta, 44 kD) (EIF3S4); eukaryotic translation initiation factor 3, subunit 6 (48 kD) (EIF3S6); eukaryotic translation initiation factor 3, subunit 6 (EIF3S6); eukaryotic translation initiation factor 3, subunit 7 (zeta, 66/67 kD) (EIF3S7); eukaryotic translation initiation factor 3, subunit 8, 110 KD (EIF3S8); eukaryotic translation initiation factor 4 gamma, 1 (EIF4G); eukaryotic translation initiation factor 4 gamma, 1 (EIF4G1); eukaryotic translation initiation factor 4 gamma, 2 (EIF4G2); eukaryotic translation initiation factor 4 gamma, 2 (EIFG2); eukaryotic translation initiation factor 4A, isoform 1 (EIF4A1); eukaryotic translation initiation factor 4A, isoform 2 (EIF4A2); eukaryotic translation initiation factor 4B (EIF4B); Eukaryotic translation initiation factor 4E binding protein 2 (EIF4EBP2); eukaryotic translation initiation factor 5 (EIF5); eukaryotic translation termination factor 1 (ETF1); EV12 protein; Ewing sarcoma breakpoint region 1 (EWSR1); EWS/FLI1 activated transcript 2 homolog (EAT-2); EWS-E1A-F chimeric protein; excision repair cross-complementing rodent repair deficiency, complementation group 1 (includes overlapping antisense sequence) (ERCC1); excision repair cross-complementing rodent repair deficiency, complementation group 5 (xeroderma pigmentosum, complementation group G (Cockayne syndrome)) (ERCC5); exostoses (multiple)-like 3 (EXTL3); F11; F1-ATPase beta subunit (F-1 beta); Fanconi anaemia group A; Fanconi anemia, complementation group A (FANCA); far upstream element (FUSE) binding protein 1 (FUBP1); farnesyl diphosphate synthase (farnesyl pyrophosphate synthetase, dimethylallyltranstransferase, geranyltranstransferase) (FDPS); farnesyl-diphosphate farnesyltransferase 1 (FDFT1); farnesyltransferase, CAAX box, beta (FNTB); Fas-ligand associated factor 1; fatty-acid-Coenzyme A ligase, long-chain 1 (FACL1); Fc fragment of IgA, receptor for (FCAR); Fc fragment of IgE, high affinity I, receptor for; gamma polypeptide (FCER1G); Fc fragment of IgE, low affinity II, receptor for (CD23A) (FCER2); Fc fragment of IgG, low affinity IIa, receptor for (CD32); Fc fragment of IgG, low affinity IIa, receptor for (CD32) (FCGR2A); Fc fragment of IgG, low affinity IIIa, receptor for (CD16) (FCGR3A); Fc fragment of IgG, receptor, transporter, alpha (FCGRT); fc-fgr; Fc-gamma-receptor IIIB (FCGR3B); feline sarcoma (Snyder-Theilen) viral (v-fes)/Fujinami avian sarcoma (PRCII) viral (v-fps) oncogene homolog (FES) c-fes/fps); female sterile homeotic-related gene 1 (mouse homolog) (FSRG1); ferritin L-chain; ferritin, heavy polypeptide 1 (FTH1); fetal Alzheimer antigen (FALZ); fetal Ig heavy chain variable region; fibrillarin (FBL); fibrinogen-like protein 2 (T49); ficolin (collagen/fibrinogen domain-containing) 1 (FCN1); filamin A, alpha (actin-binding protein-280) (FLNA); filamin B, beta (actin-binding protein-278) (FLNB); Finkel-Biskis-Reilly murine sarcoma virus (FBR-MuSV) ubiquitously expressed (fox derived); ribosomal protein S30 (FAU); FK-506 binding protein; FK506-binding protein 1A (12 kD) (FKBP1A); FK506-binding protein 1B (12.6 kD) (FKBP1B); FK506-binding protein 5 (FKBP5); Flightless I (*Drosophila*) homolog (FLII); FLN29 (FLN29); flotillin 2 (FLOT2); folate receptor 2 (fetal) (FOLR2); forkhead (*Drosophila*) homolog (rhabdomyosarcoma) like 1 (FKHRL1); Formyl peptide receptor 1 (FPR1); formyl peptide receptor-like 1 (FPRL1); fragile X mental retardation 1 (FMR1); fragile X mental retardation, autosomal homolog 1 (FXR1); Friend leukemia virus integration 1 (FLI1); fructose-bisphosphatase 1 (FBP1); FSHD-associated repeat DNA, proximal region; fucose-1-phosphate guanylyltransferase (FPGT); full length insert cDNA clone ZA78A09; full length insert cDNA YP07G10; fumarate hydratase (FH); FYN-binding protein (FYB-120/130) (FYB); G protein beta subunit-like protein 12.3; G protein-coupled receptor kinase 6 (GPRK6); G1 to S phase transition 1 (GSPT1); GA-binding protein transcription factor, beta subunit 2 (47 kD) (GABPB2); galactose-1-phosphate uridylyltransferase (GALT); galactosidase, beta 1 (GLB1); galectin-9 isoform; gamma2-adaptin (G2AD); gamma-actin; gamma-aminobutyric acid (GABA) B receptor 1 (GABBR1); GATA-binding protein 2 (GATA2); GATA-binding protein 3 (GATA3); GCN5 (general control of amino-acid synthesis, yeast, homolog)-like 1 (GCN5L1); GDP dissociation inhibitor 1 (GDI1); GDP dissociation inhibitor 2 (GCI2); GDS-related protein (HKE1.5); gelsolin (amyloidosis, Finnish type) (GSN); general transcription factor II, I (GTF2I); general transcription factor II, i, pseudogene 1 (GTF2IP1); general transcription factor IIF, polypeptide 1 (74 kD subunit) (GTF2F1); general transcription factor IIH, polypeptide 3 (34 kD subunit) (GTF2H3); general transcription factor IIH, polypeptide 4 (52 kD subunit) (GTF2H4); general transcription factor IIIA (GTF3A); general transcription factor IIIC, polypeptide 1 (alpha subunit, 220 kD) (GTF3C1); general transcription factor IIIC, polypeptide 2 (beta subunit, 110 kD) (GTF3C2); germline immunoglobulin heavy chain (IGHV@); germline immunoglobulin heavy chain, variable region; germline immunoglobulin heavy chain, variable region, (21-2); GLE1 (yeast homolog)-like, RNA export mediator (GLE1L); glia maturation factor, beta (GMFB); glioma-associated oncogene homolog (zinc finger protein) (GLI); globin, alpha 2; glucocorticoid receptor (GRL); glucos phosphate isomerase (CONTAINS LARGE REPEAT); glucosamine (N-acetyl)-6-sulfatase (Sanfilippo disease IIID) (GNS); glucose transporter-like protein-III (GLUT3); glucosidase, alpha; acid (Pompe disease, glycogen storage disease type II) (GAA); glucosidase, beta; acid (includes glucosylceramidase) (GBA); glutamate dehydrogenase 1 (GLUD1); glutamate-ammonia ligase (glutamine synthase) (GLUL); glutamate-cysteine ligase (gamma-glutamylcysteine synthetase), catalytic (72.8 kD) (GLCLC); glutamine cyclotransferase; glutamine-fructose-6-phosphate transaminase 1 (GFPT1); glutaminyl-tRNA synthetase; glutaminyl-tRNA synthetase (QARS); glutamyl-prolyl-tRNA synthetase (EPRS); glutathione peroxidase 1 (GPX1); glutathione peroxidase 4 (phospholipid hydroperoxidase) (GPX4); glutathione S-transferase pi (GSTP1); glutathione S-transferase subunit 13 homolog; glyceraldehyde-3-phosphate dehydrogenase (GAPD); glycogenin (GYG); glycophorin C (Gerbich blood group) (GYPC); glycoprotein M6B (GPM6B); glycyl-tRNA synthetase (GARS); glyoxalase I (lactoyl glutathione lyase) (GLYI); golgi autoantigen, golgin subfamily a, 1 (GOLGA1); golgi autoantigen, golgin subfamily a, 4 (GOLGA4); golgi autoantigen, golgin subfamily b, macrogolgin (with transmembrane signal), 1 (GOLGB1); gp25L2 protein; grancalcin; granulin (GRN); Granulysin (NKG5); granzyme A (granzyme 1, cytotoxic T-lymphocyte-associated serine esterase 3) (GZMA); GRB2-related adaptor protein (GRAP); Grb2-related adaptor protein 2 (GRAP2); GRO1 oncogene (melanoma growth stimulating activity, alpha) (GRO1); growth arrest and DNA-damage-inducible gene (GADD153); growth arrest-specific 7 (GAS7); growth factor receptor-bound protein 2 (GRB2); GS1 (protein of unknown function); GS3955; GTP binding protein 1 (GTPBP1); GTPase activating protein-like (GAPL); Gu protein (GURDB); guanine nucleotide binding protein (G protein), alpha inhibiting activity polypeptide 2 (GNAI2); guanine nucleotide binding protein (G protein), alpha inhibiting activity polypeptide 3 (GNAI3); guanine nucleotide binding protein (G protein), alpha stimulating activity polypeptide 1 (GNAS1); guanine nucleotide binding protein (G protein), alpha transducing activity polypeptide 2 (GNAT2); guanine nucleotide binding protein (G protein), beta 5 (GNB5); guanine nucleotide binding protein (G protein), beta polypeptide 1 (GNB1); guanine nucleotide binding protein (G protein), q polypeptide (GNAQ); guanine nucleotide binding protein-like 1 (GNL1); guanine nucleotide exchange factor; guanine nucleotide regulatory factor (LFP40); GUANINE-MONOPHOSPHATE SYNTHETASE (GMPS); guanosine-diphosphatase like protein; guanylate binding protein 1, interferon-inducible, 67 kD (GBP1); guanylate binding protein 2, interferon-inducible (GBP2); H2A histone family, member C(H2AFC); H2A histone family, member Y (H2AY); H2B histone family, member L (H2BFL); h2-calponin; H-2K binding factor-2; H3 histone family, member K (H3FK); H3 histone, family 3A (H3F3A); H3 histone, family 3B (H3.3B) (H3F3B); hbc647; heat shock 27 kD protein 1 (HSPB1); heat shock 40 kD protein 1 (HSPF1); heat shock 60 kD protein 1 (chaperonin) (HSPD1); heat shock 70 kD protein 1 (HSPA1A); heat shock 70 kD protein 5 (glucose-regulated protein, 78 kD) (HSPA5); heat shock 70 kD protein 6 (HSP70B') (HSPA6); heat shock 70 kD protein 9B (mortalin-2) (HSPA9B); heat shock factor binding protein 1 (HSBP1); heat shock protein 90; heat shock protein, DNAJ-like 2 (HSJ2); Hect (homologous to the E6-AP (UBE3A) carboxyl terminus) domain and RCC1 (CHC1)-like domain (RLD) 1 (HERC1); hect domain and RLD 2 (HERC2); helicase-like protein (HLP); helix-loop-helix protein HE47 (E2A); hematopoietic cell-specific Lyn substrate 1 (HCLS1); heme oxygenase (decycling) 1 (HMOX1); hemoglobin beta (beta globin); hemoglobin, alpha 1 (HBA1); hemoglobin, beta (HBB); emokine (C-X-C motif), receptor 4 (fusin) (CXCR4); hemopoietic cell kinase (HCK); hepatitis C-associated microtubular aggregate protein p44; hepatoma-derived growth factor; Hermansky-Pudlak syndrome (HPS); heterogeneous nuclear ribonucleoprotein (C1/C2) (HNRPC); heterogeneous nuclear ribonucleoprotein A/B (HNRPAB); heterogeneous nuclear ribonucleoprotein A1 (HNRPA1); heterogeneous nuclear ribonucleoprotein A2/B1 (HNRPA2B1); heterogeneous nuclear ribonucleoprotein D (hnRNP D); heterogeneous nuclear ribonucleoprotein D-like (HNRPDL); heterogeneous nuclear ribonucleoprotein F (HNRPF); heterogeneous nuclear ribonucleoprotein G (HNRPG); heterogeneous nuclear ribonucleoprotein H1 (H) (HNRPH1); heterogeneous nuclear ribonucleoprotein K (HNRPK); heterogeneous nuclear ribonucleoprotein R (HNRPR); heterogeneous nuclear ribonucleoprotein U (scaffold attachment factor A) (HNRPU); hexokinase 1 (HK1); hexokinase 2 (HK2); hexokinase 3 (HK3); hexosaminidase A (alpha polypeptide) (HEXA; HGMP07I gene for olfactory receptor; High density lipoprotein binding protein (HDLBP); high-mobility group (nonhistone chromosomal) protein 1 (HMG1); High-mobility group (nonhistone chromosomal) protein 17 (HMG17); high-mobility group (nonhistone chromosomal) protein 2 (HMG2); high-mobility group (nonhistone chromosomal) protein isoforms I and Y; histidine ammonia-lyase (HAL); histidyl-tRNA synthetase (HARS); histocompatibility antigen (HLA-Cw3), class I; histone deacetylase 1 (HDAC); histone deacetylase 1 (HDAC1); histone deacetylase 5 (NY-CO-9); HK2 gene for hexokinase II; HL9 monocyte inhibitory receptor precursor; HLA class I heavy chain (HLA-Cw*1701); HLA class I locus C heavy chain; HLA class II SB 4-beta chain; HLA class III region containing NOTCH4 gene; HLA-A; HLA-A*7402; HLA-A11; HLA-B; HLA-B associated transcript-1 (D6S81E); HLA-B associated transcript-2 (D6S51E); HLA-B*1529; HLA-Bw72 antigen; HLA-C gene (HLA-Cw*0701 allele); HLA-Cw*0701; HLA-Cw*0801; HLA-Cw*1203; HLA-DR alpha-chain; HLA-F (leukocyte antigen F); HMG box containing protein 1; Hmob33; HMT1 (hnRNP methyltransferase, *S. cerevisiae*)-like 1 (HRMT1L1); homeodomain-interacting protein kinase 3 (HIPK3); homolog of *Drosophila* past (PAST); homolog of yeast (*S. cerevisiae*) ufd2 (UFD2); HPV16 E1 protein binding protein; HRIHFB2157; hsc70 gene for 71 kd heat shock cognate protein; HSPC012; HSPC021; HsPex13p; htra2-beta-2; HU-K4; hunc18b2; HUNKI; huntingtin-interacting protein HYPA/FBP11 (HYPA); hVps41p (HVPS41); hydroxyacyl-Coenzyme A dehydrogenase/3-ketoacyl-Coenzyme A thiolase/enoyl-Coenzyme A hydratase (trifunctional protein), alpha subunit (HADHA); hydroxyacyl-Coenzyme A dehydrogenase/3-ketoacyl-Coenzyme A thiolase/enoyl-Coenzyme A hydratase (trifunctional protein), beta subunit (HADHB); hydroxysteroid (17-beta) dehydrogenase 1 (HSD17B1); hypoxia-inducible factor 1, alpha subunit (basic helix-loop-helix transcription factor) (HIF1A); Ia-associated invariant gamma-chain (clones lambda-y (1,2,3)); iduronate 2-sulfatase (Hunter syndrome) (IDS); Ig heavy chain variable region; Ig heavy chain variable region (VH4DJ) (clone T14.4); Ig heavy chain variable region (VH4DJ) (clone T22.18); Ig J chain; Ig kappa; IG kappa light chain variable region A20; Ig lambda light chain variable region (26-34ITIIIF120); Ig mu-chain VDJ4-region; Ig rearranged anti-myelin kappa-chain (V-J4-region, hybridoma AE6-5); Ig rearranged H-chain mRNA V-region; IgG Fc binding protein (FC(GAMMA)BP); IgG heavy chain variable region (vH26); IgM heavy chain (C mu, membrane exons); IkB kinase-beta (IKK-beta); IL-1 receptor type II; IL2-inducible T-cell kinase (ITK); immediate early protein (ETR101); immunoglobulin light chain (lambda); Immunoglobulin (CD79A) binding protein 1 (IGBP1); immunoglobulin G Fc receptor IIIB; immunoglobulin gamma 3 (Gm marker) (IGHG3); immunoglobulin heavy chain (VI-3B); immunoglobulin heavy chain J region; immunoglobulin heavy chain J region, B1 haplotype; immunoglobulin heavy chain variable region (IGH) (clone 21u-48); immunoglobulin heavy chain variable region (IGH) (clone 23u-1); immunoglobulin heavy chain variable region V3-43 (IGHV@); immunoglobulin heavy chain variable region V3-7 (IGHV@); immunoglobulin IgH heavy chain Fd fragment; immunoglobulin kappa light chain; immunoglobulin kappa light chain V-segment A27; immunoglobulin light chain; immunoglobulin light chain variable region (lambda IIIb subgroup) from IgM rheumatoid factor; immunoglobulin M heavy chain V region=anti-lipid A antibody; immunoglobulin mu (IGHM); immunoglobulin mu binding protein 2 (IGHMBP2); immunoglobulin superfamily, member 2 (IGSF2); imogen 38 (IMOGEN38); IMP (inosine monophosphate) dehydrogenase 1 (IMPDH1); IMP (inosine monophosphate) dehydrogenase 2 (IMPDH2); inc finger protein 151 (pHZ-67) (ZNF151); inc finger protein, C2H2, rapidly turned over (ZNF20); inducible poly(A)-binding protein (IPABP); inducible protein (Hs.80313); inhibitor of DNA binding 2, dominant negative helix-loop-helix protein (ID2); inhibitor of kappa light polypeptide gene enhancer in B-cells, kinase complex-associated protein (IKBKAP); inositol 1,3,4-trisphosphate 5/6-kinase; inositol 1,4,5 trisphosphate receptor type 1 (ITPR1); inositol 1,4,5-trisphosphate 3-kinase B (ITPKB); inositol monophosphatase; inositol polyphosphate-5-phosphatase, 145 kD (INPP5D); Ins(1,3,4,5)P4-binding protein; insulin (INS); insulin like growth factor 2 receptor (IGF2R); integral membrane protein 1 (ITM1); integral membrane protein 2C (ITM2C); integral membrane protein Tmp21-I (p23); integrin beta 4 binding protein (ITGB4BP); integrin, alpha 2b (platelet glycoprotein IIb of IIb/IIIa complex, antigen CD41B) (ITGA2B); integrin, alpha 5 (fibronectin receptor, alpha polypeptide) (ITGA5); integrin, alpha L (antigen CD11A (p180), lymphocyte function-associated antigen 1; alpha polypeptide) (ITGAL); integrin, alpha M (complement component receptor 3, alpha; also known as CD11b (p170), macrophage antigen alpha polypeptide) (ITGAM); integrin, alpha X (antigen CD11C (p150), alpha polypeptide) (ITGAX); integrin, beta 1 (fibronectin receptor, beta polypeptide, antigen CD29 includes MDF2 MSK12) (ITGB1); integrin, beta 2 (antigen CD18 (p95), lymphocyte function-associated antigen 1; macrophage antigen 1 (mac-1) beta subunit) (ITGB2); integrin, beta 7 (ITGB7); Integrin-linked kinase (ILK); intercellular adhesion molecule 1 (CD54), human rhinovirus receptor (ICAM1); intercellular adhesion molecule 2 (ICAM2); intercellular adhesion molecule 3 (ICAM3); intercellular adhesion molecule 4, Landsteiner-Wiener blood group (ICAM4); Interferon consensus sequence binding protein 1 (ICSBP1); interferon regulatory factor 2 (IRF2); interferon regulatory factor 1 (IRF1); interferon regulatory factor 5 (IRF5); interferon, gamma-inducible protein 16 (IFI16); interferon, gamma-inducible protein 30 (IFI30); interferon-induced protein 17 (IFI17); interferon-induced protein 54 (IFI54); interferon-inducible (1-8D); interferon-inducible (1-8U); interferon-related developmental regulator 1 (IFRD1); interferon-stimulated transcription factor 3, gamma (48 kD) (ISGF3G); interleukin 1 receptor, type II (IL1R2); Interleukin 10 receptor, beta (I.10RB); interleukin 12 receptor, beta 1 (IL12RB1); interleukin 13 receptor, alpha 1 (IL13RA1); interleukin 16 (lymphocyte chemoattractant factor) (IL16); interleukin 18 receptor 1 (IL18R1); interleukin 2 receptor, beta (IL2RB); interleukin 2 receptor, gamma (severe combined immunodeficiency) (IL2RG); interleukin 4 receptor (IL4R); interleukin 6 receptor (IL6R); interleukin 6 signal transducer (gp130, oncostatin M receptor) (IL6ST); interleukin 7 receptor (IL7R); interleukin 8 (IL8); interleukin 8 receptor alpha (IL8RA); interleukin 8 receptor, beta (IL8RB); interleukin enhancer binding factor 2, 45 kD (ILF2); interleukin enhancer binding factor 3, 90 kD (ILF3); interleukin-1 receptor-associated kinase 1 (IRAK1); interleukin-10 receptor, alpha (IL10RA); interleukin-11 receptor, alpha (IL11RA); intestinal carboxylesterase; IQ motif containing GTPase activating protein 1 (IQGAP1); IQ motif containing GTPase activating protein 2 (IQGAP2); isocitrate dehydrogenase 1 (NADP+), soluble (IDH1); isocitrate dehydrogenase 2 (NADP+), mitochondrial (IDH2); isocitrate dehydrogenase 3 (NAD+) alpha (DH3A); isocitrate dehydrogenase 3 (NAD+) gamma (IDH3G); isolate TzCCR5-179 CCR5 receptor (CCR5); isopentenyl-diphosphate delta isomerase (IDI1); Janus kinase 1 (a protein tyrosine kinase) (JAK1); Janus kinase 2 (a protein tyrosine kinase) (JAK2); Jk-recombination signal binding protein (RBPJK); JM1 protein; jumonji (mouse) homolog (JMJ); jun D proto-oncogene (JUND); jun dimerization protein; junction plakoglobin (JUP); kangai 1 (suppression of tumorigenicity 6, prostate; CD82 antigen (R2 leukocyte antigen, antigen detected by monoclonal and antibody IA4)) (KAI1); karyopherin (importin) beta 1 (KPNB1); karyopherin (importin) beta 2 (KPNB2); karyopherin alpha 1 (importin alpha 5) (KPNA1); karyopherin alpha 2 (RAG cohort 1, importin alpha 1) (DPNA2); karyopherin alpha 3 (importin alpha 4) (KPNA3); karyopherin alpha 4 (KPNA4); Katanin (80 kDa) (KAT); KE03 protein; Keratin 8 (KRT8); ketohexokinase (fructokinase) (KHK); KIAA0002 (KIAA0002); KIAA0005 (KIAA0005); KIAA0010 (KIAA0010); KIAA0016 (KIAA0016); KIAA0017 (KIAA0017); KIAA0022 (KIAA0022); KIAA0023 (KIAA0023); KIAA0024 (KIAA0024); KIAA0025 (KIAA0025); KIAA0026 (KIAA0026); KIAA0027; KIAA0032 (KIAA0032); KIAA0040 (KIAA0040); KIAA0050 (KIAA0050); KIAA0053 (KIAA0053); KIAA0057 (KIAA0057); KIAA0058 (KIAA0058); KIAA0063 (KIAA0063); KIAA0064 (KIAA0064); KIAA0066; KIAA0068; KIAA0073; KIAA0081; KIAA0084; KIAA0085; KIAA0088; KIAA0090; KIAA0092 (KIAA0092); KIAA0094; KIAA0095 (KIAA0095); KIAA0096; KIAA0097 (KIAA0097); KIAA0099 (KIAA0099); KIAA0102 (KIAA0102); KIAA0105; KIAA0121 (KIAA0121); KIAA0123; KIAA0128; KIAA0129 (KIAA0129); KIAA0130 (KIAA0130); KIAA0136; KIAA0137 (KIAA0137); KIAA0140 (KIAA0140); KIAA0141 (KIAA0141); KIAA0144 (KIAA0144); KIAA0146; KIAA0148 (KIAA0148); KIAA0154; KIAA0156; KIAA0160; KIAA0161 (KIAA0161); KIAA0164 (KIAA0164); KIAA0167 (KIAA0167); KIAA0168 (KIAA0168); KIAA0169; KIAA0171 (KIAA0171); KIAA0174 (KIAA0174); KIAA0179; KIAA0181; KIAA0183; KIAA0184; KIAA0193 (KIAA0193); KIAA0200 (KIAA0200); KIAA0210 (KIAA0210); KIAA0217; KIAA0219; KIAA0222 (KIAA0222); KIAA0223; KIAA0229; KIAA0232 (KIAA0232); KIAA0233 (KIAA0233); KIAA0235; KIAA0239; KIAA0240; KIAA0242; KIAA0248; KIAA0249 (KIAA0249); KIAA0253; KIAA0254 (KIAA0254); KIAA0255 (KIAA0255); KIAA0262 (KIAA0262); KIAA0263 (KIAA0263); KIAA0264; KIAA0268; KIAA0275 (KIAA0275); KIAA0304 (KIAA0304); KIAA0308; KIAA0310 (KIAA0310); KIAA0315 (KIAA0315); KIAA0329 (KIAA0329); KIAA0330; KIAA0332; KIAA0333; KIAA0336 (KIAA0336); KIAA0342 (KIAA0342); KIAA0344 (KIAA0344); KIAA0354 (KIAA0354); KIAA0365 (KIAA0365); KIAA0370; KIAA0372 (KIAA0372); KIAA0373 (KIAA0373); KIAA0375 (KIAA0375); KIAA0377 (KIAA0377); KIAA0379; KIAA0380 (KIAA0380); KIAA0382 (KIAA0382); KIAA0383; KIAA0386 (KIAA0386); KIAA0392; KIAA0397 (KIAA0397); KIAA0403; KIAA0404; KIAA0409; KIAA0421; KIAA0428 (KIAA0428); KIAA0429 (KIAA0429); KIAA0430 (KIAA0430); KIAA0432

(KIAA0432); KIAA0435 (KIAA0435); KIAA0438 (KIAA0438); KIAA0447 (KIAA0447); KIAA0449; KIAA0456; KIAA0458 (KIAA0458); KIAA0462; KIAA0465; KIAA0476 (KIAA0476); KIAA0489; KIAA0494 (KIAA0494); KIAA0515; KIAA0521; KIAA0525; KIAA0530; KIAA0532; KIAA0537 (KIAA0537); KIAA0540; KIAA0543; KIAA0544; KIAA0549; KIAA0551; KIAA0554; KIAA0561; KIAA0562 (KIAA0562); KIAA0563 (KIAA0563); KIAA0569 (KIAA0569); KIAA0571 (KIAA0571); KIAA0573; KIAA0576; KIAA0580; KIAA0584; KIAA0592; KIAA0596; KIAA0598 (KIAA0598); KIAA0608; KIAA0614; KIAA0615 (KIAA0615); KIAA0621; KIAA0648; KIAA0652 (KIAA0652); KIAA0668; KIAA0669; KIAA0671 (KIAA0671); KIAA0675 (KIAA0675); KIAA0676; KIAA0677 (KIAA0677); KIAA0678; KIAA0679; KIAA0680 (KIAA0680); KIAA0692; KIAA0697; KIAA0699; KIAA0700; KIAA0737 (KIAA0737); KIAA0748 (KIAA0748); KIAA0763 (KIAA0763); KIAA0769 (KIAA0769); KIAA0782; KIAA0796; KIAA0798 (KIAA0798); KIAA0823; KIAA0854; KIAA0856; KIAA0860; KIAA0862; KIAA0873; KIAA0892; KIAA0906; KIAA0991; killer cell lectin-like receptor subfamily B, member 1 (KLRB1); killer cell lectin-like receptor subfamily C, member 4 (KLRC4); kinectin 1 (kinesin receptor) (KTN1); kinesin family member 5B (KIF5B); kinesin-like DNA binding protein; Kruppel related gene (clone pHKR1RS); Kruppel-like zinc finger protein Zf9; kruppel-type zinc finger protein, ZK1; L apoferritin; lactate dehydrogenase A (LDHA); lactate dehydrogenase B (LDHB); lactotransferrin (LTF); laminin receptor 1 (67 kD); Ribosomal protein SA (LAMR1); laminin receptor homolog {3' region}; laminin, gamma 1 (formerly LAMB2) (LAMC1); latent transforming growth factor beta binding protein 1 (LTBP1); LDLC; lectin, galactoside-binding, soluble, 2 (galectin 2) (LGALS2); lectin, galactoside-binding, soluble, 3 binding protein (galectin 6 binding protein) (LGALS3BP); leucine rich repeat (in FLII) interacting protein 1 (LRRFIP1); leucocyte immunoglobulin-like receptor-5 (LIR-5); leucocyte immunoglobulin-like receptor-6a (LIR-6); leucocyte immunoglobulin-like receptor-7 (LIR-7); leukemia virus receptor 1 (GLVR1); leukocyte adhesion protein p150, 95 alpha subunit; leukocyte antigen, HLA-A2; leukocyte immunoglobulin-like receptor (MIR-10); leukocyte tyrosine kinase (LTK); leukocyte-associated Ig-like receptor 1 (LIAR1); leukotriene A4 hydrolase (LTA4H); leupaxin (LDPL); ligase I, DNA, ATP-dependent (LIG1); LIM and SH3 protein 1 (LASP1); LIM domain kinase 2 (LIMK2); Line-1 repeat mRNA with 2 open reading frames; Line-1 repeat with 2 open reading frames; lipase A, lysosomal acid, cholesterol esterase (Wolman disease) (LIPA); lipase, hormone-sensitive (LIPE); LMP7; Lon protease-like protein (LONP); low density lipoprotein-related protein 1 (alpha-2-macroglobulin receptor) (LRP1); low density lipoprotein-related protein-associated protein 1 (alpha-2-macroglobulin receptor-associated protein 1) (LRPAP1); low-affinity Fc-gamma receptor IIA; LPS-induced TNF-alpha factor (PIG7); Lst-1; L-type amino acid transporter subunit LAT1; lung resistance-related protein (LRP); Lymphocyte antigen 75 (LY75); lymphocyte antigen 9 (LY9); lymphocyte antigen HLA-B*4402 and HLA-B*5101; lymphocyte cytosolic protein 1 (L-plastin) (LCP1); lymphocyte cytosolic protein 2 (SH2 domain-containing leukocyte protein of 76 kD) (LCP2); lymphocyte glycoprotein T1/Leu-1; lymphocyte-specific protein 1 (LSP1); lymphocyte-specific protein tyrosine kinase (LCK); lymphoid phosphatase LyP1; lymphoid-restricted membrane protein (LRMP); lymphoid-specific SP100 homolog (LYSP100-A); lymphoma proprotein convertase (LPC); lysosomal-associated membrane protein 1 (LAMP1); Lysosomal-associated membrane protein 2 (LAMP2); lysozyme (renal amyloidosis) (LYZ); lysyl-tRNA synthetase (KARS); M phase phosphoprotein 10 (U3 small nucleolar ribonucleoprotein) (MPP-10); M1-type and M2-type pyruvate kinase; m6A methyltransferase (MT-A70); mab-21 (*C. elegans*)-like 1 (MAB21L1); MacMarcks; macrophage-associated antigen (MM130); MADS box transcription enhancer factor 2, polypeptide A (myocyte enhancer factor 2A) (MEF2A); MADS box transcription enhancer factor 2, polypeptide C (myocyte enhancer factor 2C) (MEF2C); major histocompatibility complex class I beta chain (HLA-B); major histocompatibility complex, class I, A (HLA-A); major histocompatibility complex, class I, C (HAL-C); major histocompatibility complex, class I, E (HLA-E); major histocompatibility complex, class II, DM BETA (HLA-DMB); major histocompatibility complex, class II, DP beta 1 (HLA-DPB1); major histocompatibility complex, class II, DR beta 1 (HLA-DRB1); Major histocompatibility complex, class II, Y box-binding protein I; DNA-binding protein B (YB1); malate dehydrogenase 1, NAD (soluble) (mdh1); malate dehydrogenase 1, NAD (soluble) (MDH1); malonyl-CoA decarboxylase precursor; maltase-glucoamylase (mg); manic fringe (*Drosophila*) homolog (MFNG); mannose phosphate isomerase (MPI); mannose phosphate isomerase (mpi); mannose-6-phosphate receptor (cation dependent) (M6PR); mannose-P-dolichol utilization defect 1 (MPDU1); mannosidase, alpha B, lysosomal (MANB); mannosyl (alpha-1,3-)-glycoprotein beta-1,2-N-acetylglucosaminyltransferase (MGAT1); map 4q35 repeat region; MAP kinase-interacting serine/threonine kinase 1 (MKNK1); MAP/ERK kinase kinase 3 (MEKK3); MAP/ERK kinase kinase 5 (MEKK5); MAP/microtubule affinity-regulating kinase 3 (MARK3); Marenostrin protein; MASL1; MAX dimerization protein (MAD); MaxiK potassium channel beta subunit; MBP-2 for MHC binding protein 2; Meis (mouse) homolog 3 (MEIS3); melanoma-associated antigen p97 (melanotransferrin); membrane cofactor protein (CD46, trophoblast-lymphocyte cross-reactive antigen) (MCP); membrane component, chromosome 17, surface marker 2 (ovarian carcinoma antigen CA125) (M17S2); membrane metallo-endopeptidase (neutral endopeptidase, enkephalinase, CALLA, CD10) (MME); membrane protein, palmitoylated 1 (55 kD) (MPP1); meningioma expressed antigen (MGEA); meningioma-expressed antigen 11 (MEA11); Menkes Disease (ATP7A) putative Cu++-transporting P-type ATPase; metallothionein 2A (MT2A); metaxin 1 (MTX1); methionine adenosyltransferase II, alpha (MAT2A); methylene tetrahydrofolate dehydrogenase (NAD+ dependent), methenyltetrahydrofolate cyclohydrolase (MTHFD2); methylenetetrahydrofolate dehydrogenase (NADP+ dependent), methenyltetrahydrofolate cyclohydrolase, formyltetrahydrofolate synthetase (MTHFD1); methyltransferase, putative; MHC class 1 region; MHC class I antigen (HLA-A2); MHC class I antigen (HLA-A33); MHC class I antigen (HLA-C); MHC class I antigen B*5801 (HLA-B); MHC class I antigen HLA-A (HLA-A); MHC class I antigen HLA-A (HLA-A-2402 allele); MHC class I antigen HLA-A11K; MHC class I antigen HLA-B (B*48 allele); MHC class I antigen HLA-B (HLA-B*1502 allele); MHC class I antigen HLA-B (HLA-B*40MD); MHC class I antigen HLA-B (HLA-B*4103 allele); MHC class I antigen HLA-B gene (HLA-B*4402 variant allele); MHC class I antigen HLA-B GN00110-B*3910; MHC class I antigen HLA-Cw*04011; MHC class I antigen R69772HLA-A (A*0302); MHC class I antigen SHCHA (HLA-B*4403 variant); MHC class I histocompatibility antigen (HLA-B) (clone C21/14); MHC class I HLA B71; MHC class I HLA-A (Aw33.1); MHC class I HLA-B; MHC class I HLA-B (HLA-B-08NR allele); MHC class I HLA-B*3512; MHC class I HLA-B44.2 chain; MHC class I HLA-B51-cd3.3; MHC class I HLA-C allele; MHC class I HLA-Cw*0803; MHC class I HLA-Cw6; MHC class I lymphocyte antigen A2 (A2.1) variant DK1; MHC class I mic-B antigen; MHC class I polypeptide-related sequence A (MICA); MHC class II DNA Sequence (clone A37G7-1C11); MHC class II DQ-alpha associated with DRw6, DQw1 protein; MHC class II DQ-beta associated with DR2, DQw1 protein; MHC class II HAL-DQ-LTR5 (DQ,w8) DNA fragment, long terminal repeat region; MHC class II HLA-DRB1; MHC class II HLA-DRw11-beta-I chain (DRw11.3); MHC class II lymphocyte antigen (DPw4-beta-1); microsomal stress 70 protein ATPase core (stch); microtubule-associated protein 4 (MAP4); microtubule-associated protein 7 (MAP7); mineralocorticoid receptor (aldosterone receptor) (MLR); minichromosome maintenance deficient (S. cerevisiae) 3 (MCM31); minichromosome maintenance deficient (S. cerevisiae) 3-associated protein (MCM3AP); minichromosome maintenance deficient (S. cerevisiae) 5 (cell division cycle 46) (MCM5); mitochondrial 16S rRNA; mitochondrial ATP synthase (F1-ATPase) alpha subunit; mitochondrial ATP synthase c subunit (P1 form); mitochondrial cytochrome b small subunit of complex II; mitochondrial DNA loop attachment sequences (clone LAS34); mitochondrial DNA polymerase accessory subunit precursor (MtPolB) nuclear gene encoding mitochondrial protein; mitochondrial DNA, complete genome; mitochondrial inner membrane preprotein translocase Tim17a; mitochondrial loop attachment sequence (clone LAS88); mitochondrial NADH dehydrogenase subunit 2 (ND2); mitochondrial translational initiation factor 2 (MTIF2); mitochondrion cytochrome b; mitogen inducible gene mig-2; mitogen-activated protein kinase-activated protein kinase 3 (MAPKAPK3); MLN51; moesin (MSN); monocytic leukaemia zinc finger protein (MOZ); MOP1 ( ); motor protein (Hs.78504); mouse double minute 2, human homolog of; p53-binding protein (MDM2); M-phase phosphoprotein 6 (MPP-6); M-phase phosphoprotein, mpp11; MPS1; Mr 110,000 antigen; mu-adaptin-related protein-2; mu subunit of AP-4 (MU-ARP2); murine leukemia viral (bmi-1) oncogene homolog (BMI1); mutant (Daudi) beta2-microglobulin; mutated in Alzheimer's diseases (MCC); myeloid cell leukemia sequence 1 (BCL2-related) (MCL1); myeloid cell nuclear differentiation antigeN (MNDA); myeloid differentiation primary response gene (88) (MYD88); myeloid leukemia factor 2 (MLF2); myeloid/lymphoid or mixed-lineage leukemia (trithorax (Drosophila) homolog); translocated to, 7 (MLLT7); MYH9 (cellular myosin heavy chain); myomesin (M-protein) 2 (165 kD) (MYOM2); myosin IE (MYO1E); myosin light chain kinase (MLCK); myosin phosphatase, target subunit 1 (MYPT1); myosin, heavy polypeptide 9, non-muscle (MYH9); myosin, light polypeptide, regulatory, non-sarcomeric (20 kD) (MLCB); myosin-I beta; myristoylated alanine-rich protein kinase C substrate (MARCKS, 80K-L) (MACS); myxovirus (influenza) resistance 1, homolog of murine (interferon-inducible protein p78) (MX1); myxovirus (influenza) resistance 2, homolog of murine (MX2); N-acetylgalactosaminidase, alpha-(NAGA); N-acetylglucosamine receptor 1 (thyroid) (NAGR1); NACP/alpha-synuclein; N-acylaminoacyl-peptide hydrolase (APEH); N-acylsphingosine amidohydrolase (acid ceramidase) (ASAH); NAD+-specific isocitrate dehydrogenase beta subunit precursor (encoding mitochondrial protein); NADH dehydrogenase (ubiquinone) 1 alpha subcomplex, 5 (13 kD, B13) (NDUFA5); NADH dehydrogenase (ubiquinone) 1 beta subcomplex, 5 (16 kD, SGDH) (NDUFB5); NADH dehydrogenase (ubiquinone) Fe-S protein 2 (49 kD) (NADH-coenzyme Q eductase) (NDUFS2); NADH dehydrogenase (ubiquinone) flavoprotein 2 (24 kD) (NDUFV2); NADH:ubiquinone dehydrogenase 51 kDa subunit (NDUFV1); Nardilysin (N-arginine dibasic convertase) (NRD1); nascent-polypeptide-associated complex alpha polypeptide (NACA); natural killer cell group 7 sequence (NKG7); natural killer cell transcript 4 (NK4); natural killer-associated transcript 3 (NKAT3); natural killer-associated transcript 5 (NKAT5); natural killer-tumor recognition sequence (NKTR); N-deacetylase/N-sulfotransferase (heparan glucosaminyl) 2 (NDST2); Ndr protein kinase; Nedd-4-like ubiquitin-protein ligase WWP1; nel (chicken)-like 2 (NELL2); N-ethylmaleimide-sensitive factor attachment protein, alpha (NAPA); N-ethylmaleimide-sensitive factor attachment protein, gamma (NAPG); neural precursor cell expressed, developmentally down-regulated 5 (NEDD5); neural precursor cell expressed, developmentally down-regulated 8 (NEDD8); neuregulin 1 (NRG1); neuroblastoma RAS viral (v-ras) oncogene homolog (NRAS); Neurofibromin 2 (bilateral acoustic neuroma) (NF2); neuronal apoptosis inhibitory protein (NAIP); neuronal cell adhesion molecule (NRCAM); neuropathy target esterase (NTE); neurotrophic tyrosine kinase, receptor, type 1 (NTRK1); neutrophil cytosolic factor 4 (40 kD); NG31; nibrin (NBS); NIK; Ninjurin 1; nerve injury-induced protein-1; Nmi; N-myristoyltransferase 1 (NMT1); No arches-like (zebrafish) zinc finger protein (NAR); non-histone chromosome protein 2 (S. cerevisiae)-like 1 (NHP2L1); non-muscle alpha-actinin; non-muscle myosin alkali light chain (Hs.77385); non-neuronal enolase (EC 4.2.1.11); non-receptor tyrosine phosphatase 1; normal keratinocyte substraction library mRNA, clone H22a; notch group protein (N); novel protein; novel T-cell activation protein; N-sulfoglucosamine sulfohydrolase (sulfamidase) (SGSH); nsulin induced gene 1 (INSIG1); integrin, alpha 4 (antigen CD49D, alpha 4 subunit of VLA-4 receptor) (ITGA14); interferon, gamma-inducible protein 16 (IFI16); interleukin 1, beta (IL1RB); nuclear antigen H731-like protein; nuclear antigen Sp100 (SP100); nuclear autoantigenic sperm protein (histone-binding) (NASP); Nuclear domain 10 protein (NDP52); Nuclear factor (erythroid-derived 2)-like 2 (NFE2L2); Nuclear factor of kappa light polypeptide gene enhancer in B-cells 1 (p105) (NFKB1); nuclear factor of kappa light polypeptide gene enhancer in B-cells inhibitor, alpha (NFKBIA);

nuclear factor related to kappa B binding protein (NFRKB); nuclear mitotic apparatus protein 1 (NUMA1); nuclear receptor coactivator 2 (GRIP1); nuclear receptor coactivator 3 (AIB3); nuclear receptor coactivator 4 (ELE1); nuclear receptor interacting protein 1 (NRIP1); nuclear respiratory factor 1 (NRF1); nuclear RNA helicase, DECD variant of DEAD box family (DDXL); nuclear transcription factor Y, alpha (NFYA); nuclear transcription factor, X-box binding 1 (NFX1); nuclear transport factor 2 (placental protein 15) (PP15); nucleobindin 1 (NUCB1); nucleolar phosphoprotein p130 (P130); nucleolar protein (KKE/D repeat) (NOP56); nucleolar protein (MSP58); nucleolar protein 1 (12 kD) (NOL1); nucleolar protein p40; nucleolin (NCL); nucleophosmin (nucleolar phosphoprotein B23, numatrin) (NPM1); nucleophosmin-retinoic acid receptor alpha fusion protein NPM-RAR long form; nucleoporin 153 kD (NUP153); nucleoporin 98 kD (NUP98); nucleosome assembly protein; nucleosome assembly protein 1-like 1 (NAP1L1); nucleosome assembly protein 1-like 4 (NAP1L4); nucleosome assembly protein, 5'UTR; olfactory receptor (OR7-141); oligodendrocyte myelin glycoprotein (OMG); O-linked N-acetylglucosamine (GlcNAc) transferase (UDP-N-acetylglucosamine:polypeptide-N-acetylglucosaminyl transferase) (OGT); ORF (Hs.77868); ORF1; MER37; origin recognition complex, subunit 2 (yeast homolog)-like (ORC2L); ornithine aminotransferase (gyrate atrophy) (OAT); ornithine decarboxylase (ODC); ornithine decarboxylase antizyme, ORF 1 and ORF 2; orphan receptor (Hs.100221); OS-9 precurosor; ovel centrosomal protein RanBPM (RANBPM); over-expressed breast tumor protein; oviductal glycoprotein 1, 120 kD (OVGP1); oxidase (cytochrome c) assembly 1-like (OXAIL); oxoglutarate dehydrogenase (lipoamide) (OGDH); oxysterol binding protein (OSBP); OZF; p21/Cdc42/Rac1-activated kinase 1 (yeast Ste20-related) (PAK1); p40; P47 LBC oncogene; p53-induced protein (PIG11); p62 nucleoporin; p63 mRNA for transmembrane protein; palmitoyl-protein thioesterase (ceroid-lipofuscinosis, neuronal 1, infantile; Haltia-Santavuori disease) (PPT); papillary renal cell carcinoma (translocation-associated) (PRCC); PAR protein; PAX3/forkhead transcription factor gene fusion; paxillin (PXN); PBK1 protein; PDZ domain protein (Drosophila inaD-like) (INALD); peptidase D (PEPD); peptidylprolyl isomerase A (cyclophilin A) (PPIA); peptidylprolyl isomerase D (cyclophilin D) (PPID); peptidylprolyl isomerase E (cyclophilin E) (PPIE); perforin 1 (preforming protein) (PRF1); peroxisomal acyl-CoA thioesterase (PTE1); Peroxisomal acyl-coenzyme A oxidase; peroxisomal farnesylated protein (PXF); phorbol-12-myristate-13-acetate-induced protein (PMAIP1); Phosphate carrier, mitochondrial (PHC); phosphate cytidylyltransferase 1, choline, alpha isoform (PCYT1A); phosphatidylinositol 3-kinase delta catalytic subunit; phosphatidylinositol 4-kinase, catalytic, beta polypeptide (PIK4CB); phosphatidylinositol glycan, class H (PIGH); phosphatidylinositol transfer protein (PI-TPbeta); phosphatidylinositol transfer protein, membrane-associated (PITPNM); phosphatidylinositol-4-phosphate 5-kinase, type II, alpha (PIP5K2A); phosphatidylinositol-4-phosphate 5-kinase, type II, beta (PIP5K2B); phosphodiesterase 7A (PDE7A); phosphodiesterase IB (PDES1B); phosphoglucomutase 1 (PGM1); phosphogluconate dehydrogenase (PGD); phosphoglycerate kinase 1 (PGK1); phosphoglycerate mutase 1 (brain) (PGAM1); phosphoglycerate mutase 2 (muscle) (PGAM2); phosphoinositide-3-kinase, catalytic, alpha polypeptide (PIK3CA); phosphoinositide-3-kinase, catalytic, delta polypeptide (PIK3CD); phosphoinositide-3-kinase, catalytic, gamma polypeptide (PIK3CG); phospholipase C; phospholipase C, delta 1 (PLCD1); phospholipase C, gamma 1 (formerly subtype 148) (PLCG1); phospholipid scramblase; phosphoribosyl pyrophosphate synthetase-associated protein 1 (PRPSAP1); phosphoribosylglycinamide formyltransferase, phosphoribosylglycinamide synthetase, phosphoribosylaminoimidazole synthetase (GART); phosphorylase kinase, alpha 2 (liver), glycogen storage disease IX (PHKA2); phosphorylase, glycogen; brain (PYGB); phosphorylase, glycogen; liver (Hers disease, lycogen storage disease type VI) (PYGL); phosphorylation regulatory protein HP-10; phosphotidylinositol transfer protein (PITPN); pigment epithelium-derived factor (PEDF); pim-1 oncogene (PIM1); pinin, desmosome associated protein (PNN); placenta (Diff33); placenta (Diff48); plasminogen activator, urokinase receptor (PLAUR); platelet factor 4 (PF4); platelet/endothelial cell adhesion molecule (CD31 antigen) (PECAM1); platelet-activating factor acetylhydrolase 2 (40 kD) (PAFAH2); platelet-activating factor acetylhydrolase, isoform Ib, alpha subunit (45 kD) (PAFAH1B1); platelet-activating factor receptor (PTAFR); pleckstrin (PLEK); pleckstrin homology, Sec7 and coiled/coil domains 1 (cytohesin 1) (PSCD1); pleckstrin homology, Sec7 and coiled/coil domains, binding protein (PSCDBP); pM5 protein; PMP69; poly (A) polymerase (PAP); poly(A)-binding protein-like 1 (PABPL1); poly(rC)-binding protein 1 (PCBP1); polyadenylate binding protein; polycystic kidney disease 1 (autosomal dominant) (PKD1); polymerase (DNA directed), beta (POLB); polymerase (DNA directed), gamma (POLG); polymerase (RNA) II (DNA directed) polypeptide A (220 kD) (POLR2A); polymyositis/scleroderma autoantigen 2 (100 kD) (PMSCL2); polypyrimidine tract binding protein (heterogeneous nuclear ribonucleoprotein I) (PTB); positive regulator of programmed cell death ICH-1L (Ich-1); postmeiotic segregation increased 2-like 12 (PMS2L12); postmeiotic segregation increased 2-like 8 (PMS2L8); potassium inwardly-rectifying channel, subfamily J, member 15 (KCNJ15); potassium voltage-gated channel, KQT-like subfamily, member 1 (KCNQ1); POU domain, class 2, associating factor 1 (POU2AF1); POU domain, class 2, transcription factor 1 (POU2F1); PPAR binding protein (PPARBP); PPAR gamma2; pre-B-cell colony-enhancing factor (PBEF); prefoldin 1 (PFDN1); prefoldin 5 (PRFLD5); pregnancy-associated plasma protein A (PAPPA); pre-mRNA splicing factor SRp20, 5'UTR; preprotein translocase (TIM17); prion protein; prion protein (p27-30) (Creutzfeld-Jakob disease, Gerstmann-Strausler-Scheinker syndrome, fatal familial insomnia) (PRNP); procollagen-lysine, 2-oxoglutarate 5-dioxygenase (lysine hydroxylase, Ehlers-Danlos syndrome type VI) (PLOD); procollagen-proline, 2-oxoglutarate 4-dioxygenase (proline 4-hydroxylase), alpha polypeptide 1 (P4HA1); procollagen-proline, 2-oxoglutarate 4-dioxygenase (proline 4-hydroxylase), beta polypeptide (protein disulfide isomerase; thyroid hormone binding protein p55) (P4HB); profilin 1 (PFN1); progesterone receptor-associated p48 protein (P48); prohibitin (PHB); proliferating cell nuclear antigen (PCNA); proliferation-associated gene A (natural iller-enhancing factor A) (PAGA); proline-serine-threonine phosphatase interacting protein 1 (PSTPIP1); prolyl endopeptidase (PREP); prolylcarboxypeptidase (angiotensinase C) (PRCP); promyelocytic leukemia (PML); properdin P factor, complement (PFC); pro-platelet basic protein (includes platelet basic protein, beta-thromboglobulin, connective tissue-activating peptide III, neutrophil-activating peptide-2) (PPBP); proprotein convertase subtilisin/kexin type 7 (PCSK7); prosaposin (variant Gaucher disease and variant metachromatic leukodystrophy) (PSAP); prostaglandin-endoperoxide synthase 1 (prostaglandin G/H synthase and cyclooxygenase) (PTGS1); prostaglandin-endoperoxide synthase 2 (prostaglandin G/H synthase and cyclooxygenase) (PTGS2); prostate carcinoma tumor antigen (pcta-1); protease inhibitor 1 (anti-elastase), alpha-1-antitrypsin (PI); protease inhibitor 2 (anti-elastase), proteasome (prosome, macropain) 26S subunit, ATPase, 1 (PSMC1); proteasome (prosome, macropain) 26S subunit, ATPase, 3 (PSMC3); proteasome (prosome, macropain) 26S subunit, ATPase, 4 (PSMC4); proteasome (prosome, macropain) 26S subunit, ATPase, 5 (PSMC5); proteasome (prosome, macropain) 26S subunit, ATPase, 6 (PMSC6); proteasome (prosome, macropain) 26S subunit, non-ATPase, 11 (PSMD11); proteasome (prosome, macropain) 26S subunit, non-ATPase, 2 (PSMD2); proteasome (prosome, macropain) 26S subunit, non-ATPase, 5 (PSMD5); proteasome (prosome, macropain) 26S subunit, non-ATPase, 7 (Mov34 homolog) (PMSD7); proteasome (prosome, macropain) 26S subunit, on-ATPase, 12 (PMSD12); proteasome (prosome, macropain) activator subunit 1 (PA28 alpha) (PSME1); proteasome (prosome, macropain) subunit, alpha type, 3 (PSMA3); proteasome (prosome, macropain) subunit, alpha type, 5 (PSMA5); proteasome (prosome, macropain) subunit, alpha type, 7 (PSMA7); proteasome (prosome, macropain) subunit, beta type, 1 (PSMB1); proteasome (prosome, macropain) subunit, beta type, 10 (PSMB10); proteasome (prosome, macropain) subunit, beta type, 6 (PMSB6); proteasome (prosome, macropain) subunit, beta type, 8 (large multifunctional protease 7) (PSMB8); proteasome (prosome, macropain) subunit, beta type, 9 (large multifunctional protease 2) (PSMB9); proteasome (prosome, macropain) subunit, beta type, 7 (PSMB7); protective protein for beta-galactosidase (galactosialidosis) (PPGB); protein A alternatively spliced form 2 (A-2); protein activator of the interferon-induced protein kinase (PACT); protein disulfide isomerase-related protein (P5); protein geranylgeranyltransferase type I, beta subunit (PGGT1B); protein homologous to chicken B complex protein, guanine nucleotide binding (H12.3); protein kinase A anchoring protein; protein kinase C substrate 80K-H (PRKCSH); protein kinase C, beta 1 (PRKCB1); protein kinase C, delta (PRKCD); protein kinase C, eta (PRKCH); Protein kinase C-like 1 (PRKCL1); protein kinase, AMP-activated, gamma 1 non-catalytic subunit (PRKAG1); protein kinase, cAMP-dependent, regulatory, type I, alpha (tissue specific extinguisher 1) (PRKAR1A); protein kinase, DNA-activated, catalytic polypeptide (PRKDC); protein kinase, mitogen-activated 1 (MAP kinase 1; p40, p41) (PRKM1); protein kinase, mitogen-activated 6 (extracellular signal-regulated kinase, p9'7) (PRKM6); protein kinase, mitogen-activated, kinase 3 (MAP kinase 3) (PRKMK3); protein phosphatase 1, catalytic subunit, alpha isoform (PPP1CA); protein phosphatase 1, regulatory subunit 10 (PPPR10); protein phosphatase 1, regulatory subunit 7 (PPP1R7); protein phosphatase 2 (formerly 2A), catalytic subunit, beta isoform (PPP2CB); protein phosphatase 2 (formerly 2A), regulatory subunit B" (PR 72), alpha isoform and (PR 130), beta isoform (PPP2R3); protein phosphatase 2, regulatory subunit B (B56), alpha isoform (PPP2R5A); protein phosphatase 2, regulatory subunit B (B56), delta isoform (PPP2R5D); protein phosphatase 2, regulatory subunit B (B56), gamma isoform (PPP2R5C); protein phosphatase 2A regulatory subunit alpha-isotype (alpha-PR65); protein phosphatase 4 (formerly X), catalytic subunit (PPP4C); protein tyrosine kinase 2 beta (PTK2B); protein tyrosine phosphatase epsilon; protein tyrosine phosphatase type IVA, member 2 (PTP4A2); protein tyrosine phosphatase, non-receptor type 1 (PTPN1); protein tyrosine phosphatase, non-receptor type 12 (PTPN12); protein tyrosine phosphatase, non-receptor type 2 (PTPN2); protein tyrosine phosphatase, non-receptor type 4 (megakaryocyte) (PTPN4); protein tyrosine phosphatase, non-receptor type 6 (PTPN6); protein tyrosine phosphatase, non-receptor type 7 (PTPN7); protein tyrosine phosphatase, receptor type, alpha polypeptide (PTPRA); protein tyrosine phosphatase, receptor type, c polypeptide (PTPRC); protein tyrosine phosphatase, receptor type, M (PTPRM); protein tyrosine phosphatase, receptor type, N polypeptide 2 (PTPRN2); protein with polyglutamine repeat (ERPROT213-21); protein-kinase, interferon-inducible double stranded RNA dependent inhibitor (PRKRI); protein-L-isoaspartate (D-aspartate) O-methyltransferase (PCMT1); proteoglycan 1, secretory granule (PRG1); prothymosin, alpha (gene sequence 28) (PTMA); prp28, U5 snRNP 100 kd protein (U5-100K); PRP4/STK/WD splicing factor (HPRP4P); PTK7 protein tyrosine kinase 7 (PTK7); purinergic receptor P2X, ligand-gated ion channel, 4 (P2RX4); purinergic receptor P2X, ligand-gated ion channel, 7 (P2RX7); puromycin-sensitive aminopeptidase (PSA); putative ATP (GTP)-binding protein; putative brain nuclearly-targeted protein (KIAA0765); putative chemokine receptor; GTP-binding protein (HM74); putative dienoyl-CoA isomerase (ECH1); putative G-binding protein; Putative human HLA class II associated protein I (PHAP1); Putative L-type neutral amino acid transporter (KIAA0436); putative mitochondrial space protein 32.1; putative nucleic acid binding protein; putative outer mitochondrial membrane 34 kDa translocase Htom34; putative translation initiation factor (SUI1); putative tumor suppressor protein (123F2); pyrroline 5-carboxylate reductase; pyruvate dehydrogenase (lipoamide) alpha 1 (PDHA1); pyruvate dehydrogenase (lipoamide) beta (PDHB); Pyruvate dehydrogenase complex, lipoyl-containing component X; E3-binding protein (PDX1); pyruvate kinase, muscle (PKM2); RAB, member of RAS oncogene family-like (RABL); RAB1, member RAS oncogene family (RAB1); RAB11A, member RAS oncogene family (RAB11A); RAB11B, member RAS oncogene family (Rab11B); RAB27A, member RAS oncogene family (RAB27A); RAB5B, member RAS oncogene family (RAB5B); RAB6, member RAS oncogene family (RAB6); RAB7, member RAS oncogene family (RAB7); RAB7, member RAS oncogene family-like 1 (RAB7L1); RAB9, member RAS oncogene family (RAB9); RAD50 (*S. cerevisiae*) homolog (RAD50); RAD51 (*S. cerevisiae*) homolog C (RAD51C); Radin blood group (RD); RAE1

(RNA export 1, S. pombe) homolog (RAE1); ralA-binding protein (RLIP76); RAN binding protein 2-like 1 (RANBP2L1); Ran GTPase activating protein 1 (RANGAP1); transforming growth factor, beta receptor II (70-80 kD) (TGFBR2); RAP1A, member of RAS oncogene family (RAP1A); RAR-related orphan receptor C (RORC); RAS guanyl releasing protein 2 (calcium and DAG-regulated); ras homolog gene family, member A (ARHA); ras homolog gene family, member G (rho G) (ARHG); ras homolog gene family, member H (ARHH); ras inhibitor (RIN1); Ras-GTPase activating protein SH3 domain-binding protein 2 (KIAA0660); Ras-GTPase-activating protein SH3-domain-binding protein (G3BP); ras-related C3 botulinum toxin substrate 2 (rho family, small GTP binding protein Rac2) (RAC2); RBQ-1; regulator of Fas-induced apoptosis (TOSO); regulator of G protein signalling 6 (RGS6); regulator of G-protein signalling 14 (RGS14); regulator of G-protein signalling 2, 24 kD (RGS2); regulatory factor X, 4 (influences HLA class II expression) (RFX4); regulatory factor X, 5 (influences HLA class II expression (RFX5); replication protein A1 (RPA1); reproduction 8 (D8S2298E); requiem, apoptosis response zinc finger gene (REQ); restin (Reed-Steinberg cell-expressed intermediate filament-associated protein) (RSN); retinoblastoma 1 (including osteosarcoma) (RB1); retinoblastoma binding protein 2 homolog 1 (RBBP2H1); retinoblastoma-binding protein 1 (RBBP1); retinoblastoma-binding protein 2 (RBBP2); retinoblastoma-binding protein 4 (RBBP4); retinoblastoma-binding protein 7 (RBBP7); retinoblastoma-like 2 (p130) (RBL2); retinoic acid receptor responder (tazarotene induced) 3 (RARRES3); retinoic acid receptor, alpha (RARA); retinoic acid responsive (NN8-4AG); retinoid X receptor beta (RXR-beta); REV3 (yeast homolog)-like, catalytic subunit of DNA polymerase zeta (REV3L); Rho GDP dissociation inhibitor (GDI) beta (ARHGDIB); Rho GTPase activating protein 4 (ARHGAP4); Rho-associated, coiled-coil containing protein kinase 2 (ROCK2); ribonuclease 6 precursor (RNASE6PL); ribonuclease, RNase A family, 2 (liver, eosinophil-derived neurotoxin) (RNASE2); ribonuclease/angiogenin inhibitor (RNH); ribonucleoside diphosphate reductase M1 subunit; ribophorin I (RPN1); ribophorin II (RPN2); ribosomal 18S rRNA; ribosomal 28S RNA; ribosomal protein L10 (RPL10); ribosomal protein L11 (RPL11); ribosomal protein L12 (RPL19); ribosomal protein L14 (RPL14); ribosomal protein L17 (RPL17); ribosomal protein L18 (RPL18); ribosomal protein L18a (RPL18A); ribosomal protein L18a homologue; ribosomal protein L19 (RPL19); ribosomal protein L21 (RPL21); ribosomal protein L22 (RPL22); ribosomal protein L23 (RPL23); ribosomal protein L23a (RPL23A); ribosomal protein L26 (RPL26); ribosomal protein L27 (RPL27); ribosomal protein L27a (RPL27A); ribosomal protein L28 (RPL28); ribosomal protein L29 (RPL29); ribosomal protein L3 (RPL3); ribosomal protein L3 homologue; ribosomal protein L30 (RPL30); ribosomal protein L31 (RPL31); ribosomal protein L32 (RPL32); ribosomal protein L33-like (RPL33L); ribosomal protein L34 (RPL34); ribosomal protein L37 (RPL37); ribosomal protein L37a; ribosomal protein L38 (PRL38); ribosomal protein L4 (RPL4); ribosomal protein L41 (RPL41); ribosomal protein L5 (RPL5); ribosomal protein L6 (RPL6); ribosomal protein L7 (RPL7); ribosomal protein L7a (RPL7A); ribosomal protein L8 (RPL8); ribosomal protein L9 (RPL9); ribosomal protein S10 (RPS10); ribosomal protein S11 (RPS11); ribosomal protein S12 (RPS12); ribosomal protein S13 (RPS13); ribosomal protein S14 (RPS14); ribosomal protein S15 (RPS15); ribosomal protein S16 (RPS16); ribosomal protein S17 (RPS17); ribosomal protein S18; ribosomal protein S19 (RPS19); ribosomal protein S2 (RPS2); ribosomal protein S20 (RPS20); ribosomal protein S21 (RPS21); ribosomal protein S23 (RPS23); ribosomal protein S24 (RPS24); ribosomal protein S25 (RPS25); ribosomal protein S26 (RPS26); ribosomal protein S27 ((metallopanstimulin 1) (RPS27); ribosomal protein S28 (RPS28); ribosomal protein S29 (RPS29); ribosomal protein S3 (RPS3); ribosomal protein S3A (RPS3A); ribosomal protein S4, X-linked (RPS4X); ribosomal protein S4, Y-linked (RPS4Y); ribosomal protein S5 (RPS5); ribosomal protein S6 (RPS6); ribosomal protein S6 kinase, 90 kD, polypeptide 1 (RPS6KA1); ribosomal protein S6 kinase, 90 kD, polypeptide 2 (RPS6KA2); ribosomal, protein S7 (RPS7); ribosomal protein S8 (RPS8); ribosomal protein S9 (RPS9); ribosomal protein, large, P0 (RPLP0); ribosomal protein, large, P1 (RPLP1); ribosomal RNA 28S; ribosomal RNA, 16S; ring finger protein 3 (RNF3); ring finger protein 4 (RNF4); ring zinc-finger protein (ZNF127-Xp); RNA (guanine-7-) methyltransferase (RNMT); RNA binding motif protein 5 (RBM5); RNA binding motif, single stranded interacting protein 2 (RBMS2); RNA helicase (putative), (Myc-regulated DEAD box protein) (MRD8); RNA helicase-related protein; RNA pol II largest subunit; RNA polymerase I subunit (RPA40); RTVP-1 protein; S100 calcium-binding protein A10 (annexin II ligand, calpactin I, light polypeptide (p11)) (S100A10); S100 calcium-binding protein A11 (calgizzarin) (S100A11); S100 calcium-binding protein A4 (calcium protein, calvasculin, metastasin, murine placental homolog) (S100A4); S100 calcium-binding protein A8 (calgranulin A) (S100A8); S100 calcium-binding protein A9 (calgranulin B) (S100A9); S164 gene; S-adenosylmethionine decarboxylase 1 (AMD1); SB class II histocompatibility antigen alpha-chain; SC35-interacting protein 1 (SRRP129); scaffold attachment factor B (SAFB); scRNA molecule, transcribed from Alu repeat; SEC14 (S. cerevisiae)-like (SEC14L); SEC23-like protein B (SEC23B); SEC63 (SEC63); secreted protein, acidic, cysteine-rich (osteonectin) (SPARC); secretory carrier membrane protein 1 (SCAMP1); secretory carrier membrane protein 2 (SCAMP2); secretory carrier membrane protein 3 (SCAMP3); secretory granule proteoglycan core (clones lambda-PG[6,7,8]); selectin L (lymphocyte adhesion molecule 1) (SELL); selectin P ligand (SELPLG); sema domain, immunoglobulin domain (Ig), transmembrane domain (TM) and short cytoplasmic domain, (semaphorin) 4D (SEMA4D); Ser/Arg-related nuclear matrix protein (plenty of prolines 101-like) (SRM160); serine palmitoyltransferase subunit I (SPTI); serine palmitoyltransferase, subunit II (LCB2); serine protease; serine protease inhibitor, Kunitz type, 2 (SPINT2); serine/threonine kinase 10 (STK10); serine/threonine kinase 19 (STK19); serine/threonine kinase 4 (STK4); serine/threonine protein kinase KKIALRE (KKIALRE); serine/threonine protein-kinase (NIK); serologically defined colon cancer antigen 16 (NY-CO-16); serologically defined colon cancer antigen 33 (SD-CCAG33); serum/glucocorticoid regulated kinase (SGK); SET domain, bifurcated 1 (SETDB1); SH2 domain protein 1A, Duncan's disease lymphoproliferative syndrome) (SH2D1A); SH3 binding protein (SAB); SH3 domain protein 1B (SH3D1B); SH3-binding domain glutamic acid-rich protein like (SH3BGRL); SH3-domain GRB2-like 1 (SH3GL1); SHC (Src homology 2 domain-containing) transforming protein 1 (SHC1); siah binding protein 1 (SiahBP1); Sialomucin CD164 (CD164); sialophorin (gpL115, leukosialin, CD43) (SNP); sialyltransferase (STHM); sialyltransferase 1 (beta-galactoside alpha-2,6-sialyltransferase) (SIAT1); sialyltransferase 4A (beta-galactosidase alpha-2,3-sialytransferase) (SIAT4A); sialyltransferase 8 (alpha-2,8-polysialytransferase) D (SIAT8D); signal peptidase 25 kDa subunit; signal recognition particle 14 kD (homologous Alu RNA-binding protein) (SRP14); signal recognition particle 54 kD (SRP54); signal recognition particle 9 kD (SRP9); signal recognition particle receptor ('docking protein') SRPR; signal regulatory protein, beta, 1 (SIRP-BETA-1); signal sequence receptor, alpha (translocon-associated protein alpha) (SSR1); signal sequence receptor, beta (translocon-associated protein beta) (SSR2); signal transducer and activator of transcription (STAT5A); signal transducer and activator of transcription 2, 113 KD (STAT2); signal transducer and activator of transcription 3 (acute-phase response factor) (STAT3); signal transducer and activator of transcription 5A (STAT5A); signal transducing adaptor molecule (SH3 domain and ITAM motif) 1 (STAM); silencing mediator of retinoid and thyroid hormone action (SMRT); SIT protein; Sjogren syndrome antigen A1 (52 kD, ribonucleoprotein autoantigen SS-A/Ro) (SSA1); SKAP55 homologue (SKAP-HOM); skb1 (*S. pombe*) homolog (SKB1); skeletal muscle abundant protein; SMA3 (SMA3); small acidic protein; small EDRK-rich factor 2 (SERF2); small inducible cytokine A5 (RANTES) (SCYA5); small inducible cytokine subfamily C, member 2 (SCYC2); small nuclear ribonucleoprotein polypeptide B" (SNRPB2); small nuclear ribonucleoprotein polypeptide N (SNRPN); small nuclear ribonucleoprotein polypeptides B and B1 (SNRPB); small nuclear RNA activating complex, polypeptide 5, 19 kD (SNAPC5); smallest subunit of ubiquinol-cytochrome c reductase; SMC (mouse) homolog, X chromosome (SMCX); SMT3B protein (2); SNC19; SNC73 protein (SNC73); solute carrier family 1 (neutral amino acid transporter), member 5 (SLC1A5); Solute carrier family 11 (proton-coupled divalent metal ion transporters), member 1 (SLC11A1); solute carrier family 17 (sodium phosphate), member 3 (SLC17A3); solute carrier family 19 (folate transporter), member 1 (SLC19A1); solute carrier family 2 (facilitated glucose transporter), member 1 (SLC2A1); solute carrier family 23 (nucleobase transporters), member 2 (SLC23A2); solute carrier family 25 (mitochondria carrier; oxoglutarate carrier), member 11 (SLC25A11); solute carrier family 31 (copper transporters), member 2 (SLC31A2); solute carrier family 4, anion exchanger, member 2 (erythrocyte membrane protein band 3-like 1) (SLC4A2); solute carrier family 4, sodium bicarbonate cotransporter, member 8 (SLC4A8); solute carrier family 7 (cationic amino acid transporter, y+ system), member 5 (SLC7A5); solute carrier family 7 (cationic amino acid transporter, y+ system), member 6 (SLC7A6); solute carrier family 9 (sodium/hydrogen exchanger), isoform 6 (SLC9A6); somatic cytochrome c (HCS); SON DNA binding protein (SON); son of sevenless (*Drosophila*) homolog 1 (SOS1); sorcin (SRI); sortilin 1 (SORT1); sortilin-related receptor, L (DLR class) A repeats-containing (SORL1); sorting nexin 1 (SNX1); sorting nexin 2 (SNX2); Sp3 transcription factor (SP3); special AT-rich sequence binding protein 1 (binds to nuclear matrix/scaffold-associating DNA's) (SATB1); speckle-type POZ protein (SPOP); spectrin SH3 domain binding protein 1 (SSH3BP1); Spectrin, alpha, non-erythrocytic 1 (alpha-fodrin) (SPTAN1); spermidine/spermine N1-acetyltransferase (SAT); spermine synthase (SMS); SPF31 (SPF31); sphingomyelin phosphodiesterase 1, acid lysosomal (acid sphingomyelinase) (SMPD1); spinocerebellar ataxia 1 (olivopontocerebellar ataxia 1, autosomal dominant, ataxin 1) (SCA1); spinocerebellar ataxia 2 (olivopontocerebellar ataxia 2, autosomal dominant, ataxin 2) (SCA2); spinocerebellar ataxia 7 (olivopontocerebellar atrophy with retinal degeneration) (SCAT); spliceosome associated protein (SAP 145); splicing factor (CC1.3) (CC1.3); splicing factor SRp40-1 (SRp40); splicing factor, arginine/serine-rich 11 (SFRS11); splicing factor, arginine/serine-rich 7 (35 kD) (SFRS7); Src-like-adapter (SLA); stannin (SNN); STAT induced STAT inhibitor 3 (SSI-3); STE20-like kinase 3 (MST-3); step 11 splicing factor SLU7 (SLUT); steroid sulfatase; steroid sulfatase (microsomal), arylsulfatase C, isozyme S (STS); sterol carrier protein 2 (SCP2); sterol O-acyltransferase (acyl-Coenzyme A: cholesterol acyltransferase) 1 (SOAT1); stimulated trans-acting factor (50 kDa) (STAF50); Stromal antigen 2 (STAG2); stromal interaction molecule 1 (STIM1); structure specific recognition protein 1 (SSRP1); succinate dehydrogenase complex, subunit A, flavoprotein (Fp) (SDHA); succinate dehydrogenase complex, subunit B, iron sulfur (Ip) (SDHB); succinate dehydrogenase complex, subunit C, integral membrane protein, 15 kD (SDHC); succinate dehydrogenase complex, subunit D, Integral membrane protein (SDHD); succinate-CoA ligase, GDP-forming, beta subunit (SUCLG2); succinyl CoA synthetase; sudD (suppressor of bimD6, *Aspergillus nidulans*) homolog (SUDD); sulfotransferase family 1A, phenol-preferring, member 1 (SULT1A1); superoxide dismutase 1, soluble (amyotrophic lateral sclerosis 1 (adult)) (SOD1); superoxide dismutase 2, mitochondrial (SOD2); supervillin (SVIL); suppression of tumorigenicity 5 (ST5); suppressor of K+ transport defect 1 (SKD1); suppressor of Ty (*S. cerevisiae*) 3 homolog (SUPT3H); suppressor of Ty (*S. cerevisiae*) 4 homolog 1 (SUPT4H1); suppressor of Ty (*S. cerevisiae*) 5 homolog (SUPT5H); suppressor of Ty (*S. cerevisiae*) 6 homolog (SUPT6H); suppressor of variegation 3-9 (*Drosophila*) homolog 1 (SUV39H1); survival of motor neuron 1, telomeric (SMN1); SWI/SNF related, matrix associated, actin dependent regulator of chromatin, subfamily a, member 2 (SMARCA2); SWI/SNF related, matrix associated, actin dependent regulator of chromatin, subfamily a, member 4 (SMARCA4); SWI/SNF related, matrix associated, actin dependent regulator of chromatin, subfamily c, member 2 (SMARCC2); SWI/SNF related, matrix associated, actin dependent regulator of chromatin, subfamily e, member 1 (SMARCE1); synaptobrevin-like 1 (SYBL1); synaptosomal-associated protein, 23 kD (SNAP23); syndecan binding protein (syntenin) (SDCBP); synovial sarcoma, translocated to X chromosome (SSXT); syntaxin 16; syntaxin 3A (STX3A); syntaxin 6 (STX6); SYNTAXIN BINDING PROTEIN 3 (UNC-18 HOMOLOG 3) (UNC-18C); syntaxin-16C; SYT interacting protein (SIP); T cell activation, increased late expression (TACTILE); T cell receptor V alpha gene segment V-alpha-7 (clone IGRa11); T cell receptor V alpha gene segment V-alpha-w27; T3 receptor-associating cofactor-1; tafazzin (cardiomyopathy, dilated 3A (X-linked); endocardial fibroelastosis 2; Barth syndrome) (TAZ); tankyrase, TRF1-interacting ankyrin-related ADP-ribose polymerase (TNKS); TAR DNA-binding protein-43; Tat interactive protein (60 kD) (TIP60); TATA box binding protein (TBP)-associated factor, RNA polymerase II, F, 55 kD (TAF2F); TATA box binding protein (TBP)-associated factor, RNA polymerase II, G, 32 kD (TAF2G); TATA box binding protein (TBP)-associated factor, RNA polymerase II, I, 28 kD (TAF2I); Tax1 (human T-cell leukemia virus type I) binding protein 1 (TAX1BP1); TBP-associated factor 172 (TAF-172); T-cell death-associated gene 8 (TDAG8); T-cell leukemia/lymphoma 1A (TCL1A); T-cell receptor (delta D2-J1-region) (clone K3B); T-cell receptor delta gene D2-J1-region, clone K3B; T-cell receptor germline beta chain gene V-region (V) V-beta-MT1-1; T-cell receptor germline beta-chain gene J2.1 exon; T-cell receptor germline delta-chain D-J region; T-cell receptor interacting molecule (TRIM) protein; T-cell receptor rearranged delta-chain, V-region (V-delta 3-J); T-cell receptor, alpha (V,D,J,C) (TCRA); T-cell receptor, beta cluster (TCRB); T-cell receptor, delta (V,D,J,C) (TCRD); T-cell, immune regulator 1 (TCIRG1); TCF-1 mRNA for T cell factor 1; TCR eta=T cell receptor (eta-exon); TCR V Beta 13.2; TERA; testis enhanced gene transcript (TEGT); tetracycline transporter-like protein (TETRAN); tetratricopeptide repeat domain 1' (TTC1); tetratricopeptide repeat domain 2 (TTC2); tetratricopeptide repeat domain 3 (TTC3); TGFB1-induced anti-apoptotic factor 1 (TIAF1); thioredoxin reductase 1 (TXNRD1); threonyl-tRNA synthetase (TARS); thrombin inhibitor; thrombospondin 1 (THBS1); thromboxane A synthase 1 (platelet, cytochrome P450, subfamily V) (TBXAZ1); thymidine kinase 2, mitochondrial (TK2); thymidylate kinase (CDC8); thymine-DNA glycosylase (TDG); Thymosin, beta 10 (TMSB10); thymosin, beta 4, X chromosome (TMSB4X); thyroid autoantigen 70 kD (Ku antigen) (G22P1); thyroid hormone receptor coactivating protein (SMAP); thyroid hormone receptor interactor 7 (TRIP7); thyroid hormone receptor interactor 8r (TRIP8); thyroid hormone receptor-associated protein, 230 kDa subunit (TRAP230); thyroid receptor interacting protein 15 (TRIP15); TI-227H; TIA1 cytotoxic granule-associated RNA-binding protein (TIA1); tissue inhibitor of metalloproteinase 1 (erythroid potentiating activity, collagenase inhibitor) (TIMP1); tissue inhibitor of metalloproteinase 2 (TIMP2); tissue specific transplantation antigen P35B (TSTA3); titin (TTN); TNF receptor-associated factor 2 (TRAF2); TNF receptor-associated factor 3 (TRAF3); toll-like receptor 1 (TLR1); toll-like receptor 2 (TLR2); toll-like receptor 4 (TLR4); toll-like receptor 5 (TILR5); topoisomerase (DNA) I (TOP1); topoisomerase (DNA) II beta (180 kD) (TOP2B); topoisomerase (DNA) III beta (TOP3B); TR3beta; TRAF family member-associated NF-kB activator (TANK); transaldolase 1 (TALDO1); transaldolase-related protein; transcobalamin II (TCII); transcription elongation factor B (SIII), polypeptide 1-like (TCEB1L); transcription elongation factor B (SIII), polypeptide 3 (110 kD, elongin A) (TCEB3); transcription factor 12 (HTF4, helix-loop-helix transcription factors 4) (TCF12); transcription factor 17 (TCF17); transcription factor 4 (TCR4); transcription factor 6-like 1 (mitochondrial transcription factor 1-like) (TCF6L1); transcription factor 7-like 2 (T-cell specific, HMG-box) (TCF7L2); transcription factor binding to IGHM enhancer 3 (TFE3; transcription factor IL-4 Stat; transcription factor TFIID; transcriptional adaptor 2 (ADA2, yeast, homolog)-like (TADA2L); transducin (beta)-like 1 (TBL1); transducin-like enhancer of split 3, homolog of *Drosophila* E(sp1) (TLE3); Transformation/transcription domain-associated protein (TRRAP); transformation-sensitive, transforming growth factor beta-stimulated protein TSC-22 (TSC22); transforming growth factor, beta receptor III (betaglycan, 300 kD) (TGFBR3); transforming growth factor, beta-induced, 68 kD (TGFBI); transgelin 2 (TAGLN2); trans-Golgi network protein (46, 48, 51 kD isoforms) (TGN51); transient receptor potential channel 1 (TRPC1); transketolase (Wernicke-Korsakoff syndrome) (TKT); translation factor sui1 homolog (GC20); translin (TSN); translin-associated factor X (TSNAX); transmembrane glycoprotein (A33); transmembrane protein (63 kD), endoplasmic reticulum/Golgi intermediate compartment (P63); transmembrane protein 1 (TMEM2); transmembrane trafficking protein (TMP21); transporter 1, ABC (ATP binding cassette) (TAP1); Treacher Collins-Franceschetti syndrome 1 (TCOF1); triosephosphate isomerase 1 (TPI1); tropomyosin; tropomyosin 4 (TPM4); TRPM-2 protein; tryptophan rich basic protein (WRB); tryptophanyl-tRNA synthetase (WARS); Ts translation elongation factor, mitochondrial (TSFM); ttopoisomerase (DNA) II beta (180 kD); Tu translation elongation factor, mitochondrial (TUFM); tuberous sclerosis 1 (TSC1); tuberous sclerosis 2 (TSC2); tubulin, alpha 1 (testis specific) (TUBA1); tubulin, alpha, ubiquitous (K-ALPHA-1); tubulin-specific chaperone c (TBCC); tumor necrosis factor (ligand) superfamily, member 10 (TNFSF10); tumor necrosis factor (ligand) superfamily, member 13 (TNFSF13); tumor necrosis factor (ligand) superfamily, member 14 (TNFSF14); tumor necrosis factor (ligand) superfamily, member 6 (TNFSF6); tumor necrosis factor (ligand) superfamily, member 8 (TNFSF8); tumor necrosis factor alpha-inducible cellular protein containing leucine zipper domains (FIP2); Tumor necrosis factor receptor superfamily member 7 (TNFRSF7); tumor necrosis factor receptor superfamily, member 10b (TNFRSF10B); tumor necrosis factor receptor superfamily, member 10c, decoy without an intracellular domain (TNFRSF10C); tumor necrosis factor receptor superfamily, member 12 (translocating chain-association membrane protein) (TNFRSF12); tumor necrosis factor receptor superfamily, member 14 (herpesvirus entry mediator) (TNFRSF14); tumor necrosis factor receptor superfamily, member 1B (TNFRSF1B); tumor necrosis factor receptor superfamily, member 6 (TNFRSF6); tumor necrosis factor receptor superfamily, member 7 (TNFRSF7); tumor necrosis, factor, alpha-induced protein 2 (TNFAIP2); tumor necrosis factor, alpha-induced protein 3 (TNFAIP3); tumor protein 53-binding protein, 1 (TP53BP1); tumor protein p53 (Li-Fraumeni syndrome) (TP53); Tumor protein p53-binding protein (TP53BPL); tumor protein, translationally-controlled 1 (TPT1); tumor rejection antigen (gp96) 1 (TRA1); tumorous imaginal discs (*Drosophila*) homolog (TID1); TXK tyrosine kinase (TXK); type II integral membrane protein (NKG2-E); TYRO protein tyrosine kinase binding protein (TYROBP); tyrosine 3-monooxygenase/ tryptophan 5-monooxygenase activation protein, beta polypeptide (YWHAB); tyrosine 3-monooxygenase/tryptophan 5-monooxygenase activation protein, zeta polypeptide (YWHAZ); Tyrosine kinase 2 (TYK2); tyrosyl-tRNA synthetase (YARS); U1 small nuclear RNA; U2 (RNU2) small nuclear RNA auxiliary factor 1 (non-standard symbol) (U2AF1); U22 snoRNA host gene (UHG); U4/U6-associated RNA splicing factor (HPRP3P); U49 small nuclear RNA; U5 snRNP-specific protein (220 kD), ortholog of S. cerevisiae Prp8p (PRP8); U5 snRNP-specific protein, 116 kD (U5-116 KD); U5 snRNP-specific protein, 200 kDa (DEXH RNA helicase family) (U5-200-KD); Uba80 mRNA for ubiquitin; ubiquinol-cytochrome c reductase (6.4 kD) subunit (UQCR); ubiquitin A-52 residue ribosomal protein fusion product 1 (UBA52); ubiquitin activating enzyme E1-like protein (GSA7); ubiquitin C (UBC); ubiquitin carboxyl-terminal esterase L3 (ubiquitin thiolesterase) (UCHL3); ubiquitin fusion degradation 1-like (UFD1L); ubiquitin protein ligase E3A (human papilloma virus E6-associated protein, Angelman syndrome) (UBE3A); ubiquitin specific protease 10 (USP10); ubiquitin specific protease 11 (USP11); ubiquitin specific protease 15 (USP15); ubiquitin specific protease 19 (USP19); ubiquitin specific protease 4 (proto-oncogene) (USP4); ubiquitin specific protease 7 (herpes virus-associated) (USP7); ubiquitin specific protease 8 (USP8); ubiquitin-activating enzyme E1 (A1S9T and BN75 temperature sensitivity complementing) (UBE1); ubiquitin-activating enzyme E1, like (UBE1L); UBIQUITIN-BINDING PROTEIN P62; phosphotyrosine independent ligand for the Lck SH2 domain p62 (P62); ubiquitin-conjugating enzyme E2 variant 1 (UBE2V1); ubiquitin-conjugating enzyme E2 variant 2 (UBE2V2); ubiquitin-conjugating enzyme E2B (RAD6 homolog) (UBE2B); ubiquitin-conjugating enzyme E2G 2 (homologous to yeast UBC7) (UBE2G2); ubiquitin-conjugating enzyme E2H (homologous to yeast UBC8) (UBE2H); ubiquitin-conjugating enzyme E2L 1 (UBE2L1); ubiquitin-conjugating enzyme E2L 3 (UBE2L3); ubiquitin-conjugating enzyme E2L 6 (UBE2L6); ubiquitin-like 1 (sentrin) (UBL1); UDP-N-acetyl-alpha-D-galactosamine:polypeptide N-acetylgalactosaminyltransferase 2 (GalNAc-T2) (GALNT2); unactive progesterone receptor, 23 Kd (P23); unconventional myosin-ID (MYO1F); uncoupling protein homolog (UCPH); uppressor of Ty (S. cerevisiae) 6 homolog; upregulated by 1,25-dihydroxyvitamin D-3 (VDUP1); upstream binding factor (hUBF); UV radiation resistance associated gene (UVRAG); vacuolar proton-ATPase, subunit D; V-ATPase, subunit D (ATP6DV); v-akt murine thymoma viral oncogene homolog 1 (AKT1); Vanin 2 (VNN2); vasodilator-stimulated phosphoprotein (VASP); vav 1 oncogene (VAV1); vav 2 oncogene (VAV2); v-crk avian sarcoma virus CT10 oncogene homolog (CRK); v-erb-b2 avian erythroblastic leukemia viral oncogene homolog 3 (ERBB3); Vesicle-associated membrane protein 1 (synaptobrevin 1) (VAMP1); vesicle-associated membrane protein 3 (cellubrevin) (VAMP3); v-fos FBJ murine osteosarcoma viral oncogene homolog (FOS); villin 2 (ezrin) (VIL2); villin-like protein; vimentin (VIM); vinculin (VCL); vitamin A responsive; cytoskeleton related (JWA); v-jun avian sarcoma virus 17 oncogene homolog (JUN); v-myb avian myeloblastosis viral oncogene homolog (MYB); voltage-dependent anion channel 1 (VDAC1); voltage-dependent anion channel 3 (VDAC3); von Hippel-Lindau syndrome (VHL); v-raf murine sarcoma 3611 viral oncogene homolog 1 (ARAF1); v-raf-1 murine leukemia viral oncogene homolog 1 (RAF1); v-ral simian leukemia viral oncogene homolog B (ras related; GTP binding protein) (RALB); V-rel avian reticuloendotheliosis viral oncogene homolog A (nuclear factor of kappa light polypeptide gene enhancer in B-cells 3 (p65)) (RELA); v-yes-1 Yamaguchi sarcoma viral related oncogene homolog (LYN); WD repeat domain 1 (WDR1); WD-repeat protein (HAN11); Williams-Beuren syndrome chromosome region 1 (WBSCR1); Wiskott-Aldrich syndrome protein interacting protein (WASPIP); X (inactive)-specific-transcript (XIST); xeroderma pigmentosum, complementation group C (XPC); XIAP associated factor-1; XIB; X-linked anhidroitic ectodermal dysplasia; X-ray repair complementing defective repair in Chinese hamster cells 5 (double-strand-break rejoining; Ku autoantigen, 80 kD) (XRCC5); XRP2 protein; yeloid differentiation primary response gene (88) (MYD88); zeta-chain (TCR) associated protein kinase (70 kD) (ZAP70); zinc finger protein (Hs.47371); zinc finger protein (Hs.78765); zinc finger protein 10 (KOX 1) (ZNF10); zinc finger protein 136 (clone pHZ-20) (ZNF136); zinc finger protein 140 (clone pHZ-39) (ZNF140); zinc finger protein 143 (clone pHZ-1) (ZNF143); zinc finger protein 148 (pHZ-52) (ZNF148); zinc finger protein 173 (ZNF173); zinc finger protein 198 (ZNF198); zinc finger protein 200 (ZNF200); zinc finger protein 207 (ZNF207); zinc finger protein 216 (ZNF216); zinc finger protein 217 (ZNF217); zinc finger protein 230 (ZNF230); Zinc finger protein 239 (ANF239); zinc finger protein 261 (ZNF261); zinc finger protein 262 (ANF262); zinc finger protein 263 (ZNF263); zinc finger protein 264 (ZNF264); zinc finger protein 42 (myeloid-specific retinoic cid-responsive) (ZNF42); zinc finger protein 45 (a Kruppel-associated box (KRAB) domain polypeptide) (ZNF45); zinc finger protein 76 (expressed in testis) (ZNF76); zinc finger protein 84 (HPF2) (ZNF84); zinc finger protein 85 (ZNF85)); zinc finger protein 9 (ZNF9); zinc finger protein C2H2-25 (ZNF25); zinc finger protein clone L3-4; zinc finger protein homologous to Zfp-36 in mouse (ZFP36); zinc finger protein HZF4; zinc finger' protein RIZ; zinc finger protein, subfamily 1A, 1 (Ikaros) (LYF1); zinc finger transcriptional regulator (GOS24); zinc-finger helicase (hZFH); Zn-15 related zinc finger protein (rlf); ZNF80-linked ERV9 long terminal repeat; ZW10 (Drosophila) homolog, centromere/kinetochore protein (ZW10); and zyxin (ZYX); thereby profiling gene expression in a human subject.

2. The method of claim 1, wherein determining the level is performed using at least one oligonucleotide of predetermined sequence.

3. The method of claim 2, wherein the at least one oligonucleotide is specific for RNA encoded only by the gene in blood of human subjects, and/or is specific for cDNA complementary to RNA encoded only by the gene in blood of human subjects.

4. The method of claim 3, wherein determining the level is performed by amplifying of RNA encoded by the gene to form amplified product, using at least one primer, and quantifying the amplified product, wherein the at least one oligonucleotide comprises the at least one primer.

5. The method of claim 3, wherein determining the level is performed by hybridizing cDNA complementary to RNA encoded by the gene with at least one immobilized probe to form hybridization product, and quantifying the hybridization product, wherein the at least one oligonucleotide comprises the at least one probe.

6. The method of claim 1, wherein determining the level is performed by amplifying RNA encoded by the gene.

7. The method of claim 1, wherein determining the level is performed using an immobilized probe.

8. The method of claim 1, wherein determining the level is performed by quantifying cDNA generated from RNA encoded by said gene.

9. The method of claim 1, wherein determining the level is performed by quantifying EST generated from RNA encoded by the gene.

10. The method of claim 1, wherein the level of RNA encoded by the gene is determined relative to a level of RNA encoded by an internal control gene in the blood sample.

* * * * *